(12) United States Patent
Basarab et al.

(10) Patent No.: US 8,399,489 B2
(45) Date of Patent: Mar. 19, 2013

(54) ANTIBACTERIAL PIPERDINE DERIVATIVES

(75) Inventors: Gregory Basarab, Sudbury, MA (US); Brian Dangel, Somerville, MA (US); Paul Robert Fleming, Waltham, MA (US); Michael Barry Gravestock, Holliston, MA (US); Oluyinka Green, Burlington, MA (US); Sheila Irene Hauck, Waltham, MA (US); Pamela Hill, Waltham, MA (US); Kenneth Gregory Hull, Marlborough, MA (US); George Mullen, Wilmington, NC (US); Haihong Ni, Lexington, MA (US); Brian Sherer, Nashua, NH (US); Fei Zhou, Southborough, MA (US)

(73) Assignee: Astrazeneca AB, Macclesfield, Cheshire (GB)

( * ) Notice: Subject to any disclaimer, the term of this patent is extended or adjusted under 35 U.S.C. 154(b) by 848 days.

(21) Appl. No.: 11/816,612

(22) PCT Filed: Feb. 16, 2006

(86) PCT No.: PCT/GB2006/000529
§ 371 (c)(1),
(2), (4) Date: Nov. 12, 2009

(87) PCT Pub. No.: WO2006/087543
PCT Pub. Date: Aug. 24, 2006

(65) Prior Publication Data
US 2010/0179150 A1 Jul. 15, 2010

Related U.S. Application Data

(60) Provisional application No. 60/654,670, filed on Feb. 18, 2005.

(51) Int. Cl.
*A61K 31/454* (2006.01)
*C07D 401/14* (2006.01)

(52) U.S. Cl. ...................................... 514/326; 546/208
(58) Field of Classification Search .................. 514/326; 546/208
See application file for complete search history.

(56) References Cited

U.S. PATENT DOCUMENTS

| | | | |
|---|---|---|---|
| 3,963,480 A | 6/1976 | Bailey | |
| 4,046,775 A | 9/1977 | Bailey | |
| 4,791,112 A | 12/1988 | Bagley et al. | |
| 4,912,109 A | 3/1990 | Bagley et al. | |
| 5,712,279 A | 1/1998 | Biller et al. | |
| 5,739,135 A | 4/1998 | Biller et al. | |
| 7,709,503 B2 * | 5/2010 | Green et al. | 514/326 |
| 2005/0234033 A1 | 10/2005 | Anandan et al. | |
| 2005/0250784 A1 | 11/2005 | Anandan et al. | |
| 2008/0312255 A1 * | 12/2008 | Basarab et al. | 514/255.05 |

FOREIGN PATENT DOCUMENTS

| | | |
|---|---|---|
| EP | 0894805 A1 | 2/1999 |
| EP | 1253142 A1 | 10/2002 |
| EP | 1431267 A1 | 6/2004 |
| WO | 96/26205 A1 | 8/1996 |
| WO | 01/12601 A1 | 2/2001 |
| WO | 01/52845 A1 | 7/2001 |
| WO | 01/52846 A1 | 7/2001 |
| WO | 01/53267 A1 | 7/2001 |
| WO | 01/96307 A2 | 12/2001 |
| WO | 02/085886 A2 | 10/2002 |
| WO | 02/096908 A1 | 12/2002 |
| WO | 03/016254 A1 | 2/2003 |
| WO | 2003/048129 A1 | 6/2003 |
| WO | 03/072554 A1 | 9/2003 |
| WO | 2003/072553 A1 | 9/2003 |
| WO | 2004/002490 A2 | 1/2004 |
| WO | 2004/083177 A2 | 9/2004 |
| WO | 2004/089947 A2 | 10/2004 |
| WO | 2004/089954 A1 | 10/2004 |
| WO | 2005/014579 A1 | 2/2005 |
| WO | 2005/026149 A1 | 3/2005 |
| WO | 2005026149 A1 | 3/2005 |
| WO | 2005/044797 A1 | 5/2005 |
| WO | 2005/086898 A2 | 9/2005 |
| WO | 2006/030975 A1 | 3/2006 |
| WO | 2006/047277 A2 | 5/2006 |
| WO | 2006/047504 A1 | 5/2006 |
| WO | 2006/087544 A2 | 8/2006 |
| WO | 2006/087548 A2 | 8/2006 |
| WO | 2006087543 A1 | 8/2006 |
| WO | 2006/092599 A2 | 9/2006 |
| WO | 2006/092608 A1 | 9/2006 |
| WO | 2007/071965 A2 | 6/2007 |
| WO | 2008020222 A1 | 2/2008 |
| WO | 2008152418 A1 | 12/2008 |

OTHER PUBLICATIONS

CHEMCATS 0078994164 (2011).*
Eakin Novel DNA Gyrase Inhibitors: Fragment-Based NMR Screening to Antibacterial Agents. Presentation at 48th Interscience Conference on Antimicrobial Agents and Chemotherapy (Washington, DC, Oct. 25, 2008).
Green et al. "Novel DNA Gyrase Inhibitors: Structure Guided Discovery and Optimization of Pyrrolamides" Poster at 48th Interscience Conference on Antimicrobial Agents and Chemotherapy (Washington, DC, Oct. 25, 2008) F1-2025.

(Continued)

*Primary Examiner* — Celia Chang
(74) *Attorney, Agent, or Firm* — Astrazeneca AB

(57) ABSTRACT

Compounds of formula (I) and their pharmaceutically acceptable salts are described. Processes for their preparation, pharmaceutical compositions containing them, their use as medicaments and their use in the treatment of bacterial infections are also described.

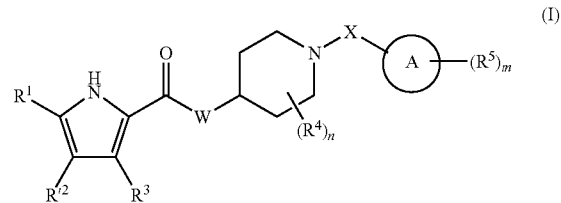

9 Claims, No Drawings

OTHER PUBLICATIONS

Hull et al. "Novel DNA Gyrase Inhibitors: The Effect of Pyrrolamide Variations at Site 1 and Site 2 Upon Potency" Poster at 48th Interscience Conference on Antimicrobial Agents and Chemotherapy (Washington, DC, Oct. 25, 2008) F1-2027
Illingworth et al. "Novel DNA Gyrase Inhibitors: Microbiological Characterization and In Vivo Efficacy of Pyrrolamides" Poster at 48th Interscience Conference on Antimicrobial Agents and Chemotherapy (Washington, DC, Oct. 25, 2008) F1-2028.
Sherer et al. "Novel DNA Gyrase Inhibitors: The Effects of Pyrrolamide Linker Variations Upon Potency" Poster at 48th Interscience Conference on Antimicrobial Agents and Chemotherapy (Washington, DC, Oct. 25, 2008) F1-2026.
Sherer et al. "Novel DNA Gyrase Inhibitors: Improvement of Pyrrolamide Antibacterial Activity by 3-Fluoropiperidine Linkers" Poster at 49th Interscience Conference on Antimicrobial Agents and Chemotherapy (San Francisco, CA, Sep. 15, 2009) F1-1977.
Uria-Nickelsen et al. "Novel DNA Gyrase Inhibitors: Investigation of the Mechanism of Action of Pyrrolamides" Poster at 49th Interscience Conference on Antimicrobial Agents and Chemotherapy (San Francisco, CA, Sep. 15, 2009) F1-2029.
Uria-Nickelsen et al. "Novel DNA Gyrase Inhibitors: Microbiological Characterization and In Vivo Efficacy 3-Fluoropiperidine Pyrrolamides" Poster at 49th Interscience Conference on Antimicrobial Agents and Chemotherapy (San Francisco, CA, Sep. 15, 2009) F1-1978.
Bisacchi et al. "Recent Advances in the Inhibition of Bacterial Type 11 Topoisomerases" in Annual Reports in Medicinal Chemistry; John E. Macon Ed. (Elsevier); 2009; pp. 379 to 396; vol. 44.
Ann E. Eakin; "Inhibition of Bacterial DNA Replication: Novel DNA Gyrase Inhibitors" Presentation at Gordon Research Conferences (Lucca, Italy) Mar. 10, 2008.
Beccalli, Egle M., et al., Pd-catalyzed intramolecular cyclization of pyrrolo-2-carboxamides: regiodivergent routes to pyrrolo-pyrazines and pyrrolo-pyridines, Tetrahedon, 2005, pp. 1077-1082, vol. 61.
Brown, J.W. et al., Some Three-Ring Esters Containing a Five-Membered Heteroaromatic Ring. A Comparison of Liquid Crystal Properties, Mol. Cryst. Liq. Cryst., 1989, pp. 121-140, vol. 173.
XP002397870 retrieved from STN, Database accession No. 784198-11-4 abstract; 784198-11-4 compounds, Nov. 19, 2004, Database Registry [Online], Chemical Abstracts Service, Columbus, OH.
XP002397871 retrieved from STN, Database accession No. 785802-22-4 abstract; 785802-22-4 compounds, Nov. 22, 2004, Database Registry [Online], Chemical Abstracts Service, Columbus, OH.
XP002397872 retrieved from STN, Database accession No. 784198-41-0 abstract; 784198-41-0 compounds, Nov. 19, 2004, Database Registry [Online], Chemical Abstracts Service, Columbus, OH.
XP002397873 retrieved from MDL, Database accession No. 432931, compounds 13254-12-1 & NL 6 510 290 a, Feb. 8, 2006, Database Beilstein [Online], Chemical Abstracts Service, Columbus, OH.
Gilles Klopman et al., Computer Automated Structure Evaluation of Quinolone Antibacterial Agents, Antimicrobial Agents and Chemotherapy, Nov. 1987, 1831-1840, 31(11).
Patrick Laurin et al., Structure-Activity Relationship in Two Series of Aminoalkyl Substituted Coumarin Inhibitors of Gyrase B, Bioorganic & Medicinal Chemistry Letters, 1999, 2875-2880, 9.
Laurent Schio et al., Fine Tuning of Physico-Chemical Parameters to Optimise a New Series of Novobiocin Analogues, Bioorganic & Medicinal Chemistry Letters, 2001, 1461-1464, 11.
Richard L. Wynn et al., Evaluation of the Morphine Reversal Actions and Antinociceptive Activity of a New Class of Opiate Antagonists Structurally Related to Fentanyl, Drug Development Research, 1991, 189-195, 22.
Yuichi Kanaoka et al., Synthesis of Thieno[2,3-c]-, Pyrrolo[2,3-c]- and Indolo[2,3-c]diazanaphthalenes by Photocyclization of Acylaminopyridines, Heterocycles, 1977, 29-32, 6(1).
John M. Domagala et al., New Structure-Activity Relationships of the Quinolone Antibacterials Using the Target Enzyme. The Development and Application of an DNA Gyrase Assay, J. Med. Chem., 1986, 394-404, 29(3).
James A. Waters et al., Anticonvulsant Activity of Piperidinol and (Dialkylamino)alkanol Esters, J. Med. Chem., 1986, 1512-1516, 29(8).
Krzysztof Sieradzki et al., Suppression of B-Lactam Antibiotic Resistance in a Methicillin-Resistant *Staphyloccous aureus* through synergic action of early cell wall inhibitors and some other antibiotics, Journal of Antimicrobial Chemotherapy, 1997, 47-51, 39, Suppl. A.
Branislav Musicki et al., Noviose Mimics of the Coumarin Inhibitors of Gyrase B, Tetrahedron Letters, 2003, 9259-9262, 44.

* cited by examiner

ANTIBACTERIAL PIPERDINE DERIVATIVES

This application is a US National Stage under 35 U.S.C. §371 of International Application No. PCT/GB2006/000529 filed 16 Feb. 2006, the text of which is hereby incorporated by reference, which claims priority under 35 U.S.C. §119(e) to Application No. 60/654,670 filed on 18 Feb. 2005.

BACKGROUND OF THE INVENTION

The present invention relates to compounds which demonstrate antibacterial activity, processes for their preparation, pharmaceutical compositions containing them as the active ingredient, to their use as medicaments and to their use in the manufacture of medicaments for use in the treatment of bacterial infections in warm-blooded animals such as humans. In particular this invention relates to compounds useful for the treatment of bacterial infections in warm-blooded animals such as humans, more particularly to the use of these compounds in the manufacture of medicaments for use in the treatment of bacterial infections in warm-blooded animals such as humans.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded as effective against both Gram-positive and certain Gram-negative pathogens.

Gram-positive pathogens, for example Staphylococci, Enterococci, Streptococci and mycobacteria, are particularly important because of the development of resistant strains which are both difficult to treat and difficult to eradicate from the hospital environment once established. Examples of such strains are methicillin resistant *staphylococcus aureus* (MRSA), methicillin resistant coagulase negative staphylococci (MRCNS), penicillin resistant *Streptococcus pneumoniae* and multiple resistant *Enterococcus faecium*.

The preferred clinically effective antibiotic for treatment of last resort of such resistant Gram-positive pathogens is vancomycin. Vancomycin is a glycopeptide and is associated with various toxicities, including nephrotoxicity. Furthermore, and most importantly, antibacterial resistance to vancomycin and other glycopeptides is also appearing. This resistance is increasing at a steady rate rendering these agents less and less effective in the treatment of Gram-positive pathogens. There is also now increasing resistance appearing towards agents such as β-lactams, quinolones and macrolides used for the treatment of upper respiratory tract infections, also caused by certain Gram negative strains including *H. influenzae* and *M. catarrhalis*.

Consequently, in order to overcome the threat of widespread multi-drug resistant organisms, there is an on-going need to develop new antibiotics, particularly those with either a novel mechanism of action and/or containing new pharmacophoric groups.

Deoxyribonucleic acid (DNA) gyrase is a member of the type II family of topoisomerases that control the topological state of DNA in cells (Champoux, J. J.; 2001. Ann. Rev. Biochem. 70: 369-413). Type II topoisomerases use the free energy from adenosine triphosphate (ATP) hydrolysis to alter the topology of DNA by introducing transient double-stranded breaks in the DNA, catalyzing strand passage through the break and resealing the DNA. DNA gyrase is an essential and conserved enzyme in bacteria and is unique among topoisomerases in its ability to introduce negative supercoils into DNA. The enzyme consists of two subunits, encoded by gyrA and gyrB, forming an $A_2B_2$ tetrameric complex. The A subunit of gyrase (GyrA) is involved in DNA breakage and resealing and contains a conserved tyrosine residue that forms the transient covalent link to DNA during strand passage. The B subunit (GyrB) catalyzes the hydrolysis of ATP and interacts with the A subunit to translate the free energy from hydrolysis to the conformational change in the enzyme that enables strand-passage and DNA resealing.

Another conserved and essential type II topoisomerase in bacteria, called topoisomerase IV, is primarily responsible for separating the linked closed circular bacterial chromosomes produced in replication. This enzyme is closely related to DNA gyrase and has a similar tetrameric structure formed from subunits homologous to Gyr A and to Gyr B. The overall sequence identity between gyrase and topoisomerase IV in different bacterial species is high. Therefore, compounds that target bacterial type II topoisomerases have the potential to inhibit two targets in cells, DNA gyrase and topoisomerase IV; as is the case for existing quinolone antibacterials (Maxwell, A. 1997, Trends Microbiol. 5: 102-109).

DNA gyrase is a well-validated target of antibacterials, including the quinolones and the coumarins. The quinolones (e.g. ciprofloxacin) are broad-spectrum antibacterials that inhibit the DNA breakage and reunion activity of the enzyme and trap the GyrA subunit covalently complexed with DNA (Drlica, K., and X. Zhao, 1997, Microbiol. Molec. Biol. Rev. 61: 377-392). Members of this class of antibacterials also inhibit topoisomerase IV and as a result, the primary target of these compounds varies among species. Although the quinolones are successful antibacterials, resistance generated primarily by mutations in the target (DNA gyrase and topoisomerase IV) is becoming an increasing problem in several organisms, including *S. aureus* and *Streptococcus pneumoniae* (Hooper, D. C., 2002, The Lancet Infectious Diseases 2: 530-538). In addition, quinolones, as a chemical class, suffer from toxic side effects, including arthropathy that prevents their use in children (Lipsky, B. A. and Baker, C. A., 1999, Clin. Infect. Dis. 28: 352-364). Furthermore, the potential for cardiotoxicity, as predicted by prolongation of the $QT_c$ interval, has been cited as a toxicity concern for quinolones.

There are several known natural product inhibitors of DNA gyrase that compete with ATP for binding the GyrB subunit (Maxwell, A. and Lawson, D. M. 2003, Curr. Topics in Med. Chem. 3: 283-303). The coumarins are natural products isolated from *Streptomyces* spp., examples of which are novobiocin, chlorobiocin and coumermycin A1. Although these compounds are potent inhibitors of DNA gyrase, their therapeutic utility is limited due to toxicity in eukaryotes and poor penetration in Gram-negative bacteria (Maxwell, A. 1997, Trends Microbiol. 5: 102-109). Another natural product class of compounds that targets the GyrB subunit is the cyclothialidines, which are isolated from *Streptomyces filipensis* (Watanabe, J. et al 1994, *J. Antibiot.* 47: 32-36). Despite potent activity against DNA gyrase, cyclothialidine is a poor antibacterial agent showing activity only against some eubacterial species (Nakada, N, 1993, *Antimicrob. Agents Chemother.* 37: 2656-2661).

Synthetic inhibitors that target the B subunit of DNA gyrase and topoisomerase IV are known in the art. For example, coumarin-containing compounds are described in patent application number WO 99/35155, 5,6-bicyclic heteroaromatic compounds are described in patent application WO 02/060879, and pyrazole compounds are described in patent application WO 01/52845 (U.S. Pat. No. 6,608,087).

We have discovered a new class of compounds which are useful for inhibiting DNA gyrase and topoisomerase IV.

SUMMARY OF THE INVENTION

Therefore the present invention provides a compound of formula (I):

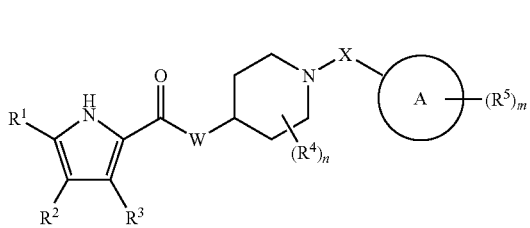

wherein:

R¹ is selected from hydrogen, nitro, hydroxy, halo, cyano, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl; wherein R¹ may be optionally substituted on carbon by one or more halo or cyclopropyl;

R² is selected from hydrogen, nitro, hydroxy, halo, cyano, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl; wherein R² may be optionally substituted on carbon by one or more halo or $C_{3-6}$cycloalkyl;

R³ is selected from hydrogen, nitro, hydroxy, halo, cyano, —C≡N—OR' wherein R' is H or $C_{1-4}$alkyl, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl; wherein R³ may be optionally substituted on carbon by one or more halo or $C_{3-6}$cycloalkyl;

W is —O—, —N(R⁶)— or —C(R⁷)(R⁸)—;

X is a direct bond, —CH$_2$—, —C(O)— or S(O)$_q$— (wherein q is 1 or 2);

Ring A is carbocyclyl or heterocyclyl; wherein if said heterocyclyl contains an —NH— moiety that nitrogen may be optionally substituted by a group selected from R⁹;

R⁴ and R⁵ are substituents on carbon and are independently selected from halo, nitro, cyano, hydroxy, trifluoromethoxy, amino, carboxy, carbamoyl, mercapto, sulphamoyl, sulfo, formyl, ureido, hydroxyiminomethyl, $C_{1-4}$alkoxyiminomethyl, N-hydroxyformamido, $C_{1-4}$hydrazino, hydrazinocarbonyl, N-hydroxyethanimidoyl, amino(hydroxyimino)methyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, N—($C_{1-4}$alkoxy)carbamoyl, N'—($C_{1-4}$alkyl)ureido, N',N'—($C_{1-4}$alkyl)$_2$ureido, N—($C_{1-4}$alkyl)-N—($C_{1-4}$alkoxy)carbamoyl, $C_{1-4}$alkylS(O)$_a$ wherein a is 0 to 2, $C_{1-4}$alkoxycarbonyl, $C_{1-4}$alkoxycarbonylamino, N—($C_{1-4}$alkyl)sulphamoyl, N,N—($C_{1-4}$alkyl)$_2$sulphamoyl, $C_{1-4}$alkylsulphonylamino, $C_{1-4}$alkylsulphonylaminocarbonyl, N'—($C_{1-4}$alkyl)hydrazinocarbonyl, N',N'—($C_{1-4}$alkyl)$_2$hydrazinocarbonyl, carbocyclyl-R¹⁰— or heterocyclyl-R¹¹—; wherein R⁴ and R⁵ independently of each other may be optionally substituted on carbon by one or more R¹²; and wherein if said heterocyclyl contains an —NH— moiety that nitrogen may be optionally substituted by a group selected from R¹³;

R⁶, R⁷ and R⁸ are independently selected from hydrogen or $C_{1-4}$alkyl;

n is 1-4; wherein the values of R⁴ may be the same or different;

m is 0-4; wherein the values of R⁵ may be the same or different;

R¹² is selected from azido, halo, nitro, cyano, hydroxy, trifluoromethoxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl, N,N—($C_{1-4}$alkyl)$_2$sulphamoyl, $C_{1-4}$alkylsulphonylamino, $C_{1-4}$alkoxycarbonylamino, carbocyclyl-R¹⁴— or heterocyclyl-R¹⁵—; wherein R¹² independently of each other may be optionally substituted on carbon by one or more R¹⁶; and wherein if said heterocyclyl contains an —NH— moiety that nitrogen may be optionally substituted by a group selected from R¹⁷;

R⁹, R¹³ and R¹⁷ are independently selected from $C_{1-4}$alkyl, $C_{1-4}$alkanoyl, $C_{1-4}$alkylsulphonyl, $C_{1-4}$alkoxycarbonyl, carbamoyl, N—($C_{1-4}$alkyl)carbamoyl, N,N—($C_{1-4}$alkyl)carbamoyl, benzyl, benzyloxycarbonyl, benzoyl and phenylsulphonyl;

R¹⁰, R¹¹, R¹⁴ and R¹⁵ are independently selected from a direct bond, —O—, —N(R¹⁸)—, —C(O)—, —N(R¹⁹)C(O)—, —C(O)N(R²⁰)—, —S(O)$_p$—, —SO$_2$N(R²¹)— or —N(R²²)SO$_2$—; wherein R¹⁸, R¹⁹, R²⁰, R²¹ and R²² are independently selected from hydrogen or $C_{1-4}$alkyl and p is 0-2;

R¹⁶ is selected from halo, nitro, cyano, hydroxy, trifluoromethoxy, trifluoromethyl, amino, carboxy, carbamoyl, mercapto, sulphamoyl, methyl, ethyl, ethenyl, ethynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or a pharmaceutically acceptable salt thereof.

The present invention also provides a compound of formula (IA):

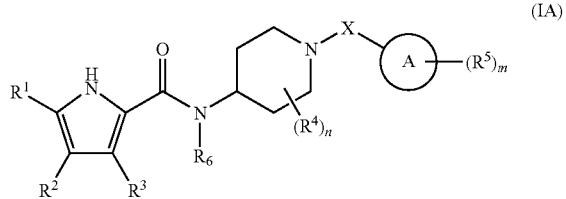

wherein:

R¹ is selected from hydrogen, nitro, hydroxy, halo, cyano, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl; wherein R¹ may be optionally substituted on carbon by one or more halo or cyclopropyl;

R² is selected from hydrogen, nitro, hydroxy, halo, cyano, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl;

wherein R² may be optionally substituted on carbon by one or more halo or $C_{3-6}$cycloalkyl; R³ is selected from hydrogen, nitro, hydroxy, halo, cyano, —C=N—OR' wherein R' is H or $C_{1-4}$alkyl, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl; wherein R³ may be optionally substituted on carbon by one or more halo or $C_{3-6}$cycloalkyl; X is a direct bond, —CH$_2$—, —C(O)— or S(O)$_q$— (wherein q is 1 or 2);

Ring A is carbocyclyl or heterocyclyl; wherein if said heterocyclyl contains an —NH— moiety that nitrogen may be optionally substituted by a group selected from R⁹;

R⁴ and R⁵ are substituents on carbon and are independently selected from halo, nitro, cyano, hydroxy, trifluoromethoxy, amino, carboxy, carbamoyl, mercapto, sulphamoyl, sulfo, formyl, ureido, hydroxyiminomethyl, N-hydroxyformamido, hydrazinocarbonyl, N-hydroxyethanimidoyl, amino(hydroxyimino)methyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, N—($C_{1-4}$alkoxy)carbamoyl, N'—($C_{1-4}$alkyl)ureido, N',N'—($C_{1-4}$alkyl)$_2$ureido, N—($C_{1-4}$alkyl)-N—($C_{1-4}$alkoxy)carbamoyl, $C_{1-4}$alkylS(O)$_a$ wherein a is 0 to 2, $C_{1-4}$alkoxycarbonyl, $C_{1-4}$alkoxycarbonylamino, N—($C_{1-4}$alkyl)sulphamoyl, N,N—($C_{1-4}$alkyl)$_2$sulphamoyl, $C_{1-4}$alkylsulphonylamino, $C_{1-4}$alkylsulphonylaminocarbonyl, N'—($C_{1-4}$alkyl)hydrazinocarbonyl, N',N'—($C_{1-4}$alkyl)$_2$hydrazinocarbonyl, carbocyclyl-R¹⁰— or heterocyclyl-R¹¹—; wherein R⁴ and R⁵ independently of each other may be optionally substituted on carbon by one or more R¹²; and wherein if said heterocyclyl contains an —NH— moiety that nitrogen may be optionally substituted by a group selected from R¹³;

R⁶, R⁷ and R⁸ are independently selected from hydrogen or $C_{1-4}$alkyl;

n is 1-4; wherein the values of R⁴ may be the same or different;

m is 0-4; wherein the values of R⁵ may be the same or different;

R¹² is selected from azido, halo, nitro, cyano, hydroxy, trifluoromethoxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl, N,N—($C_{1-4}$alkyl)$_2$sulphamoyl, $C_{1-4}$alkylsulphonylamino, $C_{1-4}$alkoxycarbonylamino, carbocyclyl-R¹⁴— or heterocyclyl-R¹⁵—; wherein R¹² independently of each other may be optionally substituted on carbon by one or more R¹⁶; and wherein if said heterocyclyl contains an —NH— moiety that nitrogen may be optionally substituted by a group selected from R¹⁷;

R⁹, R¹³ and R¹⁷ are independently selected from $C_{1-4}$alkyl, $C_{1-4}$alkanoyl, $C_{1-4}$alkylsulphonyl, $C_{1-4}$alkoxycarbonyl, carbamoyl, N—($C_{1-4}$alkyl)carbamoyl, N,N—($C_{1-4}$alkyl)carbamoyl, benzyl, benzyloxycarbonyl, benzoyl and phenylsulphonyl;

R¹⁰, R¹¹, R¹⁴ and R¹⁵ are independently selected from a direct bond, —O—, —N(R¹⁸)—, —C(O)—, —N(R¹⁹)C(O)—, —C(O)N(R²⁰)—, —S(O)$_p$—, —SO$_2$N(R²¹)— or —N(R²²)SO$_2$—; wherein R¹⁸, R¹⁹, R²⁰, R²¹ and R²² are independently selected from hydrogen or $C_{1-4}$alkyl and p is 0-2;

R¹⁶ is selected from halo, nitro, cyano, hydroxy, trifluoromethoxy, trifluoromethyl, amino, carboxy, carbamoyl, mercapto, sulphamoyl, methyl, ethyl, ethenyl, ethynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or a pharmaceutically acceptable salt thereof.

The present invention also provides a compound of formula (IB):

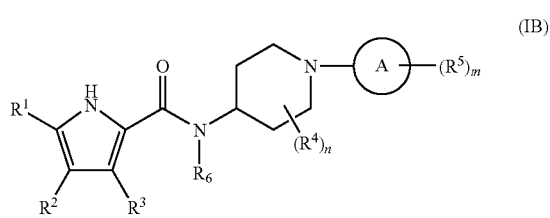

(IB)

wherein:

R¹ is selected from hydrogen, nitro, hydroxy, halo, cyano, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl; wherein R¹ may be optionally substituted on carbon by one or more halo or cyclopropyl;

R² is selected from hydrogen, nitro, hydroxy, halo, cyano, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl; wherein R² may be optionally substituted on carbon by one or more halo or $C_{3-6}$cycloalkyl;

R³ is selected from hydrogen, nitro, hydroxy, halo, cyano, —C=N—OR' wherein R' is H or $C_{1-4}$alkyl, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl; wherein R³ may be optionally substituted on carbon by one or more halo or $C_{3-6}$cycloalkyl;

Ring A is carbocyclyl or heterocyclyl; wherein if said heterocyclyl contains an —NH— moiety that nitrogen may be optionally substituted by a group selected from R⁹;

R⁴ and R⁵ are substituents on carbon and are independently selected from halo, nitro, cyano, hydroxy, trifluoromethoxy, amino, carboxy, carbamoyl, mercapto, sulphamoyl, sulfo, formyl, ureido, hydroxyiminomethyl, N-hydroxyformamido, hydrazinocarbonyl, N-hydroxyethanimidoyl, amino(hydroxyimino)methyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, N—($C_{1-4}$alkoxy)carbamoyl, N'—($C_{1-4}$alkyl)ureido, N',N'—($C_{1-4}$alkyl)$_2$ureido, N—($C_{1-4}$alkyl)-N—($C_{1-4}$alkoxy)carbamoyl, $C_{1-4}$alkylS(O)$_a$ wherein a is 0 to 2, $C_{1-4}$alkoxycarbonyl, $C_{1-4}$alkoxycarbonylamino, N—($C_{1-4}$alkyl)sulphamoyl, N,N—($C_{1-4}$alkyl)$_2$sulphamoyl, $C_{1-4}$alkylsulphonylamino, $C_{1-4}$alkylsulphonylaminocarbonyl, N'—($C_{1-4}$alkyl)hydrazinocarbonyl, N',N'—($C_{1-4}$alkyl)$_2$hydrazinocarbonyl, carbocyclyl-R¹⁰— or heterocyclyl-R¹¹—; wherein R⁴ and R⁵ independently of each other may be optionally substituted on carbon by one or more R¹²; and wherein if said heterocyclyl contains an —NH— moiety that nitrogen may be optionally substituted by a group selected from R¹³;

$R^6$, $R^7$ and $R^8$ are independently selected from hydrogen or $C_{1-4}$alkyl;

n is 1-4; wherein the values of $R^4$ may be the same or different;

m is 0-4; wherein the values of $R^5$ may be the same or different;

$R^{12}$ is selected from azido, halo, nitro, cyano, hydroxy, trifluoromethoxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl, N,N—($C_{1-4}$alkyl)$_2$sulphamoyl, $C_{1-4}$alkylsulphonylamino, $C_{1-4}$alkoxycarbonylamino, carbocyclyl-$R^{14}$— or heterocyclyl-$R^{15}$—; wherein $R^{12}$ independently of each other may be optionally substituted on carbon by one or more $R^{16}$; and wherein if said heterocyclyl contains an —NH— moiety that nitrogen may be optionally substituted by a group selected from $R^{17}$;

$R^9$, $R^{13}$ and $R^{17}$ are independently selected from $C_{1-4}$alkyl, $C_{1-4}$alkanoyl, $C_{1-4}$alkylsulphonyl, $C_{1-4}$alkoxycarbonyl, carbamoyl, N—($C_{1-4}$alkyl)carbamoyl, N,N—($C_{1-4}$alkyl)carbamoyl, benzyl, benzyloxycarbonyl, benzoyl and phenylsulphonyl;

$R^{10}$, $R^{11}$, $R^{14}$ and $R^{15}$ are independently selected from a direct bond, —O—, —N($R^{18}$)—, —C(O)—, —N($R^{19}$)C(O)—, —C(O)N($R^{20}$)—, —S(O)$_p$—, —SO$_2$N($R^{21}$)— or —N($R^{22}$)SO$_2$—; wherein $R^{18}$, $R^{19}$, $R^{20}$, $R^{21}$ and $R^{22}$ are independently selected from hydrogen or $C_{1-4}$alkyl and p is 0-2;

$R^{16}$ is selected from halo, nitro, cyano, hydroxy, trifluoromethoxy, trifluoromethyl, amino, carboxy, carbamoyl, mercapto, sulphamoyl, methyl, ethyl, ethenyl, ethynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or a pharmaceutically acceptable salt thereof.

The present invention also provides a compound of formula (IC):

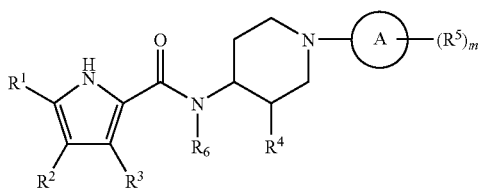

(IC)

wherein:

$R^1$ is selected from hydrogen, nitro, hydroxy, halo, cyano, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl; wherein $R^1$ may be optionally substituted on carbon by one or more halo or cyclopropyl;

$R^2$ is selected from hydrogen, nitro, hydroxy, halo, cyano, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl; wherein $R^2$ may be optionally substituted on carbon by one or more halo or $C_{3-6}$cycloalkyl;

$R^3$ is selected from hydrogen, nitro, hydroxy, halo, cyano, —C=N—OR' wherein R' is H or $C_{1-4}$alkyl, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl; wherein $R^3$ may be optionally substituted on carbon by one or more halo or $C_{3-6}$cycloalkyl;

Ring A is carbocyclyl or heterocyclyl; wherein if said heterocyclyl contains an —NH— moiety that nitrogen may be optionally substituted by a group selected from $R^9$;

$R^4$ and $R^5$ are substituents on carbon and are independently selected from halo, nitro, cyano, hydroxy, trifluoromethoxy, amino, carboxy, carbamoyl, mercapto, sulphamoyl, sulfo, formyl, ureido, hydroxyiminomethyl, N-hydroxyformamido, hydrazinocarbonyl, N-hydroxyethanimidoyl, amino(hydroxyimino)methyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, N—($C_{1-4}$alkoxy)carbamoyl, N'—($C_{1-4}$alkyl)ureido, N',N'—($C_{1-4}$alkyl)$_2$ureido, N—($C_{1-4}$alkyl)-N—($C_{1-4}$alkoxy)carbamoyl, $C_{1-4}$alkylS(O)$_a$ wherein a is 0 to 2, $C_{1-4}$alkoxycarbonyl, $C_{1-4}$alkoxycarbonylamino, N—($C_{1-4}$alkyl)sulphamoyl, N,N—($C_{1-4}$alkyl)$_2$sulphamoyl, $C_{1-4}$alkylsulphonylamino, $C_{1-4}$alkylsulphonylaminocarbonyl, N'—($C_{1-4}$alkyl)hydrazinocarbonyl, N',N'—($C_{1-4}$alkyl)$_2$hydrazinocarbonyl, carbocyclyl-$R^{10}$— or heterocyclyl-$R^{11}$—; wherein $R^4$ and $R^5$ independently of each other may be optionally substituted on carbon by one or more $R^{12}$; and wherein if said heterocyclyl contains an —NH— moiety that nitrogen may be optionally substituted by a group selected from $R^{13}$;

$R^6$, $R^7$ and $R^8$ are independently selected from hydrogen or $C_{1-4}$alkyl;

m is 0-4; wherein the values of $R^5$ may be the same or different;

$R^{12}$ is selected from azido, halo, nitro, cyano, hydroxy, trifluoromethoxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl, N,N—($C_{1-4}$alkyl)$_2$sulphamoyl, $C_{1-4}$alkylsulphonylamino, $C_{1-4}$alkoxycarbonylamino, carbocyclyl-$R^{14}$— or heterocyclyl-$R^{15}$—; wherein $R^{12}$ independently of each other may be optionally substituted on carbon by one or more $R^{16}$; and wherein if said heterocyclyl contains an —NH— moiety that nitrogen may be optionally substituted by a group selected from $R^{17}$;

$R^9$, $R^{13}$ and $R^{17}$ are independently selected from $C_{1-4}$alkyl, $C_{1-4}$alkanoyl, $C_{1-4}$alkylsulphonyl, $C_{1-4}$alkoxycarbonyl, carbamoyl, N—($C_{1-4}$alkyl)carbamoyl, N,N—($C_{1-4}$alkyl)carbamoyl, benzyl, benzyloxycarbonyl, benzoyl and phenylsulphonyl;

$R^{10}$, $R^{11}$, $R^{14}$ and $R^{15}$ are independently selected from a direct bond, —O—, —N($R^{18}$)—, —C(O)—, —N($R^{19}$)C(O)—, —C(O)N($R^{20}$)—, —S(O)$_p$—, —SO$_2$N($R^{21}$)— or —N($R^{22}$)SO$_2$—; wherein $R^{18}$, $R^{19}$, $R^{20}$, $R^{21}$ and $R^{22}$ are independently selected from hydrogen or $C_{1-4}$alkyl and p is 0-2;

$R^{16}$ is selected from halo, nitro, cyano, hydroxy, trifluoromethoxy, trifluoromethyl, amino, carboxy, carbamoyl, mercapto, sulphamoyl, methyl, ethyl, ethenyl, ethynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or a pharmaceutically acceptable salt thereof.

The present invention also provides a compound of formula (IC):

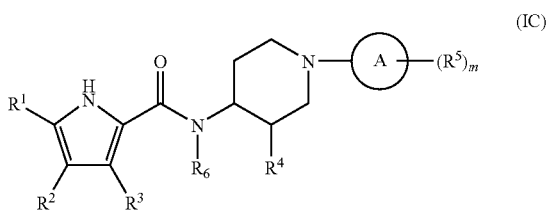

(IC)

wherein:

$R^1$ is selected from hydrogen, nitro, hydroxy, halo, cyano, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl; wherein $R^1$ may be optionally substituted on carbon by one or more halo or cyclopropyl;

$R^2$ is selected from hydrogen, nitro, hydroxy, halo, cyano, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl; wherein $R^2$ may be optionally substituted on carbon by one or more halo or $C_{3-6}$cycloalkyl;

$R^3$ is selected from hydrogen, nitro, hydroxy, halo, cyano, —C=N—OR' wherein R' is H or $C_{1-4}$alkyl, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl; wherein $R^3$ may be optionally substituted on carbon by one or more halo or $C_{3-6}$cycloalkyl;

Ring A is heterocyclyl; wherein if said heterocyclyl contains an —NH— moiety that nitrogen may be optionally substituted by a group selected from $R^9$;

$R^4$ and $R^5$ are substituents on carbon and are independently selected from halo, nitro, cyano, hydroxy, trifluoromethoxy, amino, carboxy, carbamoyl, mercapto, sulphamoyl, sulfo, formyl, ureido, hydroxyiminomethyl, N-hydroxyformamido, hydrazinocarbonyl, N-hydroxyethanimidoyl, amino(hydroxyimino)methyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, N—($C_{1-4}$alkoxy)carbamoyl, N'—($C_{1-4}$alkyl)ureido, N',N'—($C_{1-4}$alkyl)$_2$ureido, N—($C_{1-4}$alkyl)-N—($C_{1-4}$alkoxy)carbamoyl, $C_{1-4}$alkylS(O)$_a$ wherein a is 0 to 2, $C_{1-4}$alkoxycarbonyl, $C_{1-4}$alkoxycarbonylamino, N—($C_{1-4}$alkyl)sulphamoyl, N,N—($C_{1-4}$alkyl)$_2$sulphamoyl, $C_{1-4}$alkylsulphonylamino, $C_{1-4}$alkylsulphonylaminocarbonyl, N'—($C_{1-4}$alkyl)hydrazinocarbonyl, N',N'—($C_{1-4}$alkyl)$_2$hydrazinocarbonyl, carbocyclyl-$R^{10}$— or heterocyclyl-$R^{11}$—; wherein $R^4$ and $R^5$ independently of each other may be optionally substituted on carbon by one or more $R^{12}$; and wherein if said heterocyclyl contains an —NH— moiety that nitrogen may be optionally substituted by a group selected from $R^{13}$;

$R^6$, $R^7$ and $R^8$ are independently selected from hydrogen or $C_{1-4}$alkyl;

m is 0-4; wherein the values of $R^5$ may be the same or different;

$R^{12}$ is selected from azido, halo, nitro, cyano, hydroxy, trifluoromethoxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl, N,N—($C_{1-4}$alkyl)$_2$sulphamoyl, $C_{1-4}$alkylsulphonylamino, $C_{1-4}$alkoxycarbonylamino, carbocyclyl-$R^{14}$— or heterocyclyl-$R^{15}$—; wherein $R^{12}$ independently of each other may be optionally substituted on carbon by one or more $R^{16}$; and wherein if said heterocyclyl contains an —NH— moiety that nitrogen may be optionally substituted by a group selected from $R^{17}$;

$R^9$, $R^{13}$ and $R^{17}$ are independently selected from $C_{1-4}$alkyl, $C_{1-4}$alkanoyl, $C_{1-4}$alkylsulphonyl, $C_{1-4}$alkoxycarbonyl, carbamoyl, N—($C_{1-4}$alkyl)carbamoyl, N,N—($C_{1-4}$alkyl)carbamoyl, benzyl, benzyloxycarbonyl, benzoyl and phenylsulphonyl;

$R^{10}$, $R^{11}$, $R^{14}$ and $R^{15}$ are independently selected from a direct bond, —O—, —N($R^{18}$)—, —C(O)—, —N($R^{19}$)C(O)—, —C(O)N($R^{20}$)—, —S(O)$_p$—, —SO$_2$N($R^{21}$)— or —N($R^{22}$)SO$_2$—; wherein $R^{18}$, $R^{19}$, $R^{20}$, $R^{21}$ and $R^{22}$ are independently selected from hydrogen or $C_{1-4}$alkyl and p is 0-2;

$R^{16}$ is selected from halo, nitro, cyano, hydroxy, trifluoromethoxy, trifluoromethyl, amino, carboxy, carbamoyl, mercapto, sulphamoyl, methyl, ethyl, ethenyl, ethynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or a pharmaceutically acceptable salt thereof.

The present invention also provides a compound of formula (IE):

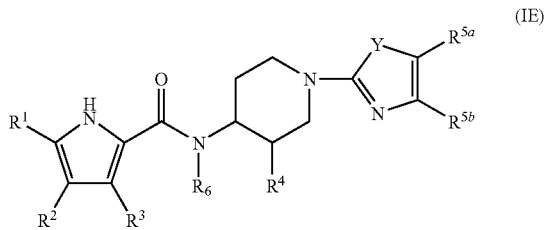

(IE)

wherein: Y is NH, N($C_{1-4}$alkyl) or S;

$R^1$ is selected from hydrogen, nitro, hydroxy, halo, cyano, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl; wherein $R^1$ may be optionally substituted on carbon by one or more halo or cyclopropyl;

$R^2$ is selected from hydrogen, nitro, hydroxy, halo, cyano, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl; wherein $R^2$ may be optionally substituted on carbon by one or more halo or $C_{3-6}$cycloalkyl;

$R^3$ is selected from hydrogen, nitro, hydroxy, halo, cyano, —C=N—OR' wherein R' is H or $C_{1-4}$alkyl, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl; wherein $R^3$ may be optionally substituted on carbon by one or more halo or $C_{3-6}$cycloalkyl;

X is a direct bond, —CH$_2$—, —C(O)— or S(O)$_q$— (wherein q is 1 or 2);

Ring A is heterocyclyl; wherein if said heterocyclyl contains an —NH— moiety that nitrogen may be optionally substituted by a group selected from $R^9$;

$R^4$ is a substitutent on carbon selected from halo, nitro, cyano, hydroxy, trifluoromethoxy, amino, carboxy, carbamoyl, mercapto, sulphamoyl, sulfo, formyl, ureido, hydroxyiminomethyl, N-hydroxyformamido, hydrazinocarbonyl, N-hydroxyethanimidoyl, amino(hydroxyimino)methyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, N—($C_{1-4}$alkoxy)carbamoyl, N'—($C_{1-4}$alkyl)ureido, N',N'—($C_{1-4}$alkyl)$_2$ureido, N—($C_{1-4}$alkyl)-N—($C_{1-4}$alkoxy)carbamoyl, $C_{1-4}$alkylS(O)$_a$ wherein a is 0 to 2, $C_{1-4}$alkoxycarbonyl, $C_{1-4}$alkoxycarbonylamino, N—($C_{1-4}$alkyl)sulphamoyl, N,N—($C_{1-4}$alkyl)$_2$sulphamoyl, $C_{1-4}$alkylsulphonylamino, $C_{1-4}$alkylsulphonylaminocarbonyl, N'—($C_{1-4}$alkyl)hydrazinocarbonyl, N',N'—($C_{1-4}$alkyl)$_2$hydrazinocarbonyl, carbocyclyl-$R^{10}$— or heterocyclyl-$R^{11}$—; wherein $R^4$ and $R^5$ independently of each other may be optionally substituted on carbon by one or more $R^{12}$; and wherein if said heterocyclyl contains an —NH— moiety that nitrogen may be optionally substituted by a group selected from $R^{13}$;

$R^{5a}$ and $R^{5b}$ are substituents as defined for $R^4$ or taken together with the carbons to which they are attached form a 6-membered carbocyclyl ring substituted by one or two groups which may be the same or different and which are selected from $R^5$;

$R^6$, $R^7$ and $R^8$ are independently selected from hydrogen or $C_{1-4}$alkyl;

$R^{12}$ is selected from halo, nitro, cyano, hydroxy, trifluoromethoxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl, N,N—($C_{1-4}$alkyl)$_2$sulphamoyl, $C_{1-4}$alkylsulphonylamino, $C_{1-4}$alkoxycarbonylamino, carbocyclyl-$R^{14}$— or heterocyclyl-$R^{15}$—; wherein $R^{12}$ independently of each other may be optionally substituted on carbon by one or more $R^{16}$; and wherein if said heterocyclyl contains an —NH— moiety that nitrogen may be optionally substituted by a group selected from $R^{17}$;

$R^9$, $R^{13}$ and $R^{17}$ are independently selected from $C_{1-4}$alkyl, $C_{1-4}$alkanoyl, $C_{1-4}$alkylsulphonyl, $C_{1-4}$alkoxycarbonyl, carbamoyl, N—($C_{1-4}$alkyl)carbamoyl, N,N—($C_{1-4}$alkyl)carbamoyl, benzyl, benzyloxycarbonyl, benzoyl and phenylsulphonyl;

$R^{10}$, $R^{11}$, $R^{14}$ and $R^{15}$ are independently selected from a direct bond, —O—, —N($R^{18}$)—, —C(O)—, —N($R^{19}$)C(O)—, —C(O)N($R^{20}$)—, —S(O)$_p$—, —SO$_2$N($R^{21}$)— or —N($R^{22}$)SO$_2$—; wherein $R^{18}$, $R^{19}$, $R^{20}$, $R^{21}$ and $R^{22}$ are independently selected from hydrogen or $C_{1-4}$alkyl and p is 0-2;

$R^{16}$ is selected from halo, nitro, cyano, hydroxy, trifluoromethoxy, trifluoromethyl, amino, carboxy, carbamoyl, mercapto, sulphamoyl, methyl, ethyl, ethenyl, ethynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or a pharmaceutically acceptable salt thereof.

The present invention also provides a compound of formula (IF):

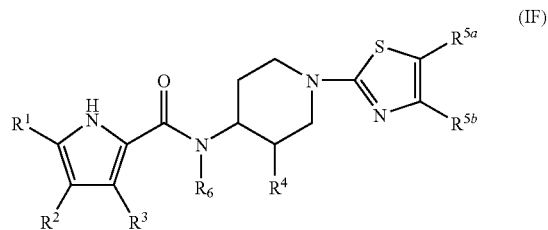

(IF)

wherein:

$R^1$ is selected from hydrogen, nitro, hydroxy, halo, cyano, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl; wherein $R^1$ may be optionally substituted on carbon by one or more halo or cyclopropyl;

$R^2$ is selected from hydrogen, nitro, hydroxy, halo, cyano, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl; wherein $R^2$ may be optionally substituted on carbon by one or more halo or $C_{3-6}$cycloalkyl;

$R^3$ is selected from hydrogen, nitro, hydroxy, halo, cyano, —C=N—OR' wherein R' is H or $C_{1-4}$alkyl, $C_{1-4}$alkyl, $C_{1-4}$alkoxy, $C_{2-4}$alkenyl, $C_{2-4}$alkynyl, $C_{1-4}$alkanoyl, $C_{1-4}$alkylS(O)$_a$ wherein a is 0 to 2 and $C_{3-6}$cycloalkyl; wherein $R^3$ may be optionally substituted on carbon by one or more halo or $C_{3-6}$cycloalkyl;

X is a direct bond, —CH$_2$—, —C(O)— or S(O)$_q$— (wherein q is 1 or 2);

$R^4$ is a substitutent on carbon selected from halo, nitro, cyano, hydroxy, trifluoromethoxy, amino, carboxy, carbamoyl, mercapto, sulphamoyl, sulfo, formyl, ureido, hydroxyiminomethyl, N-hydroxyformamido, hydrazinocarbonyl, N-hydroxyethanimidoyl, amino(hydroxyimino)methyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, N—($C_{1-4}$alkoxy)carbamoyl, N'—($C_{1-4}$alkyl)ureido, N',N'—($C_{1-4}$alkyl)$_2$ureido, N—($C_{1-4}$alkyl)-N—($C_{1-4}$alkoxy)carbamoyl, $C_{1-4}$alkylS(O)$_a$ wherein a is 0 to 2, $C_{1-4}$alkoxycarbonyl, $C_{1-4}$alkoxycarbonylamino, N—($C_{1-4}$alkyl)sulphamoyl, N,N—($C_{1-4}$alkyl)$_2$sulphamoyl, $C_{1-4}$alkylsulphonylamino, $C_{1-4}$alkylsulphonylaminocarbonyl, N'—($C_{1-4}$alkyl)hydrazinocarbonyl, N',N'—($C_{1-4}$alkyl)$_2$hydrazinocarbonyl, carbocyclyl-$R^{10}$— or heterocyclyl-$R^{11}$—; wherein $R^4$ and $R^5$ independently of each other may be optionally substituted on carbon by one or more $R^{12}$; and wherein if said heterocyclyl contains an —NH— moiety that nitrogen may be optionally substituted by a group selected from $R^{13}$;

$R^{5a}$ and $R^{5b}$ are substituents as defined for $R^4$ or taken together with the carbons to which they are attached form a 6-membered carbocyclyl ring substituted by one or two groups which may be the same or different and which are selected from $R^5$;

R⁶, R⁷ and R⁸ are independently selected from hydrogen or $C_{1-4}$alkyl;

$R^{12}$ is selected from halo, nitro, cyano, hydroxy, trifluoromethoxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)₂amino, $C_{1-4}$alkanoylamino, N—($C_{1-4}$alkyl)carbamoyl, N,N—($C_{1-4}$alkyl)₂carbamoyl, $C_{1-4}$alkylS(O)$_a$ wherein a is 0 to 2, $C_{1-4}$alkoxycarbonyl, N—($C_{1-4}$alkyl)sulphamoyl, N,N—($C_{1-4}$alkyl)₂sulphamoyl, $C_{1-4}$alkylsulphonylamino, $C_{1-4}$alkoxycarbonylamino, carbocyclyl-$R^{14}$— or heterocyclyl-$R^{15}$—; wherein $R^{12}$ independently of each other may be optionally substituted on carbon by one or more $R^{16}$; and wherein if said heterocyclyl contains an —NH— moiety that nitrogen may be optionally substituted by a group selected from $R^{17}$;

R⁹, $R^{13}$ and $R^{17}$ are independently selected from $C_{1-4}$alkyl, $C_{1-4}$alkanoyl, $C_{1-4}$alkylsulphonyl, $C_{1-4}$alkoxycarbonyl, carbamoyl, N—($C_{1-4}$alkyl)carbamoyl, N,N—($C_{1-4}$alkyl)carbamoyl, benzyl, benzyloxycarbonyl, benzoyl and phenylsulphonyl;

$R^{10}$, $R^{11}$, $R^{14}$ and $R^{15}$ are independently selected from a direct bond, —O—, —N($R^{18}$)—, —C(O)—, —N($R^{19}$)C(O)—, —C(O)N($R^{20}$)—, —S(O)$_p$—, —SO₂N($R^{21}$)— or —N($R^{22}$)SO₂—; wherein $R^{18}$, $R^{19}$, $R^{20}$, $R^{21}$ and $R^{22}$ are independently selected from hydrogen or $C_{1-4}$alkyl and p is 0-2;

$R^{16}$ is selected from halo, nitro, cyano, hydroxy, trifluoromethoxy, trifluoromethyl, amino, carboxy, carbamoyl, mercapto, sulphamoyl, methyl, ethyl, ethenyl, ethynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or a pharmaceutically acceptable salt thereof.

The invention also provides a compound which is 2-((3S,4R)-4-{[(3,4-dichloro-5-methyl-1H-pyrrol-2-yl)carbonyl]amino}-3-fluoropiperidin-1-yl)-1,3-thiazole-5-carboxylic acid;

2-((3S,4R)-4-{[(3,4-dichloro-5-methyl-1H-pyrrol-2-yl)carbonyl]amino}-3-methoxypiperidin-1-yl)-4-{[(2-methoxyethyl)amino]carbonyl}-1,3-thiazole-5-carboxylic acid;

2-((3S,4R)-4-{[(3,4-dichloro-5-methyl-1H-pyrrol-2-yl)carbonyl]amino}-3-methoxypiperidin-1-yl)-4-({[(1S)-2-methoxy-1-methylethyl]amino}carbonyl)-1,3-thiazole-5-carboxylic acid;

2-((3S,4R)-4-{[(3,4-dichloro-5-methyl-1H-pyrrol-2-yl)carbonyl]amino}-3-methoxypiperidin-1-O-4-[(methylamino)carbonyl]-1,3-thiazole-5-carboxylic acid;

2-((3S,4R)-4-{[(3,4-Dichloro-5-methyl-1H-pyrrol-2-yl)carbonyl]amino}-3-methoxypiperidin-1-yl)-4-methyl-1,3-thiazole-5-carboxylic acid;

2-((3S,4R)-4-{[(3,4-dichloro-5-methyl-1H-pyrrol-2-yl)carbonyl]amino}-3-methoxypiperidin-1-yl)-1,3-thiazole-5-carboxylic acid;

4-acetyl-2-((3S,4R)-4-{[(3,4-dichloro-5-methyl-1H-pyrrol-2-yl)carbonyl]amino}-3-methoxypiperidin-1-yl)-1,3-thiazole-5-carboxylic acid;

2-((3S,4R)-4-{[(3,4-dichloro-5-methyl-1H-pyrrol-2-yl)carbonyl]amino}-3-methoxypiperidin-1-yl)-4-({[(1R)-2-methoxy-1-methylethyl]amino}carbonyl)-1,3-thiazole-5-carboxylic acid;

2-((3S,4R)-4-{[(3,4-dichloro-5-methyl-1H-pyrrol-2-yl)carbonyl]amino}-3-methoxypiperidin-1-yl)-4-({[(2S)-2-methoxypropyl]amino}carbonyl)-1,3-thiazole-5-carboxylic acid;

2-((3S,4R)-4-{[(3,4-dichloro-5-methyl-1H-pyrrol-2-yl)carbonyl]amino}-3-methoxypiperidin-1-yl)-4-({[(2R)-2-methoxypropyl]amino}carbonyl)-1,3-thiazole-5-carboxylic acid;

2-((3S,4R)-4-{[(3,4-dichloro-5-methyl-1H-pyrrol-2-yl)carbonyl]amino}-3-methoxypiperidin-1-yl)-4-({[(1R,2S)-2-fluorocyclopropyl]amino}carbonyl)-1,3-thiazole-5-carboxylic acid;

Cis(±)2-(4-{[(3,4-dichloro-5-methyl-1H-pyrrol-2-yl)carbonyl]amino}-3-methoxypiperidin-1-yl)-1,3-benzothiazole-7-carboxylic acid;

Cis(±)2-(4-{[(3,4-dichloro-5-methyl-1H-pyrrol-2-yl)carbonyl]amino}-3-methoxypiperidin-1-yl)-4-(methoxymethyl)-1,3-thiazole-5-carboxylic acid;

Cis(±)2-(4-{[(3,4-dichloro-5-methyl-1H-pyrrol-2-yl)carbonyl]amino}-3-methoxypiperidin-1-yl)isonicotinic acid;

2-((3S,4R)-4-{[(4-chloro-5-methyl-1H-pyrrol-2-yl)carbonyl]amino}-3-methoxypiperidin-1-yl)-1,3-benzothiazole-7-carboxylic acid;

Cis(±)-2-(3-chloro-4-{[(3,4-dichloro-5-methyl-1H-pyrrol-2-yl)carbonyl]amino}piperidin-1-yl)-4-(methoxymethyl)-1,3-thiazole-5-carboxylic acid;

2-((3S,4R)-4-{[(3,4-Dichloro-5-methyl-1H-pyrrol-2-yl)carbonyl]amino}-3-fluoropiperidin-1-yl)-4-methyl-1,3-thiazole-5-carboxylic acid;

Cis(±)-2-[4-{[(3,4-dichloro-5-methyl-1H-pyrrol-2-yl)carbonyl]amino}-3-(prop-2-yn-1-yloxy)piperidin-1-yl]-1,3-thiazole-5-carboxylic acid;

Cis(±)2-((3S,4R)-4-{[(3,4-dichloro-5-methyl-1H-pyrrol-2-yl)carbonyl]amino}-3-fluoropiperidin-1-yl)-1,3-thiazole-4-carboxylic acid; or 2-((3S,4R)-4-{[(3,4-dichloro-5-methyl-1H-pyrrol-2-yl)carbonyl]amino}-3-methoxypiperidin-1-yl)-4-({[2-methoxy-1-(methoxymethyl)ethyl]amino}carbonyl)-1,3-thiazole-5-carboxylic acid;

or a pharmaceutically acceptable salt thereof.

The invention also provides a pharmaceutical composition that comprises a compound of formula I, IA, IB, IC, or IE or a pharmaceutically-acceptable salt thereof, and a pharmaceutically-acceptable diluent or carrier.

The invention also provides a method of treating a bacterial infection in a warm-blooded animal, such as a human being, in need of such treatment, which comprises administering to said animal an effective amount of a compound of formula I, IA, IB, IC, or IE, or a pharmaceutically-acceptable salt thereof.

The invention also provides a method for inhibiting bacterial DNA gyrase in a warm-blooded animal, such as a human being, in need of such treatment which comprises administering to said animal an effective amount of a compound of formula I, IA, IB, IC, or IE or a pharmaceutically acceptable salt.

The invention also provides a compound of formula I, IA, IB, IC, or IE and pharmaceutically acceptable salts thereof for use as a medicament.

The invention also provides the use of a compound of formula I, IA, IB, IC, or IE, or a pharmaceutically acceptable salt thereof in the manufacture of a medicament for use in the production of an anti-bacterial effect in a warm-blooded animal such as a human being.

The invention also provides the use of a compound of formula I, IA, IB, IC, or IE, or a pharmaceutically acceptable salt thereof in the manufacture of a medicament for use in the treatment of a bacterial infection in a warm-blooded animal such as a human being.

The present invention also provides a process for preparing compounds of formula (I) or pharmaceutically-acceptable salts thereof, comprising:

Process a) for compounds of formula (I) wherein W is —C(R⁷)(R⁸)—; converting a compound of formula (II):

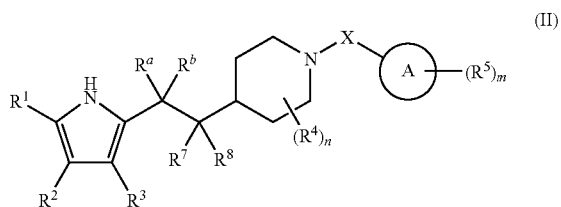

wherein $R^a$ is cyano and $R^b$ is dimethyamino or diethylamino; or $R^a$ and $R^b$ are independently selected from $C_{1-4}$alkylthio; or $R^a$ and $R^b$ together form 1,3-dithianyl or 1,3-dithiolanyl; into a compound of formula (I);

Process b) for compounds of formula (I) wherein W is —O—; reacting a compound of formula (III):

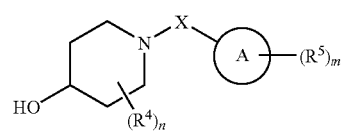

with a compound of formula (IV):

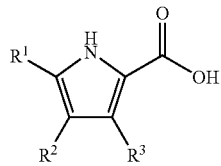

Process c) for compounds of formula (I) wherein W is —N(R⁶)—; reacting a compound of formula (V):

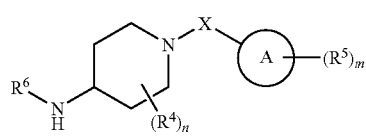

with a compound of formula (IV) or an activated acid derivative thereof;

Process d) for compounds of formula (I) wherein W is —C(R⁷)(R⁸)—; reacting a compound of formula (VI):

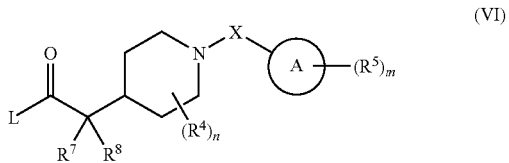

wherein L is a displaceable group; with a compound of formula (VII):

Process e) for compounds of formula (I) wherein W is —C(R⁷)(R⁸)—; reacting a compound of formula (VIII):

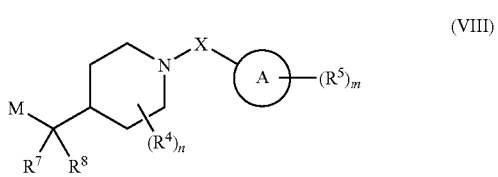

wherein M is an organometallic group; with a compound of formula (IX):

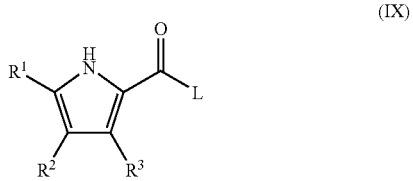

wherein L is a displaceable group;
Process f) reacting a compound of formula (X):

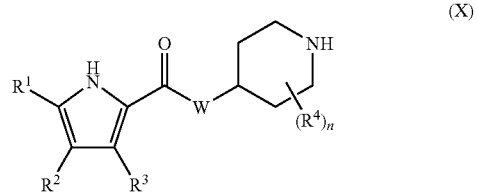

with a compound of formula (XI):

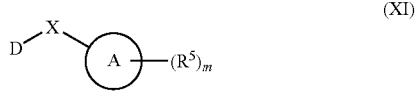

wherein D is a displaceable group;

Process g) for compounds of formula (I) wherein X is —C(O)—; reacting a compound of formula (X) with a compound of formula (XII):

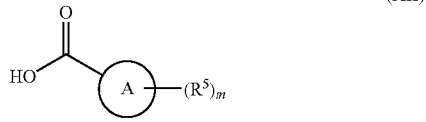

and thereafter if necessary:
i) converting a compound of the formula (I) into another compound of the formula (I);
ii) removing any protecting groups;
iii) forming a pharmaceutically acceptable salt.

DETAILED DESCRIPTION OF THE INVENTION

Definitions

In this specification the term alkyl includes both straight and branched chain alkyl groups. For example, "$C_{1-4}$alkyl" includes methyl, ethyl, propyl, isopropyl and t-butyl. However references to individual alkyl groups such as propyl are specific for the straight chain version only. An analogous convention applies to other generic terms.

Where optional substituents are chosen from one or more groups it is to be understood that this definition includes all substituents being chosen from one of the specified groups or the substituents being chosen from two or more of the specified groups.

A "heterocyclyl" is a saturated, partially saturated or unsaturated, mono or bicyclic ring containing 4-12 atoms of which at least one atom is chosen from nitrogen, sulphur or oxygen, which may, unless otherwise specified, be carbon or nitrogen linked, wherein a —$CH_2$-group can optionally be replaced by a —C(O)— and a ring nitrogen and/or a ring sulphur atom may be optionally oxidised to form the N- or S-oxide(s). In one aspect of the invention a "heterocyclyl" is a saturated, partially saturated or unsaturated, monocyclic ring containing 5 or 6 atoms of which at least one atom is chosen from nitrogen, sulphur or oxygen, it may, unless otherwise specified, be carbon or nitrogen linked, a —$CH_2$— group can optionally be replaced by a —C(O)— and a ring sulphur atom may be optionally oxidised to form the S-oxides. In a further aspect of the invention a "heterocyclyl" is an unsaturated, carbon-linked, monocyclic ring containing 5 or 6 atoms of which at least one atom is chosen from nitrogen, sulphur or oxygen. Examples and suitable values of the term "heterocyclyl" are morpholino, piperidyl, pyridyl, pyranyl, pyrrolyl, pyrazolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, pyrimidyl, pyrazinyl, pyridazinyl, isoxazolyl, N-methylpyrrolyl, 4-pyridone, 1-isoquinolone, 2-pyrrolidone, 4-thiazolidone, pyridine-N-oxide and quinoline-N-oxide. Further examples and suitable values of the term "heterocyclyl" are thiazolyl, quinolinyl, benzothiazolyl, pyrimidinyl and pyridinyl.

A "carbocyclyl" is a saturated, partially saturated or unsaturated, mono or bicyclic carbon ring that contains 3-12 atoms; wherein a —$CH_2$— group can optionally be replaced by a —C(O)—. Particularly "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl. A particular example of "carbocyclyl" is phenyl.

An example of "$C_{1-4}$alkanoyloxy" is acetoxy. Examples of "$C_{1-4}$alkoxycarbonyl" include methoxycarbonyl, ethoxycarbonyl, n- and t-butoxycarbonyl. Examples of "$C_{1-4}$alkoxycarbonylamino" include methoxycarbonylamino, ethoxycarbonylamino, n- and t-butoxycarbonylamino Examples of "$C_{1-4}$alkoxy" include methoxy, ethoxy and propoxy. Examples of "$C_{1-4}$alkanoylamino" include formamido, acetamido and propionylamino Examples of "$C_{1-4}$alkylS(O)$_a$ wherein a is 0 to 2" include methylthio, ethylthio, methylsulphinyl, ethylsulphinyl, mesyl and ethylsulphonyl. Examples of "$C_{1-4}$alkanoyl" include propionyl and acetyl. Examples of "N—($C_{1-4}$ alkyl)amino" include methylamino and ethylamino Examples of "N,N—($C_{1-4}$alkyl)$_2$amino" include di-N-methylamino, di-(N-ethyl)amino and N-ethyl-N-methylamino Examples of "$C_{2-4}$alkenyl" are vinyl, allyl and 1-propenyl. Examples of "$C_{2-4}$alkynyl" are ethynyl, 1-propynyl and 2-propynyl. Examples of "N—($C_{1-4}$alkyl)sulphamoyl" are N-(methyl)sulphamoyl and N-(ethyl)sulphamoyl. Examples of "N,N—($C_{1-4}$alkyl)$_2$sulphamoyl" are N,N-(dimethyl)sulphamoyl and N-(methyl)-N-(ethyl)sulphamoyl. Examples of "N—($C_{1-4}$alkyl)carbamoyl" are methylaminocarbonyl and ethylaminocarbonyl. Examples of "N,N—($C_{1-4}$alkyl)$_2$carbamoyl" are dimethylaminocarbonyl and methylethylaminocarbonyl. Examples of "N—($C_{1-4}$alkoxy)carbamoyl" are methoxyaminocarbonyl and isopropoxyaminocarbonyl. Examples of "N—($C_{1-4}$alkyl)-N—($C_{1-4}$alkoxy)carbamoyl" are N-methyl-N-methoxyaminocarbonyl and N-methyl-N-ethoxyaminocarbonyl. Examples of "$C_{3-6}$cycloalkyl" are cyclopropyl, cyclobutyl, cyclopropyl and cyclohexyl. Examples of "N'—($C_{1-4}$alkyl)ureido" are N'-methylureido and N'-isopropylureido. Examples of "N',N'—($C_{1-4}$alkyl)$_2$ureido" are N'N'-dimethylureido and N'-methyl-N'-isopropylureido. Examples of "N'—($C_{1-4}$alkyl)hydrazinocarbonyl" are N'-methylhydrazinocarbonyl and N'-isopropylhydrazinocarbonyl. Examples of "N',N'—($C_{1-4}$alkyl)$_2$hydrazinocarbonyl" are N'N'-dimethylhydrazinocarbonyl and N'-methyl-N'-isopropylhydrazinocarbonyl. Examples of "$C_{1-4}$alkylsulphonylamino" include methylsulphonylamino, isopropylsulphonylamino and t-butylsulphonylamino Examples of "$C_{1-4}$alkylsulphonylaminocarbonyl" include methylsulphonylaminocarbonyl, isopropylsulphonylaminocarbonyl and t-butylsulphonylaminocarbonyl. Examples of "$C_{1-4}$alkylsulphonyl" include methylsulphonyl, isopropylsulphonyl and t-butylsulphonyl.

A compound of formula (I) may form stable acid or basic salts, and in such cases administration of a compound as a salt may be appropriate, and pharmaceutically acceptable salts may be made by conventional methods such as those described following.

Suitable pharmaceutically-acceptable salts include acid addition salts such as methanesulfonate, tosylate, α-glycerophosphate, fumarate, hydrochloride, citrate, maleate, tartrate and (less preferably) hydrobromide. Also suitable are salts formed with phosphoric and sulfuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine, tris-(2-hydroxyethyl)amine, tromethamine, N-methyl d-glucamine and amino acids such as glycine or lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

Within the present invention it is to be understood that a compound of the formula (I) or a salt thereof may exhibit the phenomenon of tautomerism and that the formulae drawings within this specification can represent only one of the possible tautomeric forms. It is to be understood that the invention encompasses any tautomeric form which inhibits DNA gyrase and/or topoisomeraseIV and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein. The same applies to compound names. It will be appreciated by those skilled in the art that certain compounds of formula (I) contain an asymmetrically substituted carbon and/or sulphur atom, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the inhibition of DNA gyrase and/or topoisomeraseIV, it being well known in the art how to prepare optically-active forms (for example, by resolution of the racemic form by recrystallization techniques, by synthesis from optically-active starting materials, by chiral synthesis, by enzymatic resolution, by biotransformation, or by chromatographic separation using a chiral stationary phase) and how to determine efficacy for the inhibition of DNA gyrase and/or topoisomeraseIV by the standard tests described hereinafter.

It is also to be understood that certain compounds of the formula (I) and salts thereof can exist in solvated as well as unsolvated forms such as, for example, hydrated forms. It is to be understood that the invention encompasses all such solvated forms which inhibit DNA gyrase and/or topoisomeraseIV.

Particular and suitable values for certain substituents and groups referred to in this specification are listed below. These values may be used where appropriate with any of the definitions and embodiments disclosed herein. Each stated species represents a particular and independent aspect of the invention.

Referring to a compound of formula I, $R^1$ is $C_{1-4}$alkyl. $R^1$ is methyl. $R^1$ is halo. $R^1$ is hydrogen.

$R^2$ is methyl. $R^2$ is halo. $R^2$ is fluoro or chloro. $R^2$ is hydrogen. $R^2$ is chloro.

$R^3$ is $C_{1-4}$alkyl. $R^3$ is methyl. $R^3$ is halo. $R^3$ is fluoro or chloro. $R^3$ is hydrogen. $R^3$ is CN. $R^3$ is C=N—OH. $R^3$ is chloro.

W is —O—. W is —N($R^6$)—. W is —NH—. W is —C($R^7$)($R^8$)—.

X is a direct bond. X is —CH$_2$—. X is —C(O)—. X is S(O)$_q$— (wherein q is 1 or 2).

Ring A is carbocyclyl. Ring A is heterocyclyl; wherein if said heterocyclyl contains an —NH— moiety that nitrogen may be optionally substituted by a group selected from $R^9$. Ring A is heterocyclyl. Ring A is thiazolyl, quinolinyl, benzothiazolyl, pyrimidinyl or pyridinyl. Ring A is thiazol-2-yl, quinolin-4-yl, benzothiazol-2-yl, pyrimidin-4-yl, pyridin-2-yl or pyridin-4-yl.

$R^4$ is a substituent on carbon and is selected from halo, hydroxy, carboxy, $C_{1-4}$alkyl, $C_{1-4}$alkoxy, N—($C_{1-4}$alkyl)carbamoyl, N,N—($C_{1-4}$alkyl)$_2$carbamoyl, N—($C_{1-4}$alkyl)-N—($C_{1-4}$alkoxy)carbamoyl, $C_{1-4}$alkoxycarbonyl or heterocyclyl-$R^{11}$—; wherein $R^4$ may be optionally substituted on carbon by one or more $R^{12}$. $R^{12}$ is selected from hydroxy, $C_{2-4}$alkenyl, $C_{1-4}$alkoxy, N—($C_{1-4}$alkyl)amino or N,N—($C_{1-4}$alkyl)$_2$ amino; and $R^{11}$ is —C(O)—.

Alternatively, $R^4$ is a substituent on carbon and is selected from fluoro, hydroxy, carboxy, methyl, methoxy, propoxy, N-ethylcarbamoyl, N,N-dimethylcarbamoyl, N-methyl-N-methoxycarbamoyl, methoxycarbonyl or morpholino-$R^{11}$—; wherein $R^4$ may be optionally substituted on carbon by one or more $R^{12}$. $R^{12}$ is selected from hydroxy, ethenyl, methoxy, N-methylamino or N,N-dimethylamino; and $R^{11}$ is —C(O)—.

Alternatively, $R^4$ is a substituent on carbon and is selected from methoxy, hydroxy, methoxycarbonyl, fluoro, allyloxy, propoxy, N,N-dimethylcarbamoyl, morpholinocarbonyl, N-ethylcarbamoyl, N-(2-hydroxyethyl)carbamoyl, dimethylaminomethyl, N-methyl-N-methoxycarbamoyl, methoxymethyl, methylaminomethyl and carboxy.

Alternatively, $R^4$ is a substituent on carbon and is selected from methoxy, hydroxy, methoxycarbonyl, fluoro, allyloxy, propoxy, N,N-dimethylcarbamoyl, morpholinocarbonyl, N-ethylcarbamoyl, N-(2-hydroxyethyl)carbamoyl, dimethylaminomethyl, N-methyl-N-methoxycarbamoyl, methoxymethyl, methylaminomethyl, carboxy, N-methyl-N-methoxycarbamoyl, N-hydroxyethylcarbamoyl, hydroxymethyl, (methylthio)methyl, (methylsulfinyl)methyl, (methylsulfonyl)methyl, benzyloxy, propynyloxy, methoxyethoxy, methoxypropoxy, chloro, methyl, cyclopropylmethoxy, thiazolylmethoxy, ethoxy, oxyacetic acid, ethylaminocarbonyloxy, allylaminocarbonyloxy, pyridinylmethoxy, hydroxypropoxy, methoxy(methyl)amino, and azido.

Alternatively $R^4$ is halo, particularly fluoro.

$R^5$ is a substituent on carbon and is selected from halo, carboxy, carbamoyl, $C_{1-4}$alkyl, $C_{1-4}$alkoxy, N—($C_{1-4}$alkyl)carbamoyl, N—($C_{1-4}$alkoxy)carbamoyl or $C_{1-4}$alkoxycarbonyl; wherein $R^5$ may be optionally substituted on carbon by one or more $R^{12}$. $R^{12}$ is selected from $C_{1-4}$alkoxy or carbocyclyl-$R^{14}$—; and $R^{14}$ is a direct bond.

Alternatively, $R^5$ is a substituent on carbon and is selected from chloro, carboxy, carbamoyl, methyl, methoxy, N-(isopropyl)carbamoyl, N-(methoxy)carbamoyl, methoxycarbonyl or ethoxycarbonyl; wherein $R^5$ may be optionally substituted on carbon by one or more $R^{12}$. $R^{12}$ is selected from methoxy or phenyl-$R^{14}$—; and $R^{14}$ is a direct bond.

Alternatively, $R^5$ is a substituent on carbon and is selected from chloro, carboxy, carbamoyl, methyl, methoxymethyl, methoxy, N-(1-methyl-1-phenylethyl)carbamoyl, N-(methoxy)carbamoyl, methoxycarbonyl or ethoxycarbonyl.

Alternatively, $R^5$ is a substituent on carbon and is selected from chloro, carboxy, carbamoyl, methyl, methoxymethyl, methoxy, N-(1-methyl-1-phenylethyl)carbamoyl, N-(methoxy)carbamoyl, methoxycarbonyl or ethoxycarbonyl, N-methoxycarbamoyl, formyl, (methoxyimino)methyl, isopropoxycarbonyl, ethoxy, morpholinocarbonyl, hydroxy-1-methylethyl, amino, methoxycarbonylamino, methylsulfonylamino, N-(1-methyl-1-phenylethyl)carbamoyl, N-2-morpholin-4-ylethylcarbamoyl, piperidinocarbonyl, N-methylcarbamoyl, N-2-hydroxyethylcarbamoyl, N-2-methoxyethylcarbamoyl, N-2-hydroxypropylcarbamoyl, N-2-hydroxy-1-methylethylcarbamoyl, N-isoxazolylcarbamoyl, N-2,2-difluoroethylcarbamoyl, N-tetrahydrofuran-3-ylcarbamoyl, N-cyclopropylcarbamoyl, N-1-cyanocyclopropylcarbamoyl, N-2-fluorocyclopropylcarbamoyl, N-2- hydroxy-1,1-dimethylethylcarbamoyl, N-1-cyano-1-methylethylcarbamoyl, N-1-(hydroxymethyl-2-methoxy-2-oxoethylcarbamoyl, N-1,3-dioxolan-2-ylmethylcarbamoyl, N-3-(2-oxopyrrolidin-1-ylpropylcarbamoyl, N-pyridin-2-ylmethylcarbamoyl, N-2-(methylthio)ethylcarbamoyl, N-1,3-oxazol-2-ylmethylcarbamoyl, N-2-fluoroethylcarbamoyl, N-(2-hydroxy-2-methylpropyl)carbamoyl, morpholin-4-ylmethyl, tert-butylaminomethyl, piperidine-1-ylmethyl, (3-hydroxypyrrolidin-1-yl)methyl, (hydroxyimino)methyl, 1,1-difluoromethyl, azidomethyl, cyano(morpholin-4-yl)methyl, N-2-(methylsulfonyl)ethylcarbamoyl, cyano, 1-hydroxy-1-methylethyl, cyclopropylmethyl, N-methylcarbamoyl, N-1-carboxycyclopropylcarbamoyl, N-isoxazol-3-ylcarbamoyl, N-prop-2-yn-1 ylcarbamoyl, N-1-carboxy-2-hydroxymethylcarbamoyl, N-[3-(2-oxopyrrolidin-1-yl)propyl]carbamoyl, N-(2-hydroxy-2-methylpropyl)carbamoyl, N-methoxy-N-methylcarbamoyl, N-2-(methylsulfonyl)ethylcarbamoyl, N-methoxypropylcarbamoyl, and methoxymethyl)ethyl]amino}carbamoyl.

Alternatively $R^5$ is carboxy.
$R^6$ is hydrogen.
n is 1.
m is 1 or 2; wherein the values of $R^5$ may be the same or different. m is 1. m is 2.

In a further aspect of the invention there is provided a compound of formula (I) (as depicted above) wherein:
$R^1$ is selected from $C_{1-4}$alkyl;
$R^2$ is selected from halo.
$R^3$ is selected from hydrogen or halo;
W is —N($R^6$)—;
X is a direct bond;
Ring A is heterocyclyl;
$R^4$ is a substituent on carbon and is selected from halo, hydroxy, carboxy, $C_{1-4}$alkyl, $C_{1-4}$alkoxy, N—($C_{1-4}$alkyl)carbamoyl, N,N—($C_{1-4}$alkyl)$_2$carbamoyl, N—($C_{1-4}$alkyl)-N—($C_{1-4}$alkoxy)carbamoyl, $C_{1-4}$alkoxycarbonyl or heterocyclyl-$R^{11}$—; wherein $R^4$ may be optionally substituted on carbon by one or more $R^{12}$;
$R^5$ is a substituent on carbon and is selected from halo, carboxy, carbamoyl, $C_{1-4}$alkyl, $C_{1-4}$alkoxy, N—($C_{1-4}$alkyl)carbamoyl, N—($C_{1-4}$alkoxy)carbamoyl or $C_{1-4}$alkoxycarbonyl; wherein $R^5$ may be optionally substituted on carbon by one or more $R^{12}$;
$R^6$ is hydrogen;
$R^{11}$ is —C(O)—;
$R^{12}$ is selected from hydroxy, $C_{2-4}$alkenyl, $C_{1-4}$alkoxy, N—($C_{1-4}$alkyl)amino, N,N—($C_{1-4}$alkyl)$_2$amino or carbocyclyl-$R^{14}$—;
$R^{14}$ is a direct bond;
n is 1; and
m is 1 or 2; wherein the values of $R^5$ may be the same or different;
or a pharmaceutically acceptable salt thereof.

In a further aspect of the invention there is provided a compound of formula (I) (as depicted above) wherein:
$R^1$ is selected from methyl;
$R^2$ is fluoro or chloro;
$R^3$ is selected from hydrogen, fluoro or chloro;
W is —NH—;
X is a direct bond;
Ring A is thiazolyl, quinolinyl, benzothiazolyl, pyrimidinyl or pyridinyl;
$R^4$ is a substituent on carbon and is selected from methoxy, hydroxy, methoxycarbonyl, fluoro, allyloxy, propoxy, N,N-dimethylcarbamoyl, morpholinocarbonyl, N-ethylcarbamoyl, N-(2-hydroxyethyl)carbamoyl, dimethylaminomethyl, N-methyl-N-methoxycarbamoyl, methoxymethyl, methylaminomethyl and carboxy;
$R^5$ is a substituent on carbon and is selected from chloro, carboxy, carbamoyl, methyl, methoxymethyl, methoxy, N-(1-methyl-1-phenylethyl)carbamoyl, N-(methoxy)carbamoyl, methoxymethyl)ethyl]amino}carbamoyl, methoxycarbonyl or ethoxycarbonyl;
n is 1; and
m is 1 or 2; wherein the values of $R^5$ may be the same or different; or a pharmaceutically acceptable salt thereof.

In a further aspect of the invention there is provided a compound of formula (I) (as depicted above) wherein:
$R^1$ is selected from hydrogen or methyl;
$R^2$ is hydrogen, bromo, fluoro, chloro, CN, or —C=NOMe;
$R^3$ is selected from hydrogen, fluoro or chloro;
W is —NH—;
X is a direct bond;
Ring A is thiazolyl, quinolinyl, benzothiazolyl, pyrimidinyl or pyridinyl;
$R^4$ is a substituent on carbon and is selected from methoxy, hydroxy, methoxycarbonyl, fluoro, allyloxy, propoxy, N,N-dimethylcarbamoyl, morpholinocarbonyl, N-ethylcarbamoyl, N-(2-hydroxyethyl)carbamoyl, dimethylaminomethyl, N-methyl-N-methoxycarbamoyl, methoxymethyl, methylaminomethyl, carboxy, N-methyl-N-methoxycarbamoyl, N-hydroxyethylcarbamoyl, hydroxymethyl, (methylthio)methyl, (methylsulfinyl)methyl, (methylsulfonyl)methyl, benzyloxy, propynyloxy, methoxyethoxy, methoxypropoxy, chloro, methyl, cyclopropylmethoxy, thiazolylmethoxy, ethoxy, oxyacetic acid, ethylaminocarbonyloxy, allylaminocarbonyloxy, pyridinylmethoxy, hydroxypropoxy, methoxy(methyl)amino, and azido;
$R^5$ is a substituent on carbon and is selected from chloro, carboxy, carbamoyl, methyl, methoxymethyl, methoxy, N-(1-methyl-1-phenylethyl)carbamoyl, N-(methoxy)carbamoyl, methoxycarbonyl or ethoxycarbonyl, N-methoxycarbamoyl, formyl, (methoxyimino)methyl, isopropoxycarbonyl, ethoxy, morpholinocarbonyl, hydroxy-1-methylethyl, amino, methoxycarbonylamino, methylsulfonylamino, N-(1-methyl-1-phenylethyl)carbamoyl, N-2-morpholin-4-ylethylcarbamoyl, piperidinocarbonyl, N-methylcarbamoyl, N-2-hydroxyethylcarbamoyl, N-2-methoxyethylcarbamoyl, N-2-hydroxypropylcarbamoyl, N-2-hydroxy-1-methylethylcarbamoyl, N-isoxazolylcarbamoyl, N2,2-difluoroethylcarbamoyl, N-tetrahydrofuran-3-ylcarbamoyl, N-cyclopropylcarbamoyl, N-1-cyanocyclopropylcarbamoyl, N-2-fluorocyclopropylcarbamoyl, N-2-hydroxy-1,1-dimethylethylcarbamoyl, N-1-cyano-1-methylethylcarbamoyl, N-1-(hydroxymethyl-2-methoxy-2-oxoethylcarbamoyl, N-1,3-dioxolan-2-ylmethylcarbamoyl, N-3-(2-oxopyrrolidin-1-ylpropylcarbamoyl, N-pyridin-2-ylmethylcarbamoyl, N-2-(methylthio)ethylcarbamoyl, N-1,3-oxazol-2-ylmethylcarbamoyl, N-2-fluoroethylcarbamoyl, N-(2-hydroxy-2-methylpropyl)carbamoyl, morpholin-4-ylmethyl, tert-butylaminomethyl, piperidine-1-ylmethyl, (3-hydroxypyrrolidin-1-yl)methyl, (hydroxyimino)methyl, 1,1-difluoromethyl, azidomethyl, cyano(morpholin-4-yl)methyl, N-2-(methylsulfonyl)ethylcarbamoyl, cyano, 1-hydroxy-1-methylethyl, cyclopropylmethyl, N-methylcarbamoyl, N-1-carboxycyclopropylcarbamoyl, N-isoxazol-3-ylcarbamoyl, N-prop-2-yn-1 ylcarbamoyl, N-1-carboxy-2-hydroxymethylcarbamoyl, N-[3-(2-oxopyrrolidin-1-yl)propyl]carbamoyl, N-(2-hydroxy-2-methylpropyl)carbamoyl, N-methoxy-N-methylcarbamoyl, N-2-(methylsulfonyl)ethylcarbamoyl, N-methoxypropylcarbamoyl, and methoxymethyl)ethyl]amino}carbamoyl;

n is 1; and m is 1 or 2; wherein the values of $R^5$ may be the same or different; or a pharmaceutically acceptable salt thereof.

In a further aspect of the invention, there is provided a compound of the invention which is a compound of formula (IA)

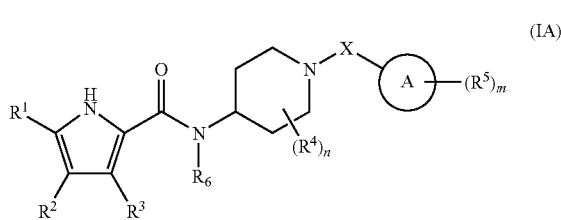

(IA)

wherein:

$R^1$ is selected from hydrogen, halo, cyano, or $C_{1-4}$alkyl;

$R^2$ is selected from hydrogen, halo, cyano, or $C_{1-4}$alkyl;

$R^3$ is selected from hydrogen, halo, cyano, $C_{1-4}$alkyl, or —C=N—OH;

X is a direct bond, —CH$_2$—, —C(O)— or S(O)$_q$— (wherein q is 1 or 2);

Ring A is carbocyclyl or heterocyclyl; wherein if said heterocyclyl contains an —NH— moiety that nitrogen may be optionally substituted by a group selected from $R^9$;

$R^4$ and $R^5$ are substituents on carbon and are independently selected from halo, nitro, cyano, hydroxy, trifluoromethoxy, amino, carboxy, carbamoyl, mercapto, sulphamoyl, sulfo, formyl, ureido, hydroxyiminomethyl, $C_{1-4}$alkoxyiminomethyl, N-hydroxyformamido, $C_{1-4}$hydrazino, hydrazinocarbonyl, N-hydroxyethanimidoyl, amino(hydroxyimino)methyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, N—($C_{1-4}$alkoxy)carbamoyl, N'—$C_{1-4}$alkyl)ureido, N',N'—($C_{1-4}$alkyl)$_2$ ureido, N—($C_{1-4}$alkyl)-N—($C_{1-4}$alkoxy)carbamoyl, $C_{1-4}$alkylS(O)$_a$ wherein a is 0 to 2, $C_{1-4}$alkoxycarbonyl, $C_{1-4}$alkoxycarbonylamino, N—($C_{1-4}$alkyl)sulphamoyl, N,N—($C_{1-4}$alkyl)$_2$sulphamoyl, $C_{1-4}$alkylsulphonylamino, $C_{1-4}$alkylsulphonylaminocarbonyl, N'—($C_{1-4}$alkyl)hydrazinocarbonyl, N',N'—($C_{1-4}$alkyl)$_2$hydrazinocarbonyl, carbocyclyl-$R^{10}$— or heterocyclyl-$R^{11}$—; wherein $R^4$ and $R^5$ independently of each other may be optionally substituted on carbon by one or more $R^{12}$; and wherein if said heterocyclyl contains an —NH— moiety that nitrogen may be optionally substituted by a group selected from $R^{13}$;

$R^6$ is hydrogen or $C_{1-4}$alkyl;

n is 1-4; wherein the values of $R^4$ may be the same or different;

m is 0-4; wherein the values of $R^5$ may be the same or different;

$R^{12}$ is selected from azido, halo, nitro, cyano, hydroxy, trifluoromethoxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl, N,N—($C_{1-4}$alkyl)$_2$sulphamoyl, $C_{1-4}$alkylsulphonylamino, $C_{1-4}$alkoxycarbonylamino, carbocyclyl-$R^{14}$— or heterocyclyl-$R^{15}$—; wherein $R^{12}$ independently of each other may be optionally substituted on carbon by one or more $R^{16}$; and wherein if said heterocyclyl contains an —NH— moiety that nitrogen may be optionally substituted by a group selected from $R^{17}$;

$R^9$, $R^{13}$ and $R^{17}$ are independently selected from $C_{1-4}$alkyl, $C_{1-4}$alkanoyl, $C_{1-4}$alkylsulphonyl, $C_{1-4}$alkoxycarbonyl, carbamoyl, N—($C_{1-4}$alkyl)carbamoyl, N,N—($C_{1-4}$alkyl)carbamoyl, benzyl, benzyloxycarbonyl, benzoyl and phenylsulphonyl;

$R^{10}$, $R^{11}$, $R^{14}$ and $R^{15}$ are independently selected from a direct bond, —O—, —N($R^{18}$)—, —C(O)—, —N($R^{19}$)C(O)—, —C(O)N($R^{20}$)—, —S(O)$_p$—, —SO$_2$N($R^{21}$)— or —N($R^{22}$)SO$_2$—; wherein $R^{18}$, $R^{19}$, $R^{20}$, $R^{21}$ and $R^{22}$ are independently selected from hydrogen or $C_{1-4}$alkyl and p is 0-2;

$R^{16}$ is selected from halo, nitro, cyano, hydroxy, trifluoromethoxy, trifluoromethyl, amino, carboxy, carbamoyl, mercapto, sulphamoyl, methyl, ethyl, ethenyl, ethynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or a pharmaceutically acceptable salt thereof.

In a further aspect of the invention, there is provided a compound of formula (IA) which is a compound of formula (IB):

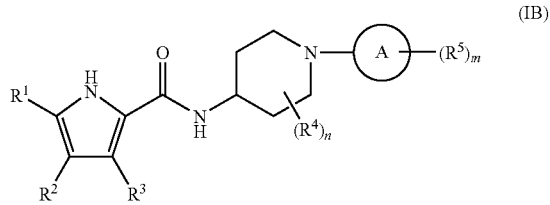

(IB)

wherein:

$R^4$ is a substituent on carbon and is selected from methoxy, hydroxy, methoxycarbonyl, fluoro, allyloxy, propoxy, N,N-dimethylcarbamoyl, morpholinocarbonyl, N-ethylcarbamoyl, N-(2-hydroxyethyl)carbamoyl, dimethylaminomethyl, N-methyl-N-methoxycarbamoyl, methoxymethyl, methylaminomethyl, carboxy, N-methyl-N-methoxyxcarbamoyl, N-hydroxyethylcarbamoyl, hydroxymethyl, (methylthio)methyl, (methylsulfinyl)methyl, (methylsulfonyl)methyl, benzyloxy, propynyloxy, methoxyethoxy, methoxypropoxy, chloro, methyl, cyclopropylmethoxy, thiazolylmethoxy, ethoxy, oxyacetic acid, ethylaminocarbonyloxy, allylaminocarbonyloxy, pyridinylmethoxy, hydroxypropoxy, methoxy(methyl)amino, and azido;

$R^5$ is a substituent on carbon and is selected from chloro, carboxy, carbamoyl, methyl, methoxymethyl, methoxy, N-(1-methyl-1-phenylethyl)carbamoyl, N-(methoxy)carbamoyl, methoxycarbonyl or ethoxycarbonyl, N-methoxycarbamoyl, formyl, (methoxyimino)methyl, isopropoxycarbonyl, ethoxy, morpholinocarbonyl, hydroxy-1-methylethyl, amino, methoxycarbonylamino, methylsulfonylamino, N-(1-methyl-1-phenylethyl)carbamoyl, N-2-morpholin-4-ylethylcarbamoyl, piperidinocarbonyl, N-methylcarbamoyl, N-2-hydroxyethylcarbamoyl, N-2-methoxyethylcarbamoyl, N-2- hydroxypropylcarbamoyl, N-2-hydroxy-1-methylethylcarbamoyl, N-isoxazolylcarbamoyl, N2,2-difluoroethylcarbamoyl, N-tetrahydrofuran-3-ylcarbamoyl, N-cyclopropylcarbamoyl, N-1-cyanocyclopropylcarbamoyl, N-2-fluorocyclopropylcarbamoyl, N-2-hydroxy-1,1-dimethylethylcarbamoyl, N-1-cyano-1-methylethylcarbamoyl, N-1-(hydroxymethyl-2-methoxy-2-oxoethylcarbamoyl, N-1,3-dioxolan-2-ylmethylcarbamoyl, N-3-(2-oxopyrrolidin-1-yl)propylcarbamoyl, N-pyridin-2-ylmethylcarbamoyl, N-2-(methylthio)ethylcarbamoyl, N-1,3-oxazol-2-ylmethylcarbamoyl, N-2-fluoroethylcarbamoyl, N-(2-hydroxy-2-methylpropyl)carbamoyl, morpholin-4-ylmethyl, tert-butylaminomethyl, piperidine-1-ylmethyl, (3-hydroxypyrrolidin-1-yl)methyl, (hydroxyimino)methyl, 1,1-difluoromethyl, azidomethyl, cyano(morpholin-4-yl)methyl, N-2-(methylsulfonyl)ethylcarbamoyl, cyano, 1-hydroxy-1-methylethyl, cyclopropylmethyl, N-methylcarbamoyl, N-1-carboxycyclopropylcarbamoyl, N-isoxazol-3-ylcarbamoyl, N-prop-2-yn-1-ylcarbamoyl, N-1-carboxy-2-hydroxymethylcarbamoyl, N-[3-(2-oxopyrrolidin-1-yl)propyl]carbamoyl, N-(2-hydroxy-2-methylpropyl)carbamoyl, N-methoxy-N-methylcarbamoyl, N-2-(methylsulfonyl)ethylcarbamoyl, N-methoxypropylcarbamoyl, and methoxymethyl)ethyl]amino}carbamoyl;

n is 1; wherein the values of $R^4$ may be the same or different; and m is 1 or 2; wherein the values of $R^5$ may be the same or different.

In a further aspect of the invention, there is provided a compound of formula (IB) which is a compound of formula (IC).

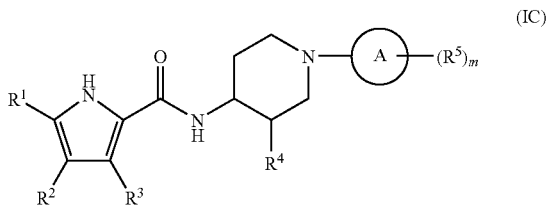

In a further aspect of the invention, there is provided a compound of formula (IC):

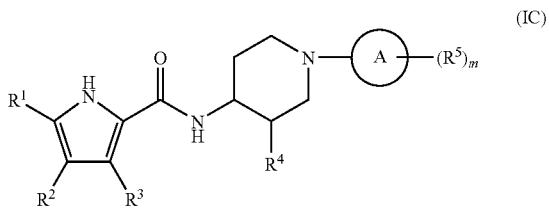

wherein:

Ring A is heterocyclyl; wherein if said heterocyclyl contains an —NH— moiety that nitrogen may be optionally substituted by a group selected from $C_{1-4}$alkyl, $C_{1-4}$alkanoyl, $C_{1-4}$alkylsulphonyl, $C_{1-4}$alkoxycarbonyl, carbamoyl, N—($C_{1-4}$alkyl)carbamoyl, N,N—($C_{1-4}$alkyl)carbamoyl, benzyl, benzyloxycarbonyl, benzoyl and phenylsulphonyl.

In a further aspect of the invention, there is provided a compound of formula (IC) which is a compound of formula (IE):

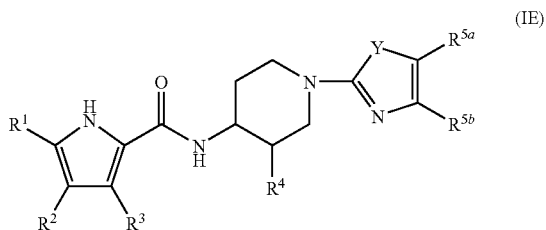

wherein:
Y is N—H, N—$C_{1-4}$alkyl, S, or O;
$R^{5a}$ is H or as defined for $R^5$;
$R^{5b}$ is H or as defined for $R^5$; or
$R^{5a}$ and $R^{5b}$ taken together with the carbons to which they are attached form a 6-membered carbocyclyl ring substituted by one or two groups selected from $R^5$ which may be the same or different.

In a further aspect of the invention, there is provided a compound of formula (IE) which is a compound of formula (IF):

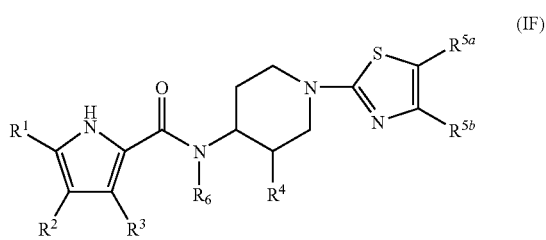

Particular compounds of the invention are the compounds of the Examples, each of which provides a further independent aspect of the invention. In further aspects, the present invention also comprises any two or more compounds of the Examples.

In one embodiment of the invention are provided compounds of formula (I), in an alternative embodiment are provided pharmaceutically-acceptable salts of compounds of formula (I).

In a further aspect the present invention provides a process for preparing a compound of formula (I) or a pharmaceutically-acceptable salt thereof.

Thus, the present invention also provides that the compounds of the formula (I) and pharmaceutically-acceptable salts thereof, can be prepared by a process as follows (wherein the variables are as defined above unless otherwise stated)
Process a) for compounds of formula (I) wherein W is —C($R^7$)($R^8$)—; converting a compound of formula (II):

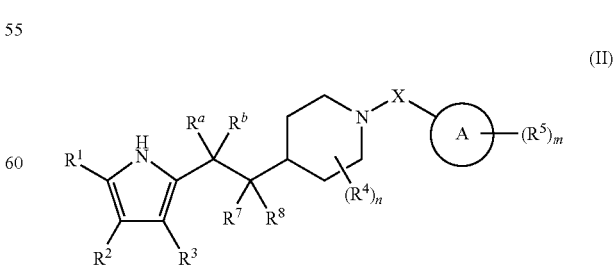

wherein $R^a$ is cyano and $R^b$ is dimethyamino or diethylamino; or $R^a$ and $R^b$ are independently selected from $C_{1-4}$alkylthio;

or $R^a$ and $R^b$ together form 1,3-dithianyl or 1,3-dithiolanyl; into a compound of formula (I);

Process b) for compounds of formula (I) wherein W is —O—; reacting a compound of formula (III):

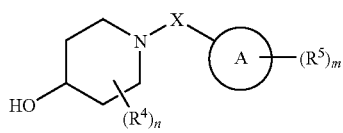
(III)

with a compound of formula (IV):

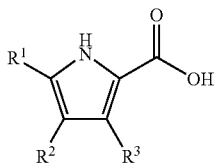
(IV)

Process c) for compounds of formula (I) wherein W is —N($R^6$)—; reacting a compound of formula (V):

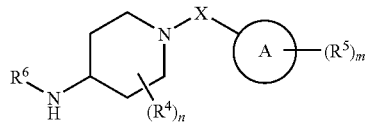
(V)

with a compound of formula (IV) or an activated acid derivative thereof;

Process d) for compounds of formula (I) wherein W is —C($R^7$)($R^8$)—; reacting a compound of formula (VI):

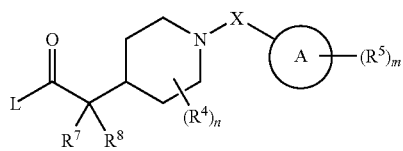
(VI)

wherein L is a displaceable group; with a compound of formula (VII):

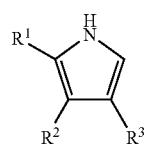
(VII)

Process e) for compounds of formula (I) wherein W is —C($R^7$)($R^8$)—; reacting a compound of formula (VIII):

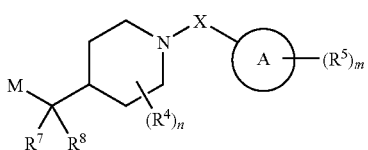
(VIII)

wherein M is an organometallic group; with a compound of formula (IX):

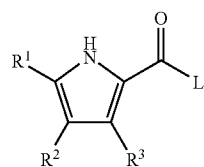
(IX)

wherein L is a displaceable group;

Process f) reacting a compound of formula (X):

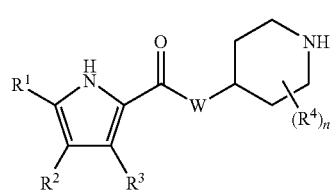
(X)

with a compound of formula (XI):

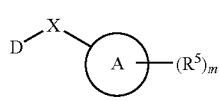
(XI)

wherein D is a displaceable group;

Process g) for compounds of formula (I) wherein X is —C(O)—; reacting a compound of formula (X) with a compound of formula (XII):

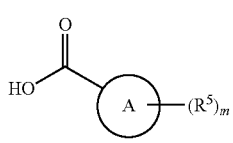
(XII)

and thereafter if necessary:
i) converting a compound of the formula (I) into another compound of the formula (I);
ii) removing any protecting groups;
iii) forming a pharmaceutically acceptable salt.

L is a displaceable group. Suitable values for L include halo, for example chloro and bromo, pentafluorophenoxy and 2,5-oxopyrrolidin-1-yloxy.

wherein D is a displaceable group;

D is a displaceable group. Suitable values for D include halo, for example chloro, bromo and iodo, tosylate and mesylate.

M is an organometallic group, suitable values for M include organocuprates, for example CuLi, organozincs, Zn, or a Grignard reagent for example MgG where G is halo for example chloro.

Specific reaction conditions for the above reaction are as follows.

Process a) Compounds of formula (II) may be converted into compounds of formula (I):
(i) where $R^a$ is cyano and $R^b$ is dimethyamino or diethylamino; in the presence of a base for example sodium hydroxide, in a suitable solvent for example aqueous methanol at room temperature.
(ii) wherein or $R^a$ and $R^b$ are independently selected from $C_{1-4}$alkylthio; or $R^a$ and $R^b$ together form 1,3-dithianyl or 1,3-dithiolanyl; in the presence of a reagent such as a mercury, copper or silver salt for example $Hg(ClO_4)_2$, $CuCl_2$ or $AgNO_3/Ag_2O$ in the presence of a suitable solvent for example methanol, acetone or ethanol from a temperature ranging from room temperature to reflux.

Compounds of formula (II) may be prepared according to Scheme 1:

Compounds of formula (III) may be prepared according to Scheme 2:

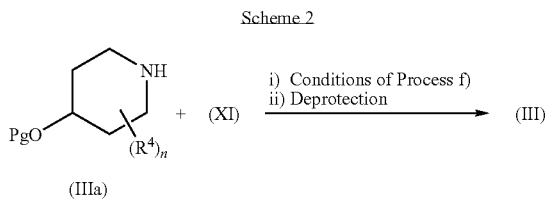

wherein Pg is a hydroxy protecting group as defined hereinbelow.

Deprotection of hydroxy protecting groups are well known in the art. Examples of such deprotections are given hereinbelow.

Compounds of formula (IIIa) and (IV) are commercially available compounds, or they are known in the literature, or they are prepared by standard processes known in the art.

Process c) Compounds of formula (V) and (IV) may be coupled together in the presence of a suitable coupling reagent. Standard peptide coupling reagents known in the art

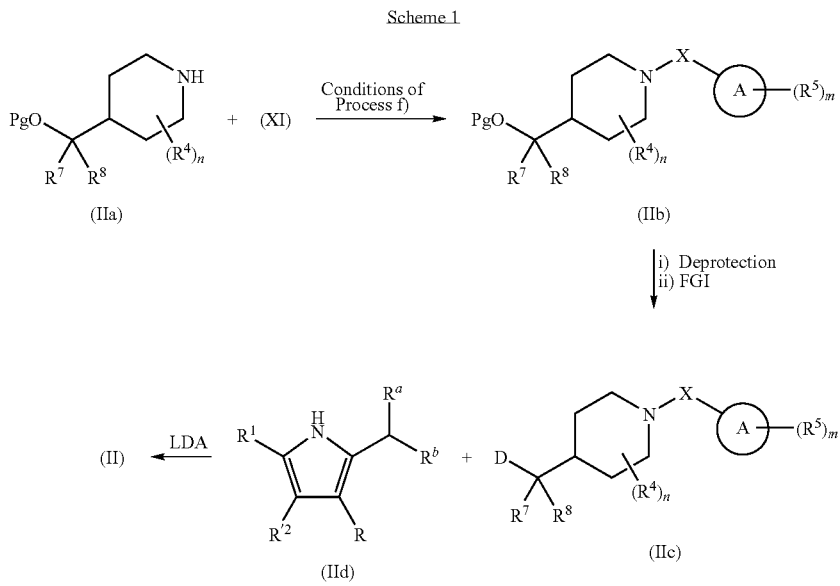

wherein Pg is a hydroxy protecting group as defined hereinbelow; and D is a displaceable group as defined hereinabove.

Deprotection of hydroxy protecting groups are well known in the art. Examples of such deprotections are given hereinbelow.

FGI stands for Functional Group Interconversion. In the above scheme such conversions between a hydroxy group and a D group are well known in the art and are well within the capabilities of a person skilled in the art.

Compounds of formula (IIa) and (IId) are known in the literature, or they are prepared by standard processes known in the art.

Process b) Compounds of formula (III) and (IV) may be reacted together may be reacted together in the presence of a coupling reagent, for example dicyclohexylcarbodiimide or EDC, in a suitable solvent, for example dichloromethane, THF or diethylether.

can be employed as suitable coupling reagents, or for example carbonyldiimidazole and dicyclohexyl-carbodiimide, optionally in the presence of a catalyst such as dimethylaminopyridine or 4-pyrrolidinopyridine, optionally in the presence of a base for example triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of −40 to 40° C.

Compounds of formula (V) may be prepared according to Scheme 3:

Scheme 3

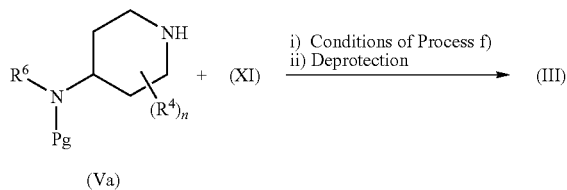

(Va)

wherein Pg is a amino protecting group as defined hereinbelow. The skilled reader will appreciate that where $R^6$ is hydrogen, this hydrogen also needs protecting by way of a suitable protecting group.

Deprotection of amino protecting groups are well known in the art. Examples of such deprotections are given hereinbelow.

Compounds of formula (Va) are commercially available compounds, or they are known in the literature, or they are prepared by standard processes known in the art.

Process d) Compounds of formula (VI) and (VII) may be reacted in a suitable solvent such a DCM or 1,2-dichloroethane, optionally in the presence of a Lewis acid, for example $AlCl_3$, from 0° C. to room temperature.

Compounds of formula (VI) may be prepared according to Scheme 4:

Scheme 4

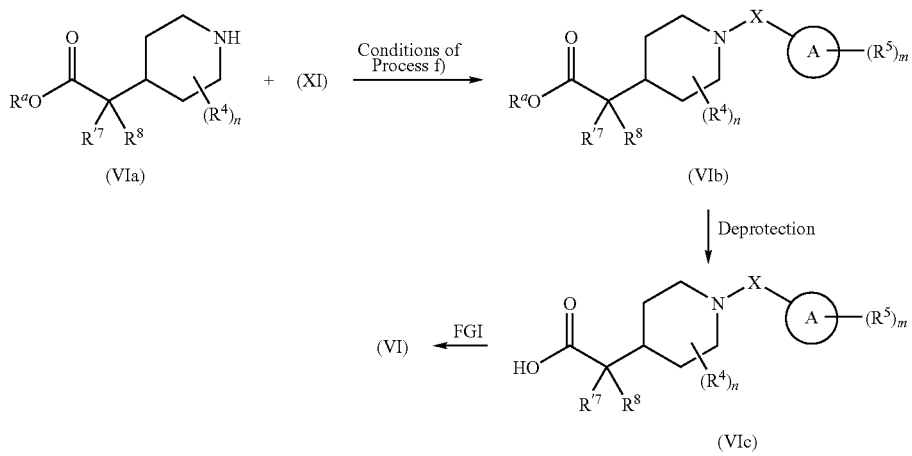

wherein $R^aOC(O)$ is an ester group.

Suitable values for $R^a$ include $C_{1-6}$alkyl. Deprotection of the $R^a$ carboxy protecting group may be achieved under standard conditions, for example acid or base hydrolysis, such as those conditions give hereinbelow.

FGI stands for Functional Group Interconversion. In the above scheme such conversions between an acid group and a —C(O)L group are well known in the art and are well within the capabilities of a person skilled in the art.

Compounds of formula (VIa) and (VII) are commercially available compounds, or they are known in the literature, or they are prepared by standard processes known in the art.

Process e) Compounds of formula (VIII) and (IX) may be reacted in a suitable aprotic solvent such as THF or ether, at temperatures in the range of −78° C. to 0° C.

Compounds of formula (VIII) may be prepared from compounds of formula (IIc) under standard conditions known in the art. For example where M is an organocuprous reagent such compounds could be prepared according to Scheme 5:

Scheme 5

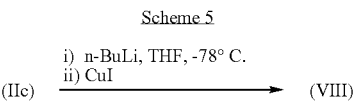

Compounds of formula (IX) are commercially available compounds, or they are known in the literature, or they are prepared by standard processes known in the art.

Process f) Compounds of formula (X) and (XI) may be reacted in a suitable solvent such as DMF, N-methylpyrrolidinone or dimethylacetamide in the presence of a base such as triethylamine or diisopropylethylamine under thermal conditions or a microwave reactor.

Compounds of formula (X) may be prepared according to Scheme 6:

Scheme 6

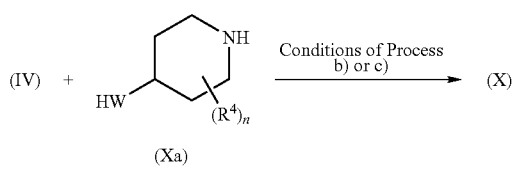

-continued

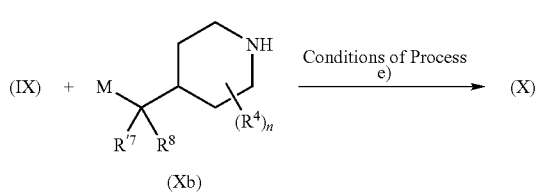

wherein M is an organometallic group as defined hereinabove.

Compounds of formula (Xa), (Xb) and (XI) are commercially available compounds, or they are known in the literature, or they are prepared by standard processes known in the art.

Process g) Compounds of formula (X) and (XII) may be coupled together under the conditions outlined in Process c).

Compounds of formula (XII) are commercially available compounds, or they are known in the literature, or they are prepared by standard processes known in the art.

The formation of a pharmaceutically-acceptable salt is within the skill of an ordinary organic chemist using standard techniques.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. The reagents used to introduce such ring substituents are either commercially available or are made by processes known in the art.

Introduction of substituents into a ring may convert one compound of the formula (I) into another compound of the formula (I). Such reactions and modifications include, for example, introduction of a substituent by means of an aromatic substitution reaction, reduction of substituents, alkylation of substituents, oxidation of substituents, esterification of substituents, amidation of substituents, formation of heteroaryl rings. The reagents and reaction conditions for such procedures are well known in the chemical art. Particular examples of aromatic substitution reactions include the introduction of alkoxides, diazotization reactions followed by introduction of thiol group, alcohol group, halogen group. Examples of modifications include; oxidation of alkylthio to alkylsulphinyl or alkylsulphonyl.

The skilled organic chemist will be able to use and adapt the information contained and referenced within the above references, and accompanying Examples therein and also the Examples herein, to obtain necessary starting materials, and products. If not commercially available, the necessary starting materials for the procedures such as those described above may be made by procedures which are selected from standard organic chemical techniques, techniques which are analogous to the synthesis of known, structurally similar compounds, or techniques which are analogous to the above described procedure or the procedures described in the examples. It is noted that many of the starting materials for synthetic methods as described above are commercially available and/or widely reported in the scientific literature, or could be made from commercially available compounds using adaptations of processes reported in the scientific literature. The reader is further referred to Advanced Organic Chemistry, 4$^{th}$ Edition, by Jerry March, published by John Wiley & Sons 1992, for general guidance on reaction conditions and reagents.

It will also be appreciated that in some of the reactions mentioned herein it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T. W. Greene, Protective Groups in Organic Synthesis, John Wiley and Sons, 1991).

Examples of a suitable protecting group for a hydroxy group is, for example, an acyl group, for example an alkanoyl group such as acetyl, an aroyl group, for example benzoyl, a silyl group such as trimethylsilyl or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively a silyl group such as trimethylsilyl may be removed, for example, by fluoride or by aqueous acid; or an arylmethyl group such as a benzyl group may be removed, for example, by hydrogenation in the presence of a catalyst such as palladium-on-carbon.

A suitable protecting group for an amino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine or 2-hydroxyethylamine, or with hydrazine.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art, or they may be removed during a later reaction step or work-up.

When an optically active form of a compound of the invention is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the invention is required, it may be obtained by carrying out one of the above procedures using a pure regioisomer as a starting material, or by resolution of a mixture of the regioisomers or intermediates using a standard procedure.

Enzyme Potency Testing Methods

Compounds were tested for inhibition of GyrB ATPase activity using an ammonium molybdate/malachite green-based phosphate detection assay (Lanzetta, P. A., L. J. Alvarez, P. S. Reinach, and O. A. Candia, 1979, 100: 95-97).

Assays were performed in multiwell plates in 100 µl reactions containing: 50 mM TRIS buffer pH 7.5, 75 mM ammonium acetate, 5.5 mM magnesium chloride, 0.5 mM ethylenediaminetetraacetic acid, 5% glycerol, 1 mM 1,4-Dithio-DL-threitol, 200 nM bovine serum albumin, 16 µg/ml sheared salmon sperm DNA, 4 nM E. coli GyrA, 4 nM E. coli GyrB, 250 µM ATP, and compound in dimethylsulfoxide. Reactions were quenched with 150 µl of ammonium molybdate/malachite green detection reagent containing 1.2 mM malachite green hydrochloride, 8.5 mM ammonium molybdate tetrahydrate, and 1 M hydrochloric acid. Plates were read in an absorbance plate reader at 625 nm and percent inhibition values were calculated using dimethylsulfoxide (2%)-containing reactions as 0% inhibition and novobiocin-containing (2 µM) reactions as 100% inhibition controls. Compounds were tested for inhibition of topoisomeraseIV ATPase activity as described above for GyrB except the 100 µl reactions contained the following: 20 mM TRIS buffer pH 8, 50 mM ammonium acetate, 8 mM magnesium chloride, 5% glycerol, 5 mM 1,4-Dithio-DL-threitol, 0.005% Brij-35, 5 µg/ml sheared salmon sperm DNA, 10 nM E. coli GyrA, 10 nM E. coli GyrB, 160 µM ATP, and compound in dimethylsulfoxide. Compound potency was based on $IC_{50}$ measurements determined from reactions performed in the presence of 10 different compound concentrations.

Compounds of the Examples generally have $IC_{50}$ values of <20 µg/ml.

Bacterial Susceptibility Testing Methods

Compounds were tested for antimicrobial activity by susceptibility testing in liquid media. Compounds were dissolved in dimethylsulfoxide and tested in 10 doubling dilutions in the susceptibility assays. The organisms used in the assay were grown overnight on suitable agar media and then suspended in a liquid medium appropriate for the growth of the organism. The suspension was a 0.5 McFarland and a further 1 in 10 dilution was made into the same liquid medium to prepare the final organism suspension in 100 µL. Plates were incubated under appropriate conditions at 37 degrees C. for 24 hrs prior to reading. The Minimum Inhibitory Concentration was determined as the lowest drug concentration able to reduce growth by 80% or more.

Example 48 had an MIC of 0.13 µg/ml against *Streptococcus pneumoniae*. Other examples are provided in the following table.

| Example No. | MIC HIN446 | MIC MCA445 | MIC SPN548 | MIC SAU516 | MIC EFM073 |
|---|---|---|---|---|---|
| 333 | 4 | 0.13 | 0.063 | 2 | 0.5 |
| 60 | 4 | 0.25 | 2 | 2 | 8 |
| 315 | 2 | 0.13 | 0.5 | 4 | 4 |
| 345 | 0.25 | 0.031 | 0.03 | 0.5 | 0.13 |
| 294 | 0.031 | 0.001 | 0.0039 | 0.031 | 0.016 |

According to a further feature of the invention there is provided a compound of the formula (I), or a pharmaceutically-acceptable salt thereof for use in a method of treatment of the human or animal body by therapy.

We have found that compounds of the present invention inhibit bacterial DNA gyrase and topoisomeraseIV and are therefore of interest for their antibacterial effects.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt thereof.

According to a further feature of the invention there is provided a method for inhibition of bacterial DNA gyrase and/or topoisomeraseIV in a warm-blooded animal, such as a human being, in need of such treatment which comprises administering to said animal an effective amount of a compound of formula (I) or a pharmaceutically acceptable salt thereof as defined hereinbefore.

According to a further feature of the invention there is provided a method of treating a bacterial infection in a warm-blooded animal, such as a human being, in need of such treatment which comprises administering to said animal an effective amount of a compound of formula (I) or a pharmaceutically acceptable salt thereof as defined hereinbefore.

A further feature of the present invention is a compound of formula (I) and pharmaceutically acceptable salts thereof for use as a medicament. Suitably the medicament is an antibacterial agent.

According to a further aspect of the invention there is provided the use of a compound of formula (I), or a pharmaceutically acceptable salt thereof in the manufacture of a medicament for use in the production of an anti-bacterial effect in a warm-blooded animal such as a human being.

According to a further aspect of the invention there is provided the use of a compound of formula (I), or a pharmaceutically acceptable salt thereof in the manufacture of a medicament for use in inhibition of bacterial DNA gyrase and/or topoisomeraseIV in a warm-blooded animal such as a human being.

Thus according to a further aspect of the invention there is provided the use of a compound of formula (I), or a pharmaceutically acceptable salt thereof in the manufacture of a medicament for use in the treatment of a bacterial infection in a warm-blooded animal such as a human being.

According to a further aspect of the invention there is provided a compound of formula (I), or a pharmaceutically acceptable salt thereof for use in the production of an anti-bacterial effect in a warm-blooded animal such as a human being.

According to a further aspect of the invention there is provided a compound of formula (I), or a pharmaceutically acceptable salt thereof for use in inhibition of bacterial DNA gyrase and/or topoisomeraseIV in a warm-blooded animal such as a human being.

Thus according to a further aspect of the invention there is provided a compound of formula (I), or a pharmaceutically acceptable salt thereof for use in the treatment of a bacterial infection in a warm-blooded animal such as a human being.

In order to use a compound of the formula (I) or a pharmaceutically-acceptable salt thereof, (hereinafter in this section relating to pharmaceutical composition "a compound of this invention") for the therapeutic (including prophylactic) treatment of mammals including humans, in particular in treating infection, it is normally formulated in accordance with standard pharmaceutical practice as a pharmaceutical composition.

Therefore in another aspect the present invention provides a pharmaceutical composition that comprises a compound of the formula (I) or a pharmaceutically-acceptable salt thereof, and a pharmaceutically-acceptable diluent or carrier.

According to a further aspect of the invention there is provided a pharmaceutical composition that comprises a compound of formula (I) as defined hereinbefore or a pharmaceutically acceptable salt thereof, in association with a pharmaceutically acceptable excipient or carrier for use in producing an anti-bacterial effect in an warm-blooded animal, such as a human being.

According to a further aspect of the invention there is provided a pharmaceutical composition that comprises a compound of formula (I) as defined hereinbefore or a pharmaceutically acceptable salt thereof, in association with a pharmaceutically acceptable excipient or carrier for use in inhibition of bacterial DNA gyrase and/or topoisomeraseIV in an warm-blooded animal, such as a human being.

According to a further aspect of the invention there is provided a pharmaceutical composition that comprises a compound of formula (I) as defined hereinbefore or a pharmaceutically acceptable salt thereof, in association with a pharmaceutically acceptable excipient or carrier for use in the treatment of a bacterial infection in an warm-blooded animal, such as a human being.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

In addition to the compounds of the present invention the pharmaceutical composition of this invention may also contain or be co-administered (simultaneously, sequentially or separately) with one or more known drugs selected from other clinically useful antibacterial agents (for example, macrolides, quinolones, β-lactams or aminoglycosides) and/or other anti-infective agents (for example, an antifungal triazole or amphotericin). These may include carbapenems, for example meropenem or imipenem, to broaden the therapeutic effectiveness. Compounds of this invention may also contain or be co-administered with bactericidal/permeability-increasing protein (BPI) products or efflux pump inhibitors to improve activity against gram negative bacteria and bacteria resistant to antimicrobial agents.

As stated above the size of the dose required for the therapeutic or prophylactic treatment of a particular disease state will necessarily be varied depending on the host treated, the route of administration and the severity of the illness being treated. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient.

In addition to its use in therapeutic medicine, compounds of formula (I) and their pharmaceutically acceptable salts are also useful as pharmacological tools in the development and standardisation of in-vitro and in-vivo test systems for the evaluation of the effects of inhibitors of DNA gyrase in laboratory animals such as cats, dogs, rabbits, monkeys, rats and mice, as part of the search for new therapeutic agents.

In the above other, pharmaceutical composition, process, method, use and medicament manufacture features, the alternative and particular embodiments of the compounds of the invention described herein also apply.

EXAMPLES

The invention is now illustrated but not limited by the following Examples in which unless otherwise stated:—
(i) evaporations were carried out by rotary evaporation in-vacuo and work-up procedures were carried out after removal of residual solids by filtration;
(ii) operations were carried out at ambient temperature, that is typically in the range 18-26° C. and without exclusion of air unless otherwise stated, or unless the skilled person would otherwise work under an inert atmosphere;
(iii) column chromatography (by the flash procedure) was used to purify compounds and was performed on Merck Kieselgel silica (Art. 9385) unless otherwise stated;
(iv) yields are given for illustration only and are not necessarily the maximum attainable;
(v) the structure of the end-products of the invention were generally confirmed by NMR and mass spectral techniques [proton magnetic resonance spectra is quoted and was generally determined in DMSO-$d_6$ unless otherwise stated using a Bruker DRX-300 spectrometer operating at a field strength of 300 MHz. Chemical shifts are reported in parts per million downfield from tetramethysilane as an internal standard (δ scale) and peak multiplicities are shown thus: s, singlet; d, doublet; AB or dd, doublet of doublets; dt, doublet of triplets; dm, doublet of multiplets; t, triplet, m, multiplet; br, broad; fast-atom bombardment (FAB) mass spectral data were generally obtained using a Platform spectrometer (supplied by Micromass) run in electrospray and, where appropriate, either positive ion data or negative ion data were collected] or using Agilent 1100 series LC/MSD equipped with Sedex 75ELSD, run in APCI mode and, where appropriate, either positive ion data or negative ion data were collected; optical rotations were determined at 589 nm at 20° C. using a Perkin Elmer Polarimeter 341; reverse phase HPLC was carried out using YMC Pack ODS-AQ (100×20 mmID, S-5μ particle size, 12 nm pore size);

(vi) each intermediate was purified to the standard required for the subsequent stage and was characterised in sufficient detail to confirm that the assigned structure was correct; purity was assessed by HPLC, TLC, or NMR and identity was determined by infra-red spectroscopy (IR), mass spectroscopy or NMR spectroscopy as appropriate;

(vii) in which the following abbreviations may be used:—

DMF is N,N-dimethylformamide; DMA is N,N-dimethylacetamide; TLC is thin layer chromatography; HPLC is high pressure liquid chromatography; DMSO is dimethylsulfoxide; $CDCl_3$ is deuterated chloroform; MS is mass spectroscopy; APCI is atmospheric pressure chemical ionisation; EtOAc is ethyl acetate; MeOH is methanol; DIEA is diisopropylethylamine; TFA is trifluoroacetic acid; HATU is N—[(dimethylamino)-1H,2,3-triazolo[4,5-b-]pyridin-1-yl-methylene]-N-methylmethanaminium hexafluorophosphate N-oxide; HOAT is 1-hydroxy-7-azabenzotriazole; NMP is N-methylpyrrolidinone; THF is tetrahydrofuran; EtOH is ethanol; LCMS is liquid chromatography/mass spectrometry; DCM is dichloromethane;

(viii) temperatures are quoted as ° C.;

(ix) Smith Microwave Synthesizer refers to an equipment that uses microwave energy to heat organic reactions in a short period of time; it was used according to the manufacturers instruction and was obtained from Personal Chemistry Uppsala AB;

(x) Kugelrohr distillation refers to a piece of equipment that distils liquids and heats sensitive compounds using air-bath oven temperature; it was used according to the manufacturers instruction and was obtained from Buchi, Switzerland or Aldrich, Milwaukee, USA;

(xi) Where cis(±) or trans(±) is used it is to be understood that this refers to a racemic mixture of the cis or the trans isomers, (–) or (+) refers to the single enantiomer as does R,R or S,S where quoted. Rotations were measured for the first chiral compound in the synthetic scheme (see for example Intermediates 57 and 58) by measuring the rotation of the effluent from the chiral column, using a Perkin Elmer Polarimeter 341, at the point at which the enantiomer eluted, the nomenclature cis(–) or cis (+) was then continued for all the compounds in the synthesis (for example, Example 42 is the final compound in the synthesis which started from Intermediate 57); and (xii) GCMS is Gas phase chromatography (model 6890N) with Mass Spectrometer (model 5973) manufactured by Agilent and was used according to manufacturers instructions.

Example 1

Cis(±)methyl 2-(4-{[(3,4-dichloro-5-methyl-1H-pyrrol-2-yl)carbonyl]amino}-3-methoxypiperidin-1-yl)-1,3-thiazole-5-carboxylate

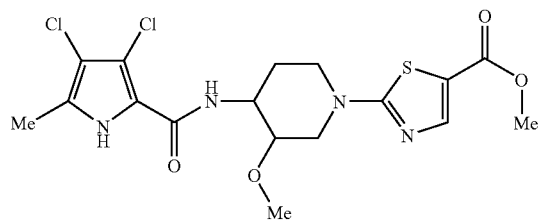 [SMILES: COC(=O)c1cnc(N2CCC(NC(=O)c3[nH]c(C)c(Cl)c3Cl)C(OC)C2)s1]

Method 1

Cis(±)3,4-dichloro-N-(3-methoxypiperidin-4-yl)-5-methyl-1H-pyrrole-2-carboxamide (Intermediate 50; 380 mg), methyl 2-bromo-1,3-thiazole-5-carboxylate (276 mg), were dissolved in anhydrous DMA (5 ml). DIEA (216 μl) was added and the mixture was heated at 120° C. for 7 hours (h). The mixture was diluted with EtOAc, washed well with citrate buffer, water, brine, and dried over $Na_2SO_4$. The organic phase was concentrated in vacuo to give the title compound as a brown solid (337 mg).

Method 2

Alternatively the title compounds were prepared using a Smith Microwave Synthesizer by subjecting the reaction mixture to single-mode microwave at 150° C. for 30 minutes (min.) or until the reaction is complete as judged by LCMS, using polar aprotic solvent such as DMA, NMP or 1-butyl-3-methyl imidazolium-tetrafluoroborate as reaction solvents. MS (ES) $MH^+$: 447 for $C_{17}H_{20}Cl_2N_4O_4S$; NMR: 1.65 (m, 2H), 2.09 (s, 3H), 3.07 (m, 3H), 3.48 (m, 1H), 3.63 (s, 3H), 3.86 (m, 1H), 4.15 (m, 2H), 6.91 (d, 1H), 7.45 (s, 1H), 11.19 (s, 1H).

Examples 2-33

The following Examples were prepared by the procedure described in Example 1 from the starting materials (SM) indicated.

| Ex | Compound | Data | SM |
|---|---|---|---|
| 2 | methyl 2-((3S,4R)-4-{[(3,4-dichloro-5-methyl-1H-pyrrol-2-yl)carbonyl]amino}-3-methoxypiperidin-1-yl)-1,3-thiazole-5-carboxylate | MS (ES) $MH^+$: 447 for $C_{17}H_{20}Cl_2N_4O_4S$; NMR: 1.87 (m, 2H), 2.05 (m, 2H), 2.27 (s, 3H), 3.01 (m, 2H), 3.25 (s, 3H), 3.65 (m, 1H), 3.83 (s, 3H), 4.12 (m, 1H), 4.46 (m, 2H), 7.40 (d, 1H), 8.00 (s, 1H), 12.38 (s, 1H) | Intermediate 51 and methyl 2-bromo-1,3-thiazole-5-carboxylate |
| 3 | methyl 2-((3R,4S)-4-{[(3,4-dichloro-5-methyl-1H-pyrrol-2-yl)carbonyl]amino}-3-methoxypiperidin-1-yl)-1,3-thiazole-5-carboxylate | MS (ES) $MH^+$: 447 for $C_{17}H_{20}Cl_2N_4O_4S$; NMR: 1.89 (m, 2H), 2.11 (m, 2H), 2.23 (s, 3H), 3.33 (m, 2H), 3.46 (s, 3H), 3.59 (m, 1H), 3.85 (s, 3H), 4.09 (m, 1H), 4.46 (m, 2H), 7.31 (d, 1H), 7.92 (s, 1H), 12.30 (s, 1H) | Intermediate 52 and methyl 2-bromo-1,3-thiazole-5-carboxylate |
| 4 | Cis(±)methyl 2-(4-{[(3,4-difluoro-5-methyl-1H-pyrrol-2-yl)carbonyl]amino}-3-methoxypiperidin-1-yl)-1,3-thiazole-5-carboxylate | MS (ES) $MH^+$: 414 for $C_{17}H_{20}F_2N_4O_4S$; NMR: 1.72 (m, 2H), 1.79 (s, 3H), 2.3 (m, 2H), 3.45 (s, 3H), 3.61 (s, 1H), 3.8 (s, 3H), 4.08 (m, 1H), 4.41 (m, 2H), 6.88 (d, 1H), 8.00 (s, 1H), 11.5 (brs, 1H) | Intermediate 56 and methyl 2-bromo-1,3-thiazole-5-carboxylate |
| 5 | Cis(±)methyl 2-(4-{[(3,4-dichloro-5-methyl-1H-pyrrol-2-yl)carbonyl]amino}-3-propoxypiperidin-1-yl)-1,3-thiazole-5-carboxylate | MS (ES) $MH^+$: 475 for $C_{19}H_{24}Cl_2N_4O_4S$; NMR: 0.89 (m, 3H), 1.54 (m, 2H), 1.87 (m, 2H), 2.26 (s, 3H), 3.37 (m, 2H), 3.71 (m, 2H), 3.81 (s, 3H), 4.15 (m, 1H), 4.42 (m, 2H), 7.18 (d, 1H), 7.98 (s, 1H), 12.29 (s, 1H) | Intermediate 53 and methyl 2-bromo-1,3-thiazole-5-carboxylate |
| 6 | Cis(±)methyl 2-(3-(allyloxy)-4-{[(3,4- | MS (ES) $MH^+$: 473 for $C_{19}H_{22}Cl_2N_4O_4S$; NMR: 1.94 | Intermediate 54 and methyl 2-bromo-1,3- |

| Ex | Compound | Data | SM |
|---|---|---|---|
| | dichloro-5-methyl-1H-pyrrol-2-yl)carbonyl]amino}piperidin-1-yl)-1,3-thiazole-5-carboxylate | (m, 2H), 2.23 (s, 3H), 3.56 (m, 2H), 3.58 (m, 2H), 3.84 (s, 3H), 4.07 (m, 2H), 4.21 (m, 1H), 4.46 (m, 2H), 5.37 (m, 2H), 5.95 (m, 1H), 7.29 (d, 1H), 7.96 (s, 1H), 12.32 (s, 1H) | thiazole-5-carboxylate |
| 7 | Cis(±)ethyl 4-(3-(allyloxy)-4-{[(3,4-dichloro-5-methyl-1H-pyrrol-2-yl)carbonyl]amino}piperidin-1-yl)quinoline-2-carboxylate | MS (ES) MH$^+$: 531 for $C_{26}H_{28}Cl_2N_4O_4$ | Intermediate 54 and Intermediate 10 |
| 8 | Cis(±)ethyl 4-(4-{[(3,4-dichloro-5-methyl-1H-pyrrol-2-yl)carbonyl]amino}-3-propoxypiperidin-1-yl)quinoline-2-carboxylate | MS (ES) MH$^+$: 533 for $C_{26}H_{30}Cl_2N_4O_4$ | Intermediate 53 and Intermediate 10 |
| 9 | Cis(±)methyl-2-(4-{[(3,4-dichloro-5-methyl-1H-pyrrol-2-yl)carbonyl]amino}-3-fluoropiperidin-1-yl)-1,3-thiazole-5-carboxylate | MS (ES) MH$^+$: 435, 437 for $C_{16}H_{17}Cl_2FN_4O_3S$; NMR: 1.77-1.79 (m, 2H), 2.12 (s, 3H), 3.25-3.27 (m, 2H), 3.49-3.62 (dd, 1H), 3.68 (s, 3H), 3.95 (m, 1H), 4.00-4.24 (m, 1H), 4.82-4.99 (m, 1H), 7.21 (d, 1H), 7.79 (s, 1H), 12.05 (brs, 1H) | Intermediate 32 and methyl 2-bromo-1,3-thiazole-5-carboxylate |
| 10 | Trans(±)methyl-2-(4-{[(3,4-dichloro-5-methyl-1H-pyrrol-2-yl)carbonyl]amino}-3-fluoropiperidin-1-yl)-1,3-thiazole-5-carboxylate | MS (ES) MH$^+$: 435, 437 for $C_{16}H_{17}Cl_2FN_4O_3S$ | Intermediate 34 and methyl 2-bromo-1,3-thiazole-5-carboxylate |
| 11 | methyl 2-((3R,4S)-4-{[(3,4-dichloro-5-methyl-1H-pyrrol-2-yl)carbonyl]amino}-3-fluoropiperidin-1-yl)-1,3-thiazole-5-carboxylate | MS (ES) MH$^+$: 435, 437 for $C_{16}H_{17}Cl_2FN_4O_3S$; NMR: 1.77-1.79 (m, 2H), 2.12 (s, 3H), 3.25-3.27 (m, 2H), 3.49-3.62 (dd, 1H), 3.68 (s, 3H), 3.95 (m, 1H), 4.00-4.24 (m, 1H), 4.82-4.99 (m, 1H), 7.21 (d, 1H), 7.79 (s, 1H), 12.05 (brs, 1H) | Intermediate 33 and methyl 2-bromo-1,3-thiazole-5-carboxylate |
| 12 | Cis(±)ethyl 2-(4-{[(3,4-dichloro-5-methyl-1H-pyrrol-2-yl)carbonyl]amino}-3-fluoropiperidin-1-yl)-1,3-benzothiazole-7-carboxylate | MS (ES) MH$^+$: 499, 501 for $C_{16}H_{17}Cl_2FN_4O_3S$ | Intermediate 32 and ethyl 2-bromo-1,3-benzothiazole-7-carboxylate (U.S. Pat. No. 5,770,758) |
| 13 | Cis(±)Ethyl 2-(4-{[(3,4-dichloro-5-methyl-1H-pyrrol-2-yl)carbonyl]amino}-3-methoxypiperidin-1-yl)-1,3-benzothiazole-7-carboxylate | MS (ES) MH$^+$: 511, 513 for $C_{22}H_{24}Cl_2N_4O_4S$; NMR: 1.45 (t, 3H), 1.87 (m, 2H), 3.44 (s, 3H), 3.46 (m, 2H), 3.67 (m, 1H), 4.23 (m, 1H), 4.28 (m, 1H), 4.36 (m, 1H), 4.47 (q, 2H), 7.27 (d, 1H), 7.50 (t, 1H), 7.77 (t, 1H0, 12.26 (s, 1H) | Intermediate 50 and ethyl 2-bromo-1,3-benzothiazole-7-carboxylate (U.S. Pat. No. 5,770,758) |
| 14 | Cis(±)Methyl 2-chloro-6-(4-{[(3,4-dichloro-5- | MS (ES) MH$^+$: 477, 479 for $C_{18}H_{20}Cl_3N_5O_4$; NMR: 1.62 | Intermediate 50 and methyl 2,6- |

| Ex | Compound | Data | SM |
|---|---|---|---|
|  | methyl-1H-pyrrol-2-yl)carbonyl]amino}-3-methoxypiperidin-1-yl)pyrimidine-4-carboxylate | (m, 1H), 1.77 (m, 1H), 2.18 (s, 3H), 3.15 (m, 1H), 3.28 (s, 3H), 3.56 (m, 1H), 3.87 (s, 3H), 4.11 (m, 1H), 4.30 (m, 1H), 5.00 (m, 1H), 7.15 (m, 1H0, 7.36-7.48 (m, 1H), 12.16 (m, 1H) | dichloropyrimidine-4-carboxylate |
| 15 | Cis(±)Ethyl 2-(4-{[(4-chloro-5-methyl-1H-pyrrol-2-yl)carbonyl]amino}-3-methoxypiperidin-1-yl)-1,3-thiazole-4-carboxylate | MS (ES) MH$^+$: 427, 429 for C$_{18}$H$_{23}$ClN$_4$O$_3$S; NMR: 1.27 (t, 3H), 1.60 (m, 1H), 1.93 (m, 1H), 2.14 (s, 3H), 3.23 (m, 1H), 3.28 (s, 3H), 3.43 (m, 1H), 3.53 (m, 1H), 3.85 (m, 1H), 4.12 (m, 1H), 4.24 (m, 2H), 6.89 (s, 1H) | Intermediate 55 and ethyl 2-bromo-1,3-thiazole-4-carboxylate |
| 16 | Cis(±)ethyl 2-(4-{[(3,4-dichloro-5-methyl-1H-pyrrol-2-yl)carbonyl]amino}-3-methoxypiperidin-1-yl)-1,3-thiazole-4-carboxylate | MS (ES) (M + H): 461, 463 for C$_{18}$H$_{22}$Cl$_2$N$_4$O$_4$S | Intermediate 50 and ethyl 2-bromo-1,3-thiazole-4-carboxylate |
| 17 | Cis(±)ethyl 4-(4-{[(3,4-dichloro-5-methyl-1H-pyrrol-2-yl)carbonyl]amino}-3-methoxypiperidin-1-yl)pyridine-2-carboxylate | MS (ES) MH$^+$: 455 for C$_{20}$H$_{24}$Cl$_2$N$_4$O$_4$ | Intermediate 50 and ethyl 4-chloropyridine-2-carboxylate (WO 2004007657) |
| 18 | Cis(±)methyl 2-[4-{[(3,4-dichloro-5-methyl-1H-pyrrol-2-yl)carbonyl]amino}-3-(methoxymethyl)piperidin-1-yl]-1,3-thiazole-5-carboxylate | MS (ES) MH$^+$: 461 for C$_{18}$H$_{22}$Cl$_2$N$_4$O$_4$S | Intermediate 74 and methyl-2-bromothiazole-5-carboxylate |
| 19 | Cis(±)methyl-2-{4-{[(3,4-dichloro-5-methyl-1H-pyrrol-2-yl)carbonyl]amino}-3-[(methylamino)methyl]piperidin-1-yl}-1,3-thiazole-5-carboxylate | MS (ES) MH$^+$: 460 for C$_{18}$H$_{23}$Cl$_2$N$_5$O$_3$S | Intermediate 75 and methyl-2-bromothiazole-5-carboxylate |
| 20 | Cis(±)methyl 2-{4-{[(3,4-dichloro-5-methyl-1H-pyrrol-2-yl)carbonyl]amino}-3-[(dimethylamino)methyl]piperidin-1-yl}-1,3-thiazole-5-carboxylate | MS (ES) MH$^+$: 474 for C$_{19}$H$_{25}$Cl$_2$N$_5$O$_3$S | Intermediate 76 and methyl-2-bromothiazole-5-carboxylate |

| Ex | Compound | Data | SM |
|---|---|---|---|
| | (structure: 3,4-dichloro-5-methyl-1H-pyrrole-2-carboxamide linked to piperidine with CH₂N(Me)₂ substituent, N-substituted with methyl thiazole-5-carboxylate) | | |
| 21 | Cis(±)methyl-2-(4-{[(4-chloro-5-methyl-1H-pyrrol-2-yl)carbonyl]amino}-3-methoxypiperidin-1-yl)-4-{[(1-methyl-1-phenylethyl)amino]carbonyl}-1,3-thiazole-5-carboxylate | MS (ES) MH⁺: 574 for C₂₇H₃₂ClN₅O₅S | Intermediate 16 and Intermediate 55 |
| 22 | Cis(±)methyl-2-(4-{[(4-chloro-5-methyl-1H-pyrrol-2-yl)carbonyl]amino}-3-methoxypiperidin-1-yl)-1,3-thiazole-5-carboxylate | MS (ES) MH⁺: 413 for C₁₇H₂₁ClN₄O₄S; NMR: 1.63 (s, 1H), 1.90 (s, 1H), 2.14 (s, 3H), 3.28 (s, 3H), 3.39 (s, 1H), 3.47 (s, 2H), 3.74 (s, 3H), 3.93 (s, 1H), 4.21 (s, 2H), 6.89 (d, J = 2.64 Hz, 1H), 7.71 (d, J = 7.91 Hz, 1H), 7.84 (s, 1H), 11.64 (s, 1H) | Intermediate 55 and methyl 2-bromo-1,3-thiazole-5-carboxylate |
| 23 | Cis(±)methyl-2-chloro-6-(4-{[(4-chloro-5-methyl-1H-pyrrol-2-yl)carbonyl]amino}-3-methoxypiperidin-1-yl)pyrimidine-4-carboxylate | MS (ES) MH⁺: 442 for C₁₈H₂₁Cl₂N₅O₄; NMR: 1.63 (s, 1H), 1.79 (s, 1H), 2.09-2.20 (m, 3H), 3.08 (s, 1H), 3.17 (d, J = 5.27 Hz, 1H), 3.25 (s, 3H), 3.30 – 3.81 – 3.89 (m, 3H), 4.22 (s, 2H), 4.91 (s, 1H), 6.87 (d, J = 2.64 Hz, 1H), 7.37 (s, 1H), 7.67 (d, J = 7.72 Hz, 1H), 11.62 (s, 1H) | Intermediate 55 and methyl 2,6-dichloropyrimidine-4-carboxylate |
| 24 | Cis(±)methyl-2-(4-{[(4-chloro-5-methyl-1H-pyrrol-2-yl)carbonyl]amino}-3-methoxypiperidin-1-yl)-4-(methoxymethyl)-1,3-thiazole-5-carboxylate | MS (ES) MH⁺: 457 for C₁₉H₂₅ClN₄O₅S; NMR: 1.63 (s, 1H), 1.84-1.99 (m, 1H), 2.12-2.19 (m, 3H), 3.33 (s, 3H), 3.35-3.38 (m, 1H), 3.52-3.57 (m, 1H), 3.72 (s, 3H), 3.97 (s, 1H), 4.15-4.29 (m, 3H), 4.52-4.61 (m, 2H), 6.89 (d, J = 2.64 Hz, 1H), 7.70 (d, J = 7.91 Hz, 1H), 11.63 (s, 1H) | Intermediate 55 and Intermediate 17 |

| Ex | Compound | Data | SM |
|---|---|---|---|
| 25 | Cis(±)methyl-2-(4-{[(3,4-dichloro-5-methyl-1H-pyrrol-2-yl)carbonyl]amino}-3-methoxypiperidin-1-yl)-4-(methoxymethyl)-1,3-thiazole-5-carboxylate | MS (ES) MH⁺: 491 for $C_{19}H_{24}Cl_2N_4O_5S$; NMR: 1.66-1.81 (m, 2H), 2.14-2.22 (m, 3H), 3.29 (s, 3H), 3.33 (s, 2H), 3.36 (s, 3H), 3.55 (s, 1H), 3.73 (s, 3H), 3.97 (s, 1H), 4.20-4.35 (m, 2H), 4.57 (d, J = 1.32 Hz, 2H), 7.15 (d, J = 8.29 Hz, 1H), 12.15 (s, 1H) | Intermediate 50 and Intermediate 17 |
| 26 | Cis(±)ethyl 4-(4-{[(4-chloro-5-methyl-1H-pyrrol-2-yl)carbonyl]amino}-3-methoxypiperidin-1-yl)quinoline-2-carboxylate | MS (ES) MH⁺: 471 for $C_{24}H_{27}ClN_4O_4$; NMR: 1.38 (t, J = 7.06 Hz, 3H), 1.80 (s, 1H), 2.15 (s, 3H), 3.27 (s, 3H), 3.36-3.42 (m, 3H), 3.64 (s, 3H), 3.84 (s, 1H), 4.41 (q, J = 7.10 Hz, 2H), 6.95 (d, J = 2.64 Hz, 1H), 7.57 (s, 1H), 7.69 (d, J = 7.16 Hz, 1H), 7.73-7.82 (m, 2H), 8.11 (dd, J = 17.14, 8.29 Hz, 2H), 11.65 (s, 1H | Intermediate 55 and Intermediate 10 |
| 27 | Cis(±)ethyl-2-(4-{[(3,4-dichloro-5-methyl-1H-pyrrol-2-yl)carbonyl]amino}-3-methoxypiperidin-1-yl)isonicotinate | MS (ES) MH⁺: 455 for $C_{20}H_{24}Cl_2N_4O_4$; NMR: 1.32 (t, J = 7.06 Hz, 3H), 1.72 (d, J = 0.75 Hz, 2H), 2.18 (s, 3H), 3.13 (d, J = 13.38 Hz, 2H), 3.29-3.31 (m, 3H), 3.50 (s, 1H), 4.23 (s, 2H), 4.32 (q, J = 7.03 Hz, 2H), 4.67 (s, 1H), 6.97 (dd, J = 5.09, 0.94 Hz, 1H), 7.14 (d, J = 8.10 Hz, 1H), 7.23 (s, 1H), 8.24 (d, J = 5.09 Hz, 1H), 12.15 (s, 1H) | Intermediate 50 and ethyl 2-fluoroisonicotinate (Konno, Akinori J. Fluorine Chemistry (1998), 87(2), 137-140) |
| 28 | Cis(±)ethyl-4-(4-{[(4-chloro-5-methyl-1H-pyrrol-2-yl)carbonyl]amino}-3-methoxypiperidin-1-yl)pyridine-2-carboxylate | MS (ES) MH⁺: 421 for $C_{20}H_{25}ClN_4O_4$; NMR: 1.31 (t, J = 7.06 Hz, 3H), 1.61 (s, 1H), 1.85 (s, 1H), 2.12-2.18 (m, 3H), 3.23 (s, 3H), 3.50 (s, 1H), 3.89 (s, 2H), 4.19 (s, 3H), 4.30 (q, J = 7.16 Hz, 2H), 6.89 (d, J = 2.83 Hz, 1H), 7.05 (dd, J = 6.03, 2.64 Hz, 1H), 7.44 (d, J = 2.64 Hz, 1H), 7.67 (d, J = 8.10 Hz, 1H), 8.20 (d, J = 5.84 Hz, 1H), 11.63 (s, 1H) | Intermediate 55 and ethyl 4-chloropyridine-2-carboxylate (WO 2004007657) |
| 29 | Cis(±)3,4-dicholoro-N-[3-methoxy-1-(2-methylquinolin-4-yl)piperidin-4-yl]-5-methyl-1H-pyrrole-2-carboxamide | MS (ES) MH⁺: 447 for $C_{22}H_{24}Cl_2N_4O_2$ | Intermediate 50 and 4-chloro-2-methylquinoline |

| Ex | Compound | Data | SM |
|---|---|---|---|
| 30 | Cis(±)Methyl 4-{[(3,4-dichloro-5-methyl-1H-pyrrol-2-yl)carbonyl]amino}-1-[5-(methoxycarbonyl)-1,3-thiazol-2-yl]piperidine-3-carboxylate | MS (ES) MH+: 474 $C_{18}H_{22}ClN_5O_5S$; NMR: 1.98 (m, 2H), 2.23 (s, 3H), 3.08 (m, 1H), 3.24 (m, 1H), 3.55 (m, 1H), 3.66 (s, 3H), 3.79 (s, 3H), 3.97 (m, 1H), 4.23 (m, 1H), 4.63 (m, 1H), 7.64 (d, 1H), 7.95 (s, 1H), 12.01 (s, 1H) | Intermediate 35 and methyl 2-bromo-1,3-thiazole-5-carboxylate |
| 31 | Cis(±)ethyl 2-(4-{[(4-chloro-5-methyl-1H-pyrrol-2-yl)carbonyl]amino}-3-methoxypiperidin-1-yl)-1,3-benzothiazole-7-carboxylate | MS(ES) MH+: 477, 479 for $C_{22}H_{25}ClN_4O_4S$; NMR: 1.33 (t, 3H), 1.76 (m, 1H), 1.83 (m, 1H), 2.10 (s, 3H), 3.37 (m, 2H), 3.45 (s, 3H), 3.54 (m, 1H), 4.21-4.29 (m, 3H), 4.36 (q, 2H), 6.86 (m, 1H), 7.38 (t, 1H), 7.62-7.69 (m, 3H), 11.60 (s, 1H) | Intermediate 55 and ethyl 2-bromo-1,3-benzothiazole-7-carboxylate (U.S. Pat. No. 5,770,758) |
| 32 | Cis(±)ethyl 4-(4-{[(3,4-difluoro-5-methyl-1H-pyrrol-2-yl)carbonyl]amino}-3-methoxypiperidin-1-yl)quinoline-2-carboxylate | MS (ES) MH: 472 for for $C_{24}H_{26}F_2N_4O_4$ | Intermediate 56 and Intermediate 10 |
| 33 | methyl 2-((3S,4R)-4-{[(3,4-dichloro-5-methyl-1H-pyrrol-2-yl)carbonyl]amino}-3-fluoropiperidin-1-yl)-1,3-thiazole-5-carboxylate | MS (ES) MH+: 435, 437 for $C_{16}H_{17}Cl_2FN_4O_3S$; NMR: 1.77-1.79 (m, 2H), 2.12 (s, 3H), 3.25-3.27 (m, 2H), 3.49-3.62 (dd, 1H), 3.68 (s, 3H), 3.95 (m, 1H), 4.00-4.24 (m, 1H), 4.82-4.99 (m, 1H), 7.21 (d, 1H), 7.79 (s, 1H), 12.05 (br s, 1H) | Intermediate 36 and methyl 2-bromo-1,3-thiazole-5-carboxylate |

Example 34

Cis(±)methyl 4-(aminocarbonyl)-2-(4-{[(4-chloro-5-methyl-1H-pyrrol-2-yl)carbonyl]amino}-3-methoxypiperidin-1-yl)-1,3-thiazole-5-carboxylate Cis(±)methyl-2-(4-{[(4-chloro-5-methyl-1H-pyrrol-2-yl)carbonyl]amino}-3-methoxypiperidin-1-yl)-4-{[(1-methyl-1-phenylethyl)amino]carbonyl}-1,3-thiazole-5-carboxylate (Example 21; 0.058 g, 0.1 mmol) was dissolved in equal volumes of TFA and DCM. The reaction was heated in a sealed tube to an external temperature of 85° C. overnight. The reaction mixture was concentrated to remove the DCM and excess TFA. The residue was partitioned with EtOAc and NaHCO₃ and the organic extracts were dried with MgSO₄ and concentrated to a yellow solid (0.050 g, 100%). MS (ES) MH+: 456 for $C_{18}H_{22}ClN_5O_5S$.

Example 35

Cis(±)2-(4-{[(3,4-dichloro-5-methyl-1H-pyrrol-2-yl)carbonyl]amino}-3-methoxypiperidin-1-yl)-1,3-thiazole-5-carboxylic acid

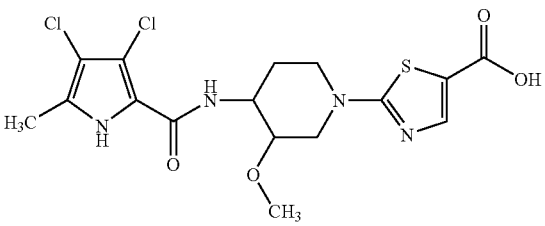 [SMILES: COC1CN(c2ncc(C(=O)O)s2)CCC1NC(=O)c1[nH]c(C)c(Cl)c1Cl]

Cis(±)methyl 2-(4-{[(3,4-dichloro-5-methyl-1H-pyrrol-2-yl)carbonyl]amino}-3-methoxypiperidin-1-yl)-1,3-thiazole-5-carboxylate (Example 1; 200 mg) was dissolved in THF (50 ml). 2N LiOH (100 ml) was added and the mixture was heated at 50° C. for 18 h. The reaction mixture was cooled to ambient and acidified with 20% aqueous citric acid. The aqueous phase was extracted with EtOAc and the organic phase was washed with water, brine, dried over Na₂SO₄. The organic phase was concentrated in vacuo and triturated with diethyl ether to give the title compound as an off white solid. (164 mg). MS (ES) MH+: 433, 431 for $C_{16}H_{18}Cl_2N_4O_4S$; NMR: 1.87 (m, 2H), 2.28 (s, 3H), 3.32 (m, 6H), 3.63 (s, 1H), 3.87 (m, 1H), 4.45 (m, 2H), 7.04 (d, 1H), 7.90 (s, 1H), 11.97 (s, 1H), 12.30 (s, 1H).

Examples 36-71

The following Examples were synthesized by an analogous method to Example 35 from the starting materials (SM) given in the table below.

| Ex | Compound | NMR | m/z | SM |
|---|---|---|---|---|
| 36 | Cis(±)2-(4-{[(3,4-dichloro-5-methyl-1H-pyrrol-2-yl)carbonyl]amino}-3-propoxypiperidin-1-yl)-1,3-thiazole-5-carboxylic acid | 0.87 (m, 3H), 1.57 (m, 2H), 1.93 (m, 2H), 2.24 (s, 3H), 2.6 (m, 2H), 3.45 (m, 2H), 3.69 (m, 2H), 4.36 (m, 2H), 7.23 (d, 1H), 7.87 (s, 1H), 12.34 (s, 1H) | 461 | Example 5 |
| 37 | Cis(±)2-(3-(allyloxy)-4-{[(3,4-dichloro-5-methyl-1H-pyrrol-2-yl)carbonyl]amino}piperidin-1-yl)-1,3-thiazole-5-carboxylic acid | 1.79 (m, 2H), 2.20 (s, 3H), 3.38 (m, 2H), 3.71 (s, 1H), 3.95 (m, 2H), 4.15 (m, 2H), 5.26 (m, 2H), 5.91 (m, 1H), 7.18 (d, 1H), 7.76 (s, 1H), 12.19 (s, 1H) | 459 | Example 6 |
| 38 | Cis(±)4-(3-(allyloxy)-4-{[(3,4-dichloro-5-methyl-1H-pyrrol-2-yl)carbonyl]amino}piperidin-1-yl)quinoline-2-carboxylic acid | 2.06 (m, 2H), 2.20 (s, 3H), 3.1-4.0 (m, 4H), 4.51 (m, 3H), 5.18 (m, 2H), 5.82 (m, 1H), 7.29 (d, 1H), 7.57 (s, 1H), 7.71 (m, 1H), 7.95 (m, 1H), 8.36 (m, 2H), 12.23 (s, 1H) | 503 | Example 7 |
| 39 | Cis(±)4-(4-{[(3,4-dichloro-5-methyl-1H-pyrrol-2-yl)carbonyl]amino}-3-propoxypiperidin-1-yl)quinoline-2-carboxylic acid | 0.62 (t, 3H), 1.35 (m, 2H), 2.13 (s, 3H), 5.36 (m, 2H), 3.5-4.0 (m, 4H), 4.05 (m, 2H), 4.43 (m, 2H), 7.20 (d, 1H), 7.55 (s, 1H), 7.71 (m, 1H), 8.00 (m, 1H), 8.22 (m, 2H), 12.24 (s, 1H) | 505 | Example 8 |
| 40 | Cis(±)2-(4-{[(3,4-dichloro-5-methyl-1H-pyrrol-2-yl)carbonyl]amino}-3-fluoropiperidin-1-yl)-1,3-thiazole-5-carboxylic acid | 1.75-1.79 (m, 2H), 2.13 (s, 3H), 3.39-3.57 (m, 2H), 3.93-3.96 (d, 1H), 4.25 (m, 2H), 4.81-4.97 (m, 1H), 7.28 (d, 1H), 7.63 (s, 1H), 12.12 (s, 1H) | 421, 423 | Example 9 |

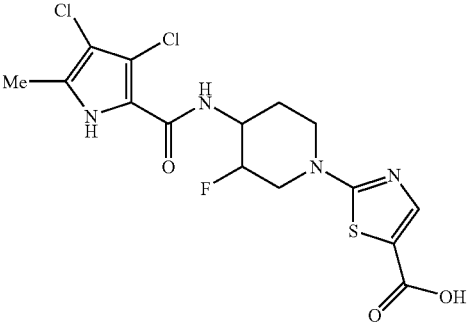 [SMILES: Cc1[nH]c(C(=O)NC2CCN(c3ncc(C(=O)O)s3)CC2F)c(Cl)c1Cl]

| Ex | Compound | NMR | m/z | SM |
|---|---|---|---|---|
| 41 | Trans(±)2-(4-{[(3,4-dichloro-5-methyl-1H-pyrrol-2-yl)carbonyl]amino}-3-fluoropiperidin-1-yl)-1,3-thiazole-5-carboxylic acid | 1.74-1.79 (m, 2H), 2.11 (s, 3H), 3.49-3.58 (m, 2H), 3.86-3.92 (d, 1H), 4.22 (m, 2H), 4.84-4.97 (m, 1H), 7.26 (d, 1H), 7.61 (s, 1H), 12.11 (s, 1H) | 421, 423 | Example 10 |
| 42 | 2-((3S,4R)-4-{[(3,4-dichloro-5-methyl-1H-pyrrol-2-yl)carbonyl]amino}-3-fluoropiperidin-1-yl)-1,3-thiazole-5-carboxylic acid | 1.62-1.90 (m, 2H), 2.12 (s, 3H), 3.23 (m, 1H), 3.50 (dd, 1H), 3.83-4.03 (m, 1H), 4.12-4.43 (m, 2H), 4.90 (d, 1H), 7.21 (d, 1H), 7.69 (s, 1H), 12.04 (s, 1H), 12.61 (brs, 1H) | 421, 423 | Example 33 |
| 43 | 2-((3R,4S)-4-{[(3,4-dichloro-5-methyl-1H-pyrrol-2-yl)carbonyl]amino}-3-fluoropiperidin-1-yl)-1,3-thiazole-5-carboxylic acid | 1.63-1.92 (m, 2H), 2.13 (s, 3H), 3.21 (m, 1H), 3.50 (dd, 1H), 3.87-4.02 (m, 1H), 4.14-4.42 (m, 2H), 4.90 (d, 1H), 7.21 (d, 1H), 7.69 (s, 1H), 12.04 (s, 1H), 12.61 (brs, 1H) | 421, 423 | Example 11 |
| 44 | Cis(±)2-(4-{[(3,4-dichloro-5-methyl-1H-pyrrol-2-yl)carbonyl]amino}-3-fluoropiperidin-1-yl)-1,3-benzothiazole-7-carboxylic acid | 1.82 (m, 2H), 2.13 (s, 3H), 3.48-3.67 (m, 2H), 4.12-4.41 (m, 3H), 4.92 (d, 1H), 7.22 (d, 1H), 7.34 (t, 1H), 7.62 (m, 1H), 12.06 (s, 1H), 13.45 (brs, 1H) | 471, 473 | Example 12 |

| Ex | Compound | NMR | m/z | SM |
|---|---|---|---|---|
| 45 | Cis(±)2-(4-{[(3,4-dichloro-5-methyl-1H-pyrrol-2-yl)carbonyl]amino}-3-methoxypiperidin-1-yl)-1,3-benzothiazole-7-carboxylic acid | 1.86 (m, 2H), 2.25 (s, 3H), 3.46 (s, 3H), 3.48 (m, 2H), 3.65 (m, 1H), 4.35 (m, 2H), 4.46 (m, 1H), 7.25 (d, 1H), 7.48 (t, 1H), 7.73 (t, 1H), 12.26 (s, 1H) | 483, 485 | Example 13 |
| 46 | Cis(±)2-(4-{[(4-chloro-5-methyl-1H-pyrrol-2-yl)carbonyl]amino}-3-methoxypiperidin-1-yl)-1,3-benzothiazole-7-carboxylic acid | 1.60 (m, 1H), 1.83 (m, 1H), 2.07 (s, 3H), 3.25 (s, 3H), 3.35 (m, 2H), 3.52 (m, 1H), 4.09-4.17 (m, 3H), 6.84 (d, 1H), 7.37 (t, 1H), 7.58-7.67 (m, 3H), 11.58 (s, 1H) | 449, 451 | Example 31 |
| 47 | Cis(±)2-(4-{[(3,4-dichloro-5-methyl-1H-pyrrol-2-yl)carbonyl]amino}-3-methoxypiperidin-1-yl)-1,3-thiazole-4-carboxylic acid | 1.74 (m, 2H), 2.17 (s, 3H), 3.26 (m, 2H), 3.35 (s, 3H), 3.52 (m, 1H), 3.84 (m, 1H), 4.21 (m, 2H), 7.13 (d, 1H), 7.57 (s, 1H), 12.15 (s, 1H), 12.61 (brs, 1H) | 433, 435 | Example 16 |
| 48 | Cis(±)2-Chloro-6-(4-{[(3,4-dichloro-5-methyl-1H-pyrrol-2-yl)carbonyl]amino}-3-methoxypiperidin-1-yl)pyrimidine-4-carboxylic acid | 1.59 (m, 1H), 1.77 (m, 1H), 2.18 (s, 3H), 3.16 (m, 1H), 3.17 (m, 1H), 3.56 (m, 1H), 4.11 (m, 1H), 4.30 (m, 1H), 4.55 (m, 1H), 4.98 (m, 1H), 7.15 (m, 1H), 7.38 (m, 1H), 12.10 (m, 1H) | 463, 465 | Example 14 |
| 49 | 2-((3S,4R)-4-{[(3,4-dichloro-5-methyl-1H-pyrrol-2-yl)carbonyl]amino}-3-methoxypiperidin-1-yl)-1,3-thiazole-5-carboxylic acid | 1.85 (m, 2H), 2.24 (s, 3H), 3.32 (s, 3H), 3.42 (m, 2H), 3.69 (s, 3H), 4.07 (m, 1H), 4.49 (m, 2H), 7.31 (d, 1H), 7.87 (s, 1H), 12.27 (s, 1H), 12.69 (s, 1H) | 433 | Example 2 |
| 50 | Cis(±)2-(4-{[(4-chloro-5-methyl-1H-pyrrol-2-yl)carbonyl]amino}-3-methoxypiperidin-1-yl)-1,3-thiazole-4-carboxylic acid | 1.61 (m, 1H), 1.92 (m, 1H), 2.14 (s, 3H), 3.24 (m, 1H), 3.28 (s, 3H), 3.43 (m, 1H), 3.53 (m, 1H), 3.84 (m, 1H), 4.10 (m, 1H), 4.21 (m, 1H), 6.91 (s, 1H), 7.51 (s, 1H), 7.69 (m, 1H), 11.64 (s, 1H) | 399, 401 | Example 15 |
| 51 | 2-((3S,4S)-4-{[(3,4-Dichloro-5-methyl-1H-pyrrol-2-yl)carbonyl]amino}-3-methoxypiperidin-1-yl)-1,3-thiazole-5-carboxylic acid | 1.64 (m, 1H), 1.88 (m, 1H), 2.11 (s, 3H), 3.13-3.20 (m, 3H), 3.29 (s, 3H), 3.68 (m, 1H), 4.03 (m, 1H), 7.29 (d, 1H0, 7.71 (s, 1H), 11.95 (s, 1H), 12.63 (brs, 1H) | 433, 435 | Example 86 |
| 52 | 2-((3R,4R)-4-{[(3,4-Dichloro-5-methyl-1H-pyrrol-2-yl)carbonyl]amino}-3- | 1.63 (m, 1H), 1.88 (m, 1H), 2.11 (s, 3H), 3.16-3.27 (m, 3H), 3.29 (s, 3H), 3.69 (m, | 433, 435 | Example 85 |

-continued

| Ex | Compound | NMR | m/z | SM |
|---|---|---|---|---|
| | methoxypiperidin-1-yl)-1,3-thiazole-5-carboxylic acid | 1H), 4.03-4.07 (m, 2H), 7.37 (d, 1H), 7.69 (s, 1H), 12.03 (s, 1H) | | |
| 53 | Cis(±)2-[4-{[(3,4-dichloro-5-methyl-1H-pyrrol-2-yl)carbonyl]amino}-3-(methoxymethyl)piperidin-1-yl]-1,3-thiazole-5-carboxylic acid | 1.62 (m, 1H), 2.03 (m, 1H), 2.16 (s, 3H), 2.98 (m, 1H), 3.21 (s, 3H), 3.25 (m, 3H), 3.41 (dd, 1H), 3.89 (m, 2H), 4.06 (dd, 1H), 7.51 (d, 1H), 7.63 (s, 1H) | 447 | Example 18 |
| 54 | Cis(±)2-{4-{[(3,4-dichloro-5-methyl-1H-pyrrol-2-yl)carbonyl]amino}-3-[(methylamino)methyl]piperidin-1-yl}-1,3-thiazole-5-carboxylic acid | 1.63 (m, 1H), 1.83 (m, 1H), 1.97 (m, 1H), 2.18 (s, 3H), 2.44 (s, 3H), 2.64 (m, 1H), 2.79 (m, 1H), 2.98 (m, 2H), 3.87 (m, 1H), 4.07 (m, 2H), 7.33 (s, 1H), 8.14 (d, 1H) | 446 | Example 19 |
| 55 | Cis(±)2-{4-{[(3,4-dichloro-5-methyl-1H-pyrrol-2-yl)carbonyl]amino}-3-[(dimethylamino)methyl]piperidin-1-yl}-1,3-thiazole-5-carboxylic acid | 1.66 (m, 1H), 1.88 (m, 1H0, 2.05 (m, 1H), 2.16 (s, 3H), 2.26 (s, 6H), 2.40 (m, 2H), 2.94 (t, 1H), 3.18 (t, 1H), 3.86 (m, 1H), 3.98 (dd, 2H), 7.63 (s, 1H), 7.67 (d, 1H), 12.3 (brs, 1H) | 460 | Example 20 |
| 56 | Cis(±)2-(4-{[(4-chloro-5-methyl-1H-pyrrol-2-yl)carbonyl]amino}-3-methoxypiperidin-1-yl)-1,3-thiazole-5-carboxylic acid | 1.63 (d, J = 3.39 Hz, 1H), 1.84-1.99 (m, 1H), 2.14 (s, 3H), 3.28 (s, 3H), 3.54 (s, 1H), 3.91 (s, 1H), 4.15-4.29 (m, 1H), 6.90 (d, J = 2.83 Hz, 1H), 7.71 (d, J = 8.10 Hz, 1H), 7.74 (s, 1H), 11.64 (d, J = 1.70 Hz, 1H), 12.62 (s, 1H) | 399 | Example 22 |
| 57 | Cis(±)2-chloro-6-{4-{[(4-chloro-5-methyl-1H-pyrrol-2-yl)carbonyl]amino}-3-methoxypiperidin-1-yl)pyrimidine-4-carboxylic acid | 1.64 (s, 1H), 1.78 (s, 1H), 2.13 (s, 3H), 3.13 (s, 1H), 3.25 (s, 3H), 3.54 (s, 1H), 4.22 (s, 2H), 4.60 (s, 1H), 4.93 (s, 1H), 6.87 (d, J = 2.45 Hz, 1H), 7.34 (s, 1H), 7.65 (s, 1H), 11.62 (s, 1H), 13.69 (s, 1H) | 428 | Example 23 |
| 58 | Cis(±)2-(4-{[(4-chloro-5-methyl-1H-pyrrol-2-yl)carbonyl]amino}-3-methoxypiperidin-1-yl)-4-(methoxymethyl)-1,3-thiazole-5-carboxylic acid | 1.62 (s, 1H), 1.93 (s, 1H), 2.14 (s, 3H), 3.28 (d, J = 2.26 Hz, 3H), 3.36 (s, 3H), 3.54 (s, 2H), 3.91 (s, 1H), 4.19 (s, 2H), 4.56 (s, 2H), 6.89 (s, 1H), 7.69 (s, 1H), 11.63 (s, 1H) | 443 | Example 24 |
| 59 | Cis(±)2-(4-{[(3,4-dichloro-5-methyl-1H-pyrrol-2-yl)carbonyl]amino}-3-methoxypiperidin-1-yl)-4-(methoxymethyl)-1,3-thiazole-5-carboxylic acid | 1.75 (s, 2H), 2.18 (s, 3H), 3.28 (s, 3H), 3.37 (s, 3H), 3.54 (s, 3H), 3.91 (s, 1H), 4.26 (s, 2H), 4.56 (s, 2H), 7.14 (s, 1H), 12.15 (s, 1H) | 477 | Example 25 |

| Ex | Compound | NMR | m/z | SM |
|---|---|---|---|---|
| 60 | Cis(±)4-(4-{[(4-chloro-5-methyl-1H-pyrrol-2-yl)carbonyl]amino}-3-methoxypiperidin-1-yl)quinoline-2-carboxylic acid | 1.80 (s, 1H), 2.15 (s, 3H), 3.15 (s, 3H), 3.64 (s, 3H), 3.80 (s, 2H), 4.09 (s, 1H), 4.30 (s, 1H), 6.93 (d, J = 2.45 Hz, 1H), 7.57 (s, 1H), 7.68 (s, 1H), 7.85 (s, 2H), 8.19 (s, 2H), 11.65 (s, 1H) | 443 | Example 26 |
| 61 | Cis(±)4-(4-{[(3,4-dichloro-5-methyl-1H-pyrrol-2-yl)carbonyl]amino}-3-methoxypiperidin-1-yl)pyridine-2-carboxylic acid | 1.67 (s, 1H), 1.81 (s, 1H), 2.18 (s, 3H), 3.28 (s, 3H), 3.59 (s, 2H), 4.20 (s, 2H), 4.32 (s, 1H), 4.55 (d, J = 12.43 Hz, 1H), 7.14 (d, J = 8.29 Hz, 1H), 7.18 (dd, J = 7.06, 2.92 Hz, 1H), 7.44 (d, J = 2.64 Hz, 1H), 7.97 (d, J = 6.97 Hz, 1H), 12.18 (s, 1H) | 393 | Example 17 |
| 62 | Cis(±)2-(4-{[(3,4-dichloro-5-methyl-1H-pyrrol-2-yl)carbonyl]amino}-3-methoxypiperidin-1-yl)isonicotinic acid | 1.72 (s, 2H), 2.18 (s, 3H), 3.04-3.18 (m, 2H), 3.30 (s, 3H), 3.49 (s, 1H), 4.25 (s, 2H), 4.66 (s, 1H), 6.97 (d, J = 4.71 Hz, 1H), 7.16 (s, 1H), 7.24 (s, 1H), 8.22 (d, J = 4.90 Hz, 1H), 12.16 (s, 1H), 13.39 (s, 1H) | 427 | Example 27 |
| 63 | Cis(±)2-[4-{[(3,4-Dichloro-5-methyl-1H-pyrrol-2-yl)carbonyl]amino}-3-(morpholin-4-ylcarbonyl)piperidin-1-yl]-1,3-thiazole-5-carboxylic acid | MS (ES+): 516, 518 for $C_{20}H_{23}Cl_2N_4O_5S$; NMR: 1.82 (m, 2H), 2.15 (s, 3H), 3.32 (m, 6H), 3.61 (m, 5H), 3.99 (t, 2H), 4.40 (m, 1H), 7.18 (d, 1H), 7.78 (s, 1H), 12.03 (s, 1H), 12.8 (brs, 1H) | | Example 78 |
| 64 | Cis(±)2-{4-{[(3,4-Dichloro-5-methyl-1H-pyrrol-2-yl)carbonyl]amino}-3-[(dimethylamino)carbonyl]piperidin-1-yl}-1,3-thiazole-5-carboxylic acid | 1.75 (m, 1H), 1.89 (m, 1H), 2.14 (s, 3H), 2.87 (s, 3H), 3.09 (s, 3H), 3.36 (m [under water peak], 3H), 4.00 (m, 2H), 4.36 (m, 1H), 7.19 (d, 1H), 7.78 (s, 1H), 11.98 (s, 1H), 12.71 (brs, 1H) | 474, 476 | Example 79 |
| 65 | Cis(±)2-{4-{[(3,4-dichloro-5-methyl-1H-pyrrol-2-yl)carbonyl]amino}-3-[(ethylamino)carbonyl]piperidin-1-yl}-1,3-thiazole-5-carboxylic acid | 0.92 (t, 3H), 1.58 (m 1H), 1.99 (d, 1H), 2.15 (s, 3H), 2.62 (dd, 1H), 3.02 (m, 2H), 3.30 (q, 2H), 3.92 (d, 1H), 4.07 (d, 1H), 4.27 (m, 1H), 7.03 (d, 1H), 7.77 (s, 1H), 7.92 (t, 1H), 12.01 (s, 1H), 12.71 (brs, 1H) | 474, 476 | Example 80 |
| 66 | Cis(±)2-(4-{[(3,4-dichloro-5-methyl-1H-pyrrol-2-yl)carbonyl]amino}-3-{[(2-hydroxyethyl)amino]carbonyl}piperidin-1-yl)-1,3-thiazole-5-carboxylic acid | 1.50 (m, 1H), 1.96 (d, 1H), 2.41 (s, 3H), 2.61 (m, 1H), 3.07 (m, 2H), 3.26 (q, 2H), 3.32 (under water peak, 2H), 3.89 (d, 1H), 4.04 (d, 1H), 4.22 (m, 1H), 4.72 (brs, 1H), 7.39 (brs, 1H), 7.62 (s, 1H), 8.07 (t, 1H), 12.32 (brs, 1H) | 490, 492 | Example 81 |

-continued

| Ex | Compound | NMR | m/z | SM |
|---|---|---|---|---|
| 67 | Cis(±)2-(4-{[(3,4-dichloro-5-methyl-1H-pyrrol-2-yl)carbonyl]amino}-3-{[methoxy(methyl)amino]carbonyl}piperidin-1-yl)-1,3-thiazole-5-carboxylic acid | 1.66 (m, 1H), 1.85 (m, 1H), 2.14 (s, 3H), 3.08 (m, 1H), 3.09 (s, 3H), 3.15 (m, 1H), 3.33 (under water peak, 1H), 3.74 (brs, 3H), 3.83 (m, 1H), 4.00 (m, 1H), 4.33 (m, 1H), 7.19 (s, 1H), 7.81 (brs, 1H), 12.98 (brs, 1H) | 490, 492 | Example 82 |
| 68 | Cis(±)4-(aminocarbonyl)-2-(4-{[(4-chloro-5-methyl-1H-pyrrol-2-yl)carbonyl]amino}-3-methoxypiperidin-1-yl)-1,3-thiazole-5-carboxylic acid | 1.63 (s, 1H), 1.90 (s, 1H), 2.14 (s, 3H), 3.17 (s, 1H), 3.37 (s, 3H), 3.54 (s, 2H), 4.14-4.28 (m, 2H), 6.90 (s, 1H), 7.72 (s, 1H), 8.93 (s, 2H), 11.63 (s, 1H) | 442 | Example 34 |
| 69 | 2-((3R,4S)-4-{[(3,4-dichloro-5-methyl-1H-pyrrol-2-yl)carbonyl]amino}-3-methoxypiperidin-1-yl)-1,3-thiazole-5-carboxylic acid1,3-thiazole-5-carboxylic acid | 1.89 (m, 2H), 2.11 (s, 3H), 2.23 (s, 3H), 3.33 (m, 2H), 3.46 (s, 3H), 3.59 (s, 1H), 4.09 (m, 1H), 4.46 (m, 2H), 7.31 (d, 1H), 7.92 (s, 1H), 12.28 (s, 1H), 12.67 (brs, 1H) | 433 | Example 3 |
| 70 | Cis(±)2-(4-{[(3,4-difluoro-5-methyl-1H-pyrrol-2-yl)carbonyl]amino}-3-methoxypiperidin-1-yl)-1,3-thiazole-5-carboxylic acid 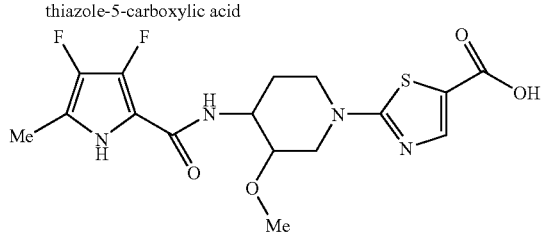 | 1.75 (m, 2H), 2.13 (s, 3H), 3.33 (s, 3H), 3.36 (m, 2H), 3.54 (s, 1H), 3.89 (m, 1H), 3.94 (m, 2H), 6.73 (d, 1H), 7.90 (s, 1H), 11.40 (s, 1H) | 441 | Example 4 |
| 71 | Cis(±)4-(4-{[(3,4-difluoro-5-methyl-1H-pyrrol-2-yl)carbonyl]amino}-3-methoxypiperidin-1-yl)quinoline-2-carboxylic acid | 1.69 (m, 2H), 2.01 (s, 3H), 3.16 (m, 1H), 3.16 (s, 3H), 3.8-4.02 (m, 2H), 4.18-4.38 (m, 2H), 6.57-6.84 (d, 1H), 7.44-7.56 (s, 1H), 7.56-7.72 (m, 1H), 7.78-7.94 (m, 1H), 8.04-8.27 (m, 2H), 11.23 (br, 1H) | 444 | Example 32 |

Example 72

Cis(±)2-(4-{[(3,4-dichloro-5-methyl-1H-pyrrol-2-yl)carbonyl]amino}-3-methoxypiperidin-1-yl)-N-methoxy-1,3-thiazole-5-carboxamide Cis(±)2-(4-{[(3,4-dichloro-5-methyl-1H-pyrrol-2-yl)carbonyl]amino}-3-methoxypiperidin-1-yl)-1,3-thiazole-5-carboxylic acid (Example 35; 100 mg) was dissolved in anhydrous DMA (2 ml). HATU (97 mg), HOAT (31 mg), DIEA (41 µl) were added and the mixture was stirred for 30 min. N-Methoxyamine hydrochloride (19.3 mg) was added followed by DIEA (41 µl), and the mixture was stirred at room temperature for 16 h. The reaction mixture was diluted with EtOAc, washed with $H_2O$, 20% citric acid solution, $H_2O$, sat. $NaHCO_3$, $H_2O$, brine and dried over $Na_2SO_4$. The organic phase was concentrated in vacuo to give the title compound as an off-white solid (82 mg). MS (ES)(MH$^+$): 462, 460 for $C_{17}H_{21}Cl_2N_5O_4S$; NMR: 1.64 (m, 2H), 1.85 (m, 1H), 2.05 (s, 3H), 2.83 (m, 1H), 3.33 (m, 5H), 3.73 (s, 3H), 4.07 (m, 1H), 4.38 (m, 2H), 7.24 (d, 1H), 7.74 (s, 1H), 11.39 (s, 1H), 12.05 (s, 1H).

Example 73

The following Example was prepared by the procedure described in Example 72 from the starting material (SM) indicated.

| Ex | Compound | Data | SM |
|---|---|---|---|
| 73 | 2-((3R,4R)-4-{[(3,4-Dichloro-5-methyl-1H-pyrrol-2-yl)carbonyl]amino}-3-methoxypiperidin-1-yl)-N-methoxy-1,3-thiazole-5-carboxamide | MS (ES) (M + H): 462, 464 (M + H), for $C_{17}H_{21}Cl_2N_5O_4S$; NMR: 1.61 (m, 1H), 1.87 (m, 1H), 2.11 (s, 3H), 3.14 (m, 1H), 3.29 (s, 3H), 3.33 (m, 1H), 3.59 (s, 3H), 3.64 (m, 1H,) 3.95-4.06 (m, 3H), | Example 52 |

| Ex | Compound | Data | SM |
|---|---|---|---|
|  |  | 7.29 (d, 1H), 7.66 (s, 1H), 11.31 (brs, 1H), 11.95 (s, 1H) |  |

Example 74

Cis(±)2-(4-{[(3,4-dichloro-5-methyl-1H-pyrrol-2-yl)carbonyl]amino}-3-hydroxypiperidin-1-yl)-1,3-thiazole-5-carboxylic acid Cis(±)2-(4-{[(3,4-dichloro-5-methyl-1H-pyrrol-2-yl)carbonyl]amino}-3-methoxypiperidin-1-yl)-1,3-thiazole-5-carboxylic acid (Example 35; 100 mg) was suspended in anhydrous DCM. $BBr_3$/DCM (15 ml) was added and the mixture was heated at 40° C. for 18 h. The reaction mixture was cooled to −50° C. and water was added. The mixture was extracted with EtOAc and the organic phase was washed with water, dried over $Na_2SO_4$. The organic phase was concentrated in vacuo to yield a pale brown solid which was dissolved in acetonitrile/water mixture and was lyophilized (46 mg). MS (ES) MH$^+$: 419 for $C_{15}H_{16}Cl_2N_4O_4S$; NMR: 1.87 (m, 2H), 2.20 (s, 3H), 3-4 (brm, 6H), 6.9 (d, 1H), 7.51 (s, 1H), 12.19 (s, 1H).

Example 75

The following Example was prepared by the procedure described in Example 74 from the starting material (SM) indicated.

Example 76

Cis(±)-4-(4-{[(3,4-dichloro-5-methyl-1H-pyrrol-2-yl)carbonyl]amino}-3-methoxypiperidin-1-yl)quinoline-2-carboxylic acid Cis(±)3,4-dicholoro-N-[3-methoxy-1-(2-methylquinolin-4-yl)piperidin-4-yl]-5-methyl-1H-pyrrole-2-carboxamide (Example 29; 170 mg) was dissolved in pyridine (5 ml). Selenium dioxide (211 mg) was added and the mixture was heated at 130° C. for 3 h. The brown solution was cooled to room temperature, diluted with water and filtered through a bed of celite. The filtrate was extracted with EtOAc, washed with water and dried over $Na_2SO_4$, concentrated in vacuo. The brown solid that separated was triturated with $Et_2O$, filtered, washed well with n-hexanes and dried in vacuo to give the title compound as a brown solid (176 mg). MS (ES) MH$^+$: 477 for $C_{22}H_{22}Cl_2N_4O_4$; NMR: 1.34 (m, 1H), 2.01 (m, 1H), 2.28 (s, 3H), 3.10 (s, 3H), 3.42 (m, 3H), 3.72 (m, 2H), 4.23 (m, 1H), 7.36 (d, 1H), 7.63 (s, 1H), 7.78 (m, 1H), 7.92 (m, 1H), 8.30 (m, 2H), 12.30 (brs, 1H).

Example 77

Cis(±)4-{[(3,4-Dichloro-5-methyl-1H-pyrrol-2-yl)carbonyl]amino}-1-[5-(methoxycarbonyl)-1,3-thiazol-2-yl]piperidine-3-carboxylic acid Cis(±)4-{[(3,4-Dichloro-5-methyl-1H-pyrrol-2-yl)carbonyl]amino}piperidine-3-carboxylic acid hydrochloride (Intermediate 79; 1.84 g) was dissolved in anhydrous DMF (20 ml) under an argon atmosphere in a 100-ml round bottom flask. Methyl 2-bromothiazole-5-carboxylate (1.43 g) was added followed by N,N-diisopropylethylamine (3.6 ml) at room temperature. The reaction was heated to 55° C. for 14 h cooled to room temperature. The reaction mixture was diluted with EtOAc (250 ml) and washed with a saturated aqueous ammonium chloride solution (125 ml), followed by a satu-

| Ex | Compound | Data | SM |
|---|---|---|---|
| 75 | Cis(±)4-(4-{[(3,4-dichloro-5-methyl-1H-pyrrol-2-yl)carbonyl]amino}-3-hydroxypiperidin-1-yl)quinoline-2-carboxylic acid | MS (ES) MH$^+$: 463 for $C_{21}H_{20}Cl_2N_4O_4$; NMR: 1.24 (m, 2H), 2.13 (m, 2H), 2.38 (s, 3H), 3.54 (m, 2H), 4.14 (m, 2H), 4.57 (m, 1H), 7.07 (s, 1H), 7.87 (m, 1H), 8.23 (m, 2H), 8.52 (m, 2H), 12.06 (s, 1H) | Example 76 | rated aqueous sodium chloride solution (100 ml). The EtOAc solution was dried over anhydrous $MgSO_4$ and concentrated in vacuo. The crude product was purified by silica gel chromatography using 0-10% $CH_3OH$ in DCM. The recovered product was recrystallised from EtOAc to further enhance the diastereomeric excess, increasing it from a 90:10 cis:trans mixture to a 96:4 cis:trans mixture (by HPLC analysis). The recrystallised product was carried on to the next reaction (2 g). MS (ES−(M+H)$^+$): 461, 463 for $C_{17}H_{18}Cl_2N_4O_5S$; NMR: 1.71 (m, 1H), 1.91 (m, 1H), 2.16 (s, 3H), 2.81 (dt, 1H), 3.42 (m, 2H), 3.74 (s, 3H), 3.86 (m, 1H), 4.34 (m, 2H), 7.43 (d, 1H), 7.88 (s, 1H), 8.50 (brs, 1H), 12.06 (s, 1H).

Example 78

Cis(±)methyl 2-[4-{[(3,4-dichloro-5-methyl-1H-pyrrol-2-yl)carbonyl]amino}-3-(morpholin-4-ylcarbonyl)piperidin-1-yl]-1,3-thiazole-5-carboxylate The title compound was prepared in a manner analogous to (Intermediate 37) starting from cis(±)4-{[(3,4-dichloro-5-methyl-1H-pyrrol-2-yl)carbonyl]amino}-1-[5-(methoxycarbonyl)-1,3-thiazol-2-yl]piperidine-3-carboxylic acid (Example 77) and morpholine. MS (ES$^+$): 530, 532 for $C_{21}H_{25}Cl_2N_5O_5S$.

Examples 79-82

The following compounds were synthesized by an analogous method to Example 78 from Example 77 and the starting materials given in the table below.

Example 83

Cis(±)6-(4-{[(4-chloro-5-methyl-1H-pyrrol-2-yl)carbonyl]amino}-3-methoxypiperidin-1-yl)-2-methoxypyrimidine-4-carboxylic acid Cis(±)methyl 2-chloro-6-(4-{[(4-chloro-5-methyl-1H-pyrrol-2-yl)carbonyl]amino}-3-methoxypiperidin-1-yl)pyrimidine-4-carboxylate (Example 23; 0.12 g, 0.27 mmol) was dissolved in 0.5 M sodium methoxide in MeOH (5.4 ml, 2.7 mmol) and heated in the microwave for 1.5 h at 85° C. The reaction mixture was acidified with 1N HCl and the product was extracted with EtOAc, dried with MgSO$_4$ and concentrated to a solid which was purified by reverse phase chromatography (gradient elution from 20-50% CH$_3$CN in water with 0.5% TFA). Freeze drying yielded product as a white solid. MS (ES) MH$^+$: 424 for $C_{18}H_{22}ClN_5O_5$; NMR: 1.62 (s, 1H), 1.75 (s, 1H), 2.14 (s, 3H), 3.26 (s, 3H), 3.53 (m, 3H), 3.87 (s, 3H), 4.22 (s, 2H), 6.88 (d, J=2.64 Hz, 1H), 7.07 (s, 1H), 7.66 (d, J=7.91 Hz, 1H), 11.63 (s, 1H).

| Ex | Compound | m/z | SM |
|---|---|---|---|
| 79 | Cis(±)methyl 2-{4-{[(3,4-dichloro-5-methyl-1H-pyrrol-2-yl)carbonyl]amino}-3-[(dimethylamino)carbonyl]piperidin-1-yl}-1,3-thiazole-5-carboxylate | M/z 488, 490 | Dimethylamine (2 M in THF) |
| 80 | Cis(±)methyl 2-{4-{[(3,4-dichloro-5-methyl-1H-pyrrol-2-yl)carbonyl]amino}-3-[(ethylamino)carbonyl]piperidin-1-yl}-1,3-thiazole-5-carboxylate | M/z 488, 490 | Ethylamine (2 M in THF) |
| 81 | Cis(±)methyl 2-(4-{[(3,4-dichloro-5-methyl-1H-pyrrol-2-yl)carbonyl]amino}-3-{[(2-hydroxyethyl)amino]carbonyl}piperidin-1-yl)-1,3-thiazole-5-carboxylate | M/z 504, 506 | Ethanolamine |
| 82 | Cis(±)methyl 2-(4-{[(3,4-dichloro-5-methyl-1H-pyrrol-2-yl)carbonyl]amino}-3-{[methoxy(methyl)amino]carbonyl}piperidin-1-yl)-1,3-thiazole-5-carboxylate | M/z 504, 506; NMR: 1.78 (m, 1H), 1.93 (m, 1H), 2.14 (s, 3H), 3.06 (brs, 3H), 3.24 (m, 1H), 3.32 (s, 1H), 3.38 (m, 1H), 3.72 (brs, 1H), 3.74 (s, 3H), 3.98 (m, 1H), 4.12 (m, 1H), 4.38 (m, 1H), 7.19 (d, 1H), 7.88 (s, 1H), 11.99 (s, 1H) | N,O-Dimethylhydroxylamine hydrochloride |

Example 84

The following compound was prepared by the procedure of Example 83 from the starting material (SM) indicated.

| Ex | Compound | NMR | M/z | SM |
|---|---|---|---|---|
| 84 | Cis(±)6-(4-{[(3,4-dichloro-5-methyl-1H-pyrrol-2-yl)carbonyl]amino}-3-methoxypiperidin-1-yl)-2-methoxypyrimidine-4-carboxylic acid | 1.61 (m, 1H), 1.74 (m, 1H), 2.18 (s, 3H), 3.21 (m, 1H), 3.33 (s, 3H), 3.51 (m, 1H), 3.53 (m, 1H), 3.85 (s, 3H), 4.28 (m, 2H), 5.10 (m, 1H), 7.03 (m, 1H), 7.12 (m, 1H), 12.15 (m, 1H) | 458, 460 | Example 14 |

Examples 85-86

The following compounds were prepared by the procedure of Intermediate 37 using the starting materials (SM) indicated.

| Ex | Compound | Data | SM |
|---|---|---|---|
| 85 | Methyl 2-((3R,4R)-4-{[(3,4-dichloro-5-methyl-1H-pyrrol-2-yl)carbonyl]amino}-3-methoxypiperidin-1-yl)-1,3-thiazole-5-carboxylate | MS (ES) MH+: 447 for $C_{17}H_{20}ClN_4O_4S$; NMR: 1.71 (m, 1H), 1.93 (m, 1H), 2.18 (s, 3H), 3.24-3.28 (m, 2H), 3.31 (s, 3H), 3.75 (s, 3H), 3.79 (m, 1H), 4.02-4.11 (m, 2H), 7.35 (d, 1H), 7.88 (s, 1H0, 12.00 (s, 1H) | Intermediate 30 and Intermediate 1 |
| 86 | Methyl 2-((3S,4S)-4-{[(3,4-dichloro-5-methyl-1H-pyrrol-2-yl)carbonyl]amino}-3-methoxypiperidin-1-yl)-1,3-thiazole-5-carboxylate | MS (ES) MH+: 447 for $C_{17}H_{20}ClN_4O_4S$; NMR: 1.71 (m, 1H), 1.93 (m, 1H), 2.18 (s, 3H), 3.24-3.28 (m, 2H), 3.31 (s, 3H), 3.75 (s, 3H), 3.79 (m, 1H), 4.02-4.11 (m, 2H), 7.35 (d, 1H), 7.88 (s, 1H0, 12.00 (s, 1H) | Intermediate 31 and Intermediate 1 |

Preparation of Starting Materials for Examples 1-86

Intermediate 1

3,4-Dichloro-5-methyl-1H-pyrrole-2-carboxylic acid

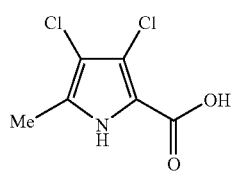 [SMILES: Cc1[nH]c(C(=O)O)c(Cl)c1Cl]

Ethyl 3,4-dichloro-5-methyl-1H-pyrrole-2-carboxylate (Intermediate 2; 7.765 g, 0.03496 mol) was dissolved in MeOH (80 ml) and DCM (10 ml) and slowly added to a 70° C. solution of 2 N LiOH (105 ml, 0.21 mol). After 2 h, the reaction mixture was cooled to room temperature and then in an ice bath, followed by acidification with 2 N HCl. The mixture was stirred at 0° C. for 1 h, and a purple solid was filtered, washed with water and lyophilized overnight to give 4.314 g (0.0222 mol, 64% yield) of the desired product. MS (ES−): 192.13, 194.13 for $C_6H_5Cl_2NO_2$; NMR: 2.17 (s, 3H).

Intermediate 2

Ethyl 3,4-dichloro-5-methyl-1H-pyrrole-2-carboxylate

Method 1

A solution of ethyl 5-methyl-1H-pyrrole-2-carboxylate (Intermediate 3; 7.00 g, 0.0457 mol) in tetrachloromethane (30 ml) was cooled to 0° C. under nitrogen. The rubber septum used in the apparatus was pierced with a needle, and $SO_2Cl_2$ (7.8 ml, 0.096 mol) was then added dropwise over 25 min. Within 1 h, the reaction mixture had formed a slurry. The solid was collected by suction filtration, washed with cold tetrachloromethane, and dried under vacuum overnight to give the title product as a peach coloured solid (7.84 g, 0.0353 mol, 77% yield). MS (ES): 222.00, 224.00 for $C_8H_9Cl_2NO_2$; NMR: 1.34-1.40 (t, 3H), 2.28 (s, 3H), 4.32-4.38 (m, 2H).
Method 2

A 4-neck 22 L round bottom flask equipped with an overhead stirrer, reflux condenser, nitrogen inlet and an internal temperature probe was charged with (Intermediate 253, 1000 g, 3.9 mol), 1-methyl-2-pyrrolidinone (10 L) and sodium cyanoborohydride (382 g, 6.1 mol, 1.56 eq). The resulting solution was heated at 75-80° C. for 6 h and allowed to cool to ambient overnight. Reaction solution was poured into water (20 L) resulting in a light brown suspension and product was extracted with methyl tert-butyl ether (2×10 L). Organic layer was dried with sodium sulfate and concentrated under reduced pressure to a thick slurry, which was filtered and solid dried in convection oven yielding 4 (518 g, 60%) as a light brown solid.

Intermediate 3

Ethyl 5-methyl-1H-pyrrole-2-carboxylate

Sodium (2.79 g, 0.121 mmol) was dissolved in anhydrous EtOH (100 ml), then 2,2,2-trichloro-1-(5-methyl-1H-pyrrol-2-yl)ethanone (Intermediate 4; 22.5 g, 0.099 mmol) was added in small portions. The dark brown solution was stirred at room temperature for 30 min then concentrated under vacuum to a small volume. The mixture was cooled in an ice bath and 3 N HCl was added slowly then extracted with diethyl ether (3×100 ml). The ether extracts were washed with 10% $NaHCO_3$, water and brine, dried over $Na_2SO_4$ and concentrated in vacuo to give the title compound as a brown solid. (15.04 g). NMR: 1.32 (t, 3H), 2.1 (s, 3H), 4.371 (q, 2H), 5.96 (dd, 1H), 6.78 (dd, 1H), 11.67 (s, 1H).

Intermediate 4

2,2,2-Trichloro-1-(5-methyl-1H-pyrrol-2-yl)ethanone

2-Methyl-1H-pyrrole (Intermediate 5; 10 g, 0.123 mmol) in anhydrous diethyl ether (30 ml) was added dropwise over 1 h to a stirred solution of triacetyl chloride (29 g, 0.16 mmol) in anhydrous $Et_2O$ (100 ml). The mixture was stirred for a further 1 h then $K_2CO_3$ (10 g/30 ml) was added slowly through a dropping funnel. The organic phase was dried over $Na_2SO_4$ and treated with decolourizing charcoal (3 g) for 30 min at room temperature. The resulting purple solution was concentrated and triturated with n-hexanes to give the title compound as a purple solid. (16.72 g). NMR ($CDCl_3$): 2.36 (s, 3H), 6.04 (dd, 1H), 7.45 (dd, 1H), 10.344 (s, 1H).

Intermediate 5

2-Methyl-1H-pyrrole

Potassium hydroxide (50 g, 0.89 mmol) was added to a solution of ethylene glycol (750 ml) and 1H-pyrrole-2-carbaldehyde (50 g, 0.53 mmol). Hydrazine hydrate (37 ml, 0.745 mmol) was added slowly over 15 min. The reaction mixture was refluxed at 90° C. for 90 min. The mixture was cooled to room temperature and cold water (250 ml) was added. The aqueous mixture was extracted with DCM (250 ml). The organic phase was washed with water (250 ml), dried over $Na_2SO_4$ and concentrated in vacuo. Kugelrohr distillation gave the title compound as a clear colourless liquid (29.75 g). NMR: 2.1 (s, 3H), 5.77 (s, 1H), 5.9 (dd, 1H), 6.25 (dd, 1H), 10.54 (s, 1H).

Intermediate 6

4-Chloro-5-methyl-1H-pyrrole-2-carboxylic acid

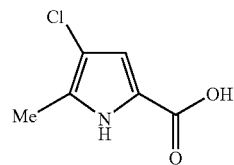

Lithium hydroxide (2 M, 4 ml) was warmed to 50° C. and a solution of ethyl 4-chloro-5-methyl-1H-pyrrole-2-carboxylate (Intermediate 7; 0.30 g, 1.60 mmol) in MeOH was added to it. The reaction was heated to 80° C. and stirred for two hours. The MeOH was removed and the aqueous solution was cooled to 0° C. and acidified with 30% HCl. The precipitated product (0.23 g, 92%) was filtered and dried. MS (ES): 160 (M+1) for $C_6H_6ClNO_2$; NMR ($CDCl_3$): 2.25 (s, 3H), 6.85 (s, 1H), 8.98 (brs, 1H).

Intermediate 7

Ethyl 4-chloro-5-methyl-1H-pyrrole-2-carboxylate

N-Chlorosuccinimide (0.67 g, 5.08 mmol) was added to a solution of ethyl 5-methyl-1H-pyrrole-2-carboxylate (Intermediate 3; 0.65 g, 4.23 mmol) in chloroform (20 ml). The reaction was warmed to 40° C. and stirred for 4 h, then poured to a beaker containing 2 N NaOH (20 ml) at 0° C. The layers were separated and the aqueous layer was extracted with chloroform (×3). The combined organic extracts were dried over magnesium sulfate and concentrated. The resultant off-white solid was purified by flash chromatography (hexanes/EtOAc, 16:1) to give the title product as a white solid (0.3 g, 38%). MS (ES): 188 (M+1) for $C_8H_{10}ClNO_2$; NMR ($CDCl_3$): 1.34 (t, 3H), 2.27 (s, 3H), 4.30 (q, 2H), 6.76 (s, 1H), 9.07 (brs, 1H).

Intermediate 8

3,4-Difluoro-2-methyl-1H-pyrrole $BH_3$THF (400 ml, 1M in THF) was added dropwise to a solution of 3,4-difluoro-1H-pyrrole-2-carbaldehyde (Intermediate 19; 3.82 g) in THF (50 ml) cooled in an ice-water bath under $N_2$. The reaction mixture was stirred at room temperature for 3 days. MeOH was added slowly to quench excess of $BH_3$ and then the solvent was removed in vacuo at 0° C. The resulting yellow oil was triturated with hexanes/DCM and the yellow precipitate was removed by filtration. The filtrate was washed with $NaHCO_3$, $H_2O$ and brine, dried over $Na_2SO_4$, filtered and concentrated at 0° C. in vacuo to give a pale yellow oil (3.8 g). MS (ES) $MH^+$: 116 for $C_5H_5F_2N$; NMR ($CDCl_3$): 2.15 (s, 3H), 6.22 (m, 1H).

Intermediate 9

1-tert-Butyl-3-methyl-4-hydroxy-5,6-dihydropyridine-1,3-(2H)-dicarboxylate

Methyl-4-hydroxy-1,2,5,6-tetrahydropyridine-3-carboxylate-hydrochloride (25 g) was suspended in DCM (250 ml). DIEA (41.6 g) was added in a single portion and the resultant homogeneous solution was cooled to 0° C. A DCM solution of di-tert-butyl dicarbonate (29.5 g, 1.05 moles) was added dropwise over a 1 h period. After the addition, the reaction was warmed to room temperature and stirred overnight. The reaction mixture was concentrated to one-half the volume and washed with water, brine, dried over $Na_2SO_4$, filtered and concentrated in vacuo to an oil. The crude product was purified by flash column chromatography eluting with (20% EtOAc/80% hexanes) to give the title product (33 g). NMR ($CDCl_3$): 1.48 (s, 9H), 2.37 (m, 2H), 3.57 (t, 2H), 3.78 (s, 3H), 4.06 (brs, 2H), 11.9 (s, 1H).

Intermediate 10

Ethyl 4-chloroquinoline-2-carboxylate

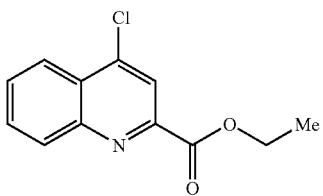 [SMILES: CCOC(=O)c1cc(Cl)c2ccccc2n1]

Phosphorous oxychloride (5 ml) was added to ethyl 4-hydroxyquinoline-2-carboxylate (1.01 g). The reaction mixture was subjected to single-mode microwave at 100° C. for 30 min using a Smith Microwave Synthesizer. The solvent was removed in vacuo and recrystallized with acetone to gave the title compound as a white solid (1.90 g). MS (ES) $MH^+$: 235, 237 for $C_{12}H_{10}ClNO_2$; NMR ($CDCl_3$): 1.44 (t, 3H, J=7.16), 4.51 (q, 2H, J=7.16), 7.19 (s, 1H), 7.71 (m, 1H), 7.81 (m, 1H), 8.22 (m, 1H), 8.36 (d, 1H, J=8.29).

Intermediate 11

2-(Methylthio)-1,3-thiazole-4-carboxylic acid

Ethyl 2-(methylthio)-1,3-thiazole-4-carboxylate (5.0 g) (Sinha, Subhash C et al. *Tet. Lett.* 2000, 41 (43), 8243-8246) was dissolved in MeOH (50 ml) and 2N LiOH (74 ml) was added. After stirring at room temperature for five minutes the reaction mixture was concentrated to remove MeOH and the residue was suspended in water and acidified with conc. HCl to pH 3. The white precipitate was filtered and dried to yield the title compound (3.42 g). NMR: 2.72 (s, 3H), 8.35 (s, 1H).

Intermediate 12

2-(Methylthio)-4-thiazolecarbonyl chloride 2-(Methylthio)-1,3-thiazole-4-carboxylic acid (Intermediate 11; 1.0 g) in thionyl chloride (10 ml) was heated to reflux for 30 min. The solution was cooled to room temperature and concentrated in vacuo. The residue was washed with anhydrous THF and concentrated to yield a black solid which was dried and stored cold under nitrogen (1.2 g). NMR ($CDCl_3$): 2.76 (s, 3H), 8.32 (s, 1H).

Intermediate 13

N-(1-Methyl-1-phenylethyl)-2-(methylthio)-1,3-thiazole-4-carboxamide

Triethylamine (2.24 ml) was added to a solution of cumylamine (3.2 ml) in anhydrous THF (30 ml). After stirring for 15 min, a solution of 2-(methylthio)-4-thiazolecarbonyl chloride (Intermediate 12; 3.1 g) in anhydrous THF was added and the reaction mixture was concentrated in vacuo after 15 min. The residue was partitioned with EtOAc and water, dried with $MgSO_4$, and concentrated to an orange oil. Flash purification on silica gel with isocratic elution of DCM yielded the product as a yellow oil (3.7 g). MS (ES) $MH^+$: 293 for $C_{14}H_{16}N_2OS_2$; NMR: 1.68 (s, 6H), 2.76 (s, 3H), 7.20 (d, J=7.16 Hz, 1H), 7.29 (t, J=7.54 Hz, 2H), 7.36-7.41 (m, 2H), 8.04 (s, 1H), 8.08 (s, 1H).

Intermediate 14

4-{[(1-Methyl-1-phenylethyl)amino]carbonyl}-2-(methylthio)-1,3-thiazole-5-carboxylic acid Diisopropylamine (4.2 ml) was dissolve in anhydrous THF (100 ml) was cooled to −78° C. and to this was added n-butyl lithium (12 ml) slowly. The solution was slowly warmed to 0° C. and then cooled back to −78° C. A solution of N-(1-methyl-1-phenylethyl)-2-(methylthio)-1,3-thiazole-4-carboxamide (Intermediate 13; 2.8 g) in anhydrous THF was added slowly maintaining the temperature below −70° C. After stirring for 30 min, a solution of methyl cyano formate (1.6 ml) in anhydrous THF was added in one portion and the reaction was stirred at −78° C. for 30 min followed by slow warming to room temperature. The reaction mixture was diluted with water and extracted with ether. The aqueous portion was acidified with conc. HCl, extracted with EtOAc, dried with $MgSO_4$ and concentrated to an orange solid (0.9 g). MS (ES) $MH^+$: 337 for $C_{15}H_{16}N_2O_3S_2$; NMR: 1.66-1.74 (m, 6H), 2.80 (s, 3H), 7.23 (d, J=7.16 Hz, 1H), 7.33 (t, J=7.54 Hz, 2H), 7.45 (s, 2H), 9.07 (s, 1H).

Intermediate 15

Methyl 4-{[(1-methyl-1-phenylethyl)amino]carbonyl}-2-(methylthio)-1,3-thiazole-5-carboxylate

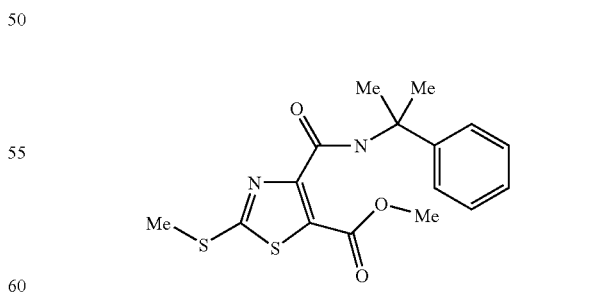

Potassium carbonate (0.37 g) and iodomethane (0.17 ml) were added to a solution of 4-{[(1-methyl-1-phenylethyl)amino]carbonyl}-2-(methylthio)-1,3-thiazole-5-carboxylic acid (Intermediate 14; 0.9 g) in DMF (20 ml) and heated in a sealed tube at an external temperature of 85° C. for 30 min. The reaction mixture was concentrated to remove DMF and partitioned with EtOAc and water. The combined organic extracts were washed with water, dried with MgSO$_4$, and concentrated to an orange solid (0.63 g). NMR: 1.60-1.65 (m, 6H), 2.76 (s, 3H), 3.78-3.83 (m, 3H), 7.22 (d, J=7.16 Hz, 1H), 7.33 (t, J=7.63 Hz, 2H), 7.46 (d, J=7.35 Hz, 2H), 8.75 (s, 1H).

Intermediate 16

Methyl 4-{[(1-methyl-1-phenylethyl)amino]carbonyl}-2-(methylsulfonyl)-1,3-thiazole-5-carboxylate 3-Chloroperbenzoic acid (0.89 g) was added to a solution of methyl 4-{[(1-methyl-1-phenylethyl)amino]carbonyl}-2-(methylthio)-1,3-thiazole-5-carboxylate (Intermediate 15; 0.63 g) in DCM (25 ml). After stirring overnight the reaction was complete. Aqueous sodium bisulfite was added to quench any unreacted peroxides and the solution was washed with sat. NaHCO$_3$. The organic portion was dried with MgSO$_4$ and concentrated to a yellow solid (0.6 g). NMR: 1.63-1.68 (m, 6H), 3.58 (s, 3H), 3.89 (s, 3H), 7.23 (d, J=7.16 Hz, 1H), 7.34 (t, J=7.63 Hz, 2H), 7.47 (d, J=7.54 Hz, 2H), 8.91 (s, 1H).

Intermediate 17

Methyl-2-chloro-4-(methoxymethyl)-1,3-thiazole-5-carboxylate tert-Butyl nitrite (2.2 ml, 18.6 mmol) and cuprous chloride (1.5 g) were suspended in anhydrous CH$_3$CN (100 ml). Methyl 2-amino-4-(methoxymethyl)-1,3-thiazole-5-carboxylate (2.5 g) prepared as described in (Kennedy, Alan R. et al. *Acta Crystallographica, Section C: Crystal Structure Communications* (1999, C55 (7) 2) was added in one portion. The mixture was stirred at room temperature for 2 h and the temperature was raised to 70° C. for 1 h. The mixture was cooled to room temperature and filtered. The filtrate was poured into 6 N HCl, extracted with EtOAc, dried with MgSO$_4$ and concentrated to a black oil. Flash purification on silica gel with gradient elution (hexane to EtOAc) yielded product as a yellow liquid (0.82 g). NMR: 3.31 (s, 3H), 3.85 (s, 3H), 4.71 (s, 2H).

Intermediate 18

3,4-Difluoro-1H-pyrrole 3,4-Difluoro-1H-pyrrole was prepared as described in Eric K. Woller et al., *J. Org. Chem.*, 1998 63(16), 5706-5707) and references therein. Thus, to a solution of 3,3,4,4-tetrafluoropyrrolidine hydrochloride (30.2 g) in dry DMSO (250 ml) cooled in an ice-water bath, t-BuOK was added (100 g) under N$_2$. After the addition was complete (~0.5 h), the reaction mixture was stirred at room temperature for another 0.5 h. It was cooled to 0° C. and quenched with ice water (300 ml). After the solid dissolved, the mixture was diluted to ~1.5l with water, neutralized to pH 7 with HCl, and extracted with DCM. The combined DCM extracts were washed with water, brine, dried over MgSO$_4$ and filtered. DCM was removed in vacuo at 0° C., and the resulting orange oil was dissolved in pentane at room temperature, cooled to -20° C. overnight and filtered under N$_2$ to give the title compound as golden crystals (4.6 g). NMR (CDCl$_3$): 6.38 (d, 1H), 6.41 (d, 1H).

Intermediate 19

3,4-Difluoro-1H-pyrrole-2-carbaldehyde

DMF (4.3 ml) was cooled in ice-water bath under N$_2$ and POCl$_3$ (5.2 ml) was added dropwise. The mixture was stirred at room temperature for 10 min. The ice-water bath was replaced, and the mixture was diluted with DCM (45 ml). A solution of 3,4-difluoro-1H-pyrrole (Intermediate 18; 4.57 g) in DCM (45 ml) was added dropwise. The mixture was refluxed for 30 min, cooled to room temperature and a solution of NaOAc (23 g) in water (60 ml) was added slowly. The resulting mixture was refluxed for 30 min, organic phase was separated and aqueous phase was extracted with DCM. The combined organic phase was washed with NaHCO$_3$, dried over Na$_2$SO$_4$, and concentrated in vacuo. The crude solid was triturated with DCM (20 ml)/pentane (100 ml), and then cooled to -20° C. to give the title compound as pale brown needles (4.73 g). NMR (CDCl$_3$): 6.87 (m, 1H), 9.6 (m, 1H).

Intermediate 20

3,4-Difluoro-5-methyl-1H-pyrrole-2-carboxylic acid

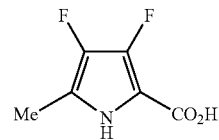 [SMILES: Cc1[nH]c(C(=O)O)c(F)c1F]

2,2,2-Trichloro-1-(3,4-difluoro-5-methyl-1H-pyrrol-2-yl)ethanone (Intermediate 80; 1.03 g) was added to an aqueous solution of NaOH (18 ml) at 0° C. under N$_2$. The mixture was stirred at room temperature for a further 2 h, cooled to 0° C. and acidified with HCl to ~pH 2. A brown precipitate of product was collected by filtration. The crude product was purified by column chromatography on silica gel elution with EtOAc/hexanes (1:1). Trituration with DCM (1 ml)/pentane (6 ml) gave the title compound as a pale brown solid (306 mg). M.p. 140° C. (dec.). MS (ES) MH$^+$: 160, 161 for C$_6$H$_5$F$_2$NO$_2$; NMR (CDCl$_3$): 2.15 (s, 3H), 11.5 (s, 1H), 12.8 (brs, 1H).

Intermediate 21

Cis(±)ethyl 4-amino-3-methoxypiperidine-1-carboxylate hydrochloride salt

The title compound can be prepared as described in Lee, C. et al. *Synth. Comm.* 2001, 31(7), 10881-10890 and/or WO 94/12494 or from Intermediate 157 by the following procedure;

To a stirred solution of the benzylamine (36.45 g, 125 mmol) and 10% palladium on activated carbon (50% wet; approximately 4 g) in methanol (250 mL), at room temperature and under an atmosphere of N$_2$, was added ammonium formate (31.50 g, 500 mmol) as a solid. Temperature was increased to 70° C.; the reaction was stirred overnight at this temperature, under an atmosphere of N$_2$. Complete conversion was suggested by TLC (6% methanol in ethyl acetate; Rf~0.06 in a solution of 15% methanol and 30% acetone in methylene chloride) in the morning. The reaction mixture was filtered through Celite and concentrated under vacuum. To the residue was added approximately 50 mL water; from this mixture was extracted the crude product with a solution of ~3% methanol in chloroform (4×300 mL). Organic layers were combined, dried over magnesium sulfate, and concentrated. Obtained 24.18 g (96%) of an off-white solid.

MS (ES) MH$^+$: 202 for C$_9$H$_{18}$N$_2$O$_3$.

Intermediate 22

Cis(±)ethyl 4-{[(benzyloxy)carbonyl]amino}-3-methoxypiperidine-1-carboxylate

Benzyl chloroformate (3.3 ml) was added dropwise to a cold solution of Cis(±)ethyl 4-amino-3-methoxypiperidine-1-carboxylate hydrochloride salt (Intermediate 21; 5 g) in saturated NaHCO$_3$. The mixture was stirred at room temperature for 14 h. The white precipitate was filtered, washed well with water, dried in vacuo to give the title compound as a white solid (6.66 g). MS (ES) MH$^+$: 336 for C$_{17}$H$_{24}$N$_2$O$_5$; NMR: 1.21 (t, 3H), 1.52-1.67 (m, 2H), 3.08 (m, 2H), 3.28 (s, 3H), 3.41 (s, 2H), 3.74-3.92 (m, 2H), 3.96 (m, 2H), 4.14 (m, 1H), 5.10 (s, 2H), 7.24 (d, 1H), 7.44 (m, 5H).

Intermediate 23 and Intermediate 24 ethyl (3R,4S)-4-{[(benzyloxy)carbonyl]amino}-3-methoxypiperidine-1-carboxylate and ethyl (3S,4R)-4-{[(benzyloxy)carbonyl]amino}-3-methoxypiperidine-1-carboxylate Cis(±)ethyl 4-{[(benzyloxy)carbonyl]amino}-3-methoxypiperidine-1-carboxylate (Intermediate 22; 6.2 g) were separated into its enantiomers by chiral chromatography over a Chiralcel OJ column (eluant: hexanes/MeOH/EtOH; 70/15/15; 0.1% diethylamine). The fractions corresponding to the first chromatographic peak (Cis(−)isomer) were collected and evaporated yielding the title compound as a white solid (2.62 g). The fractions corresponding to the second chromatographic peak (Cis(+)isomer) were collected and evaporated yielding the title compound as a white solid (2.71 g). MS (ES)(M+Na)$^+$: 360 for C$_{17}$H$_{24}$N$_2$O$_5$; NMR: 1.21 (t, 3H), 1.52-1.67 (m, 2H), 3.08 (m, 2H), 3.28 (s, 3H), 3.41 (s, 2H), 3.74-3.92 (m, 2H), 3.96 (m, 2H), 4.14 (m, 1H), 5.10 (s, 2H), 7.24 (d, 1H), 7.44 (m, 5H).

Intermediate 25 ethyl (3S,4R)-4-amino-3-methoxypiperidine-1-carboxylate

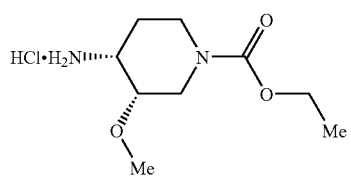

ethyl (3S,4R)-4-{[(benzyloxy)carbonyl]amino}-3-methoxypiperidine-1-carboxylate (Intermediate 24; 3.98 g) was dissolved in MeOH (100 ml) and 1N HCl (50 ml). 10% Pd-charcoal (600 mg) was added, degassed and hydrogenolysed under an atmosphere of H$_2$ gas at room temperature for 3 h. The catalyst was filtered through a bed of celite, concentrated in vacuo and lyophilized giving the title compound (2.8 g). MS (ES) MH$^+$: 202 for C$_9$H$_{18}$N$_2$O$_3$.

Intermediate 26

The following compound was prepared in a manner analogous to Intermediate 25 from the starting material indicated.

| Int | Compound | MS | SM |
|---|---|---|---|
| 26 | ethyl (3R,4S)-4-amino-3-methoxypiperidine-1-carboxylate | MS (ES) MH$^+$: 202 for C$_9$H$_{18}$N$_2$O$_3$ | Intermediate 23 |

Intermediate 27

Cis(±)ethyl-3-(allyloxy)-4-[(tert-butoxycarbonyl)amino]piperidine-1-carboxylate

A 50% aqueous solution of sodium hydroxide (3 ml) was added to a suspension of allyl bromide (693 mg, 5.70 mmol), cis(±)ethyl 4-[(tert-butoxycarbonyl)amino]-3-hydroxypiperidine-1-carboxylate (reference: C. H. Lee et al. *Syn. Commun.*, 2001, 31, 1081), (750 mg, 2.6 mmol), benzyltriethylammonium chloride (4 mg, cat.) and toluene (8 ml). The resultant mixture was stirred overnight at room temperature. The reaction mixture was diluted with EtOAc (150 ml) and water (35 ml). The organic phase was separated and the aqueous phase was back extracted with EtOAc (2×30 ml). The combined organic phase was washed with brine, dried over sodium sulfate, filtered and concentrated. The crude residue was purified by flash column chromatography (hexane/EtOAc, 3:2) to yield 734 mg of the title compound. MS (ES)(M+H): 329. for C$_{16}$H$_{28}$N$_2$O$_5$; NMR: 1.28 (t, 3H), 1.47 (s, 9H), 1.68 (m, 2H), 2.88 (brt, 2H), 3.50 (m, 1H), 3.68 (m, 1H), 3.90 (m, 1H), 4.00-4.45 (m, 3H), 4.10 (q, 2H), 4.92 (brs, 1H), 5.20 (m, 2H), 5.86 (m, 1H).

Intermediate 28

Cis(±)ethyl-3-(allyloxy)-4-amino]piperidine-1-carboxylate hydrochloride salt

4N HCl/dioxane (20 ml) was added to cis(±)ethyl-3-(allyloxy)-4-[(tert-butoxycarbonyl)amino]piperidine-1-carboxylate (Intermediate 27; 572 mg). The mixture was stirred at room temperature for 90 min. The solvent was removed in vacuo, dried in vacuo to give the title compound as an oily foam which was used without further purification (449 mg). MS (ES)(M+H): 228. for C$_{11}$H$_{20}$N$_2$O$_3$.

Intermediates 29-36

The following compounds were prepared in a manner analogous to Intermediate 28 from the starting material (SM) indicated.

| Int | Compound | Data | SM |
|---|---|---|---|
| 29 | Cis(±)ethyl-4-amino-3-propyoxypiperidine-1-carboxylate hydrochloride salt | MS (ES)(M + H): 220 for C$_{11}$H$_{22}$N$_2$O$_3$ | Intermediate 81 |

-continued

| Int | Compound | Data | SM |
|---|---|---|---|
| 30 | Methyl 2-[(3R,4R)-4-amino-3-methoxypiperidin-1-yl]-1,3-thiazole-5-carboxylate hydrochloride salt | NMR: 1.63 (m, 1H), 2.08 (d, 1H), 2.97-3.01 (m, 1H), 3.21-3.24 (m, 2H), 3.25 (m, 2H), 3.40 (s, 3H), 3.73 (s, 3H), 3.88 (d, 1H), 4.34 (m, 1H), 7.87 (s, 1H), 8.28 (brs, 3H) | Intermediate 68 |
| 31 | Methyl 2-[(3S,4S)-4-amino-3-methoxypiperidin-1-yl]-1,3-thiazole-5-carboxylate hydrochloride salt | NMR: 1.63 (m, 1H), 2.08 (d, 1H), 2.97-3.01 (m, 1H), 3.21-3.24 (m, 2H), 3.25 (m, 2H), 3.40 (s, 3H), 3.73 (s, 3H), 3.88 (d, 1H), 4.34 (m, 1H), 7.87 (s, 1H), 8.28 (brs, 3H) | Intermediate 69 |
| 32 | Cis(±)3,4-dichloro-N-[3-fluoropiperidin-4-yl]-5-methyl-1H-pyrrole-2-carboxamide hydrochloride salt | NMR: 1.92-1.96 (m, 2H), 2.20 (s, 3H), 3.10 (m, 1H), 3.43-3.51 (m, 2H), 3.64 (m, 1H), 4.27-4.38 (m, 1H), 5.05 (d, 1H), 7.58 (d, 1H), 8.75 (brs, 1H), 9.43 (brs, 1H), 12.32 (s, 1H) | Intermediate 49 |
| 33 | 3,4-dichloro-N-[(3R,4S)-3-fluoropiperidin-4-yl]-5-methyl-1H-pyrrole-2-carboxamide hydrochloride | MS (ES) (M + H): 294, 296 for $C_{11}H_{14}Cl_2FN_3O$ | Intermediate 45 |
| 34 | Trans(±)3,4-dichloro-N-[3-fluoropiperidin-4-yl]-5-methyl-1H-pyrrole-2-carboxamide hydrochloride | MS (ES) (M + H): 294, 296 for $C_{11}H_{14}Cl_2FN_3O$ | Intermediate 44 |
| 35 | Cis(±)methyl 4-{[(3,4-dichloro-5-methyl-1H-pyrrol-2-yl)carbonyl]amino}piperidine-3-carboxylate hydrochloride salt | MS (ES) (M + H): 332 for $C_{13}H_{17}Cl_2N_3O_3$ | Intermediate 46 |
| 36 | 3,4-dichloro-N-[(3S,4R)-3-fluoropiperidin-4-yl]-5-methyl-1H-pyrrole-2-carboxamide hydrochloride | MS (ES) M + H): 294, 296 for $C_{11}H_{14}Cl_2FN_3O$ | Intermediate 48 |

Intermediate 37

Cis(±)ethyl 4-{[(3,4-dichloro-5-methyl-1H-pyrrol-2-yl)carbonyl]amino}-3-methoxypiperidine-1-carboxylate 3,4-Dichloro-5-methyl-1H-pyrrole-2-carboxylic acid (Intermediate 1; 304 mg) was dissolved in anhydrous DMF. HATU (596 mg), HOAT (213 mg) and DIEA (274 μl) were added and stirred at ambient for 15 min. Cis(±)ethyl 4-amino-3-methoxypiperidine-1-carboxylate (Intermediate 21; 317 mg) was added and the mixture was stirred at ambient for 18 h. The mixture was diluted with EtOAc and washed with water, 1N HCl, bicarbonate buffer, water, brine and dried over $Na_2SO_4$. The solution was concentrated in vacuo to give the title compound as a brown solid (503 mg). MS (ES) MH+: 378, 380 for $C_{15}H_{21}Cl_2N_3O_4$; NMR: 1.29 (t, 3H), 1.79 (m, 2H), 2.27 (s, 3H), 3.12 (m, 2H), 3.30 (s, 3H), 3.37 (m, 1H), 3.83-4.16 (m, 5H), 7.25 (d, 1H), 12.23 (s, 1H).

Intermediates 38-49

The following compounds were prepared in a manner analogous to Intermediate 37 from the starting material (SM) indicated.

| Int | Compound | Data | SM |
|---|---|---|---|
| 38 | Cis(±)ethyl-4-{[(3,4-difluoro-5-methyl-1H-pyrrol-2-yl)carbonyl]amino}-3-methoxypiperidine-1-carboxylate | MS (ES) MH⁺: 344 for $C_{15}H_{21}F_2N_3O_4$; NMR: 1.3 (t, 3H), 1.69 (m, 2H), 2.21 (s, 3H), 3.11 (m, 2H), 3.22 (s, 3H), 3.39 (m, 2H), 3.85 (q, 2H), 4.41 (m, 1H), 6.83 (d, 1H), 11.54 (s, 1H) | Intermediate 20 and Intermediate 21 |
| 39 | ethyl (3S,4R)-4-{[(3,4-dichloro-5-methyl-1H-pyrrol-2-yl)carbonyl]amino}-3-methoxypiperidine-1-carboxylate | MS (ES) MH⁺: 377 for $C_{15}H_{21}Cl_2N_3O_4$; NMR: 1.32 (t, 3H), 1.74 (m, 2H), 2.31 (s, 3H), 3.14 (m, 2H), 3.18-3.52 (s, 3H), 3.75-4.44 (m, 5H), 7.30 (d, 1H), 12.39 (s, 1H) | Intermediate 25 and Intermediate 1 |
| 40 | ethyl (3R,4S)-4-{[(3,4-dichloro-5-methyl-1H-pyrrol-2-yl)carbonyl]amino}-3-methoxypiperidine-1-carboxylate | MS (ES) MH⁺: 377 for $C_{15}H_{21}Cl_2N_3O_4$; NMR: 1.32 (t, 3H), 1.74 (m, 2H), 2.31 (s, 3H), 3.14 (m, 2H), 3.18-3.52 (s, 3H), 3.75-4.44 (m, 5H), 7.30 (d, 1H), 12.39 (s, 1H) | Intermediate 26 and Intermediate 1 |
| 41 | Ethyl 4-{[(4-chloro-5-methyl-1H-pyrrol-2-yl)carbonyl]amino}-3-methoxypiperidine-1-carboxylate | MS (ES) MH⁺: for $C_{15}H_{22}ClN_3O_4$; NMR: 1.18 (t, J = 7.06 Hz, 3H), 1.48 (d, J = 3.58 Hz, 1H), 1.75 (td, J = 12.29, 7.82 Hz, 1H), 2.10-2.18 (m, 3H), 2.95 (d, J = 13.38 Hz, 2H), 3.20-3.27 (m, 3H), 3.27-3.35 (m, 2H), 3.38 (s, 1H), 3.97-4.09 (m, J = 10.53, 7.08, 7.08, 3.39 Hz, 2H), 4.19 (s, 1H), 6.88 (d, J = 2.64 Hz, 1H), 7.62 (d, J = 7.91 Hz, 1H), 11.60 (s, 1H) | Intermediate 21 and Intermediate 6 |
| 42 | Cis(±)ethyl 3-(allyloxy)-4-{[(3,4-dichloro-5-methyl-1H-pyrrol-2-yl)carbonyl]amino}piperidine-1-carboxylate | MS (ES) MH⁺: 402, 404 for $C_{17}H_{23}Cl_2N_3O_4$ | Intermediate 1 and Intermediate 28 |
| 43 | Cis(±)ethyl 4-{[(3,4-dichloro-5-methyl-1H-pyrrol-2-yl)carbonyl]amino}-3-propoxypiperidine-1-carboxylate | MS (ES) MH⁺: 404, 406 for $C_{17}H_{25}Cl_2N_3O_4$ | Intermediate 1 and Intermediate 29 |
| 44 | Trans(±)tert-butyl-4-{[(3,4-dichloro-5-methyl-1H-pyrrol-2-yl)carbonyl]amino}-3-fluoropiperidine-1-carboxylate | MS (ES) (M + Na): 416, 418 for $C_{16}H_{22}Cl_2FN_3O_3$ | Intermediate 60 and Intermediate 1 |
| 45 | tert-butyl (3R,4S)-4-{[(3,4-dichloro-5-methyl-1H-pyrrol-2-yl)carbonyl]amino}-3-fluoropiperidine-1-carboxylate | MS (ES) (M + Na): 416, 418 for $C_{16}H_{22}Cl_2FN_3O_3$ | Intermediate 61 and Intermediate 1 |
| 46, 47 | 1-tert-Butyl 3-methyl 4-{[(3,4-dichloro-5-methyl-1H-pyrrol-2-yl)carbonyl]amino}piperidine-1,3-dicarboxylate | 46: MS (ES − (M + H)⁺): 434, 436 for $C_{18}H_{25}Cl_2N_3O_5$; NMR 1.45 (s, 9H), 2.16 (m, 1H), 2.27 (s, 3H), 2.55 (dt, 1H), | Intermediate 70 and Intermediate 1 |

| Int | Compound | Data | SM |
|---|---|---|---|
| | Note for Examples 46 and 47: The resultant crude mixture dissolved in DCM, added to a silica gel column, and was purified using a gradient of 10-50% EtOAc in hexanes. The recovered mixture of diastereomers were taken up in EtOAc (200 ml), heated to 50° C., and filtered. The solid was washed with EtOAc and dried, to show a 90:10 cis:trans mixture of diastereomers (2.3 g, 30.6% yield) (Intermediate 46). The filtrate was then subjected to a recrystallisation using EtOAc and n-heptane, and a 90:10 trans:cis mixture (2.65 g, 35.3% yield) (Intermediate 47) was recovered. | 2.93 (m, 1H), 3.09 (m, 2H), 3.66 (s, 3H), 4.08 (m, 1H), 4.29 (m, 2H), 6.68 (d, 1H), 9.66 (s, 1H) 47: MS (ES) MH+: 434, 436 for $C_{18}H_{25}Cl_2N_3O_5$; NMR: 1.44 (s, 9H), 1.75 (m, 1H), 2.09 (m, 1H), 2.26 (s, 3H), 2.86 (m, 1H), 2.98 (m, 1H), 3.17 (dd, 1H), 3.71 (s, 3H), 4.04 (m, 1H), 4.44 (m, 2H), 7.57 (d, 1H), 9.53 (s, 1H) | |
| 48 | tert-butyl (3S,4R)-4-{[(3,4-dichloro-5-methyl-1H-pyrrol-2-yl)carbonyl]amino}-3-fluoropiperidine-1-carboxylate | MS (ES) (M + Na): 416, 418 for $C_{16}H_{22}Cl_2FN_3O_3$ | Intermediate 64 and Intermediate 1 |
| 49 | Cis(±)tert-butyl-4-{[(3,4-dichloro-5-methyl-1H-pyrrol-2-yl)carbonyl]amino}-3-fluoropiperidine-1-carboxylate | NMR (CDCl$_3$): 1.47 (s, 9H), 1.84-1.88 (m, 2H), 2.28 (s, 3H), 2.76-3.02 (m, 2H), 4.11-4.26 (m, 2H), 4.43-4.51 (m, 1H), 4.77 (d, 1H) | Intermediate 59 and Intermediate 1 |

Intermediate 50

Cis(±)3,4-dichloro-N-(3-methoxypiperidin-4-yl)-5-methyl-1H-pyrrole-2-carboxamide

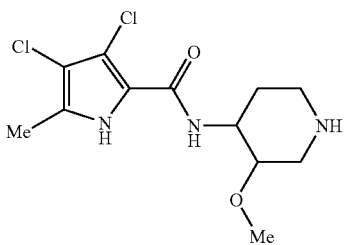 [SMILES: COC1CNCCC1NC(=O)c1[nH]c(C)c(Cl)c1Cl]

The title compound was prepared by the methods described below:
Method A
Cis(±)ethyl 4-{[(3,4-dichloro-5-methyl-1H-pyrrol-2-yl)carbonyl]amino}-3-methoxypiperidine-1-carboxylate (Intermediate 37; 503 mg) was dissolved in MeOH (30 ml). 1 M NaOH was added and the mixture was heated at 100° C. for 12 h. The reaction mixture was cooled to ambient and extracted with EtOAc, washed with water, dried over Na$_2$SO$_4$ and concentrated in vacuo to give the title compound as a brown oily gum which was used without further purification (336 mg).
Method B
Cis(±)ethyl-4-{[(3,4-dichloro-5-methyl-1H-pyrrol-2-yl)carbonyl]amino}-3-methoxypiperidine-1-carboxylate (Intermediate 37; 3.85 g) was suspended in anhydrous CH$_3$CN. Iodotrimethylsilane (2.2 ml) was added slowly. The reaction was heated to reflux for several hours until complete by LCMS. The crude reaction mixture was diluted with water and acidified with 1N HCl to pH 3. The solution was extracted with EtOAc. The aqueous layer was basified with 50% NaOH to pH 10. The aqueous layer as saturated with sodium chloride and extracted with THF, dried with MgSO$_4$ and concentrated to a tan solid (2.1 g). MH+: 306 for $C_{12}H_{17}Cl_2N_3O_2$; NMR: 1.61 (d, J=3.77 Hz, 2H), 1.76 (dt, J=6.50, 3.16 Hz, 1H), 2.16-2.20 (m, 3H), 2.56-2.69 (m, 2H), 2.90 (d, J=13.19 Hz, 1H), 3.18 (dd, J=13.75, 3.01 Hz, 1H), 3.30-3.35 (m, 3H), 3.56-3.64 (m, 1H), 4.04-4.15 (m, J=8.10, 7.72, 7.72, 3.01 Hz, 1H), 7.14 (d, J=8.29 Hz, 1H).

Intermediates 51-56

The following Intermediates were prepared as described by the general methods described in Intermediate 50 from the starting materials (SM) indicated.

| Int | Compound | Data | SM |
|---|---|---|---|
| 51 | 3,4-dichloro-N-[(3S,4R)-3-methoxypiperidin-4-yl]-5-methyl-1H-pyrrole-2-carboxamide | M/z 306; 1.73 (m, 2H), 2.31 (s, 3H), 2.64 (m, 1H), 2.98 (m, 1H), 3.22 (m, 1H), 3.34 (m, 1H), 3.34 (s, 3H), 3.42 (m, 2H), 4.25 (m, 1H), 7.31 (d, 1H). | Intermediate 39 |
| 52 | 3,4-dichloro-N-(3R,4S)[3-methoxypiperidin-4-yl]-5-methyl-1H-pyrrole-2-carboxamide | M/z 306; 1.73 (m, 2H), 2.31 (s, 3H), 2.64 (m, 1H), 2.98 (m, 1H), 3.22 (m, 1H), 3.34 (m, 1H), 3.34 (s, 3H), 3.42 (m, 2H), 4.25 (m, 1H), 7.31 (d, 1H). | Intermediate 40 |

-continued

| Int | Compound | Data | SM |
|---|---|---|---|
| 53 | Cis(±)3,4-dichloro-5-methyl-N-(3-propoxypiperidin-4-yl)-1H-pyrrole-2-carboxamide | M/z 334 | Intermediate 43 |
| 54 | Cis(±)3,4-dichloro-5-methyl-N-(3-allyoxypiperidin-4-yl)-1H-pyrrole-2-carboxamide | M/z 332 | Intermediate 42 |
| 55 | Cis(±)4-chloro-N-(3-methoxypiperidin-4-yl)-5-methyl-1H-pyrrole-2-carboxamide | M/z 272; 1.41 (s, 1H), 1.67 (s, 1H), 2.13 (s, 3H), 2.47 (s, 1H), 2.55 (s, 1H), 2.86 (s, 1H), 3.08 (d, J = 13.19 Hz, 1H), 3.25 (s, 3H), 3.31 (s, 1H), 6.89 (d, J = 2.45 Hz, 1H), 7.52 (s, 1H), 11.59 (s, 1H) | Intermediate 41 |
| 56 | Cis(±)3,4-difluoro-N-(3-methoxypiperidin-4-yl)-5-methyl-1H-pyrrole-2-carboxamide | M/z 273; 1.74 (m, 2H), 2.24 (s, 3H), 3.00 (m, 1H), 3.21 (m, 1H), 3.36 (s, 3H), 3.42 (m, 4H), 4.20 (brm, 1H), 6.74 (brm, 1H), 11.60 (brs, 1H). | Intermediate 38 |

Intermediate 57 and Intermediate 58 tert-Butyl-(3S,4R)-4-(benzylamino)-3-fluoropiperidine-1-carboxylate and tert-Butyl-(3R,4S)-4-(benzylamino)-3-fluoropiperidine-1-carboxylate

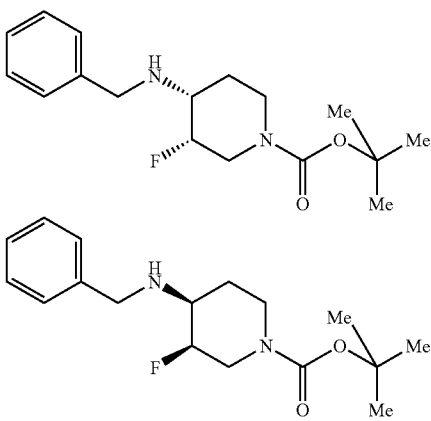

Cis(±)tert-butyl-4-(benzylamino)-3-fluoropiperidine-1-carboxylate (Intermediate 82; 2.2 g) was separated into the title compounds using chiral HPLC, in a manner analogous to Intermediate 23 and Intermediate 24 over a Chiralpak AD column (eluent: hexanes/MeOH/EtOH; 90/2.5/2.5; 0.1% diethylamine). The fractions corresponding to the first chromatographic peak (Cis(+) isomer; Intermediate 57) were collected and evaporated yielding the title compound as a white solid (942 mg). The fractions corresponding to the second chromatographic peak (Cis(−) isomer; Intermediate 58) were collected and evaporated yielding the title compound as a white solid (980 mg). NMR (CDCl$_3$): 1.40 (s, 9H), 1.88 (m, 2H), 3.01 (m, 2H), 3.55 (m, 2H), 3.77 (m, 1H), 4.66 (d, 1H).

Intermediate 59

Cis(±)tert-butyl-4-amino-3-fluoropiperidine-1-carboxylate

Cis(±)tert-butyl-4-(benzylamino)-3-fluoropiperidine-1-carboxylate (Intermediate 82; 711 mg), ammonium formate (582 mg), and 10% Pd/C (200 mg) in MeOH (10 ml) was heated to 50° C. for 1 h. The reaction mixture was cooled to room temperature, filtered through diatomaceous earth and concentrated under reduced pressure to give the title compound (503 mg, quantitative). NMR (CDCl$_3$): 1.40 (s, 9H), 1.88 (m, 2H), 3.01 (m, 2H), 3.55 (m, 2H), 3.77 (m, 1H), 4.66 (d, 1H).

Intermediates 60-64

The following Intermediates were prepared by the procedure described in Intermediate 59 from the starting materials (SM) indicated.

| Int | Compound | Data | SM |
|---|---|---|---|
| 60 | Trans(±)tert-butyl-4-amino-3-fluoropiperidine-1-carboxylate | NMR (CDCl$_3$): 1.38 (s, 9H), 1.88 (m, 2H), 2.87 (m, 2H), 3.59 (m, 2H), 3.77 (m, 1H), 4.66 (d, 1H) | Intermediate 65 |
| 61 | tert-butyl (3R,4S)-4-amino-3-fluoropiperidine-1-carboxylate | NMR (CDCl$_3$): 1.40 (s, 9H), 1.88 (m, 2H), 3.01 (m, 2H), 3.55 (m, 2H), 3.77 (m, 1H), 4.66 (d, 1H) | Intermediate 58 |
| 62 | tert-Butyl [(3R,4R)-3-methoxypiperidin-4- | NMR (CDCl$_3$): 1.45 (s, 9H), 2.43 (m, 1H), 2.50-2.57 (m, | Intermediate 66 |

-continued

| Int | Compound | Data | SM |
|---|---|---|---|
| | yl]carbamate | 1H), 2.59-2.66 (m, 1H), 2.89 (m, 1H), 3.01 (m, 1H), 3.24 (m, 1H), 3.41 (s, 3H), 3.67 (m, 1H), 4.71 (m, 1H) | |
| 63 | tert-Butyl [(3S,4S)-3-methoxypiperidin-4-yl]carbamate | NMR (CDCl$_3$): 1.45 (s, 9H), 2.43 (m, 1H), 2.50-2.57 (m, 1H), 2.59-2.66 (m, 1H), 2.89 (m, 1H), 3.01 (m, 1H), 3.24 (m, 1H), 3.41 (s, 3H), 3.67 (m, 1H), 4.71 (m, 1H) | Intermediate 67 |
| 64 | tert-butyl (3S,4R)-4-amino-3-fluoropiperidine-1-carboxylate | NMR (CDCl$_3$): 1.40 (s, 9H), 1.88 (m, 2H), 3.01 (m, 2H), 3.55 (m, 2H), 3.77 (m, 1H), 4.66 (d, 1H) | Intermediate 57 |

Intermediate 65

Trans(±)tert-butyl 4-(benzylamino)-3-fluoropiperidine-1-carboxylate

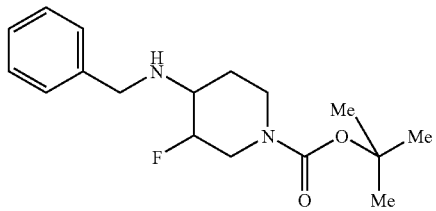 [SMILES: CC(C)(C)OC(=O)N1CCC(NCc2ccccc2)C(F)C1]

The title compound was prepared as described in Monique B. van Neil et al. *J. Med. Chem.*, 1999, 42, 2087-2104 and the references therein. NMR (CDCl$_3$): 1.40 (s, 9H), 1.88 (m, 2H), 3.01 (m, 2H), 3.55 (m, 2H), 3.77 (m, 1H), 4.66 (d, 1H).

Intermediate 66 tert-Butyl [(3R,4R)-1-benzyl-3-methoxypiperidin-4-yl]carbamate

The title compound (150 mg) was prepared from tert-butyl [(3R,4R)-1-benzyl-3-hydroxypiperidin-4-yl]carbamate by the procedure described (for similar compounds) in *Synth. Commun.*, 2001, 31, 1081-1089. NMR (CDCl$_3$): 1.44 (s, 9H), 1.97-2.11 (m, 3H), 2.68 (d, 1H), 3.07-3.12 (m, 2H), 3.36 (s, 3H), 3.41 (m, 1H), 3.52 (m, 2H), 4.51 (m, 1H), 7.23-7.32 (m, 5H).

Intermediate 67 tert-Butyl [(3 S,4 S)-1-benzyl-3-methoxypiperidin-4-yl]carbamate

The title compound (426 mg) was prepared from tert-butyl [(3S,4S)-1-benzyl-3-hydroxypiperidin-4-yl]carbamate by the procedure described (for similar compounds) in *Synth. Commun.*, 2001, 31, 1081-1089. NMR (CDCl$_3$): 1.44 (s, 9H), 1.97-2.11 (m, 3H), 2.68 (d, 1H), 3.07-3.12 (m, 2H), 3.36 (s, 3H), 3.41 (m, 1H), 3.52 (m, 2H), 4.51 (m, 1H), 7.23-7.32 (m, 5H).

Intermediates 68-69

The following Intermediates were prepared by the procedure described in Example 1 from the starting materials (SM) indicated.

| Int | Compound | Data | SM |
|---|---|---|---|
| 68 | 2-{(3R,4R)-4-[(tert-Butoxycarbonyl)amino]-3-methoxypiperidin-1-yl}-1,3-thiazole-5-carboxylate | MS (ES) (M + Na): 394 for C$_{16}$H$_{25}$N$_3$O$_5$S; NMR (CDCl$_3$): 1.46 (s, 9H), 1.66 (m, 1H), 1.89 (m, 1H), 2.29 (m, 1H), 3.13-3.20 (m, 3H), 3.47 (s, 3H), 3.75 (m, 1H), 3.83 (s, 3H), 4.20 (m, 1H), 4.60 (brs, 1H), 7.85 (s, 1H) | Intermediate 62 and methyl 2-bromo-1,3-thiazole-5-carboxylate |
| 69 | 2-{(3S,4S)-4-[(tert-Butoxycarbonyl)amino]-3-methoxypiperidin-1-yl}-1,3-thiazole-5-carboxylate | MS (ES) (M + Na): 394 for C$_{16}$H$_{25}$N$_3$O$_5$S; NMR (CDCl$_3$): 1.46 (s, 9H), 1.66 (m, 1H), 1.89 (m, 1H), 2.29 (m, 1H), 3.13-3.20 (m, 3H), 3.47 (s, 3H), 3.75 (m, 1H), 3.83 (s, 3H), 4.20 (m, 1H), 4.60 (brs, 1H), 7.85 (s, 1H) | Intermediate 63 and methyl 2-bromo-1,3-thiazole-5-carboxylate |

Intermediate 70

1-tert-Butyl-3-methyl-4-aminopiperidine-1,3-dicarboxylate

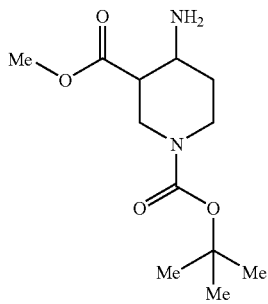 [SMILES: COC(=O)C1CN(C(=O)OC(C)(C)C)CCC1N]

The title compound was prepared according to (Cordero, F. M et al. *Gazz. Chim. Ital.* 1997, 127, 25-29). Thus, 1-tert-butyl-3-methyl-4-hydroxy-5,6-dihydropyridine-1,3-(2H)-dicarboxylate (Intermediate 9; 33 g) and $NH_4OAc$ (100 g) were dissolved in dry MeOH (250 ml). $NaCNBH_3$ (8.1 g) was added in three equal portions at 1 h intervals. The reaction mixture was stirred at room temperature overnight. The reaction was monitored by GC/MS and additional $NH_4OAc$ (2.5 equiv.) and $NaCNBH_3$ (0.25 equiv.) were added until reaction was completed. The reaction was cooled to −10° C. and acidified to pH=2 with concentrated HCl and solvent was removed in vacuo. The solid residue was dissolved in water, and extracted with $Et_2O$. The pH of the aqueous phase was adjusted to 8-9 with solid KOH, solution saturated with NaCl and extracted with EtOAc. The organic layer was dried over $K_2CO_3$, filtered and concentrate to an oil (25 g). GC/MS: 258 for $C_{12}H_{22}N_2O_4$.

Intermediate 71

Cis(±)tert-butyl-4-{[(3,4-dichloro-5-methyl-1H-pyrrol-2-yl)carbonyl]amino}-3-(hydroxymethyl)piperidine-1-carboxylate Cis(±)1-tert-butyl-3-methyl-4-{[(3,4-dichloro-5-methyl-1H-pyrrol-2-yl)carbonyl]amino}-piperidine-1,3-dicarboxylate (Intermediate 46; 4.26 g) and $LiBH_4$ (321 mg) were combined in dry THF (20 ml). MeOH (600 µl) was added in a single portion. The reaction was heated to reflux for 1 h. The mixture was cooled to room temperature, diluted with EtOAc and washed with 0.5% HCl. The organic layer was dried over $Na_2SO_4$, filtered and concentrated to a solid which was purified by flash column chromatography eluting with (60% EtOAc/40% hexanes), to yield title compound (3.11 g). MS (ES)($MH^+$): 406 for $C_{17}H_{25}Cl_2N_3O_4$; NMR ($CDCl_3$): 1.47 (s, 9H), 1.56 (m, 1H), 1.96 (m, 1H), 2.27 (s, 3H), 2.84 (m, 1H), 2.9 (m, 1H), 3.49 (m, 1H), 3.71 (m, 1H), 4.16 (m, 5H), 6.58 (d, 1H), 10.1 (brs, 1H).

Intermediate 72

Cis(±)tert-butyl-4-{[(3,4-dichloro-5-methyl-1H-pyrrol-2-yl)carbonyl]amino}-3-({[(4-methylphenyl)sulfonyl]oxy}methyl)piperidine-1-carboxylate Cis(±)tert-butyl-4-{[(3,4-dichloro-5-methyl-1H-pyrrol-2-yl)carbonyl]amino}-3-(hydroxymethyl)piperidine-1-carboxylate (Intermediate 71; 1.46 g) was dissolved in dry pyridine (20 ml) and cooled to 0° C. Tosylchloride (822 mg) was added in a single portion. The reaction was allowed to slowly warm to room temperature and stirred overnight. The mixture was diluted with EtOAc and washed with water, dried over $Na_2SO_4$, filtered and concentrated in vacuo. The foam was purified by flash column chromatography eluting with (40% EtOAc/60% hexanes) to give title compound (1.58 g). MS (ES)($MH^+$): 560 for $C_{24}H_{31}Cl_2N_3O_6S$; NMR ($CDCl_3$): 1.46 (brs, 11H), 1.89 (m, 1H), 1.98 (m, 1H), 2.31 (s, 3H), 2.35 (s, 3H), 2.8 (m, 2H), 3.96-4.23 (m, 4H), 6.4 (d, 1H), 7.19 (d, 2H), 7.68 (d, 2H), 10.3 (brs, 1H).

Intermediate 73

Cis(±)4-[(3,4-Dichloro-5-methyl-1H-pyrrole-2-carbonyl)-amino]-3-methoxymethyl-piperidine-1-carboxylic acid tert-butyl ester Cis-tert-butyl-4-{[(3,4-dichloro-5-methyl-1H-pyrrol-2-yl)carbonyl]amino}-3-({[(4-methylphenyl)sulfonyl]oxy}methyl)piperidine-1-carboxylate (Intermediate 72; 325 mg) was dissolved in 5 ml of a 30 wt % MeOH solution containing NaOMe and an additional 5 ml of dry MeOH. The homogeneous reaction was stirred at room temperature for 2 days. Upon reacting, solids began to precipitate from solution. The reaction was concentrated to a solid residue, re-dissolved in EtOAc and washed with saturated $NH_4Cl$ (2×10 ml). The organic layer was dried over $Na_2SO_4$, filtered and concentrated. The residual material was purified by flash column chromatography eluting with (1:1 EtOAc/hexanes) to give the title compound (192 mg). MS (ES)($MH^+$): 420 for $C_{19}H_{27}Cl_2N_3O_4$.

Intermediate 74

Cis(±)3,4-dichloro-N-[3-(methoxymethyl)piperidin-4-yl]-5-methyl-1H-pyrrole-2-carboxamide hydrochloride Cis(±)tert-butyl 4-{[(3,4-dichloro-5-methyl-1H-pyrrol-2-yl)carbonyl]amino}-3-(methoxymethyl)piperidine-1-carboxylate (Intermediate 73; 192 mg, 0.45 mmol) was dissolved in 4N HCl in dioxane (10 ml) and 10 ml of MeOH. The mixture was stirred at room temperature for 3 h, concentrated to dryness and azeotroped with MeOH to remove excess HCl (5×20 ml) to yield the title compound which was used without purification. (crude mixture 195 mg). MS (ES)($MH^+$): 320 for $C_{13}H_{19}Cl_2N_3O_2$.

Intermediates 75-76

The following Intermediates were prepared by the procedure described in Intermediate 74 from the starting materials (SM) indicated.

| Int | Compound | Data | SM |
|---|---|---|---|
| 75 | Cis(±)3,4-Dichloro-5-methyl-1H-pyrrole-2-carboxylic acid (3-methylaminomethyl-piperidin-4-yl)-amide hydrochloride | MS (ES) MH$^+$: 319 for $C_{13}H_{20}Cl_2N_4O$ | Intermediate 77 |
| 76 | Cis-3,4-dichloro-5-methyl-1H-pyrrole-2-carboxylic acid (3-dimethylaminomethyl-piperidin-4-yl)-amide hydrochloride | MS (ES) MH$^+$: 333 for $C_{14}H_{22}Cl_2N_4O$ | Intermediate 78 |

Intermediate 77

Cis(±)4-[(3,4-Dichloro-5-methyl-1H-pyrrole-2-carbonyl)-amino]-3-methylaminomethyl-piperidine-1-carboxylic acid tert-butyl ester Cis(±)tert-butyl-4-{[(3,4-dichloro-5-methyl-1H-pyrrol-2-yl)carbonyl]amino}-3-({[(4-methylphenyl)sulfonyl]oxy}methyl)-piperidine-1-carboxylate (Intermediate 72; 500 mg, 0.89 mmol) was dissolved in 5 ml of a 2.0 M THF solution containing MeNH$_2$. The reaction vessel was sealed and heated to 100° C. for 2 h. The mixture was cooled to room temperature and diluted with EtOAc, then washed with water. The organic layer was dried over Na$_2$SO$_4$, filtered and concentrated to a crude solid foam which was used without further purification. MS (ES)MH$^+$: 419 for $C_{18}H_{28}Cl_2N_4O_3$.

Intermediate 78

The title compound was prepared in a manner analogous to Intermediate 77 from the starting material indicated.

| Int | Compound | MS | SM |
|---|---|---|---|
| 78 | Cis(±)4-[(3,4-Dichloro-5-methyl-1H-pyrrole-2-carbonyl)-amino]-3-dimethylaminomethyl-piperidine-1-carboxylic acid tert-butyl ester | MS (ES) MH$^+$: 433 for $C_{19}H_{30}Cl_2N_4O_3$ | Intermediate 72 and dimethylamine |

Intermediate 79

Cis(±)4-{[(3,4-Dichloro-5-methyl-1H-pyrrol-2-yl)carbonyl]amino}piperidine-3-carboxylic acid hydrochloride THF (10 ml) and MeOH (8 ml) were added to cis(±)1-tert-butyl 3-methyl 4-{[(3,4-dichloro-5-methyl-1H-pyrrol-2-yl)carbonyl]amino}piperidine-1,3-dicarboxylate (Intermediate 46; 2.24 g). The resultant mixture was cooled to 0° C., and a solution of lithium hydroxide (0.37 g) in water (5 ml) at 0° C. was added dropwise via pipette, producing a clear, lightly yellow solution. The reaction was stirred at 0° C. for 2 h, stored overnight in a freezer without stirring, then stirred again at 0° C. for six hours. The reaction was acidified to pH 3 with 2N HCl 9-7 ml), and was concentrated in vacuo. The resultant mixture was dissolved in EtOAc (125 ml) and a saturated aqueous sodium chloride solution (40 ml), followed by the addition of 2N HCl (~1 ml) to acidify the aqueous layer to pH 1. The phases were separated and the aqueous layer was washed with EtOAc (2×60 ml). The combined EtOAc layers were dried over anhydrous MgSO$_4$ and concentrated in vacuo. The resultant white solid was suspended in anhydrous THF (35 ml) under an argon atmosphere, cooled to 0° C., followed by the addition of 4 M HCl in 1,4-dioxane (10 ml, 40 mmol). The reaction was warmed to room temperature, producing a clear orange-red solution. The reaction was stirred overnight at room temperature, followed by the addition of 5 ml of 4 M HCl in 1,4-dioxane. The reaction was stirred for two days at room temperature, then heated to 50° C. for two hours, and allowed to slowly cool to room temperature overnight. The reaction was concentrated in vacuo, and carried on to the next reaction without further purification (5.16 mmol). MS (ES)(M+H)): 320, 322 for $C_{12}H_{15}Cl_2N_3O_3$.

Intermediate 80

2,2,2-Trichloro-1-(3,4-difluoro-5-methyl-1H-pyrrol-2-yl)ethanone

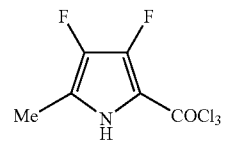

3,4-Difluoro-2-methyl-1H-pyrrole (Intermediate 8; 3.8 g) was dissolved in anhydrous diethyl ether (100 ml). Anhydrous K$_2$CO$_3$ (12.5 g) was added followed by trichloroacetyl chloride (10 ml). The mixture was stirred at room temperature under N$_2$ for 2 h, poured into a cold saturated solution of NaHCO$_3$, stirred for 10 min, and extracted with ether. The combined organic layers were dried over Na$_2$SO$_4$ and concentrated in vacuo to give a red brown oil. Trituration with pentane (50 ml)/DCM (2 ml), at −20° C. overnight to gave the title compound as a brown powder (1.3 g). MS (ES) MH$^+$: 262 for $C_7H_4Cl_3F_2NO$; NMR (CDCl$_3$): 2.35 (d, 3H), 9.0 (brs, 1H).

Intermediate 81

Cis(±)ethyl-4-[(tert-butoxycarbonyl)amino]-3-(propoxypiperidine-1-carboxylate

Cis(±)ethyl-3-(allyloxy)-4-[(tert-butoxycarbonyl)amino]piperidine-1-carboxylate (Intermediate 27; 528 mg) was dissolved in MeOH (20 ml). 10% Pd—C (100 mg) was added and the mixture was evacuated and replaced with $H_2$ gas twice. The mixture was stirred under an atmosphere of $H_2$ gas for 12 h. The catalyst was removed over a bed of celite and solvent was removed in vacuo to give the title compound as an oil (445 mg). NMR: 0.94 (m, 3H), 1.25 (m, 3H), 1.43 (s, 9H), 1.53 (m, 2H), 1.71 (m, 1H), 3.04 (m, 2H), 3.37 (m, 2H), 3.50 (m, 2H), 3.69 (m, 1H), 3.89 (m, 1H), 4.15 (m, 2H), 6.5 (d, 1H).

Intermediate 82

Cis(±)tert-butyl 4-(benzylamino)-3-fluoropiperidine-1-carboxylate

The title compound was prepared as described in Monique B. van Neil et al. *J. Med. Chem.*, 1999, 42, 2087-2104 and the references therein. NMR (CDCl$_3$): 1.40 (s, 9H), 1.88 (m, 2H), 3.01 (m, 2H), 3.55 (m, 2H), 3.77 (m, 1H), 4.66 (d, 1H).

Examples 87-193

The following Examples were prepared by the procedure described in Example 1 from the starting materials (SM) indicated.

| Ex | Compound | Data | SM |
|---|---|---|---|
| 87 | Cis(±)-methyl 2-[4-{[(3,4-dichloro-5-methyl-1H-pyrrol-2-yl)carbonyl]amino}-3-(hydroxymethyl)piperidin-1-yl]-1,3-thiazole-5-carboxylate. | MS (ES) MH$^+$: 447, 449 for C$_{17}$H$_{20}$Cl$_2$N$_4$O$_4$S. | Intermediate 115 and methyl 2-bromo-1,3-thiazole-5-carboxylate |
| 88 | Cis(±)-methyl 2-{4-{[(3,4-dichloro-5-methyl-1H-pyrrol-2-yl)carbonyl]amino}-3-[(methylthio)methyl]piperidin-1-yl}-1,3-thiazole-5-carboxylate. | MS (ES) MH$^+$: 477, 479 for C$_{18}$H$_{22}$Cl$_2$N$_4$O$_3$S$_2$. | Intermediate 116 and methyl 2-bromo-1,3-thiazole-5-carboxylate |
| 89 | Cis(±)-methyl 2-{4-{[(3,4-dichloro-5-methyl-1H-pyrrol-2-yl)carbonyl]amino}-3-[(methylsulfinyl)methyl]piperidin-1-yl}-1,3-thiazole-5-carboxylate | MS (ES) MH$^+$: 493, 495 for C$_{18}$H$_{22}$Cl$_2$N$_4$O$_4$S$_2$. | Example 88 and methyl 2-bromo-1,3-thiazole-5-carboxylate |
| 90 | Cis(±)-methyl 2-{4-{[(3,4-dichloro-5-methyl-1H-pyrrol-2-yl)carbonyl]amino}-3-[(methylsulfonyl)methyl]piperidin-1-yl}-1,3-thiazole-5-carboxylate | MS (ES) MH$^+$: 509, 511 for C$_{18}$H$_{22}$Cl$_2$N$_4$O$_5$S$_2$. | Example 88 and methyl 2-bromo-1,3-thiazole-5-carboxylate |
| 91 | Ethyl 2-((3S,4R)-4-{[(3,4-dichloro-5-methyl-1H-pyrrol-2-yl)carbonyl]amino}-3-fluoropiperidin-1-yl)-5-methyl-1,3-thiazole-4-carboxylate. | MS (ES) MH$^+$: 463, 465 for C$_{18}$H$_{21}$Cl$_2$FN$_4$O$_3$S. | Intermediate 36 and Intermediate 179 |
| 92 | Ethyl 2-((3S,4R)-4-{[(3,4-dichloro-5-methyl-1H-pyrrol-2-yl)carbonyl]amino}-3-methoxypiperidin-1-yl)-5-methyl-1,3-thiazole-4-carboxylate | MS (ES) MH$^+$: 475, 477 for C$_{19}$H$_{24}$Cl$_2$N$_4$O$_4$S. | Intermediate 51 and Intermediate 179 |
| 93 | Ethyl 2-((3S,4R)-4-{[(3,4-dichloro-5-methyl-1H-pyrrol-2-yl)carbonyl]amino}-3-fluoropiperidin-1-yl)-5-formyl-1,3-thiazole-4-carboxylate | MS (ES) MH$^+$: 477, 479 for C$_{18}$H$_{19}$Cl$_2$FN$_4$O$_4$S. | Intermediate 36 and Intermediate 181 |
| 94 | Ethyl 2-((3S,4R)-4-{[(3,4-dichloro-5-methyl-1H-pyrrol-2-yl)carbonyl]amino}-3-fluoropiperidin-1-yl)-5-[(methoxyimino)methyl]-1,3-thiazole-4-carboxylate | MS (ES) MH$^+$: 506, 508 for C$_{19}$H$_{22}$Cl$_2$FN$_5$O$_4$S; $^1$H NMR (CDCl$_3$): 1.41 (m, 6H), 2.0 (m, 4H), 2.3 (s, 6H), 3.2 (m, 4H), 3.9 (s, 3H), 4.0 (s, 3H), 4.4 (m, 10H), 4.8 (s, 1H), | Intermediate 93 and methoxyamine hydrochloride |

| Ex | Compound | Data | SM |
|---|---|---|---|
| | | 4.9 (s, 1H), 7.0 (s, 2H), 8.5 (s, 1H); 8.8 (s, 1H), 9.6 (s, 2H) | |
| 95 | Cis(±)-methyl 2-[(-4-{[(3,4-dichloro-5-methyl-1H-pyrrol-2-yl)carbonyl]amino}-3-(methylthio)piperidin-1-yl]-1,3-thiazole-5-carboxylate | MS (ES) MH+: 463.1 for $C_{17}H_{20}Cl_2N_4O_3S_2$; NMR: 1.90 (m, 2H); 2.14 (s, 3H); 2.28 (s, 3H); 3.28-3.45 (m, 2H); 3.74 (s, 3H); 3.77 (m, 1H); 3.95 (m, 2H); 4.44 (m, 1H); 7.25 (d, 1H); 7.85 (s, 1H); 12.14 (s, 1H) | Intermediate 117 and Intermediate 1 |
| 96 | Cis(±)-methyl 2-[4-{[(3,4-dichloro-5-methyl-1H-pyrrol-2-yl)carbonyl]amino}-3-(methylsulfonyl)piperidin-1-yl]-1,3-thiazole-5-carboxylate | MS (ES) MH+: 495 for $C_{17}H_{20}Cl_2N_4O_5S_2$; NMR: 1.88 (m, 2H); 2.18 (s, 3H); 3.07 (s, 3H); 3.45 (t, 1H); 3.61 (t, 1H); 3.60-3.85 (m, 2H); 3.77 (s, 3H); 4.48 (m, 1H); 4.68 (m, 1H); 7.52 (d, 1H); 7.93 (s, 1H); 12.07 (s, 1H) | Intermediate 95 |
| 97 | Cis(±)methyl 2-(3-(benzyloxy)-4-{[(3,4-dichloro-5-methyl-1H-pyrrol-2-yl)carbonyl]amino}piperidin-1-yl)-1,3-thiazole-5-carboxylate | MS (ES) MH+: 523 for $C_{23}H_{24}Cl_2N_4O_4S$; NMR: 1.73 (m, 2H); 2.12 (s, 3H); 3.36 (m, 2H); 3.68 (s, 3H); 3.71 (m, 2H); 3.90 (m, 1H); 4.25 (m, 1H); 4.40 (d, 1H), 4.65 (d, 1H); 7.02 (d, 1H); 7.19 (s, 5H); 7.79 (s, 1H); 12.06 (s, 1H) | Intermediate 118 and methyl 2-bromo-1,3-thiazole-5-carboxylate |
| 98 | Cis(±)-methyl 2-[4-{[(3,4-dichloro-5-methyl-1H-pyrrol-2-yl)carbonyl]amino}-3-(prop-2-yn-1-yloxy)piperidin-1-yl]-1,3-thiazole-5-carboxylate | MS (ES) MH+: 471 for $C_{19}H_{20}Cl_2N_4O_4S$; NMR: 1.76 (m, 2H); 2.18 (s, 3H); 3.36 (m, 2H); 3.44 (t, 1H); 3.74 (s, 3H); 3.87 (m, 1H); 3.98 (m, 1H); 4.22-4.36 (m, 4H); 7.15 (d, 1H); 7.83 (s, 1H); 12.15 (s, 1H) | Intermediate 119 and methyl-2-bromo-1,3-thiazole-5-carboxylate |
| 99 | Trans-(±)methyl 2-(4-{[(3,4-dichloro-5-methyl-1H-pyrrol-2-yl)carbonyl]amino}-3-hydroxypiperidin-1-yl)-1,3-thiazole-5-carboxylate | MS (ES) MH+: 433 for $C_{16}H_{18}Cl_2N_4O_4S$; NMR: 1.62 (m, 1H), 2.02 (m, 1H), 2.18 (s, 3H), 3.12 (m, 1H), 3.63 (m, 1H), 3.75 (s, 3H), 3.87 (m, 2H), 4.02 (m, 1H), 5.37 (d, 1H), 5.76 (s, 1H), 7.19 (d, 1H), 7.87 (s, 1H), 11.99 (s, 1H) | Intermediate 120 and methyl 2-bromo-1,3-thiazole-5-carboxylate |
| 100 | methyl 2-((3S,4R)-4-{[(3-chloro-5-methyl-1H-pyrrol-2-yl)carbonyl]amino}-3-fluoropiperidin-1-yl)-1,3-thiazole-5-carboxylate | 1.87 (m, 2H); 2.17 (s, 3H); 3.34 (m 1H); 3.60 (m 1H); 3.75 (s, 3H); 4.01 (m, 1H); 4.33 (m, 2H); 4.96 (d, br, 1H); 5.95 (s, 1H); 7.10 (d, 1H); 7.85 (s, 1H); 11.63 (s, 1H) | Intermediate 121 and methyl 2-bromo-1,3-thiazole-5-carboxylate |
| 101 | ethyl 2-((3S,4R)-4-{[(3-chloro-5-methyl-1H-pyrrol-2-yl)carbonyl]amino}-3-fluoropiperidin-1-yl)-1,3-thiazole-4-carboxylate | 1.37 (t, 3H); 2.00 (m, 2H); 2.26 (s, 3H); 3.31 (m 2H); 4.21 (m, 1H); 4.34 (q, 2H); 4.45 (m, 2H); 4.90 (d, br, 1H); 5.93 (s, 1H); 6.97 (d, 1H); 7.46 (s, 1H); 8.98 (s, br, 1H) | Intermediate 121 and ethyl 2-bromo-1,3-thiazole-4-carboxylate |
| 102 | ethyl 2-((3S,4R)-4-{[(3-chloro-5-methyl-1H-pyrrol-2-yl)carbonyl]amino}-3- | MS (ES) MH+: 465 for $C_{21}H_{22}ClFN_4O_3S$ NMR δ: 1.44 (t, 3H); 2.03 | Intermediate 121 and ethyl 2-bromo-1,3-benzothiazole- |

| Ex | Compound | Data | SM |
|---|---|---|---|
| | fluoropiperidin-1-yl)-1,3-benzothiazole-7-carboxylate | (m, 2H); 2.27 (s, 3H); 3.40 (m 2H); 4.36 (m, 2H); 4.44 (q, 2H); 4.67 (m, 1H); 4.90 (d, br, 1H); 5.93 (s, 1H); 7.05 (d, 1H); 7.37 (t, 1H); 7.71 (d, 1H); 7.79 (d, 1H); 9.89 (s, br, 1H) | 7-carboxylate |
| 103 | methyl 2-((3S,4R)-4-{[(4-bromo-5-methyl-1H-pyrrol-2-yl)carbonyl]amino}-3-fluoropiperidin-1-yl)-1,3-thiazole-5-carboxylate | MS (ES) MH$^+$: 446 for C$_{16}$H$_{18}$BrFN$_4$O$_3$S; NMR: 1.97 (m, 2H); 2.23 (s, 3H); 3.34 (m 2H); 3.80 (s, 3H); 4.26 (m, 2H); 4.55 (m, 1H); 4.86 (d, br, 1H); 6.0 (d, 1H); 6.53 (s, 1H); 7.82 (s, 1H); 9.83 (s, br, 1H) | Intermediate 122 and methyl 2-bromo-1,3-thiazole-5-carboxylate |
| 104 | methyl 2-((3S,4R)-4-{[(4-bromo-3-chloro-5-methyl-1H-pyrrol-2-yl)carbonyl]amino}-3-fluoropiperidin-1-yl)-1,3-thiazole-5-carboxylate | MS (ES) MH$^+$: 480 for C$_{16}$H$_{17}$BrClFN$_4$O$_3$S; NMR δ: 1.86 (m, 2H); 2.19 (s, 3H); 3.44 (m 1H); 3.60 (m 1H); 3.75 (s, 3H); 4.01 (m, 1H); 4.33 (m, 2H); 4.96 (d, br, 1H); 7.28 (d, 1H); 7.85 (s, 1H); 12.18 (s, 1H) | Intermediate 123 and methyl 2-bromo-1,3-thiazole-5-carboxylate |
| 105 | ethyl 2-((3S,4R)-4-{[(4-bromo-3-chloro-5-methyl-1H-pyrrol-2-yl)carbonyl]amino}-3-fluoropiperidin-1-yl)-1,3-thiazole-4-carboxylate | MS (ES) MH$^+$: 494 for C$_{17}$H$_{19}$BrClFN$_4$O$_3$S; NMR δ: 1.22 (t, 3H); 1.81 (m, 2H); 2.15 (s, 3H); 3.41 (m 2H); 3.90 (m, 1H); 4.20 (q, 2H); 4.30 (m, 1H); 4.92 (d, br, 1H); 5.72 (s, 1H); 7.24 (d, 1H); 7.65 (s, 1H); 12.13 (s, 1H) | Intermediate 123 and ethyl 2-bromo-1,3-thiazole-4-carboxylate |
| 106 | isopropyl 2-((3S,4R)-4-{[(4-bromo-3-chloro-5-methyl-1H-pyrrol-2-yl)carbonyl]amino}-3-fluoropiperidin-1-yl)isonicotinate | 1.32 (d, 6H); 1.80 (m, 2H); 2.19 (s, 3H); 3.07 (m 1H); 3.27 (m, 1H); 4.37 (m, 2H); 4.71 (m, 1H); 4.97 (d, br, 1H); 5.15 (m, 1H); 6.70 (d, 1H), 7.22 (d, 1H); 7.25 (s, 1H); 8.17 (d, 1H); 12.11 (s, br, 1H) | Intermediate 123 and isopropyl 2-bromo-isonicotinate |
| 107 | methyl 2-((3S,4R)-4-{[(4-bromo-3-chloro-5-methyl-1H-pyrrol-2-yl)carbonyl]amino}-3-fluoropiperidin-1-yl)-4-(methoxymethyl)-1,3-thiazole-5-carboxylate | MS (ES) MH$^+$: 524 for C$_{18}$H$_{21}$BrClFN$_4$O$_4$S; NMR δ: 1.86 (m, 2H); 2.19 (s, 3H); 3.29 (s, 2H); 3.60 (m 2H); 3.73 (s, 3H); 4.04 (m, 1H); 4.30 (m, 2H); 4.57 (s, 3H); 4.90 (d, br, 1H); 7.27 (d, 1H); 12.17 (s, 1H) | Intermediate 123 and Intermediate 17 |
| 108 | ethyl 2-((3S,4R)-4-{[(3-chloro-5-methyl-1H-pyrrol-2-yl)carbonyl]amino}-3-fluoropiperidin-1-yl)isonicotinate | MS (ES) MH$^+$: 409 for C$_{19}$H$_{22}$ClFN$_4$O$_3$ NMR: 1.40 (t, 3H); 1.98 (m, 2H); 2.27 (s, 3H); 3.09 (m 2H); 4.38 (q, 2H); 4.47 (m, 2H); 4.84 (m, 1H); 4.90 (d, br, 1H); 5.92 (s, 1H); 7.03 (d, 1H); 7.15 (d, 1H); 7.30 (s, 1H); 8.27 (d, 1H); 9.88 (s, br, 1H) | Intermediate 121 and ethyl 2-bromo-isonicotinate |
| 109 | ethyl 2-((3S,4R)-4-{[(4-bromo-5-methyl-1H-pyrrol-2-yl)carbonyl]amino}-3-fluoropiperidin-1-yl)isonicotinate | MS (ES) MH$^+$: 409 for C$_{19}$H$_{22}$BrFN$_4$O$_3$ NMR: 1.40 (t, 3H); 1.98 (m, 2H); 2.27 (s, 3H); 3.09 (m 2H); 4.38 (q, 2H); 4.43 (m, 2H); 4.84 (m, 1H); 4.90 (d, br, 1H); 6.16 (d, 1H); 6.59 (s, 1H); 7.15 (d, 1H); 7.29 (s, 1H); 8.27 (d, 1H); 9.76 (s, br, 1H) | Intermediate 122 and ethyl 2-bromo-isonicotinate |

-continued

| Ex | Compound | Data | SM |
|---|---|---|---|
| 110 | Cis(±)-Methyl 2-[4-{[(3,4-dichloro-5-methyl-1H-pyrrol-2-yl)carbonyl]amino}-3-(2-methoxyethoxy)piperidin-1-yl]-1,3-thiazole-5-carboxylate | MS (ES) MH$^+$: 491 for $C_{19}H_{24}Cl_2N_4O_5S$; NMR: 1.72-1.80 (m, 2H), 2.17 (s, 3H), 3.13 (s, 3H), 3.25-3.42 (m, 4H), 3.52-3.60 (m, 1H), 3.65-3.75 (m, 2H), 3.73 (s, 3H); 3.85-4.05 (m, 1H); 4.20-4.35 (m, 2H), 7.14 (d, 1H), 7.82 (s, 1H), 12.14 (brs, 1H) | Intermediate 124 and methyl 2-bromo-1,3-thiazole-5-carboxylate |
| 111 | Cis(±)-Ethyl 2-[4-{[(3,4-dichloro-5-methyl-1H-pyrrol-2-yl)carbonyl]amino}-3-(2-methoxyethoxy)piperidin-1-yl]-1,3-thiazole-4-carboxylate | MS (ES) MH$^+$: 505 for $C_{20}H_{26}Cl_2N_4O_5S$ | Intermediate 124 and ethyl 2-bromo-1,3-thiazole-4-carboxylate |
| 112 | Cis(±)-Ethyl 2-[4-{[(3,4-dichloro-5-methyl-1H-pyrrol-2-yl)carbonyl]amino}-3-(2-methoxyethoxy)piperidin-1-yl]-4-methyl-1,3-thiazole-5-carboxylate | MS (ES) MH$^+$: 519 for $C_{21}H_{28}Cl_2N_4O_5S$; NMR: 1.22 (t, 3H), 1.70-1.75 (m, 2H), 2.17 (s, 3H), 2.41 (s, 3H), 3.14 (s, 3H), 3.32-3.40 (m, buried under water peak), 3.45-3.62 (m, 1H), 3.67-3.73 (m, 2H), 3.86-3.98 (m, 1H), 4.16 (q, 2H), 4.19-4.30 (m, 2H), 7.13 (d, 1H), 12.14 (s, 1H) | Intermediate 124 and ethyl 2-chloro-1,3-thiazole-5-carboxylate |
| 113 | Cis(±)-Ethyl 2-[4-{[(3,4-dichloro-5-methyl-1H-pyrrol-2-yl)carbonyl]amino}-3-(2-methoxyethoxy)piperidin-1-yl]isonicotinate | MS (ES) MH$^+$: 499 for $C_{22}H_{28}Cl_2N_4O_5$ | Intermediate 124 and ethyl 2-fluoroisonicotinate (Konno, Akinori J. Fluorine Chemistry (1998), 87(2), 137-140) |
| 114 | Cis(±)-Ethyl 2-[4-{[(3,4-dichloro-5-methyl-1H-pyrrol-2-yl)carbonyl]amino}-3-(2-methoxyethoxy)piperidin-1-yl]-1,3-benzothiazole-7-carboxylate | MS (ES) MH$^+$: 555 for $C_{24}H_{28}Cl_2N_4O_5S$ | Intermediate 124 and ethyl 2-bromo-1,3-benzothiazole-7-carboxylate |
| 115 | Methyl 2-((3S,4R)-4-{[(4-chloro-1H-pyrrol-2-yl)carbonyl]amino}-3-fluoropiperidin-1-yl)-1,3-thiazole-5-carboxylate | MS (ES) MH$^+$: 387 for $C_{15}H_{16}ClFN_4O_3S$; NMR: 1.55-1.76 (m, 1H), 1.85-2.00 (m, 1H), 3.36-3.45 (m, 1H), 3.50 (dd, 1H), 3.74 (s, 3H), 4.02-4.10 (m, 1H), 4.15-4.36 (m, 2H), 4.90 (d, 1H), 6.94-6.97 (m, 2H), 7.85 (s, 1H), 8.10 (d, 1H), 11.82 (s, 1H) | Intermediate 95 and methyl 2-bromo-1,3-thiazole-5-carboxylate |
| 116 | Ethyl 2-((3S,4R)-4-{[(4-chloro-5-methyl-1H-pyrrol-2-yl)carbonyl]amino}-3-fluoropiperidin-1-yl)-4-methyl- | MS (ES) MH$^+$: 429 for $C_{18}H_{22}ClFN_4O_3S$; NMR: 1.23 (t, 3H), 1.62-1.77 (m, 1H), 1.83-2.00 (m, 1H), 2.13 | Intermediate 260 and ethyl 2-chloro-4-methyl-1,3-thiazole-5- |

-continued

| Ex | Compound | Data | SM |
|---|---|---|---|
| | 1,3-thiazole-5-carboxylate | (s, 3H), 2.43 (s, 3H), 3.33-3.41 (m, 1H), 3.50 (dd, 1H), 3.98-4.02 (m, 1H), 4.16 (q, 2H), 4.23-4.35 (m, 2H), 4.86 (d, 1H), 6.89 (d, 1H), 7.97 (d, 1H), 11.65 (s, 1H) | carboxylate |
| 117 | Ethyl 2-((3S,4R)-4-{[(4-chloro-1H-pyrrol-2-yl)carbonyl]amino}-3-fluoropiperidin-1-yl)-4-methyl-1,3-thiazole-5-carboxylate | MS (ES) MH+: 415 for $C_{17}H_{20}ClFN_4O_3S$; NMR: 1.23 (t, 3H), 1.69-1.74 (m, 1H), 1.86-2.03 (m, 1H), 2.43 (s, 3H), 3.27-3.35 (m, 1H), 3.51 (dd, 1H), 3.98-4.05 (m, 1H), 4.16 (q, 2H), 4.23-4.33 (m, 2H), 4.88 (d, 1H), 6.94-6.98 (m, 2H), 8.85 (d, 1H), 11.81 (s, 1H) | Intermediate 95 ethyl 2-chloro-4-methyl-1,3-thiazole-5-carboxylate |
| 118 | Ethyl 2-((3S,4R)-4-{[(4,5-dichloro-1H-pyrrol-2-yl)carbonyl]amino}-3-fluoropiperidin-1-yl)-4-methyl-1,3-thiazole-5-carboxylate | MS (ES) MH+: 449 for $C_{17}H_{19}Cl_2FN_4O_3S$; NMR: 1.23 (t, 3H), 1.65-1.74 (m, 1H), 1.85-2.00 (m, 1H), 2.43 (s, 3H), 3.30-3.40 (m, 1H), 3.51 (dd, 1H), 3.98-4.05 (m, 1H), 4.16 (q, 2H), 4.21-4.35 (m, 2H), 4.88 (d, 1H), 7.06 (d, 1H), 8.15 (d, 1H), 12.78 (s, 1H) | Intermediate 128 and ethyl 2-chloro-4-methyl-1,3-thiazole-5-carboxylate |
| 119 | Methyl 2-((3S,4R)-4-{[(4,5-dichloro-1H-pyrrol-2-yl)carbonyl]amino}-3-fluoropiperidin-1-yl)-1,3-thiazole-5-carboxylate | MS (ES) MH+: 421 for $C_{15}H_{15}Cl_2FN_4O_3S$ | Intermediate 128 and methyl 2-bromo-1,3-thiazole-5-carboxylate |
| 120 | Cis(±)-Methyl 2-[4-{[(3,4-dichloro-5-methyl-1H-pyrrol-2-yl)carbonyl]amino}-3-(2-hydroxypropoxy)piperidin-1-yl]-1,3-thiazole-5-carboxylate | MS (ES) MH+: 491 for $C_{19}H_{24}Cl_2N_4O_5S$; NMR: 0.95 (d, 3H), 1.75-1.90 (m, 2H), 2.17 (s, 3H), 3.15-3.47 (peaks overlapping with $H_2O$ signal), 3.55-3.68 (m, 2H), 3.73 (s, 3H), 3.94-3.97 (m, 1H), 4.23-4.35 (m, 2H), 7.17 (d, 1H), 7.82 (s, 1H), 12.11 (s, 1H) | Intermediate 126 and methyl 2-bromo-1,3-thiazole-5-carboxylate |
| 121 | Cis(±)-Methyl 2-[4-{[(3,4-dichloro-5-methyl-1H-pyrrol-2-yl)carbonyl]amino}-3-(2-methoxypropoxy)piperidin-1-yl]-1,3-thiazole-5-carboxylate | MS (ES) MH+: 505 for $C_{20}H_{26}Cl_2N_4O_5S$ | Intermediate 125 and methyl 2-bromo-1,3-thiazole-5-carboxylate |
| 122 | ethyl 2-((3S,4R)-4-{[(3,4-dichloro-5-methyl-1H-pyrrol-2-yl)carbonyl]amino}-3-methoxypiperidin-1-yl)-1,3-benzothiazole-7-carboxylate | MS (ES) MH+: 511 for $C_{22}H_{24}Cl_2N_4O_4S$; NMR: 1.36 (t, 3H), 1.79 (m, 2H), 2.18 (s, 3H), 3.32-3.59 (m, 4H), 4.21 (m, 1H), 4.37 (m, 1H), 4.37 (q, 2H), 7.19 (d, 1H), 7.41 (t, 1H), 7.66 (m, 2H), 12.17 (s, 1H) | Intermediate 51 and 2-bromo-1,3-benzothiazole-7-carboxylate (U.S. Pat. No. 5770758) |
| 123 | ethyl 2-((3R,4S)-4-{[(3,4-dichloro-5-methyl-1H-pyrrol-2-yl)carbonyl]amino}-3-methoxypiperidin-1-yl)-1,3-benzothiazole-7-carboxylate | MS (ES) MH+: 511 for $C_{22}H_{24}Cl_2N_4O_4S$; NMR: 1.36 (t, 3H), 1.79 (m, 2H), 2.18 (s, 3H), 3.32-3.59 (m, 4H), 4.21 (m, 1H), 4.37 (m, 1H), 4.37 (q, 2H), 7.19 (d, 1H), 7.41 (t, 1H), 7.66 (m, 2H), 12.17 (s, 1H) | Intermediate 52 and 2-bromo-1,3-benzothiazole-7-carboxylate (U.S. Pat. No. 5770758) |
| 124 | Cis (±)ethyl 2-(4-{[(3,4-dichloro-5-methyl-1H-pyrrol-2- | MS (ES) MH+: 448 for $C_{17}H_{19}Cl_2FN_4O_3S$ | Intermediate 32 and ethyl 2-bromo-1,3- |

| Ex | Compound | Data | SM |
|---|---|---|---|
| | yl)carbonyl]amino}-3-fluoropiperidin-1-yl)-1,3-thiazole-4-carboxylate | | thiazole-4-carboxylate |
| 125 | ethyl 2-((3S,4R)-4-{[(4-chloro-5-methyl-1H-pyrrol-2-yl)carbonyl]amino}-3-methoxypiperidin-1-yl)-1,3-benzothiazole-7-carboxylate | MS (ES) MH$^+$: 475 for $C_{22}H_{24}ClN_4O_4S$ | Intermediate 129 and 2-bromo-1,3-benzothiazole-7-carboxylate (U.S. Pat. No. 5770758) |
| 126 | Cis(±)methyl 2-(4-{[(4-chloro-3,5-dimethyl-1H-pyrrol-2-yl)carbonyl]amino}-3-methoxypiperidin-1-yl)-1,3-thiazole-5-carboxylate | MS (ES) MH$^+$: 427 for $C_{18}H_{23}ClN_4O_4S$ | Intermediate 130 and methyl 2-bromo-1,3-thiazole-5-carboxylate |
| 127 | Cis(±)ethyl 2-(4-{[(3,4-dichloro-5-methyl-1H-pyrrol-2-yl)carbonyl]amino}-3-methoxypiperidin-1-yl)[1,3]thiazolo[4,5-b]pyridine-7-carboxylate | MS (ES) MH$^+$: 513 for $C_{21}H_{23}Cl_2N_5O_4S$ | Intermediate 51 and Intermediate 204 |
| 128 | ethyl 2-((3S,4R)-4-{[(3,4-dichloro-5-methyl-1H-pyrrol-2-yl)carbonyl]amino}-3-fluoropiperidin-1-yl)-1,3-thiazole-4-carboxylate | MS (ES) MH$^+$: 448 for $C_{17}H_{19}Cl_2FN_4O_3S$ | Intermediate 31 and ethyl 2-bromo-1,3-thiazole-4-carboxylate |
| 129 | ethyl 2-((3S,4R)-4-{[(4-chloro-3,5-dimethyl-1H-pyrrol-2-yl)carbonyl]amino}-3-fluoropiperidin-1-yl)-1,3-thiazole-4-carboxylate | MS (ES) MH$^+$: 448 for $C_{18}H_{22}ClFN_4O_3S$ | Intermediate 130 and ethyl 2-bromo-1,3-thiazole-4-carboxylate |
| 130 | ethyl 2-((3R,4S)-4-{[(3,4-dichloro-5-methyl-1H-pyrrol-2-yl)carbonyl]amino}-3-fluoropiperidin-1-yl)-1,3-thiazole-4-carboxylate | MS (ES) MH$^+$: 448 for $C_{17}H_{19}Cl_2FN_4O_3S$ | Intermediate 33 and ethyl 2-bromo-1,3-thiazole-4-carboxylate |
| 131 | Cis(±)methyl 2-(3-chloro-4-{[(3,4-dichloro-5-methyl-1H-pyrrol-2-yl)carbonyl]amino}piperidin-1-yl)-1,3-thiazole-5-carboxylate | MS (ES) MH$^+$: 451 for $C_{16}H_{17}Cl_3N_4O_3S$; NMR: 1.17 (t, 3H), 1.84 (m, 1H), 1.93 (m, 1H), 2.20 (s, 3H), 3.45 (m, 1H), 3.75 (s, 3H), 3.82 (d, 1H), 4.02 (m, 1H), 4.26 (m, 1H), 4.50 (m, 1H), | Intermediate 131 and 2-bromo-1,3-thiazole-5-carboxylate |

-continued

| Ex | Compound | Data | SM |
|---|---|---|---|
| | | 4.76 (s, 1H), 7.15 (d, 1H), 7.85 (s, 1H), 12.12 (s, 1H) | |
| 132 | methyl 2-{(3S,4R)-4-[({4-chloro-3-[(E)-(methoxyimino)methyl]-5-methyl-1H-pyrrol-2-yl}carbonyl)amino]-3-fluoropiperidin-1-yl}-1,3-thiazole-5-carboxylate | MS (ES) MH+: 456 for $C_{18}H_{21}ClFN_5O_4S$; | Intermediate 132 and methyl-2-bromo-1,3-thiazole-5-carboxylate |
| 133 | Cis(±)-ethyl 2-(3-chloro-4-{[(3,4-dichloro-5-methyl-1H-pyrrol-2-yl)carbonyl]amino}piperidin-1-yl)-1,3-benzothiazole-7-carboxylate | MS (ES) MH+: 515 for $C_{21}H_{21}Cl_3N_4O_3S$ | Intermediate 131 and 2-bromo-1,3-benzothiazole-7-carboxylate (U.S. Pat. No. 5770758) |
| 134 | Cis(±)-ethyl 2-(3-chloro-4-{[(3,4-dichloro-5-methyl-1H-pyrrol-2-yl)carbonyl]amino}piperidin-1-yl)-4-(hydroxymethyl)-1,3-thiazole-5-carboxylate | MS (ES) MH+: 495 for $C_{18}H_{21}Cl_3N_4O_4S$ and Intermediate | Intermediate 131<br><br>215 |
| 135 | Cis(±)-methyl 2-(3-chloro-4-{[(4-chloro-5-methyl-1H-pyrrol-2-yl)carbonyl]amino}piperidin-1-yl)-1,3-thiazole-5-carboxylate | MS (ES) MH+: 417 for $C_{16}H_{18}Cl_2N_4O_3S$ | Intermediate 133 and methyl 2-bromo-1,3-thiazole-5-carboxylate |
| 136 | Cis(±)-methyl 2-(3-chloro-4-{[(3,4-dichloro-5-methyl-1H-pyrrol-2-yl)carbonyl]amino}piperidin-1-yl)-4-(methoxymethyl)-1,3-thiazole-5-carboxylate | MS (ES) MH+: 495 for $C_{18}H_{21}Cl_3N_4O_4S$ | Intermediate 131 and Intermediate 17 |
| 137 | Cis(±)-ethyl 2-(4-{[(3,4-dichloro-5-methyl-1H-pyrrol-2-yl)carbonyl]amino}-3-methoxypiperidin-1-yl)-5-nitroisonicotinate | MS (ES) MH+: 500 for $C_{20}H_{23}Cl_2N_5O_6$; NMR: 1.3 (t, 3H), 1.65 (m, 1H), 1.8 (m, 1H), 2.2 (s, 3H), 3.2-3.3 (m 6H), 3.6 (m 1H), 4.3 (m, 3H), 7.1 (m, 2H), 8.9 (s, 1H), 12.1 (s, 1H) | Intermediate 226 and Intermediate 50 |
| 138 | Cis(±)-methyl 2-(4-{[(3,4-dichloro-5-methyl-1H-pyrrol-2-yl)carbonyl]amino}-3-methylpiperidin-1-yl)-1,3-thiazole-5-carboxylate | MS (ES) MH+: 431 for $C_{17}H_{20}Cl_2N_4O_3S$; NMR: 0.9 (d, 3H), 1.8 (m, 2H), 2.2 (m, 4H), 3.2 (m 3H), 3.4-3.7 (m, 3H), 3.7 (s, 3H), 4.1 (m, 1H), 4.25 (m, 1H), 7.1 (d, 1H), 7.9 (s, 1H), 12.0 (s, 1H) | methyl 2-bromo-1,3-thiazole-5-carboxylate and Intermediate 134 |
| 139 | Cis(±)-methyl 2-(4-{[(3,4-dichloro-5-methyl-1H-pyrrol-2-yl)carbonyl]amino}-2-methylpiperidin-1-yl)-1,3-thiazole-5-carboxylate | MS (ES) MH+: 431 for $C_{17}H_{20}Cl_2N_4O_3S$; NMR: 1.3 (d, 1H), 1.8-2.1 (m, 4H), 2.2 (s, 3H), 3.5 (m, 1H), 3.7 (m, 4H), 4.1 (m, 2H), 7.3 (s, 1H), 7.9 (s, 1H), 12.0 (s, 1H) | methyl 2-bromo-1,3-thiazole-5-carboxylate and Intermediate 135 |

-continued

| Ex | Compound | Data | SM |
|---|---|---|---|
| 140 | Cis(±)-isopropyl 2-(4-{[(3,4-dichloro-5-methyl-1H-pyrrol-2-yl)carbonyl]amino}-3-methoxypiperidin-1-yl)-6-methylisonicotinate | MS (ES) MH+: 483 for $C_{22}H_{28}Cl_2N_4O_4$; NMR: 0.9 (m, 1H), 1.3 (d, 6H), 1.7, (m, 1H), 2.2 (s, 3H), 2.4 (s, 3H), 3.1 (m, 2H), 3.5 (m, 1H), 4.2 (m, 2H), 4.7 (d, 1H), 5.1 (m, 1H), 6.8 (s, 1H), 7.0 (s, 1H), 7.15 (s, 1H), 12.1 (s, 1H) | Intermediate 227 and Intermediate 50 |
| 141 | Cis(±)-isopropyl 5-chloro-4-(4-{[(3,4-dichloro-5-methyl-1H-pyrrol-2-yl)carbonyl]amino}-3-methoxypiperidin-1-yl)pyridine-2-carboxylate | MS (ES) MH+: 503 for $C_{21}H_{25}Cl_3N_4O_4$ | Intermediate 226 and Intermediate 50 |
| 142 | ethyl 2-((3S,4R)-4-{[(3,4-dichloro-5-methyl-1H-pyrrol-2-yl)carbonyl]amino}-3-fluoropiperidin-1-yl)-4-(hydroxymethyl)-1,3-thiazole-5-carboxylate | MS (ES) MH+: 479 for $C_{18}H_{21}Cl_2FN_4O_4S$; NMR: 1.2 (t, 3H), 1.9 (m, 2H), 2.2 (s, 3H), 3.6 (dd, 1H), 4.0-4.2 (m, 1H), 4.2 (q, 2H), 4.25-4.45 (m, 1H), 4.6 (s, 2H), 4.9 (m, 1H), 5.05 (m, 1H), 7.2 (d, 1H), 12.1 (s, 1H) | Intermediate 215 and Intermediate 36 |
| 143 | Cis(±)-ethyl 2-(4-{[(3,4-dichloro-5-methyl-1H-pyrrol-2-yl)carbonyl]amino}-3-methoxypiperidin-1-yl)-4-(hydroxymethyl)-1,3-thiazole-5-carboxylate | MS (ES) MH+: 491 for $C_{19}H_{24}Cl_2N_4O_5S$; NMR: 1.2 (t, 3H), 1.7 (m, 2H), 2.2 (s, 3H), 3.4 (s, 3H), 3.55 (m, 1H), 4.0 (m, 1H), 4.1-4.4 (m, 4H), 4.6 (s, 2H), 7.1 (d, 1H), 12.1 (s, 1H) | Intermediate 215 and Intermediate 50 |
| 144 | Cis(±)-ethyl 2-(4-{[(4-chloro-3-cyano-5-methyl-1H-pyrrol-2-yl)carbonyl]amino}-3-methoxypiperidin-1-yl)-1,3-thiazole-5-carboxylate | MS (ES) MH+: 438 for $C_{18}H_{20}ClN_5O_4S$; NMR: 1.6-1.9 (m, 2H), 2.2 (s, 3H), 3.3 (s, 3H), 3.6 (m, 1H), 3.7 (s, 3H), 3.9 (m, 1H), 4.3 (m, 3H), 7.75 (d, 1H), 12.7 (s, 1H) | Intermediate 136 and methyl 2-bromo-1,3-thiazole-5-carboxylate |
| 145 | Cis(±)-ethyl 2-(4-{[(4-chloro-3-cyano-5-methyl-1H-pyrrol-2-yl)carbonyl]amino}-3-methoxypiperidin-1-yl)-1,3-benzothiazole-7-carboxylate | MS (ES) MH+: 502 for $C_{23}H_{24}ClN_5O_4S$; NMR: 1.35 (t, 3H), 1.6-2.0 (m, 2H), 2.2 (s, 3H), 3.3 (s, 3H), 3.4 (m, 1H), 3.6 (s, 3H), 4.1 (m, 1H), 4.3 (m, 1H), 4.4 (q, 2H), 7.7 (m, 2H), 7.8 (m, 1H), 7.9 (t, 1H), 12.7 (s, 1H) | Intermediate 136 and ethyl 2-bromo-1,3-benzothiazole-7-carboxylate (U.S. Pat. No. 5770758) |
| 146 | Cis(±)-ethyl 2-(4-{[(4-chloro-3-cyano-5-methyl-1H-pyrrol-2-yl)carbonyl]amino}-3-methoxypiperidin-1-yl)-1,3-thiazole-5-carboxylate | MS (ES) MH+: 460 for $C_{22}H_{26}ClN_5O_4$ NMR: 1.3 (d, 6H), 1.7 (m, 2H), 2.2 (s, 3H), 3.1 (s, 2H), 3.3 (s, 3H), 3.5 (s, 3H), 4.2 (m, 1H), 4.6 (d, 1H), 5.1 (m, 1H), 7.0 (s, 1H), 7.2 (s, 1H), 7.7 (d, 1H), 8.2 (d, 1H), 12.7 (s, 1H) | Intermediate 136 and Intermediate 230 |
| 147 | methyl 2-((3S,4R)-4-{[(4-chloro-3-cyano-5-methyl-1H- | MS (ES) MH+: 426 for $C_{17}H_{17}ClFN_5O_3S$; NMR: 1.9 | Intermediate 137 and methyl 2- |

| Ex | Compound | Data | SM |
|---|---|---|---|
| | pyrrol-2-yl)carbonyl]amino}-3-fluoropiperidin-1-yl)-1,3-thiazole-5-carboxylate | (m, 2H), 2.2 (s, 3H), 3.3 (s, 3H), 3.5 (dd, 1H), 3.75 (s, 3H), 4.0 (m, 1H), 4.2-4.5 (m, 2H), 5.0 (d, 1H), 7.9 (s, 1H), 8.15 (m, 1H), 12.6 (s, 1H) | bromo-1,3-thiazole-5-carboxylate |
| 148 | ethyl 2-((3S,4R)-4-{[(4-chloro-3-cyano-5-methyl-1H-pyrrol-2-yl)carbonyl]amino}-3-fluoropiperidin-1-yl)-1,3-benzothiazole-7-carboxylate | MS (ES) MH⁺: 490 for $C_{22}H_{21}ClFN_5O_3S$; NMR: 1.35 (t, 3H), 1.6-2.0 (m, 2H), 2.2 (s, 3H), 3.3 (m), 3.4 (m, 1H), 3.6 (s, 3H), 4.1 (m, 1H), 4.3 (m, 1H), 4.4 (q, 2H), 7.7 (m, 2H), 7.8 (m, 1H), 7.9 (t, 1H), 12.7 (s, 1H) | Intermediate 137 and ethyl 2-bromo-1,3-benzothiazole-7-carboxylate (U.S. Pat. No. 5770758) |
| 149 | isopropyl 2-((3S,4R)-4-{[(4-chloro-3-cyano-5-methyl-1H-pyrrol-2-yl)carbonyl]amino}-3-fluoropiperidin-1-yl)isonicotinate | MS (ES) MH⁺: 460 for $C_{21}H_{23}ClFN_5O_3$ NMR: 1.3 (d, 6H), 1.8 (m, 2H), 2.2 (s, 3H), 3.0 (m, 2H), 3.3 (m), 4.1-4.2 (m, 1H), 4.45 (d, 1H), 4.9 (d, 1H), 5.0 (m, 1H), 5.1 (m, 1H), 7.0 (d, 1H), 7.3 (s, 1H), 8.1 (d, 1H), 8.3 (d, 1H), 12.6 (s, 1H) | Intermediated 137 and Intermediate 230 |
| 150 | Cis(±)-ethyl 2-(4-{[(3,4-dichloro-5-methyl-1H-pyrrol-2-yl)carbonyl]amino}-3-methoxypiperidin-1-yl)-5-(morpholin-4-ylcarbonyl)-1,3-thiazole-4-carboxylate | MS (ES) MH⁺: 579 for $C_{23}H_{29}Cl_2N_5O_6S$; NMR: 1.2 (m, 3H), 1.75 (m, 2H), 2.2 (s, 3H), 3.3 (s, 3H), 3.4 (m, 1H), 3.5-3.6 (m, 4H), 3.8 (m, 1H), 4.2 (m, 4H), 7.15 (d, 1H), 12.1 (s, 1H) | Intermediate 231 and Intermediate 50 |
| 151 | Cis(±)-isopropyl 6-cyano-4-(4-{[(3,4-dichloro-5-methyl-1H-pyrrol-2-yl)carbonyl]amino}-3-methoxypiperidin-1-yl)pyridine-2-carboxylate | MS (ES) MH⁺: 494 for $C_{22}H_{23}Cl_2N_5O_4$; NMR: 1.3 (s, 6H), 1.8 (m, 2H), 2.25 (s, 3H), 3.4 (s, 3H), 3.6 (m, 1H), 4.1 (d, 1H), 4.3 (m, 1H), 4.5 (d, 1H), 5.2 (m, 1H), 7.2 (d, 1H), 7.65 (s, 1H), 7.8 (s, 1H), 12.2 (s, 1H) | Intermediate 231 and Intermediate 50. |
| 152 | Cis(±)-2-(4-{[(3,4-dichloro-5-methyl-1H-pyrrol-2-yl)carbonyl]amino}-3-methoxypiperidin-1-yl)-1,3-thiazole-4,5-dicarboxamide | MS (ES) MH⁺: 475 for $C_{17}H_{20}Cl_2N_6O_4S$; NMR: 1.7 (m, 2H), 2.2 (s, 3H), 3.3 (s, 3H), 3.5 (m, 1H), 4.0 (m, 1H), 4.2 (m, 1H), 4.4 (m, 1H), 7.1 (d, 1H), 7.6 (s, 1H), 8.1 (s, 1H), 8.2 (s, 1H), 10.4 (s, 1H), 12.1 (s, 1H) | 2-chloro-1,3-thiazole-4,5-dicarboxamide (Robba, M.; Le Guen, Y. Bulletin de la Societe Chimique de France (1969), (6), 2152-7) and Intermediate 50. |
| 153 | 2-((3S,4R)-4-{[(3,4-dichloro-5-methyl-1H-pyrrol-2-yl)carbonyl]amino}-3-methoxypiperidin-1-yl)-1,3-thiazole-4,5-dicarboxamide | MS (ES) MH⁺: 463 for $C_{16}H_{17}Cl_2N_6O_3S$; NMR: 1.8-1.9 (m, 2H), 2.2 (s, 3H), 3.3 (s, 3H), 3.4 (dd, 1H), 4.1 (m, 1H), 4.4 (m, 2H), 4.95 (d, 1H), 7.3 (d, 1H), 7.6 (s, 1H), 8.1 (s, 1H), 8.2 (s, 1H), 10.4 (s, 1H), 12.1 (s, 1H) | 2-chloro-1,3-thiazole-4,5-dicarboxamide (Robba, M.; Le Guen, Y. Bulletin de la Societe Chimique de France (1969), (6), 2152-7) and Intermediate 36. |
| 154 | Cis(±)-ethyl 2-(4-{[(3,4-dichloro-5-methyl-1H-pyrrol-2-yl)carbonyl]amino}-3-methoxypiperidin-1-yl)-5-formylisonicotinate | MS (ES) MH⁺: 483 for $C_{21}H_{24}Cl_2N_4O_5$ | Intermediate 202 and Intermediate 50 |

| Ex | Compound | Data | SM |
|---|---|---|---|
| 155 | ethyl 2-((3S,4R)-4-{[(3,5-dichloro-4-methyl-1H-pyrrol-2-yl)carbonyl]amino}-3-fluoropiperidin-1-yl)-1,3-thiazole-5-carboxylate | MS (ES) MH$^+$: 449 for C$_{17}$H$_{19}$Cl$_2$FN$_4$O$_3$S; NMR: 1.25 (m, 5H), 1.9 (s, 3H), 3.6 (dd, 1H), 3.9 (m, 1H), 4.3 (m, 2H), 5.0 (d, 1H), 7.3(d, 1H), 7.8 (s, 1H), 12.6 (s, 1H) | Intermediate 138 and ethyl 2-bromo-1,3-thiazole-5-carboxylate |
| 156 | 2-((3S,4R)-4-{[(3,5-dichloro-4-methyl-1H-pyrrol-2-yl)carbonyl]amino}-3-fluoropiperidin-1-yl)-5-(ethoxycarbonyl)-1,3-thiazole-4-carboxylic acid | MS (ES) MH$^+$: 465 for C$_{18}$H$_{19}$Cl$_2$FN$_4$O$_5$S; NMR: 1.25 (t, 3H), 1.8 (m, 2H), 1.9 (s, 3H), 3.5-3.8 (m, 2H), 3.9 (m, 1H), 4.2 (q, 2H), 4.3 (m, 2H), 5.0 (d, 1H), 7.4 (d, 1H), 12.6 (s, 1H), 13.6 (s, 1H) | Intermediate 138 and Intermediate 252 |
| 157 | methyl 4-acetyl-2-((3S,4R)-4-{[(3,4-dichloro-5-methyl-1H-pyrrol-2-yl)carbonyl]amino}-3-methoxypiperidin-1-yl)-1,3-thiazole-5-carboxylate | MS (ES) MH$^+$: 489 for C$_{19}$H$_{24}$Cl$_2$N$_4$O$_5$S; NMR: 1.75 (m, 2H), 2.2 (s, 3H), 2.45 (s, 3H), 3.2-3.4 (m), 3.9 (m, 1H), 4.3 (m, 2H), 7.15 (d, 1H), 12.15 (s, 1H) | Intermediate 212 and Intermediate 51 |
| 158 | methyl 2-((3S,4R)-4-{[(3,4-dichloro-5-methyl-1H-pyrrol-2-yl)carbonyl]amino}-3-methoxypiperidin-1-yl)-4-(1-hydroxy-1-methylethyl)-1,3-thiazole-5-carboxylate | MS (ES) MH$^+$: 505 for C$_{20}$H$_{26}$Cl$_2$N$_4$O$_5$S; NMR: 1.5 (s, 6H), 1.75 (m, 2H), 2.2 (s, 3H), 3.3 (s, 3H), 3.55 (m, 1H), 3.8 (s, 3H), 3.8-4.0 (m, 2H), 4.2 (m, 1H), 4.5 (m, 1H), 7.15 (d, 1H), 12.2 (s, 1H) | Intermediate 214 and Intermediate 51 |
| 159 | methyl 2-((3S,4R)-4-{[(3,4-dichloro-5-methyl-1H-pyrrol-2-yl)carbonyl]amino}-3-methoxypiperidin-1-yl)thieno[2,3-d][1,3]thiazole-6-carboxylate | MS (ES) MH$^+$: 503 for C$_{19}$H$_{20}$Cl$_2$N$_4$O$_4$S$_2$; NMR: 1.8 (m, 2H), 2.2 (s, 3H), 3.3 (m), 3.6 (m, 1H), 3.95 (m, 1H), 4.3 (m, 2H), 7.2 (d, 1H), 8.0 (s, 1H), 12.2 (s, 1H) | Intermediate 213 and Intermediate 51. |
| 160 | Cis(±)-methyl 2-(3-(cyclopropylmethoxy)-4-{[(3,4-dichloro-5-methyl-1H-pyrrol-2-yl)carbonyl]amino}piperidin-1-yl)-1,3-thiazole-5-carboxylate | MS (ESI) M: 487 for C$_{20}$H$_{24}$Cl$_2$N$_4$O$_4$S; NMR 0.11 (m, 2H), 0.38 (m, 2H), 0.91 (m, 1H), 1.76 (m, 2H), 2.17 (s, 3H), 3.24-3.45 (m, 4H), 3.68 (bs, 1H), 3.73 (s, 3H), 3.94 (m, 1H), 4.25 (m, 2H), 7.14 (d, 1H), 7.82 (s, 1H), 12.16 (s, 1H) | Intermediate 139 and methyl 2-bromo-1,3-thiazole-5-carboxylate |
| 161 | Cis(±)-methyl 2-[4-{[(3,4-dichloro-5-methyl-1H-pyrrol-2-yl)carbonyl]amino}-3-(1,3-thiazol-2-ylmethoxy)piperidin-1-yl]-1,3-thiazole-5-carboxylate | MS (ESI) M: 530 for C$_{20}$H$_{21}$Cl$_2$N$_5$O$_4$S$_2$; NMR 1.66 (s, 2H), 1.91 (m, 2H), 2.10 (qd, 1H), 2.27 (s, 3H), 3.20-3.37 (m, 2H), 3.82 (s, 3H), 3.96 (m, 2H), 4.40 (m, 1H), 4.64 (d, 1H), 4.96 (dd, 2H), 7.19 (d, 1H), 7.28 (d, 1H), 9.67 (bs, 1H) | Intermediate 140 and methyl 2-bromo-1,3-thiazole-5-carboxylate |
| 162 | Cis(±)-Methyl 2-(4-{[(3,4-dichloro-5-methyl-1H-pyrrol-2-yl)carbonyl]amino}-3-ethoxypiperidin-1-yl)-1,3- | MS (ES) MH$^+$: 461, 463 for C$_{18}$H$_{22}$Cl$_2$N$_4$O$_4$S; $^1$H-NMR: 1.04 (t, 3H); 1.75 (m, 2H); 2.17 (s, 3H); 3.35-3.45 (m, | Intermediate 141 and methyl-2-bromo-1,3-thiazole-5 carboxylate |

-continued

| Ex | Compound | Data | SM |
|---|---|---|---|
| | thiazole-5-carboxylate | 3H); 3.63 (m, 2H); 3.73 (s, 3H); 3.96 (m, 1H); 4.25 (m, 2H); 7.11 (d, 1H); 7.82 (s, 1H); 12.12 (s, 1H) | |
| 163 | Cis(±)-Methyl 2-(4-{[(3,4-dichloro-5-methyl-1H-pyrrol-2-yl)carbonyl]amino}-3-ethoxypiperidin-1-yl)-4-(methoxymethyl)-1,3-thiazole-5-carboxylate | MS (ES) MH$^+$: 505, 507 for $C_{20}H_{26}Cl_2N_4O_5S$; $^1$H-NMR: 1.05 (t, 3H); 1.74 (m, 2H); 2.17 (s, 3H); 3.27 (s, 3H); 3.39-3.47 (m, 3H); 3.63 (m, 2H); 3.71 (s, 3H); 3.96 (m, 1H); 4.23 (m, 2H); 4.55 (s, 2H); 7.12 (d, 1H); 12.16 (br s, 1H) | Intermediate 141 and Intermediate 17 |
| 164 | Cis(±)-Ethyl 2-(4-{[(3,4-dichloro-5-methyl-1H-pyrrol-2-yl)carbonyl]amino}-3-methoxypiperidin-1-yl)-4-methyl-1,3-thiazole-5-carboxylate | MS (ES) MH$^+$: 475, 477 for $C_{19}H_{24}Cl_2N_4O_4S$; $^1$H-NMR: 1.22 (t, 3H); 1.72 (m, 2H); 2.17 (s, 3H); 2.42 (s, 3H); 3.31 (m, 5H); 3.52 (m, 1H); 3.90 (m, 1H); 4.16 (q, 2H); 4.26 (m, 2H); 7.14 (d, 1H); 12.14 (brs, 1H) | Intermediate 50 and Intermediate 236 |
| 165 | Ethyl 2-((3S,4R)-4-{[(3,4-dichloro-5-methyl-1H-pyrrol-2-yl)carbonyl]amino}-3-fluoropiperidin-1-yl)-4-methyl-1,3-thiazole-5-carboxylate | MS (ES) MH$^+$: 463 465 for $C_{18}H_{21}Cl_2FN_4O_3S$; NMR: 1.23 (t, 3H); 1.85 (m, 2H); 2.18 (s, 3H); 2.43 (s, 3H); 3.35 (m, 1H overlapping water) 3.53 (dd, 1H); 4.00 (m, 1H); 4.16 (q, 2H); 4.30 (m, 2H); 4.94 (d, 1H); 7.24 (d, 1H); 12.09 (s, 1H) | Intermediate 36 and Intermediate 236 |
| 166 | Ethyl 2-((3S,4R)-4-{[(3,4-dichloro-5-methyl-1H-pyrrol-2-yl)carbonyl]amino}-3-methoxypiperidin-1-yl)-4-methyl-1,3-thiazole-5-carboxylate | MS (ES) MH$^+$: 475, 477 for $C_{19}H_{24}Cl_2N_4O_4S$; NMR: 1.22 (t, 3H); 1.72 (m, 2H); 2.17 (s, 3H); 2.42 (s, 3H); 3.31 (m, 5H); 3.52 (m, 1H); 3.90 (m, 1H); 4.16 (q, 2H); 4.26 (m, 2H); 7.14 (d, 1H); 12.14 (br s, 1H) | Intermediate 51 and Intermediate 236 |
| 167 | Trans(±)methyl 2-[4-{[(3,4-dichloro-5-methyl-1H-pyrrol-2-yl)carbonyl]amino}-3-(morpholin-4-ylcarbonyl)piperidin-1-yl]-1,3-thiazole-5-carboxylate | MS (ES) MH$^+$: 530, 532 for $C_{21}H_{25}Cl_2N_5O_5S$; NMR: 1.89 (m, 1H), 2.14 (m, 1H), 2.17 (s, 3H), 3.73 (s, 3H), 3.23-3.79 (m, 12H), 3.93 (dd, 1H), 4.51 (m, 1H), 7.33 (d, 1H), 7.84 (s, 1H), 12.08 (s, 1H) | Intermediate 142 |
| 168 | Cis(±)methyl 2-[4-{[(3,4-dichloro-5-methyl-1H-pyrrol-2-yl)carbonyl]amino}-3-(morpholin-4-ylcarbonyl)piperidin-1-yl]-1,3-thiazole-5-carboxylate | MS (ES) MH$^+$: 530, 532 for $C_{21}H_{25}Cl_2N_5O_5S$; NMR: 1.79 (dq, 1H), 1.90 (m, 1H), 2.15 (s, 3H), 3.22-3.42 (m, 6H), 3.51-3.71 (m, 5H), 3.74 (s, 3H), 3.96 (m, 1H), 4.02 (m, 1H), 4.40 (m, 1H), 7.17 (d, 1H), 7.88 (s, 1H), 12.02 (s, 1H) | Intermediate 143 |
| 169 | Cis(±)({4-{[(3,4-dichloro-5-methyl-1H-pyrrol-2-yl)carbonyl]amino}-1-[5-(methoxycarbonyl)-1,3-thiazol-2-yl]piperidin-3-yl}oxy)acetic acid | MS (ES) MH$^+$: 491, 493 for $C_{18}H_{20}Cl_2N_4O_6S$; NMR: 1.61 (dq, 1H), 2.03 (m, 1H), 2.17 (s, 3H), 3.25 (dd, 1H), 3.35 (m, 1H), 3.63 (m, 1H), 3.74 (s, 3H), 3.88 (m, 1H), 4.06 (m, 1H), 4.17 (s, 2H), 4.23 (dd, 1H), 7.58 (d, 1H), 7.86 (s, 1H), 11.99 (s, 1H), 12.76 (s, 1H) | Intermediate 144 |

| Ex | Compound | Data | SM |
|---|---|---|---|
| 170 | Cis(±)methyl 2-[4-{[(3,4-dichloro-5-methyl-1H-pyrrol-2-yl)carbonyl]amino}-3-(2-morpholin-4-yl-2-oxoethoxy)piperidin-1-yl]-1,3-thiazole-5-carboxylate | MS (ES) MH+: 560, 562 for $C_{22}H_{27}Cl_2N_5O_6S$; NMR: 1.59 (dq, 1H), 2.07 (m, 1H), 2.17 (s, 3H), 3.24 (dd, 1H), 3.27-3.56 (m, 8H), 3.61 (m, 1H), 3.74 (s, 3H), 3.85 (m, 1H), 4.05 (m, 1H), 4.24 (dd, 2H), 4.35 (q, 2H), 7.78 (d, 1H), 7.86 (s, 1H), 11.95 (s, 1H) | Example 169 |
| 171 | Methyl 2-(4-{[(3,4-dichloro-5-methyl-1H-pyrrol-2-yl)carbonyl]amino}-3-hydroxypiperidin-1-yl)-1,3-thiazole-5-carboxylate | MS (ES) MH+: 433, 435 for $C_{16}H_{18}Cl_2N_4O_4S$ | Intermediate 244 |
| 172 | Methyl 2-(4-{[(3,4-dichloro-5-methyl-1H-pyrrol-2-yl)carbonyl]amino}-3-{[(ethylamino)carbonyl]oxy}piperidin-1-yl)-1,3-thiazole-5-carboxylate | MS (ES) MH+: 504, 506 for $C_{19}H_{23}Cl_2N_5O_5S$ | Example 171 |
| 173 | Methyl 2-(3-{[(allylamino)carbonyl]oxy}-4-{[(3,4-dichloro-5-methyl-1H-pyrrol-2-yl)carbonyl]amino}piperidin-1-yl)-1,3-thiazole-5-carboxylate | MS (ES) MH+: 516, 518 for $C_{20}H_{23}Cl_2N_5O_5S$ | Example 171 |
| 174 | ethyl 4-((3S,4R)-4-{[(3,4-dichloro-5-methyl-1H-pyrrol-2-yl)carbonyl]amino}-3-fluoropiperidin-1-yl)pyridine-2-carboxylate | MS (ES) MH+: 443 for $C_{19}H_{21}Cl_2FN_4O_3$; NMR: 1.31 (t, 3H) 1.81 (s, 2H) 2.19 (s, 3H) 2.69 (s, 1H) 3.33 (s, 3H) 4.05 (s, 1H) 4.30 (q, 2H) 4.40 (s, 1H) 4.86 (d, 1H) 7.07 (dd, 2.73 Hz, 1H) 7.21 (d, 1H) 7.46 (d, 1H) 8.23 (d, 1H) 12.09 (s, 1H) | Intermediate 32 and ethyl 4-chloropyridine-2-carboxylate (WO 2004007657) |
| 175 | Cis(±)-diethyl 2-(4-{[(3,4-dichloro-5-methyl-1H-pyrrol-2-yl)carbonyl]amino}-3-methoxypiperidin-1-yl)-1,3-thiazole-4,5-dicarboxylate | MS (ES) MH+: 533 for $C_{21}H_{26}Cl_2N_4O_6S$; NMR: 1.22 (t, 3H) 1.28 (t, 3H) 1.76 (d, 2H) 2.15-2.21 (m, 3H) 3.29-3.34 (m, 3H) 3.36 (s, 3H) 3.42 (s, 1H) 3.56 (s, 1H) 3.95 (s, 1H) 4.19 (q, 2H) 4.23-4.32 (m, 3H) 7.19 (d, 1H) 12.20 (s, 1H) | Intermediate 50 and Intermediate 244 |
| 176 | diethyl 2-((3S,4R)-4-{[(3,4-dichloro-5-methyl-1H-pyrrol-2-yl)carbonyl]amino}-3-fluoropiperidin-1-yl)-1,3-thiazole-4,5-dicarboxylate | MS (ES) MH+: 521 for $C_{20}H_{23}Cl_2FN_4O_5S$; NMR: 1.22 (t, 3H) 1.28 (t, 3H) 1.86 (d, 2H) 2.19 (s, 3H) 3.31 (s, 1H) 3.41 (s, 2H) 3.68-3.71 (dd, 1H) 3.99 (s, 1H) 4.20 (q, 2H) 4.29 (q, 2H) 4.89-5.05 (d, 1H) 7.27 (d, 1H) 12.09 (s, 1H) | Intermediate 32 and Intermediate 247 |

-continued

| Ex | Compound | Data | SM |
|---|---|---|---|
| 177 | Cis(±)-ethyl 4-(4-{[(4-chloro-5-methyl-1H-pyrrol-2-yl)carbonyl]amino}-3-methoxypiperidin-1-yl)pyridine-2-carboxylate | MS (ES) MH+: 521 for $C_{20}H_{25}ClN_4O_4$ NMR: 1.31 (t, 3H) 1.62 (s, 1H) 1.79-1.95 (m, 1H) 2.10-2.19 (m, 3H) 3.07-3.19 (m, 2H) 3.23 (s, 3H) 3.45-3.54 (m, 1H) 3.89 (s, 1H) 4.18 (s, 1H) 4.22 (d, 1H) 4.30 (q, 2H) 6.89 (d, 1H) 7.04 (dd, 1H) 7.44 (d, 1H) 7.67 (d, 1H) 8.20 (d, 1H) 11.63 (s, 1H) | Intermediate 55 and ethyl 4-chloropyridine-2-carboxylate (WO 2004007657) |
| 178 | Cis(±)-ethyl 2-(4-{[(3,4-dichloro-5-methyl-1H-pyrrol-2-yl)carbonyl]amino}-3-methoxypiperidin-1-yl)-4-{[(1-methyl-1-phenylethyl)amino]carbonyl}-1,3-thiazole-5-carboxylate | MS (ES) MH+: 622 for $C_{28}H_{33}Cl_2N_5O_5S$ | Intermediate 50 and Intermediate 55 |
| 179 | ethyl 2-((3S,4R)-4-{[(3,4-dichloro-5-methyl-1H-pyrrol-2-yl)carbonyl]amino}-3-fluoropiperidin-1-yl)isonicotinate | MS (ES) MH+: 443 for $C_{19}H_{21}Cl_2FN_4O_3$ | Intermediate 32 and ethyl 2-fluoroisonicotinate (Konno, Akinori J. Fluorine Chemistry (1998), 87(2), 137-140) |
| 180 | methyl 2-((3S,4R)-4-{[(3,4-dichloro-5-methyl-1H-pyrrol-2-yl)carbonyl]amino}-3-fluoropiperidin-1-yl)-4-(methoxymethyl)-1,3-thiazole-5-carboxylate | MS (ES) MH+: 479 for $C_{18}H_{21}Cl_2FN_4O_4S$ NMR: 1.86 (s, 2H) 2.19 (s, 3H) 3.25-3.31 (s, 3H) 3.53-3.67 (dd, 1H) 3.73 (s, 3H) 4.00 (s, 2H) 4.33 (s, 2H) 4.57 (s, 2H) 4.89-5.05 (d, 1H) 7.27 (d, 1H) 12.10 (s, 1H) | Intermediate 32 and Intermediate 17 |
| 181 | ethyl 4-((3S,4R)-4-{[(3,4-dichloro-5-methyl-1H-pyrrol-2-yl)carbonyl]amino}-3-fluoropiperidin-1-yl)quinoline-2-carboxylate | MS (ES) MH+: 493 for $C_{23}H_{23}Cl_2FN_4O_3$ | Intermediate 32 and Intermediate 10 |
| 182 | ethyl 2-((3S,4R)-4-{[(4-chloro-5-methyl-1H-pyrrol-2-yl)carbonyl]amino}-3-methoxypiperidin-1-yl)isonicotinate | MS (ES) MH+: 421 for $C_{20}H_{25}ClN_4O_4$ NMR: 1.32 (t, 3H) 1.60 (d, 1H) 1.84 (s, 1H) 2.14 (s, 1H) 3.13 (d, 2H) 3.20-3.24 (m, 3H) 3.49 (s, 1H) 4.20 (d, 2H) 4.33 (q, 2H) 4.56 (s, 1H) 6.89 (d, 1H) 6.97 (d, 1H) 7.23 (s, 1H) 7.64 (d, 1H) 8.24 (d, 1H) 11.62 (s, 1H) | Intermediate 55 and ethyl 2-fluoroisonicotinate (Konno, Akinori J. Fluorine Chemistry (1998), 87(2), 137-140) |
| 183 | methyl 2-((3S,4R)-4-{[(3,4-dichloro-5-methyl-1H-pyrrol-2-yl)carbonyl]amino}-3-methoxypiperidin-1-yl)-4-(methoxymethyl)-1,3-thiazole-5-carboxylate | MS (ES) MH+: 491 for $C_{19}H_{24}Cl_2N_4O_5S$ NMR: 1.86-1.95 (m, 1H) 1.97-2.04 (m, 1H) 2.26-2.31 (m, 3H) 3.16-3.31 (m, 2H) 3.47 (s, 3H) 3.48 (s, 2H) 3.50-3.55 (m, 1H) 3.82 (s, 3H) 4.05 (d, 1H) 4.25-4.37 (m, 1H) 4.54 (s, 1H) 4.69-4.81 (m, 2H) 7.19-7.27 (m, 1H) 9.54 (s, 1H) | Intermediate 51 and Intermediate 17 |
| 184 | methyl 2-((3R,4S)-4-{[(3,4-dichloro-5-methyl-1H-pyrrol-2-yl)carbonyl]amino}-3-methoxypiperidin-1-yl)-4- | MS (ES) MH+:491 for $C_{19}H_{24}Cl_2N_4O_5S$ | Intermediate 52 and Intermediate 17 |

| Ex | Compound | Data | SM |
|---|---|---|---|
| | (methoxymethyl)-1,3-thiazole-5-carboxylate | | |
| 185 | Cis(±)-isopropyl 4-(4-{[(3,4-dichloro-5-methyl-1H-pyrrol-2-yl)carbonyl]amino}-3-methoxypiperidin-1-yl)-6-(morpholin-4-ylcarbonyl)pyridine-2-carboxylate | MS (ES) MH$^+$: 582 for $C_{26}H_{33}Cl_2N_5O_6$ | Intermediate 50 and Intermediate 249 |
| 186 | isopropyl 4-((3S,4R)-4-{[(3,4-dichloro-5-methyl-1H-pyrrol-2-yl)carbonyl]amino}-3-fluoropiperidin-1-yl)-6-(morpholin-4-ylcarbonyl)pyridine-2-carboxylate | MS (ES) MH$^+$: 570 for $C_{25}H_{30}Cl_2FN_5O_5$ NMR: 1.32 (d, 6H) 1.78-1.93 (m, 2H) 2.19 (s, 3H) 3.27-3.33 (m, 4H) 3.39 (d, 2H) 3.53-3.60 (m, 2H) 3.65 (d, 4H) 4.12 (s, 1H) 4.39 (s, 1H) 5.07-5.19 (m, 1H) 7.16-7.26 (m, 2H) 7.47 (d, 1H) 12.08 (s, 1H) | Intermediate 32 and Intermediate 249 |
| 187 | isopropyl 4-((3S,4R)-4-{[(3,4-dichloro-5-methyl-1H-pyrrol-2-yl)carbonyl]amino}-3-fluoropiperidin-1-yl)-6-[(dimethylamino)carbonyl]pyridine-2-carboxylate | MS (ES) MH$^+$: 528 for $C_{23}H_{28}Cl_2FN_5O_4$ | Intermediate 32 and Intermediate 250 |
| 188 | Cis(±)-2-(4-{[(3,4-dichloro-5-methyl-1H-pyrrol-2-yl)carbonyl]amino}-3-methoxypiperidin-1-yl)-5-(ethoxycarbonyl)-1,3-thiazole-4-carboxylic acid | MS (ES) MH$^+$: 505 for $C_{19}H_{22}Cl_2N_4O_6S$ NMR: 1.24 (t, 3H) 1.74 (s, 2H) 2.18 (s, 3H) 3.36 (s, 4H) 3.56 (s, 1H) 3.93 (s, 1H) 4.19 (s, 3H) 4.29 (s, 2H) 7.13 (s, 1H) 12.11 (s, 1H) 13.51 (s, 1H) | Intermediate 50 and Intermediate 252 |
| 189 | 2-((3S,4R)-4-{[(3,4-dichloro-5-methyl-1H-pyrrol-2-yl)carbonyl]amino}-3-fluoropiperidin-1-yl)-5-(ethoxycarbonyl)-1,3-thiazole-4-carboxylic acid | MS (ES) MH$^+$: 493 for $C_{18}H_{19}Cl_2FN_4O_5S$ NMR: 1.19-1.27 (m, 3H) 1.85 (d, 2H) 2.18 (s, 3H) 3.26-3.35 (m, 1H) 3.53 (d, 1H) 3.98 (s, 2H) 4.18 (q, 1H) 4.31 (s, 2H) 4.88-5.04 (s, 1H) 7.26 (d, 1H) 12.08 (s, 1H) 13.55 (s, 1H) | Intermediate 32 and Intermediate 252 |
| 190 | 2-((3R,4S)-4-{[(3,4-dichloro-5-methyl-1H-pyrrol-2-yl)carbonyl]amino}-3-methoxypiperidin-1-yl)-5-(ethoxycarbonyl)-1,3-thiazole-4-carboxylic acid | MS (ES) MH$^+$: 505 for $C_{19}H_{22}Cl_2N_4O_6S$ NMR: 1.16 (t, 3H) 1.69 (s, 2H) 2.12 (s, 2H) 3.30 (s, 3H) 3.50 (s, 2H) 3.89 (s, 2H) 4.13 (q, 2H) 4.17-4.29 (m, 2H) 7.10 (d, 1H) 12.10 (s, 1H) 13.50 (s, 1H) | Intermediate 52 and Intermediate 252 |

| Ex | Compound | Data | SM |
|---|---|---|---|
| 191 | ethyl 2-((3S,4R)-4-{[(3,4-dichloro-5-methyl-1H-pyrrol-2-yl)carbonyl]amino}-3-methoxypiperidin-1-yl)-4-carboxy-1,3-thiazole-5-carboxylate | MS (ES) MH$^+$: 505 for $C_{19}H_{22}Cl_2N_4O_6S$ NMR: 1.22 (t, 3H) 1.75 (s, 2H) 2.18 (s, 3H) 3.31 (d, 1H) 3.36 (s, 3H) 3.42 (s, 1H) 3.56 (s, 1H) 3.95 (s, 1H) 4.14-4.22 (m, 2H) 4.29 (s, 1H) 7.16 (d, 1H) 12.16 (s, 2H) 13.56 (s, 1H) | Intermediate 51 and Intermediate 252 |
| 192 | ethyl 2-((3S,4R)-4-{[(3,4-dichloro-5-methyl-1H-pyrrol-2-yl)carbonyl]amino}-3-methoxypiperidin-1-yl)-1,3-thiazole-4-carboxylate | MS (ES) MH$^+$: 461 for $C_{18}H_{22}Cl_2N_4O_4S$ | Intermediate 51 and ethyl 2-bromo-1,3-thiazole-4-carboxylate |
| 193 | ethyl 2-((3S,4R)-4-{[(3,4-dichloro-5-methyl-1H-pyrrol-2-yl)carbonyl]amino}-3-methoxypiperidin-1-yl)isonicotinate | MS (ES) MH$^+$: 455 for $C_{20}H_{24}Cl_2N_4O_4$ NMR: 1.32 (s, 3H) 1.84 (s, 2H) 2.22 (s, 3H) 3.36 (s, 3H) 3.45 (s, 1H) 4.16 (s, 1H) 4.25 (s, 1H) 4.31 (s, 2H) 4.81 (s, 1H) 7.04 (s, 1H) 7.26 (s, 1H) 8.21 (s, 1H) 10.53 (s, 1H) | Intermediate 51 and ethyl 2-fluoroisonicotinate (Konno, Akinori J. Fluorine Chemistry (1998), 87(2), 137-140) |

Example 194

Cis(±)-ethyl 5-amino-2-(4-{[(3,4-dichloro-5-methyl-1H-pyrrol-2-yl)carbonyl]amino}-3-methoxypiperidin-1-yl)isonicotinate A solution of SnCl$_2$ dihydrate (870 mg, 3.8 mmol) in 5 ml concentrated HCl was added to a solution of 436 mg (0.87 mmol) of Cis(±)-ethyl 2-(4-{[(3,4-dichloro-5-methyl-1H-pyrrol-2-yl)carbonyl]amino}-3-methoxypiperidin-1-yl)-5-nitroisonicotinate (Example 308) in 30 ml acetic acid. The mixture was stirred at room temperature overnight. Solvent was removed and the residue was partitioned between water and EtOAc. The EtOAc was separated and washed with brine. Drying (MgSO$_4$), removal of solvent and chromatography on silica gel (100% CH$_2$Cl$_2$ followed by gradient elution to 100% EtOAc and then to 10% MeOH in EtOAc) gave 230 mg of product. MS (ES)(MH$^+$): 470 for $C_{20}H_{25}Cl_2N_5O_4$; NMR (CDCl$_3$): 1.5 (t, 3H), 2.1 (m, 2H) 2.4 (s, 3H), 3.2 (m, 2H), 3.6 (s, 3H), 3.65 (m, 1H), 4.0 (m, 1H), 4.4 (m, 1H), 4.5 (q, 2H), 7.3 (s, 1H), 8.0 (s, 1H), 9.5 (s, 1H).

Example 195

Cis(±)-ethyl 2-(4-{[(3,4-dichloro-5-methyl-1H-pyrrol-2-yl)carbonyl]amino}-3-methoxypiperidin-1-yl)-5-[(methoxycarbonyl)amino]isonicotinate

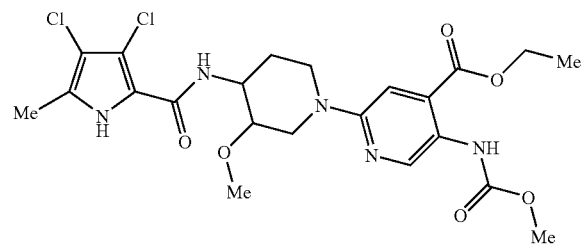 [SMILES: CCOC(=O)c1cc(N2CCC(NC(=O)c3[nH]c(C)c(Cl)c3Cl)C(OC)C2)ncc1NC(=O)OC]

Methylchlorofomate (15 μl, 0.19 mmol) was added to a solution of 60 mg (0.13 mmol) of Cis(±)-ethyl 5-amino-2-(4-{[(3,4-dichloro-5-methyl-1H-pyrrol-2-yl)carbonyl]amino}-3-methoxypiperidin-1-yl)isonicotinate (Example 194) in 3 ml pyridine. After stirring at room temperature overnight, 7 μl more methylchloroformate was added. Solvent was removed and the residue was partitioned between EtOAc and NaHCO$_3$ (aqueous). The EtOAc was separated and washed with water and brine. Drying (MgSO$_4$) and removal of solvent gave 43 mg of product. NMR (d$_6$-DMSO): 1.3 (t, 3H), 1.7 (m, 2H) 2.2 (s, 3H), 3.1 (m, 2H), 3.3 (s, 3H), 3.5 (m, 1H), 3.6 (s, 3H), 4.0-4.3 (m, 4H), 4.6 (m, 1H), 7.05 (m, 1H), 7.15 (m, 1H), 8.2 (s, 1H), 9.1 (s, 1H), 12.2 (s, 1H).

Example 196

Cis(±)-ethyl 2-(4-{[(3,4-dichloro-5-methyl-1H-pyrrol-2-yl)carbonyl]amino}-3-methoxypiperidin-1-yl)-5-[(methylsulfonyl)amino]isonicotinate Methanesulfonyl chloride (16 μl, 21 mmol) was added to 66 mg (0.14 mmol) of Cis(±)-ethyl 5-amino-2-(4-{[(3,4-dichloro-5-methyl-1H-pyrrol-2-yl)carbonyl]amino}-3-methoxypiperidin-1-yl)isonicotinate (Example 194) in 3 ml pyridine. After stirring for 1 h, 5 μl more methanesulfonyl chloride was added. Stirred at room temperature overnight. Solvent was removed, and the residue was partitioned between EtOAc and Na$_2$CO$_3$ (aqueous). The EtOAc was separated and washed with water and brine. Drying (MgSO$_4$) and removal of solvent gave 63 mg of product. MS (ES) (MH$^+$): 534 for $C_{21}H_{27}Cl_2N_5O_6S$, NMR (d$_6$-DMSO): 1.4 (t, 3H), 1.8 (m, 2H) 2.2 (s, 3H), 2.9 (s, 3H), 3.1-3.2 (m, 2H), 3.3-3.5 (m), 3.6 (m, 1H), 4.2-4.3 (m, 2H), 4.4 (q, 2H), 4.7 (m, 1H), 7.1 (s, 1H), 7.2 (d, 1H), 8.2 (s, 1H), 12.2 (s, 1H).

Example 197

Cis(±)-6-(4-{[(3,4-dichloro-5-methyl-1H-pyrrol-2-yl)carbonyl]amino}-3-methoxypiperidin-1-yl)-4-(ethoxycarbonyl)nicotinic acid A solution of 133 mg (0.84 mmol) KMnO$_4$ in 5 ml water was added to a solution of Cis(±)-ethyl 2-(4-{[(3,4-dichloro-5-methyl-1H-pyrrol-2-yl)carbonyl]amino}-3-methoxypiperidin-1-yl)-5-formylisonicotinate (Example 154) in 20 ml acetone, and the mixture was stirred at room temperature for 4 h. After quenching with aqueous NaHSO$_3$, the mixture was acidified to about pH=4 with 1N HCl and extracted twice with EtOAc. The EtOAc extracts were washed with brine, dried (MgSO$_4$) and concentrated to give a solid that was triturated with MeOH to give 175 mg of product. MS (ES) MH$^+$: 499 for C$_{21}$H$_{24}$Cl$_2$N$_4$O$_6$; NMR: 1.25 (t, 3H), 1.5-1.8, (m, 3H), 2.1 (s, 3H), 3.1 (m, 3H), 3.3 (s, 3H), 3.5 (m, 1H), 4.2 (m, 2H), 4.4 (m, 1H), 4.9 (m, 1H), 6.9 (s, 1H), 7.1 (d, 1H), 8.6 (s, 1H), 12.1 (s, 1H), 13.3 (s, 1H).

Example 198

Cis(±)-ethyl 2-(4-{[(3,4-dichloro-5-methyl-1H-pyrrol-2-yl)carbonyl]amino}-3-methoxypiperidin-1-yl)-5-{[(1-methyl-1-phenylethyl)amino]carbonyl}isonicotinate HATU (87 mg, 24 mmol) was added to a solution of 118 mg (0.24 mmol) Cis(±)-6-(4-{[(3,4-dichloro-5-methyl-1H-pyrrol-2-yl)carbonyl]amino}-3-methoxypiperidin-1-yl)-4-(ethoxycarbonyl)nicotinic acid (Example 197), 0.040 ml (28 mmol) Et$_3$N and 33 mg (0.24 mmol) cumylamine in 3 ml DMF. After stirring at room temperature overnight, the mixture was diluted with water and extracted with EtOAc. The EtOAc was washed 2 times with water and once with brine before being dried (MgSO$_4$) and concentrated to give 103 mg of a solid. MS (ES) MH$^+$: 616 for C$_{30}$H$_{35}$Cl$_2$N$_5$O$_5$.

Examples 199-200

The following Examples were prepared by the procedure described in Example 198 from the starting materials (SM) indicated.

Example 201

Cis(±)-ethyl 5-(aminocarbonyl)-2-(4-{[(3,4-dichloro-5-methyl-1H-pyrrol-2-yl)carbonyl]amino}-3-methoxypiperidin-1-yl)isonicotinate A solution of 103 mg (0.17 mmol) of Cis(±)-ethyl 2-(4-{[(3,4-dichloro-5-methyl-1H-pyrrol-2-yl)carbonyl]amino}-3-methoxypiperidin-1-yl)-5-{[(1-methyl-1-phenylethyl)amino]carbonyl} isonicotinate (Example 198) in 10 ml TFA was heated at 40° C. overnight and at 50° C. for 6 h. Solvent was removed and the residue was triturated with MeOH to give 62 mg of a white solid. MS (ES) MH$^+$: 498 for C$_{21}$H$_{25}$Cl$_2$N$_5$O$_5$.

Example 202

The following Example was prepared by the procedure described in Example 201 from the starting materials (SM) indicated.

| Ex | Compound | Data | SM |
| --- | --- | --- | --- |
| 202 | 5-thiazolecarboxylic acid, 4-(aminocarbonyl)-2-[(3S,4R)-4-[[(3,5-dichloro-4-methyl-1H-pyrrol-2-yl)carbonyl]amino]-3-fluoro-1-piperidinyl]-, ethyl ester | MS (ES) MH$^+$: 492 for C$_{18}$H$_{20}$Cl$_2$FN$_5$O$_4$SE | Example 199 |

| Ex | Compound | Data | SM |
| --- | --- | --- | --- |
| 199 | ethyl 2-((3S,4R)-4-{[(3,5-dichloro-4-methyl-1H-pyrrol-2-yl)carbonyl]amino}-3-fluoropiperidin-1-yl)-4-{[(1-methyl-1-phenylethyl)amino]carbonyl}-1,3-thiazole-5-carboxylate | MS (ES) MH$^+$: 610 for C$_{27}$H$_{30}$Cl$_2$FN$_5$O$_4$S; NMR: 1.2 (t, 3H), 1.5 (s, 6H), 1.65 (m, 2H), 1.9 (s, 3H), 3.6 (m, 1H), 4.0 (m, 1H), 4.1-4.3 (m, 4H), 4.3 (dd, 1H), 4.95 (d, 1H), 7.0-7.5 (m, 5H), 8.6 (s, 1H), 12.6 (s, 1H) | Example 156 and cumylamine |
| 200 | ethyl 2-((3S,4R)-4-{[(3,5-dichloro-4-methyl-1H-pyrrol-2-yl)carbonyl]amino}-3-fluoropiperidin-1-yl)-4-{[(2-morpholin-4-ylethyl)amino]carbonyl}-1,3-thiazole-5-carboxylate | MS (ES) MH$^+$: 605 for C$_{24}$H$_{31}$Cl$_2$FN$_6$O$_6$S; NMR: 1.2 (t, 3H), 1.8 (m, 2H), 1.9 (s, 3H), 2.3 (m, 4H), 3.6 (m, 5H), 4.0 (m, 1H), 4.2 (q, 2H), 4.3 (m, 2H), 4.95 (d, 1H), 7.35 (d, 1H), 8.4 (t, 1H), 12.6 (s, 1H) | Example 156 and (2-morpholin-4-ylethyl)amine |

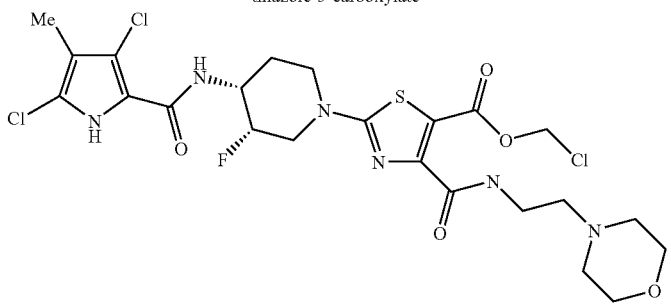

Example 203

Cis(±)-ethyl 2-(4-{[(3,4-dichloro-5-methyl-1H-pyrrol-2-yl)carbonyl]amino}-3-methoxypiperidin-1-yl)-4-[(dimethylamino)carbonyl]-1,3-thiazole-5-carboxylate A solution of Cis(±)-2-(4-{[(3,4-dichloro-5-methyl-1H-pyrrol-2-yl)carbonyl]amino}-3-methoxypiperidin-1-yl)-5-(ethoxycarbonyl)-1,3-thiazole-4-carboxylic acid (0.062 g, 0.12 mmol, Example 188), dimethylamine (0.06 mL, 2M solution in THF, Aldrich), HATU (0.05 g, 0.13 mmol) and triethylamine (0.018 mL, 0.13 mmol) was stirred at room temperature until complete by LCMS (about 30 min). The crude reaction mixture was slowly poured into water and the resulting white precipitate was filtered, washed with water and dried under vacuum to yield pure product (0.028 g). MS (ES) MH$^+$: 532 for $C_{21}H_{27}Cl_2N_5O_5S$; NMR: 1.20 (t, 3 H) 1.76 (s, 2 H) 2.18 (s, 3 H) 2.78 (s, 3 H) 2.93 (s, 3 H) 3.29 (d, 1 H) 3.36 (s, 3 H) 3.39-3.43 (m, 1 H) 3.55 (s, 1 H) 3.91 (s, 1 H) 4.15 (q, 2 H) 4.29 (s, 2 H) 7.15 (d, 1 H) 12.14 (s, 1 H).

Examples 204-241

The following Examples were prepared by the procedure described in Example 203 from the starting materials (SM) indicated

| Ex | Compound | Data | SM |
|---|---|---|---|
| 204 | Cis(±)-ethyl 2-(4-{[(3,4-dichloro-5-methyl-1H-pyrrol-2-yl)carbonyl]amino}-3-methoxypiperidin-1-yl)-4-(morpholin-4-ylcarbonyl)-1,3-thiazole-5-carboxylate | MS (ES) MH$^+$: 574 for C$_{23}$H$_{29}$Cl$_2$N$_5$O$_6$S; NMR: 1.21 (t, 3H) 1.74 (s, 2H) 2.17 (s, 3H) 3.11-3.17 (m, 2H) 3.34 (s, 3H) 3.38 (s, 1H) 3.47-3.59 (m, 5H) 3.62 (s, 2H) 3.87 (s, 1H) 4.17 (q, 2H) 4.29 (s, 2H) 7.13 (d, 1H) 12.13 (s, 1H) | Example 188 and morpholine |
| 205 | ethyl 2-(3S,4R)-4-{[(3,4-dichloro-5-methyl-1H-pyrrol-2-yl)carbonyl]amino}-3-fluoropiperidin-1-yl)-4-(morpholin-4-ylcarbonyl)-1,3-thiazole-5-carboxylate | MS (ES) MH$^+$: 562 for C$_{22}$H$_{26}$Cl$_2$FN$_5$O$_5$S; NMR: 1.16 (t, 3H) 1.80 (s, 2H) 2.12 (s, 3H) 3.09 (d, 2H) 3.45 (s, 2H) 3.50 (s, 2H) 3.57 (s, 2H) 3.92 (s, 1H) 4.12 (q, 2H) 4.26 (s, 3H) 4.82 (s, 1H) 4.99 (s, 1H) 7.19 (s, 1H) 12.02 (s, 1H) | Example 189 and morpholine |
| 206 | Cis(±)-ethyl 2-(4-{[(3,4-dichloro-5-methyl-1H-pyrrol-2-yl)carbonyl]amino}-3-methoxypiperidin-1-yl)-4-[(methoxyamino)carbonyl]-1,3-thiazole-5-carboxylate | MS (ES) MH$^+$: 534 for C$_{20}$H$_{25}$Cl$_2$N$_5$O$_6$S; NMR: 1.18-1.25 (m, 3H) 1.75 (s, 2H) 2.17 (s, 3H) 3.35 (s, 3H) 3.54 (s, 2H) 3.67 (s, 3H) 3.95 (s, 2H) 4.14-4.22 (m, 2H), 4.28 (s, 2H) 7.13 (d, 1H) 11.48 (s, 1H) 12.13 (s, 1H) | Example 188 and methoxylamine hydrochloride |
| 207 | ethyl 2-(3S,4R)-4-{[(3,4-dichloro-5-methyl-1H-pyrrol-2-yl)carbonyl]amino}-3-fluoropiperidin-1-yl)-4-[(methoxyamino)carbonyl]-1,3-thiazole-5-carboxylate | MS (ES) MH$^+$: 522 for C$_{19}$H$_{22}$Cl$_2$FN$_5$O$_5$S; NMR: 1.16 (t, 3H) 1.79 (s, 2H) 2.12 (s, 3H) 3.29 (s, 2H) 3.62 (s, 3H) 3.94 (s, 1H) 4.12 (q, 2H) 4.25 (s, 2H) 4.82-4.98 (s, 1H) 7.18 (d, 1H) 11.44 (s, 1H) 12.03 (s, 1H) | Example 189 and methoxylamine hydrochloride |
| 208 | Cis(±)-ethyl 2-(4-{[(3,4-dichloro-5-methyl-1H-pyrrol-2-yl)carbonyl]amino}-3- | MS (ES) MH$^+$: 572 for C$_{24}$H$_{31}$Cl$_2$N$_5$O$_5$S; NMR: 1.22 (s, 3H) 1.43 (s, 2H) 1.56 (s, | Example 188 and piperidine |

| Ex | Compound | Data | SM |
|---|---|---|---|
| 209 | methoxypiperidin-1-yl)-4-(piperidin-1-ylcarbonyl)-1,3-thiazole-5-carboxylate | 4H) 1.74 (s, 2H) 2.17 (s, 3 H) 3.12 (s, 2H) 3.36 (s, 3H) 3.52 (s, 3H) 4.16 (s, 2H) 4.27 (s, 2H) 7.15 (s, 1H) 12.18 (s, 1H) | Example 190 and cumylamine |
| 210 | ethyl 2-((3R,4S)-4-{[(3,4-dichloro-5-methyl-1H-pyrrol-2-yl)carbonyl]amino}-3-methoxypiperidin-1-yl)-4-{[(1-methyl-1-phenylethyl)amino]carbonyl}-1,3-thiazole-5-carboxylate | MS (ES) MH+: 622 for C$_{28}$H$_{33}$Cl$_2$N$_5$O$_5$S; NMR: 1.18 (t, 3H) 1.53 (s, 3H) 1.56 (s, 3 H) 1.71 (s, 2H) 2.13 (s, 3H) 3.34 (s, 3H) 3.51 (s, 2H) 3.92 (s, 2H) 4.15 (q, 2H) 4.26 (s, 2H) 7.12 (dd, 2H) 7.23 (t, 2H) 7.40 (d, 2H) 8.56 (s, 1H) 12.11 (s, 1H) | Example 189 and cumylamine |
| | ethyl 2-((3S,4R)-4-{[(3,4-dichloro-5-methyl-1H-pyrrol-2-yl)carbonyl]amino}-3-fluoropiperidin-1-yl)-4-{[(1-methyl-1-phenylethyl)amino]carbonyl}-1,3-thiazole-5-carboxylate | MS (ES) MH+: 610 for C$_{27}$H$_{30}$Cl$_2$FN$_5$O$_4$S; NMR: 1.23 (t, 3H) 1.61 (s, 6H) 1.86 (s, 2H) 2.19 (s, 3H) 3.31 (s, 3H) 3.55 (s, 1H) 4.04 (s, 1H) 4.22 (q, 1H) 4.32 (s, 2H) 4.90-5.06 (d, 1H) 7.20 (d, 1H) 7.31 (t, 3H) 7.47 (d, 2H) 8.63 (s, 1H) 12.12 (s, 1H) | |
| 211 | ethyl 2-((3S,4R)-4-{[(3,4-dichloro-5-methyl-1H-pyrrol-2-yl)carbonyl]amino}-3-fluoropiperidin-1-yl)-4-{[(methylamino)carbonyl]}-1,3-thiazole-5-carboxylate | MS (ES) MH+: 506 for C$_{19}$H$_{22}$Cl$_2$FN$_5$O$_4$S; NMR: 1.14 (t, 3H) 1.77 (s, 2H) 2.12 (s, 3H) 2.62 (d, 3H) 3.33 (s, 1H) 3.43-3.63 (s, 1H) 3.94 (s, 2H) 4.09 (q, 2H) 4.23 (s, 2H) 4.82-4.98 (s, 1 H) 7.20 (d, 1H) 8.27 (d, 1H) 12.03-12.12 (m, 1H) | Example 189 and methylamine |
| 212 | Cis(±)-ethyl 2-(4-{[(3,4-dichloro-5-methyl-1H-pyrrol-2-yl)carbonyl]amino}-3-methoxypiperidin-1-yl)-4-{[(2- | MS (ES) MH+: 548 for C$_{21}$H$_{27}$Cl$_2$N$_5$O$_6$S | Example 188 and 2-aminoethanol |

| Ex | Compound | Data | SM |
|---|---|---|---|
| 213 | hydroxyethyl)amino]carbonyl}-1,3-thiazole-5-carboxylate ethyl 2-((3S,4R)-4-{[(3,4-dichloro-5-methyl-1H-pyrrol-2-yl)carbonyl]amino}-3-methoxypiperidin-1-yl)-4-{[(1-methyl-1-phenylethyl)amino]carbonyl}-1,3-thiazole-5-carboxylate | MS (ES) MH⁺: 622 for C₂₈H₃₃Cl₂N₅O₅S; NMR: 1.23 (t, 3H) 1.59 (s, 3 H) 1.62 (s, 6H) 1.77 (s, 2H) 2.19 (s, 3H) 3.31 (s, 1H) 3.36 (s, 1H) 3.40 (s, 3H) 3.57 (s, 1H) 3.96 (s, 1H) 4.21 (q, 2H) 4.32 (s, 2H) 7.12-7.22 (m, 2H) 7.29 (t, 2 H) 7.46 (d, 2H) 8.62 (s, 1H) | Example 191 and cumylamine |
| 214 | Cis(±)-ethyl 2-(4-{[(3,4-dichloro-5-methyl-1H-pyrrol-2-yl)carbonyl]amino}-3-methoxypiperidin-1-yl)-4-[(methylamino)carbonyl]-1,3-thiazole-5-carboxylate | MS (ES) MH⁺: 518 for C₂₀H₂₅Cl₂N₅O₅S; NMR: 1.20 (s, 3H) 1.74 (s, 2 H) 2.17 (s, 3H) 2.68 (s, 3H) 3.30 (s, 2H) 3.36 (s, 3H) 3.55 (s, 1H) 3.99 (s, 1H) 4.15 (s, 3H) 4.26 (s, 2H) 7.14 (s, 1H) 8.32 (s, 1H) 12.18 (s, 1H) | Example 188 and methylamine |
| 215 | Cis(±)-ethyl 2-(4-{[(3,4-dichloro-5-methyl-1H-pyrrol-2-yl)carbonyl]amino}-3-methoxypiperidin-1-yl)-4-{[(2-methoxyethyl)amino]carbonyl}-1,3-thiazole-5-carboxylate | MS (ES) MH⁺: 562 for C₂₂H₂₉Cl₂N₅O₆S; NMR: 1.15-1.25 (m, 3H) 1.74 (s, 2H) 2.18 (s, 3H) 3.26 (s, 3H) 3.30 (s, 1H) 3.36 (s, 3H) 3.41 (d, 3H) 3.55 (s, 3H) 4.00 (s, 1H) 4.10-4.19 (m, 2H) 4.26 (s, 2+nlH) 7.15 (d, 1H) 8.44-8.56 (m, 1H) 12.16 (s, 1H) | Example 188 and (2-methoxyethyl)amine |
| 216 | Cis(±)-ethyl 2-(4-{[(3,4-dichloro-5-methyl-1H-pyrrol-2-yl)carbonyl]amino}-3-methoxypiperidin-1-yl)-4-{[(2-hydroxy-1-methylethyl)amino]carbonyl}-1,3-thiazole-5-carboxylate | MS (ES) MH⁺: 562 for C₂₂H₂₉Cl₂N₅O₆S; NMR: 1.08 (d, 2H) 1.22 (t, 3 H) 1.75 (s, 2H) 2.18 (s, 3H) 3.37 (s, 3H) 3.47 (d, 1H) 3.55 (s, 1H) 3.81-3.92 (m, 1 H) 3.99 (s, 1H) 4.17 (q, 2H) 4.27 (s, 2H) 4.62 (s, 2H) 7.15 (d, 1H) 8.20 (d, 1H) 12.17 (s, 1H) | Example 188 and 2-aminopropan-1-ol |
| 217 | Cis(±)-ethyl 2-(4-{[(3,4-dichloro-5-methyl-1H-pyrrol- | MS (ES) MH⁺: 562 for C₂₂H₂₉Cl₂N₅O₆S; | Example 188 and 1-aminopropan-2-ol |

| Ex | Compound | Data | SM |
|---|---|---|---|
| | 2-yl)carbonyl]amino}-3-methoxypiperidin-1-yl)-4-{[(2-hydroxypropyl)amino]carbonyl}-1,3-thiazole-5-carboxylate | NMR: 1.07 (d, 3H) 1.21 (t, 3H) 1.75 (s, 2H) 2.18 (s, 3H) 3.03-3.18 (m, 2H) 3.36 (s, 3H) 3.41 (s, 1H) 3.55 (s, 1H) 3.74 (s, 1H) 3.98 (s, 1H) 4.11-4.19 (m, 2H) 4.19 (s, 1H) 4.30 (s, 1H) 4.61 (s, 1H) 7.15 (d, 1H) 8.33-8.43 (m, 1H) 12.16 (s, 1H) | |
| 218 | ethyl 2-((3S,4R)-4-{[(3,4-dichloro-5-methyl-1H-pyrrol-2-yl)carbonyl]amino}-3-methoxypiperidin-1-yl)-4-{[(methylamino)carbonyl]-1,3-thiazole-5-carboxylate | MS (ES) MH+: 518 for $C_{20}H_{25}Cl_2N_5O_5S$; NMR: 1.21 (s, 3H) 1.74 (s, 2H) 2.18 (s, 3H) 2.69 (s, 3H) 3.17 (s, 2H) 3.36 (s, 3H) 3.55 (s, 1H) 3.98 (s, 1H) 4.14 (s, 2H) 4.27 (s, 2H) 7.13 (s, 1H) 8.33 (s, 1H) 12.17 (s, 1H) | Example 191 and methylamine hydrochloride |
| 219 | ethyl 2-((3S,4R)-4-{[(3,4-dichloro-5-methyl-1H-pyrrol-2-yl)carbonyl]amino}-3-methoxypiperidin-1-yl)-4-{[(2-methoxyethyl)amino]carbonyl}-1,3-thiazole-5-carboxylate | MS (ES) MH+: 562 for $C_{22}H_{29}Cl_2N_5O_6S$ | Example 191 and (2-methoxyethyl)amine |
| 220 | ethyl 2-((3S,4R)-4-{[(3,4-dichloro-5-methyl-1H-pyrrol-2-yl)carbonyl]amino}-3-methoxypiperidin-1-yl)-4-({[(1S)-2-hydroxy-1-methylethyl]amino}carbonyl)-1,3-thiazole-5-carboxylate | MS (ES) MH+: 562 for $C_{22}H_{29}Cl_2N_5O_6S$ | Example 191 and (2S)-2-aminopropan-1-ol |
| 221 | ethyl 2-((3S,4R)-4-{[(3,4-dichloro-5-methyl-1H-pyrrol-2-yl)carbonyl]amino}-3-methoxypiperidin-1-yl)-4-({[(1R)-2-hydroxy-1-methylethyl]amino}carbonyl)-1,3-thiazole-5-carboxylate | MS (ES) MH+: 562 for $C_{22}H_{29}Cl_2N_5O_6S$ | Example 191 and [(1R)-2-methoxy-1-methylethyl]amine |

-continued

| Ex | Compound | Data | SM |
|---|---|---|---|
| 222 | Cis(±)-ethyl 2-(4-{[(3,4-dichloro-5-methyl-1H-pyrrol-2-yl)carbonyl]amino}-3-methoxypiperidin-1-yl)-4-{[(2,2-difluoroethyl)amino]carbonyl}-1,3-thiazole-5-carboxylate | MS (ES) MH+: 568 for C₂₁H₂₅Cl₂F₂N₅O₅S; NMR: 1.21 (t, 3H) 1.75 (s, 2H) 2.18 (s, 3H) 3.36 (s, 3H) 3.44 (s, 1H) 3.55 (s, 3H) 3.98 (s, 1H) 4.16 (q, 2H) 4.26 (s, 2H) 5.88-6.26 (t, 1H) 7.15 (d, 1H) 8.88 (s, 1H) 12.16 (s, 1H) | Example 188 and difluoroethylamine |
| 223 | Cis(±)-ethyl 2-(4-{[(3,4-dichloro-5-methyl-1H-pyrrol-2-yl)carbonyl]amino}-3-methoxypiperidin-1-yl)-4-[(isoxazol-3-ylamino)carbonyl]-1,3-thiazole-5-carboxylate | MS (ES) MH+: 571 for C₂₂H₂₄Cl₂N₆O₆S; NMR: 1.12 (t, 3H) 1.77 (d, 2H) 2.18 (s, 3H) 3.38 (s, 3H) 3.56 (s, 2H) 3.98 (s, 2H) 4.14 (q, 2H) 4.19-4.34 (m, 2H) 6.99 (d, 1H) 7.16 (d, 1H) 8.86 (d, 1H) 11.59 (s, 1H) 12.17 (s, 1H) | Example 188 and isoxazol-3-amine |
| 224 | Cis(±)-ethyl 2-(4-{[(3,4-dichloro-5-methyl-1H-pyrrol-2-yl)carbonyl]amino}-3-methoxypiperidin-1-yl)-4-{[((3R)-tetrahydrofuran-3-ylamino]carbonyl}-1,3-thiazole-5-carboxylate | MS (ES) MH+: 574 for C₂₃H₂₉Cl₂N₅O₆S; NMR: 1.21 (t, 3H) 1.75 (d, 2H) 1.87 (s, 1H) 2.09 (s, 1H) 2.18 (s, 3H) 3.36 (s, 3H) 3.42 (s, 1H) 3.55 (s, 2H) 3.69 (s, 1H) 3.78 (s, 2H) 4.01 (s, 1H) 4.17 (d, 2H) 4.28 (s, 3H) 7.15 (d, 1H) 8.67 (d, 1H) 12.17 (s, 1H) | Example 188 and (3R)-tetrahydrofuran-3-amine 4-methylbenzenesulfonate |
| 225 | Cis(±)-ethyl 2-(4-{[(3,4-dichloro-5-methyl-1H-pyrrol-2-yl)carbonyl]amino}-3-methoxypiperidin-1-yl)-4-{[((1R,2S)-2-fluorocyclopropyl)amino]carbonyl}-1,3-thiazole-5-carboxylate | MS (ES) MH+: 562 for C₂₃H₂₆Cl₂FN₅O₅S; NMR: 1.07 (s, 2H) 1.21 (t, 3+nlH) 1.75 (s, 2H) 2.18 (s, 3H) 2.73 (s, 1H) 3.36 (s, 3H) 3.41 (s, 1H) 3.55 (s, 1H) 3.99 (s, 1H) 4.17 (s, 2H) 4.26 (s, 3H) 4.62-4.84 (d, 1H) 7.16 (s, 1H) 8.64 (s, 1H) 12.17 (s, 1H) | Example 188 and (1R,2S)-2-fluorocyclopropanamine 4-methylbenzenesulfonate |
| 226 | ethyl 2-(3S,4R)-4-{[(3,4-dichloro-5-methyl-1H-pyrrol- | MS (ES) MH+: 576 for C₂₃H₃₁Cl₃N₅O₆S; | Example 191 and [(1S)-2-methoxy-1- |

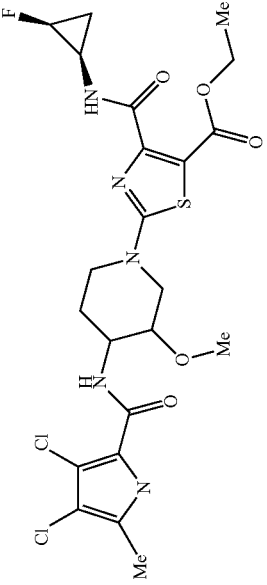

| Ex | Compound | Data | SM |
|---|---|---|---|
| | 2-yl)carbonyl]amino}-3-methoxypiperidin-1-yl)-4-({[(1S)-2-methoxy-1-methylethyl]amino}carbonyl)-1,3-thiazole-5-carboxylate | NMR: 1.09 (d, 3H) 1.22 (t, 3H) 1.75 (s, 2H) 2.18 (s, 3H) 3.17 (s, 2H) 3.26 (s, 3H) 3.37 (s, 3H) 3.55 (s, 1H) 4.01 (d, 1H) 4.17 (d, 2H) 4.27 (s, 2H) 7.16 (s, 1H) 8.32 (d, 1H) 12.16 (s, 1H) | methylethyl]amine |
| 227 | ethyl 2-((3S,4R)-4-{[(3,4-dichloro-5-methyl-1H-pyrrol-2-yl)carbonyl]amino}-3-methoxypiperidin-1-yl)-4-{[(prop-2-yn-1-ylamino)carbonyl]-1,3-thiazole-5-carboxylate | MS (ES) MH⁺: 542 for $C_{22}H_{25}Cl_2N_5O_5S$; NMR: 1.22 (s, 3H) 1.74 (s, 2H) 2.18 9s, 3H) 3.16 (s, 1H) 3.40 (m, 5H) 3.55 (d, 1H) 3.96 (s, 3H) 4.17 (s, 1H) 4.28 (s, 2H) 7.14 (s, 1H) 8.87 (s, 1H) 12.16 (s, 1H) | Example 191 and propargylamine |
| 228 | ethyl 2-((3S,4R)-4-{[(3,4-dichloro-5-methyl-1H-pyrrol-2-yl)carbonyl]amino}-3-methoxypiperidin-1-yl)-4-{[(2-hydroxy-1,1-dimethylethyl)amino]carbonyl}-1,3-thiazole-5-carboxylate | MS (ES) MH⁺: 576 for $C_{23}H_{31}Cl_2N_5O_6S$ NMR: 1.26 (s, 6H) 1.75 (s, 2H) 2.18 (s, 3H) 3.37 (s, 3H) 3.44 (s, 1H) 3.56 (s, 1H) 4.03 (s, 1H) 4.19 (s, 2H) 4.28 (s, 2H) 4.67 (s, 1H) 7.16 (s, 1H) 7.87 (s, 1H) 12.17 (s, 1H) | Example 191 and 2-amino-2-methylpropan-1-ol |
| 229 | 2-((3S,4R)-4-{[(3,4-dichloro-5-methyl-1H-pyrrol-2-yl)carbonyl]amino}-3-methoxypiperidin-1-yl)-4-{[(2-hydroxy-1,1-dimethylethyl)amino]carbonyl}-1,3-thiazole-5-carboxylic acid | MS (ES) MH⁺: 562 for $C_{22}H_{26}Cl_2FN_5O_5S$; NMR: 1.08 (s, 3H) 1.21 (t, 3H) 1.76 (s, 2H) 2.18 (s, 3H) 3.36 (s, 3H) 3.41 (s, 1H) 3.55 (s, 1H) 3.97 (s, 1H) 4.09-4.19 (m, 2H) 4.27 (s, 2H) 4.61-4.83 (s, 1H) 7.15 (d, 1H) 8.64 (s, 1H) 12.16 (s, 1H) | Example 191 and (1R,2S)-2-fluorocyclo-propanamine 4-methylbenzenesulfonate |
| 230 | ethyl 4-{[(1-cyanocyclopropyl)amino]carbonyl}-2-((3S,4R)-4-{[(3,4-dichloro-5-methyl-1H-pyrrol-2-yl)carbonyl]amino}-3-methoxypiperidin-1-yl)-1,3-thiazole-5-carboxylate | MS (ES) MH⁺: 569 for $C_{23}H_{26}Cl_2N_6O_5S$; NMR: 1.21 (s, 5H) 1.50-1.61 (m, 2H) 1.75 (s, 2H) 2.18 (s, 3H) 3.36 (s, 3H) 3.40 (s, 1H) 3.55 (s, 1H) 4.01 (s, 1H) 4.13-4.22 (m, 2H) 4.28 (s, 2H) 7.14 (d, 1H) 9.36 (s, 1H) 12.17 (s, 1H) | Example 191 and 1-aminocyclopropane carbonitrile |

| Ex | Compound | Data | SM |
|---|---|---|---|
| 231 | ethyl 4-[(cyclopropylamino)carbonyl]-2-((3S,4R)-4-{[(3,4-dichloro-5-methyl-1H-pyrrol-2-yl)carbonyl]amino}-3-methoxypiperidin-1-yl)-1,3-thiazole-5-carboxylate | MS (ES) MH+: 544 for C$_{22}$H$_{27}$Cl$_2$N$_5$O$_5$S; NMR: 0.49 (s, 2H) 0.66 (d, 2H) 1.22 (s, 3H) 1.75 (s, 2H) 2.18 (s, 3H) 2.72 (s, 1H) 3.38 (m, 4H) 3.55 (s, 1H) 3.99 (s, 1H) 4.17 (s, 2H) 4.27 (s, 2H) 7.16 (s, 1H) 8.44 (s, 1H) 12.17 (s, 1H) | Example 191 and cyclopropylamine |
| 232 | ethyl 4-{[(1-cyano-1-methylethyl)amino]carbonyl}-2-((3S,4R)-4-{[(3,4-dichloro-5-methyl-1H-pyrrol-2-yl)carbonyl]amino}-3-methoxypiperidin-1-yl)-1,3-thiazole-5-carboxylate | MS (ES) MH+: 571 for C$_{23}$H$_{28}$Cl$_2$N$_6$O$_5$S; NMR: 1.23 (t, 3H) 1.62 (s, 6H) 1.76 (s, 2H) 2.18 (s, 3H) 3.37 (s, 3H) 3.56 (s, 1H) 4.04 (s, 1H) 4.15-4.22 (m, 2H) 4.23 (s, 2H) 7.15 (d, 1H) 9.07 (s, 1H) 12.17 (s, 1H) | Example 191 and 2-amino-2-methylpropanenitrile |
| 233 | ethyl 2-((3S,4R)-4-{[(3,4-dichloro-5-methyl-1H-pyrrol-2-yl)carbonyl]amino}-3-methoxypiperidin-1-yl)-4-({[1-(hydroxymethyl)-2-methoxy-2-oxoethyl]amino}carbonyl)-1,3-thiazole-5-carboxylate | MS (ES) MH+: 606 for C$_{23}$H$_{29}$Cl$_2$N$_5$O$_8$S; NMR: 1.21 (t, 3H) 1.75 (s, 2H) 2.18 (s, 3H) 3.37 (s, 3H) 3.56 (s, 1H) 3.66 (s, 2H) 3.69-3.75 (m, 1H) 4.00 (s, 1H) 4.16 (q, 2H) 4.27 (s, 2H) 4.42-4.54 (m, 1H) 4.98 (s, 1H) 7.16 (d, 1H) 8.75 (dd, 1H) 12.17 (s, 1H) | Example 191 and methyl serinate |
| 234 | ethyl 2-((3S,4R)-4-{[(3,4-dichloro-5-methyl-1H-pyrrol-2-yl)carbonyl]amino}-3-methoxypiperidin-1-yl)-4-{[(2-morpholin-4-ylethyl)amino]carbonyl}-1,3-thiazole-5-carboxylate | MS (ES) MH+: 617 for C$_{25}$H$_{34}$Cl$_2$N$_6$O$_6$S; NMR: 1.22 (d, 3H) 1.75 (s, 2H) 2.18 (s, 3H) 3.34 (m, 5H) 3.36 (s, 3H) 3.55 (s, 1H) 3.80 (s, 2H) 3.91 (s, 2H) 4.02 (s, 1H) 4.16 (s, 2H) 4.27 (s, 2H) 4.94 (s, 1H) 7.14 (s, 1H) 8.59 (s, 1H) 12.16 (s, 1H) | Example 191 and (2-morpholin-4-ylethyl)amine |

| Ex | Compound | Data | SM |
|---|---|---|---|
| 235 | ethyl 2-((3S,4R)-4-{[(3,4-dichloro-5-methyl-1H-pyrrol-2-yl)carbonyl]amino}-3-methoxypiperidin-1-yl)-4-{[((1,3-dioxolan-2-ylmethyl)amino]carbonyl}-1,3-thiazole-5-carboxylate 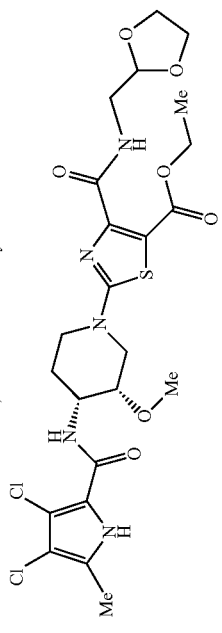 | MS (ES) MH⁺: 590 for C₂₃H₂₉Cl₂N₅O₇S NMR: 1.22 (d, 3H) 1.75 (s, 2+nH) 2.18 (s, 3H) 3.36 (s, 4H) 3.55 (s, 1H) 3.80 (s, 2H) 3.91 (s, 2H) 4.00 (s, 1H) 4.16 (s, 3H) 4.28 (s, 2H) 4.94 (s, 1H) 7.14 (s, 1H) 8.59 (s, 1H) 12.16 (s, 1H) | Example 191 and (1,3-dioxolan-2-ylmethyl)amine |
| 236 | ethyl 2-((3S,4R)-4-{[(3,4-dichloro-5-methyl-1H-pyrrol-2-yl)carbonyl]amino}-3-methoxypiperidin-1-yl)-4-({[3-(2-oxopyrrolidin-1-yl)propyl]amino}carbonyl)-1,3-thiazole-5-carboxylate | MS (ES) MH⁺: 629 for C₂₆H₃₄Cl₂N₆O₆S | Example 191 and 1-(3-aminopropyl)pyrrolidin-2-one |
| 237 | ethyl 2-((3S,4R)-4-{[(3,4-dichloro-5-methyl-1H-pyrrol-2-yl)carbonyl]amino}-3-methoxypiperidin-1-yl)-4-{[[(pyridin-2-ylmethyl)amino]carbonyl}-1,3-thiazole-5-carboxylate | MS (ES) MH⁺: 595 for C₂₅H₂₈Cl₂N₆O₅S; NMR: 1.18 (t, 3H) 1.76 (s, 2 H) 2.18 (s, 3H) 3.46 (s, 2H) 3.57 (s, 1H) 3.99 (s, 1H) 4.16 (q, 2H) 4.28 (s, 2H) 4.50 (d, 2H) 7.16 (d, 1H) 7.34 (s, 1H) 7.53 (d, 1H) 7.81-7.93 (m, 1H) 8.53 (s, 1 H) 9.07 (t, 1H) 12.17 (s, 1H) | Example 191 and (pyridin-2-ylmethyl)amine |
| 238 | ethyl 2-((3S,4R)-4-{[(3,4-dichloro-5-methyl-1H-pyrrol-2-yl)carbonyl]amino}-3-methoxypiperidin-1-yl)-4-({[2-(methylthio)ethyl]amino}carbonyl)-1,3-thiazole-5-carboxylate | MS (ES) MH⁺: 578 for C₂₂H₂₉Cl₂N₅O₅S₂ | Example 191 and [2-(methylthio) |
| 239 | ethyl 2-((3S,4R)-4-{[(3,4-dichloro-5-methyl-1H-pyrrol-2-yl)carbonyl]amino}-3-methoxypiperidin-1-yl)-4-{[[(1,3-oxazol-2-ylmethyl)amino]carbonyl}-1,3-thiazole-5-carboxylate | MS (ES) MH⁺: 585 for C₂₃H₂₆Cl₂N₆O₆S; NMR: 1.17 (t, 3H) 1.74 (s, 2 H) 2.18 (s, 3H) 3.37 (s, 3H) 3.55 (s, 1H) 4.00 (s, 1H) 4.13 (d, 2H) 4.26 (s, 2H) 4.49 (d, 2H) 7.11-7.25 (m, 2 H) 8.08 (s, 1H) 9.07 (s, 1H) | Example 191 and 1-(1,3-oxazol-2-yl)methanamine hydrochloride |

-continued

| Ex | Compound | Data | SM |
|---|---|---|---|
| 240 | ethyl 2-((3S,4R)-4-{[(3,4-dichloro-5-methyl-1H-pyrrol-2-yl)carbonyl]amino}-3-methoxypiperidin-1-yl)-4-{[(2-fluoroethyl)amino]carbonyl}-1,3-thiazole-5-carboxylate 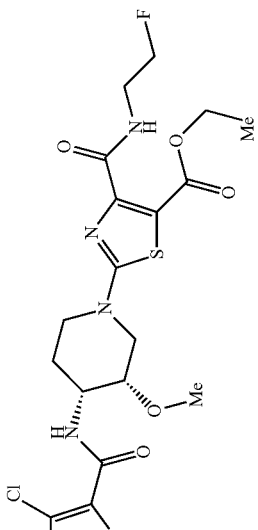 | MS (ES) MH+: 550 for $C_{21}H_{26}Cl_2FN_5O_5S$; NMR: 1.21 (t, 3H) 1.74 (d, 2+nH) 2.18 (s, 3H) 3.40 (s, 3H)3.55 (s, 3H) 3.99 (s, 1H) 4.17 (d, 2H) 4.27 (s, 2H) 4.42 (s, 1H) 4.58 (s, 1H) 7.14 (s, 1H) 8.70 (s, 1H) 12.17 (s, 1H) | Example 191 and 2-fluoroethanamine hydrochloride |
| 241 | ethyl 2-((3S,4R)-4-{[(3,4-dichloro-5-methyl-1H-pyrrol-2-yl)carbonyl]amino}-3-methoxypiperidin-1-yl)-4-{[(2-hydroxy-2-methylpropyl)amino]carbonyl}-1,3-thiazole-5-carboxylate | MS (ES) MH+: 576 for $C_{23}H_{31}Cl_2N_5O_6S$; NMR: 1.11 (s, 6H) 1.22 (d, 3H) 1.75 (s, 2H) 2.18 (s, 3H) 3.14 (s, 2H) 3.38 (s, 3H) 3.55 (s, 1H) 3.95 (s, 1H) 4.17 (s, 2H) 4.27 (s, 2H) 4.39 (s, 1H) 7.14 (s, 1H) 8.28 (s, 1H) 12.17 (s, 1H) | Example 191 and 1-amino-2-methylpropan-2-ol |

Examples 242-245

The following Examples were prepared by the procedure described in Example 34 from the starting materials (SM) indicated.

temperature and monitored by LCMS. Upon completion, the reaction mixture was diluted with 1N HCl and then partitioned with EtOAc/sat. sodium bicarbonate. Washing with brine, drying with $MgSO_4$ and concentrating yielded a solid. Purification by silica gel flash column (gradient elution

| Ex | Compound | Data | SM |
|---|---|---|---|
| 242 | Cis(±)-ethyl 4-(aminocarbonyl)-2-(4-{[(3,4-dichloro-5-methyl-1H-pyrrol-2-yl)carbonyl]amino}-3-methoxypiperidin-1-yl)-1,3-thiazole-5-carboxylate | MS (ES) MH$^+$: 504 for $C_{19}H_{23}Cl_2N_5O_5S$ | Example 178 |
| 243 | ethyl 4-(aminocarbonyl)-2-((3R,4S)-4-{[(3,4-dichloro-5-methyl-1H-pyrrol-2-yl)carbonyl]amino}-3-methoxypiperidin-1-yl)-1,3-thiazole-5-carboxylate | MS (ES) MH$^+$: 504 for $C_{19}H_{23}Cl_2N_5O_5S$ | Example 209 |
| 244 | ethyl 4-(aminocarbonyl)-2-((3S,4R)-4-{[(3,4-dichloro-5-methyl-1H-pyrrol-2-yl)carbonyl]amino}-3-fluoropiperidin-1-yl)-1,3-thiazole-5-carboxylate | MS (ES) MH$^+$: 492 for $C_{18}H_{20}Cl_2FN_5O_4S$ | Example 210 |
| 245 | ethyl 4-(aminocarbonyl)-2-((3S,4R)-4-{[(3,4-dichloro-5-methyl-1H-pyrrol-2-yl)carbonyl]amino}-3-methoxypiperidin-1-yl)-1,3-thiazole-5-carboxylate | MS (ES) MH$^+$: 504 for $C_{19}H_{23}Cl_2N_5O_5S$ NMR: 1.22 (t, 3H) 1.74 (d, 2H) 2.18 (s, 3H) 3.31 (s, 1H) 3.37 (s, 3H) 3.38-3.43 (m, 1H) 3.55 (s, 1H) 3.95 (s, 1H) 4.17 (q, 2H) 4.27 (s, 2H) 7.15 (d, 1H) 7.53 (s, 1H) 7.82 (s, 1H) 12.17 (s, 1H) | Example 213 |

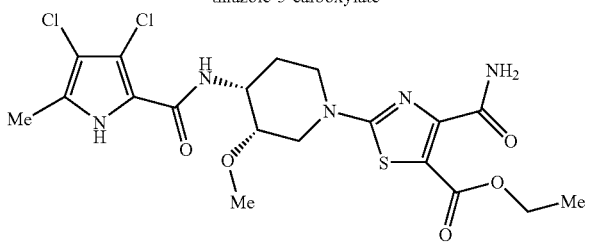

Example 246

Cis(±)-ethyl 2-(4-{[(3,4-dichloro-5-methyl-1H-pyrrol-2-yl)carbonyl]amino}-3-methoxypiperidin-1-yl)-4-(morpholin-4-ylmethyl)-1,3-thiazole-5-carboxylate To a solution of ethyl 2-(4-{[(3,4-dichloro-5-methyl-1H-pyrrol-2-yl)carbonyl]amino}-3-methoxypiperidin-1-yl)-4-formyl-1,3-thiazole-5-carboxylate (0.15 g, 0.31 mmol, Example 252) in methylene chloride (20 mL) was added sodium triacetoxyborohydride (0.1 g, 0.47 mmol) and morpholine (0.03 mL, 0.34 mmol). Reaction was stirred at room temperature and monitored by LCMS.

70-100% EtOAc/$CH_2Cl_2$) afforded pure product (0.091 g) MS (ES) M+H$^+$: 560 for $C_{23}H_{31}Cl_2N_5O_5S$; NMR: 1.24 (t, 3 H) 1.75 (s, 2 H) 2.18 (s, 3 H) 3.32 (s, 2 H) 3.36 (s, 3 H) 3.52 (s, 2 H) 3.54 (d, 4 H) 3.65-3.75 (m, 2 H) 3.76-3.86 (m, 2 H) 3.93 (s, 1 H) 4.18 (q, 2 H) 4.27 (s, 1 H) 7.16 (d, 1 H) 12.16 (s, 1 H).

Examples 247-249

The following Examples were prepared by the procedure described in Example 246 from the starting materials (SM) indicated.

| Ex | Compound | Data | SM |
|---|---|---|---|
| 247 | Cis(±)-ethyl 4-[(tert-butylamino)methyl]-2-(4-{[3,4-dichloro-5-methyl-1H-pyrrol-2-yl)carbonyl]amino}-3-methoxypiperidin-1-yl)-1,3-thiazole-5-carboxylate | MS (ES) MH$^+$: 546 for $C_{23}H_{33}Cl_2N_5O_4S$; NMR: 1.04 (s, 9 H) 1.22 (t, 3 H) 1.72 (d, 2 H) 2.17 (s, 3 H) 3.32 (s, 1 H) 3.35 (s, 3 H) 3.53 (s, 1 H) 3.78-3.92 (m, 2 H) 4.17 (q, 2 H) 4.23 (d, 1 H) 7.14 (d, 1 H) | Example 252 and tert-butylamine |
| 248 | Cis(±)-ethyl 2-(4-{[(3,4-dichloro-5-methyl-1H-pyrrol-2-yl)carbonyl]amino}-3-methoxypiperidin-1-yl)-4-(piperidin-1-ylmethyl)-1,3-thiazole-5-carboxylate | MS (ES) MH$^+$: 558 for $C_{24}H_{33}Cl_2N_5O_4S$ | Example 252 and piperidine |

| Ex | Compound | Data | SM |
|---|---|---|---|
| 249 | ethyl 2-((3S,4R)-4-{[(3,4-dichloro-5-methyl-1H-pyrrol-2-yl)carbonyl]amino}-3-methoxypiperidin-1-yl)-4-[(3-hydroxypyrrolidin-1-yl)methyl]-1,3-thiazole-5-carboxylate | MS (ES) MH+: 560 for C23H31Cl2N5O5S | Example 252 and pyrrolidin-3-ol |

Example 250

Cis(±)-ethyl 2-(4-{[(3,4-dichloro-5-methyl-1H-pyrrol-2-yl)carbonyl]amino}-3-methoxypiperidin-1-yl)-4-[(E)-(hydroxyimino)methyl]-1,3-thiazole-5-carboxylate

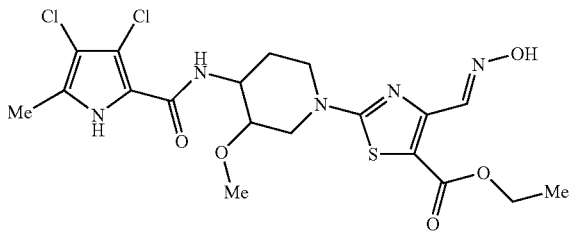 [SMILES: CCOC(=O)c1sc(N2CCC(NC(=O)c3[nH]c(C)c(Cl)c3Cl)C(OC)C2)nc1/C=N/O]

A solution of Cis(±)-ethyl 2-(4-{[(3,4-dichloro-5-methyl-1H-pyrrol-2-yl)carbonyl]amino}-3-methoxypiperidin-1-yl)-4-formyl-1,3-thiazole -5-carboxylate (0.10 g, 0.2 mmol, Example 252), sodium acetate (0.041 g, 0.5 mmol) and hydroxylamine hydrochloride (0.028 g, 0.4 mmol) were heated to reflux in absolute ethanol for 3 hours. After cooling to room temperature the ethanol was removed under reduced pressure followed by EtOAc/H$_2$O partitioning, drying with MgSO4 and concentrating to a yellow solid (0.081 g) MS (ES): 504 NMR: 1.25 (t, 3H) 1.75 (s, 2 H) 2.18 (s, 3 H) 3.31 (s, 3 H) 3.36 (s, 3 H) 3.55 (s, 1 H) 3.95 (s, 1 H) 4.18-4.26 (m, 2 H) 4.26 (d, 2 H) 7.16 (d, 1 H) 8.61 (s, 1 H) 11.72 (s, 1 H) 12.16 (s, 1 H).

Example 251

The following Example was prepared by the procedure described in Example 250 from the starting materials (SM) indicated.

Example 252

Cis(±)-ethyl 2-(4-{[(3,4-dichloro-5-methyl-1H-pyrrol-2-yl)carbonyl]amino}-3-methoxypiperidin-1-yl)-4-formyl-1,3-thiazole-5-carboxylate To a solution of Cis(±)-ethyl 2-(4-{[(3,4-dichloro-5-methyl-1H-pyrrol-2-yl)carbonyl]amino}-3-methoxypiperidin-1-yl)-4-(hydroxymethyl)-1,3-thiazole-5-carboxylate (0.63 g, 1.3 mmol, Example 143) in methylene chloride was added Dess-Martin periodinane (0.61 g, 1.4 mmol). After 1 hr stirring at room temperature the reaction was complete. The crude reaction mixture was washed with water (×2) and brine, followed by drying with MgSO4 and concentrating to a minimal volume of methylene chloride after which it was directly deposited on a silica gel flash column (gradient elution to 1:1 EtOAc in CH2 Cl2). Pure fractions concentrated to clean, yellow solid (0.56 g). NMR: 1.29 (t, 3 H) 1.75 (s, 2 H) 2.18 (s, 3 H) 3.38 (s, 4 H) 3.44 (s, 1 H) 3.57 (s, 1 H) 4.03 (d, 1H) 4.22-4.35 (m, 4 H) 7.15 (d, 1 H) 10.31 (s, 1 H) 12.16 (s, 1 H).

Example 253 ethyl 2-((3S,4R)-4-{[(3,4-dichloro-5-methyl-1H-pyrrol-2-yl)carbonyl]amino}-3-methoxypiperidin-1-yl)-4-(difluoromethyl)-1,3-thiazole-5-carboxylate Diethylaminosulfurtrifluoride (0.03 mL, 0.22 mmol) was added to a solution of ethyl 2-((3S,4R)-4-{[(3,4-dichloro-5-methyl-1H-pyrrol-2-yl)carbonyl]amino}-3-methoxypiperidin-1-yl)-4-formyl-1,3-thiazole-5-carboxylate (0.10 g, 0.2 mmol, Example 252) in methylene chloride. The reaction was complete after heating at reflux overnight. Upon cooling to room temperature, the reaction was washed with water (×3) and brine (×1), dried with MgSO$_4$ and concentrated to a yellow solid which, upon trituration, yielded a clean white solid (0.021 g). MS (ES) M+H: 511 for C$_{19}$H$_{22}$Cl$_2$F$_2$N$_4$O$_4$S; NMR: 1.26 (t, 3 H) 1.75 (s, 2 H) 2.18 (s, 3 H) 3.37 (s, 3 H) 3.43 (s, 1 H) 3.56 (s, 1 H) 3.96 (s, 1 H) 4.25 (s, 1 H) 4.36 (s, 2 H) 7.16 (s, 1 H) 7.31 (s, 1 H) 12.17 (s, 1 H).

| Ex | Compound | Data | SM |
|---|---|---|---|
| 251 | ethyl 2-((3S,4R)-4-{[(3,4-dichloro-5-methyl-1H-pyrrol-2-yl)carbonyl]amino}-3-methoxypiperidin-1-yl)-4-[(E)-(methoxyimino)methyl]-1,3-thiazole-5-carboxylate | MS (ES) MH+: 518 for C20H25Cl2N5O5S; NMR: 1.25 (t, 3 H) 1.76 (s, 2 H) 2.19 (s, 3 H) 3.30-3.32 (m, 2 H) 3.35-3.39 (m, 3 H) 3.57 (s, 1 H) 3.92 (s, 3 H) 4.04 (s, 1 H) 4.19-4.25 (m, 2 H) 4.25-4.33 (m, 2 H) 7.16 (d, 1 H) 8.66 (s, 1 H) 12.16 (s, 1 H) | Example 252 and methoxylamine hydrochloride |

Example 254 ethyl 4-(azidomethyl)-2-((3S,4R)-4-{[(3,4-dichloro-5-methyl-1H-pyrrol-2-yl)carbonyl]amino}-3-methoxypiperidin-1-yl)-1,3-thiazole-5-carboxylate To a suspension of ethyl 2-((3S,4R)-4-{[(3,4-dichloro-5-methyl-1H-pyrrol-2-yl)carbonyl]amino}-3-methoxypiperidin-1-yl)-4-(hydroxymethyl)-1,3-thiazole-5-carboxylate (0.10 g, 0.2 mmol, Example 143) in anhydrous toluene was added diphenylphosphorylazide (0.053 mL, 0.24 mmol). The reaction was cooled to 0 deg and DBU was added slowly. After stirring at 0 deg for 30 min the reaction was warmed to room temperature and stirred overnight. The biphasic reaction mixture was washed with water (×3), 1NHCl (×1), brine (×1), dried with MgSO4 and concentrated (0.048 g). MS (ES) M+H: 516 for $C_{19}H_{23}Cl_2N_7O_4S$.

Example 255

Cis(±)-ethyl 4-[cyano(morpholin-4-yl)methyl]-2-(4-{[3,4-dichloro-5-methyl-1H-pyrrol-2-yl)carbonyl]amino}-3-methoxypiperidin-1-yl)-1,3-thiazole-5-carboxylate

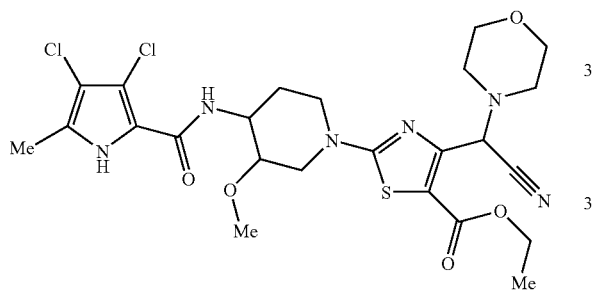

A solution of sodium cyanide (0.011 g, 0.22 mmol) and morpholine (0.018 mL, 0.21 mmol) in water (5 mL) was cooled to 0 deg. 1N HCl (0.22 mL, 0.22 mmol) was added slowly. After warming to room temperature, a solution of Cis(±)-ethyl 2-(4-{[(3,4-dichloro-5-methyl-1H-pyrrol-2-yl)carbonyl]amino}-methoxypiperidin-1-yl)-4-formyl-1,3-thiazole-5-carboxylate (0.10 g, 0.2 mmol, Example 252) in methanol (10 mL) was added. After stirring at room temperature for six weeks the reaction was complete. The reaction mixture was concentrated to remove methanol and the residue was diluted with water and extracted with EtOAc (×3), washed with brine (×1), dried with $MgSO_4$ and concentrated to a pink solid (0.055 g). MS (ES) M+H: 585 for $C_{24}H_{30}Cl_2N_6O_5S$.

Example 256 ethyl 2-((3S,4R)-4-{[(3,4-dichloro-5-methyl-1H-pyrrol-2-yl)carbonyl]amino}-3-methoxypiperidin-1-yl)-4-({[2-(methylsulfonyl)ethyl]amino}carbonyl)-1,3-thiazole-5-carboxylate m-CPBA (0.091 g, 0.37 mmol) was added to a cold solution of ethyl 2-((3S,4R)-4-{[(3,4-dichloro-5-methyl-1H-pyrrol-2-yl)carbonyl]amino}-3-methoxypiperidin-1-yl)-4-({[2-(methylthio)ethyl]amino}carbonyl)-1,3-thiazole-5-carboxylate (0.107 g, 0.18 mmol, Example 238) in methylene chloride. After stirring at room temperature for 2 hours, the reaction mixture was washed with sat. sodium bicarbonate (×3), dried with MgSO4, and concentrated to a white solid (0.092 g). MS (ES) M+H: 610 for $C_{22}H_{29}Cl_2N_5O_7S_2$; NMR: 1.21 (q, 3H) 1.66-1.80 (m, 2 H) 2.18 (s, 3 H) 3.04 (s, 3 H) 3.29 (s, 4 H) 3.36 (s, 3 H) 3.51-3.62 (m, 3 H) 3.99 (s, 1 H) 4.17 (q, 2 H) 4.28 (s, 2 H) 7.15 (d, 1 H) 8.72 (t, 1 H) 12.17 (s, 1 H).

Examples 257-381

The following Examples were synthesized by an analogous method to Example 35 from the starting materials (SM) given in the table below.

| Ex | Compound | NMR | m/z | SM |
| --- | --- | --- | --- | --- |
| 257 | Cis(±)-2-{4-{[(3,4-dichloro-5-methyl-1H-pyrrol-2-yl)carbonyl]amino}-3-[(methylsulfinyl)methyl]piperidin-1-yl}-1,3-thiazole-5-carboxylic acid | 1.85 (m, 2H), 2.16 (s, 3H), 2.2 (m, 1H), 2.5 (s, 3H), 2.6-2.9 (m, 2H), 3.0 (m, 1H), 3.2 (m, 1H), 3.9 (m, 2H), 4.17 (m, 1H), 7.4 (s, 1H), 7.7 (dd. 1H), 7.9 (broad s, 1H). | 479 | Example 89 |
| 258 | Cis(±)-2-{4-{[(3,4-dichloro-5-methyl-1H-pyrrol-2-yl)carbonyl]amino}-3-[(methylsulfonyl)methyl]piperidin-1-yl}-1,3-thiazole-5-carboxylic acid | 1.71 (m, 2H), 2.12 (s, 3H), 2.96 (s, 3H), 2.99 (m, 2H), 3.12 (m, 3H), 3.95 (m, 2H), 4.3 (m, 1H), 7.37 (d, 1H), 7.7 (s, 1H), 12 (broad s, 1H), 12.6 (broad s, 1H). | 496 | Example 90 |
| 259 | 2-((3S,4R)-4-{[(3,4-dichloro-5-methyl-1H-pyrrol-2-yl)carbonyl]amino}-3-fluoropiperidin-1-yl)-5-methyl-1,3-thiazole-4-carboxylic acid | 1.75 (m, 2H), 2.12 (s, 3H), 2.45 (s, 3H), 3.14 (m, 1H), 3.27 (dd, 1H), 3.8 (d, 1H), 4.0 (m, 2H), 4.78 (d, 1H), 5.9 (broad s, 1H), 7.16 (d, 1H), 12 (s, 1H). | 435 | Example 91 |

| Ex | Compound | NMR | m/z | SM |
|---|---|---|---|---|
| 260 | 2-((3S,4R)-4-{[(3,4-dichloro-5-methyl-1H-pyrrol-2-yl)carbonyl]amino}-3-methoxypiperidin-1-yl)-5-methyl-1,3-thiazole-4-carboxylic acid | 1.67 (m, 2H), 2.1 (s, 3H), 2.45 (s, 3H), 3.1 (m, 2H), 3.3 (s, 3H), 3.7 (d, 2H), 4.0 (dd, 2H), 4.4 (broad s, 1H), 7.0 (d, 1H), 12.1 (s, 1H). | 447 | Example 92 |
| 261 | 2-((3S,4R)-4-{[(3,4-dichloro-5-methyl-1H-pyrrol-2-yl)carbonyl]amino}-3-fluoropiperidin-1-yl)-5-[(methoxyimino)methyl]-1,3-thiazole-4-carboxylic acid | 1.86 (m, 4H), 2.2 (s, 6H), 3.4 (m, 4H), 3.8 (s, 3H), 3.9 (s, 3H), 4.0 (m, 2H), 4.3 (m, 4H), 4.9 (s, 1H), 5.0 (s, 1H), 7.2 (d, 2H), 8.4 (s, 1H), 8.7 (s, 1H), 12.1 (s, 2H), 13.2 (s, 2H). | 478 | Example 94 |
| 262 | Cis(±)-2-[4-{[(3,4-dichloro-5-methyl-1H-pyrrol-2-yl)carbonyl]amino}-3-(morpholin-4-ylcarbonyl)piperidin-1-yl]-1,3-benzothiazole-7-carboxylic acid | 1.93 (m, 2H), 2.16 (s, 3H), 3.3-3.8 (m, 11H), 4.0 (m, 2H), 4.4 (m, 1H), 7.2 (d, 1H), 7.4 (t, 1H), 7.6 (d, 1H), 7.7 (d, 1H), 9.8 (broad s, 1H), 12.0 (s, 1H). | 566 | Example 93 |
| 263 | Cis(±)-2-[4-{[(3,4-dichloro-5-methyl-1H-pyrrol-2-yl)carbonyl]amino}-3-(methylthio)piperidin-1-yl]-1,3-thiazole-5-carboxylic acid | 1.65-1.90 (m, 2H); 2.14 (s, 3H); 2.19 (s, 3H); 3.20-3.45 (m, 2H); 3.73 (d, 1H); 3.94 (d, 1H); 4.02 (dd, 1H); 4.43 (m, 1H); 7.24 (d, 1H); 7.75 (s, 1H); 12.13 (s, 1H); 12.66 (s, 1H). | 449 | Example 95 |
| 264 | Cis(±)-2-[4-{[(3,4-dichloro-5-methyl-1H-pyrrol-2-yl)carbonyl]amino}-3-(methylsulfonyl)piperidin-1-yl]-1,3-thiazole-5-carboxylic acid | 1.70 (m, 1H); 1.90 (m, 1H); 2.11 (s, 3H); 3.00 (s, 3H); 3.30-3.45 (m, 2H); 3.45 (m, 1H); 3.62 (m, 2H); 4.30 (bd, 1H); 7.39 (s, 1H); 8.20 (m, 1H); 12.10 (s, 1H); 12.60 (s, 1H). | 481 | Example 96 |
| 265 | Cis(±)2-(3-(benzyloxy)-4-{[(3,4-dichloro-5-methyl-1H-pyrrol-2-yl)carbonyl]amino}piperidin-1-yl)-1,3-thiazole-5-carboxylic acid | 1.79 (m, 2H); 2.18 (s, 3H); 3.35 (m, 2H); 3.81 (s, 1H); 3.95 (d, 1H); 4.29 (m, 1H); 4.46 (m, 2H); 4.71 (d, 1H); 7.09 (d, 1H); 7.25 (s, 5H); 7.75 (s, 1H); 12.12 (s, 1H); 12.63 (s, 1H). | 509 | Example 97 |
| 266 | Cis(±)-2-[4-{[(3,4-dichloro-5-methyl-1H-pyrrol-2-yl)carbonyl]amino}-3-(prop-2-yn-1-yloxy)piperidin-1-yl]-1,3-thiazole-5-carboxylic acid | 1.76 (m, 2H); 2.18 (s, 3H); 3.30 (m, 2H); 3.44 (t, 1H); 3.87 (s, 1H); 3.96 (m, 1H); 4.22-4.36 (m, 4H); 7.15 (d, 1H); 7.73 (s, 1H); 12.15 (s, 1H); 12.62 (s, 1H). | 457 | Example 98 |
| 267 | Trans(±)2-(3-(benzyloxy)-4-{[(3,4-dichloro-5-methyl-1H-pyrrol-2-yl)carbonyl]amino}piperidin-1-yl)-1,3-thiazole-5-carboxylic acid | 1.72 (m, 1H), 1.98 (m, 1H), 2.17 (s, 3H), 3.26 (m, 1H), 3.67 (m, 1H), 3.82 (m, 1H), 4.14 (m, 2H), 4.63 (dd, 2H), 7.28 (m, 5H), 7.34 (d, 2H), 7.76 (s, 1H), 12.00 (s, 1H), 12.66 (br s, 1H) | 509 | Example 99 and benzyl bromide |
| 268 | Trans(±)2-(3-(allyloxy)-4-{[(3,4-dichloro-5-methyl-1H-pyrrol-2-yl) | 1.67 (m, 1H), 1.98 (m, 1H), 2.17 (s, 3H), 3.22 (m, 1H), 3.37 (m, 1H), 3.57 (m, 1H), 3.79 (m, 1H), | 459 | Example 99 and allyl bromide |

-continued

| Ex | Compound | NMR | m/z | SM |
|---|---|---|---|---|
| | yl)carbonyl]amino}piperidin-1-yl)-1,3-thiazole-5-carboxylic acid | 4.09 (m, 4H), 5.10 (d, 1H), 5.23 (dd, 1H), 5.85 (m, 1H), 7.31 (d, 2H), 7.76 (s, 1H), 11.99 (s, 1H) | | |
| 269 | Trans(±)2-(4-{[(3,4-dichloro-5-methyl-1H-pyrrol-2-yl)carbonyl]amino}-3-hydroxypiperidin-1-yl)-1,3-thiazole-5-carboxylic acid | 1.60 (m, 1H), 2.01 (m, 1H), 2.17 (s, 3H), 3.07 (m, 1H), 3.30 (m, 1H), 3.61 (m, 1H), 3.82 (m, 1H), 3.90 (m, 1H) 3.99 (m, 1H), 4.58 (m, 1H), 7.18 (d, 1H), 7.31 (m, 1H), 7.75 (s, 1H), 11.97 (s, 1H) | 419 | Example 99 |
| 270 | Trans(±)2-[4-{[(3,4-dichloro-5-methyl-1H-pyrrol-2-yl)carbonyl]amino}-3-(pyridin-2-ylmethoxy)piperidin-1-yl]-1,3-thiazole-5-carboxylic acid | 1.74 (m, 1H), 2.00 (m, 1H), 2.16 (s, 3H), 3.36 (m, 2H), 3.79 (m, 2H), 4.18 (m, 2H), 4.80 (dd, 2H), 7.41 (brd, 1H), 7.46 (brt, 2H), 7.54 (brd, 1H), 7.76 (s, 1H), 7.94 (brt, 1H), 8.58 (brd, 1H), 11.99 (s, 1H) | 510 | Example 99 and 2-chloromethyl-pyridine |

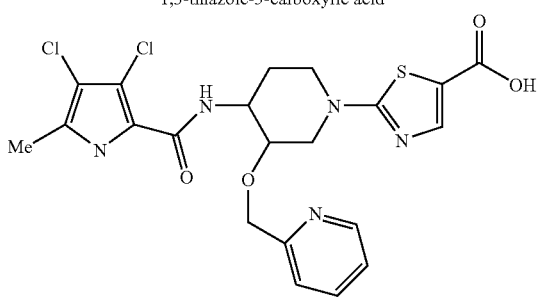

| 271 | 2-((3S,4R)-4-{[(3-chloro-5-methyl-1H-pyrrol-2-yl)carbonyl]amino}-3-fluoropiperidin-1-yl)-1,3-thiazole-5-carboxylic acid | 1.85 (m, 2H); 2.17 (s, 3H); 3.48 (m 2H); 4.0 (m, 1H); 4.33 (m, 2H); 4.96 (d, br, 1H); 5.95 (s, 1H); 7.10 (d, 1H); 7.76 (s, 1H); 11.63 (s, 1H); 12.68 (s, br 1H) | 387 | Example 100 |
| 272 | 2-((3S,4R)-4-{[(3-chloro-5-methyl-1H-pyrrol-2-yl)carbonyl]amino}-3-fluoropiperidin-1-yl)-1,3-thiazole-4-carboxylic acid | 1.88 (m, 2H); 2.17 (s, 3H); 3.31 (m 2H); 3.94 (m, 1H); 4.23 (m, 2H); 4.90 (d, br, 1H); 5.93 (s, 1H); 7.10 (d, 1H); 7.62 (s, 1H); 11.62 (s, 1H) | 387 | Example 101 |
| 273 | 2-((3S,4R)-4-{[(3-chloro-5-methyl-1H-pyrrol-2-yl)carbonyl]amino}-3-fluoropiperidin-1-yl)-1,3-benzothiazole-7-carboxylic acid | 1.88 (m, 2H); 2.17 (s, 3H); 3.31 (m 2H); 4.19 (m, 1H); 4.46 (m, 2H); 4.97 (d, br, 1H); 5.93 (s, 1H); 7.10 (d, 1H); 7.41 (t, 1H); 7.68 (d, 1H); 7.69 (d, 1H); 11.62 (s, 1H) | 437 | Example 102 |
| 274 | 2-((3S,4R)-4-{[(3-chloro-5-methyl-1H-pyrrol-2-yl)carbonyl]amino}-3-fluoropiperidin-1-yl)isonicotinic acid | 1.80 (m, 2H); 2.16 (s, 3H); 3.06 (m 2H); 4.40 (m, 2H); 4.71 (m, 1H); 4.90 (d, br, 1H); 5.94 (s, 1H); 7.03 (m, 2H); 7.26 (s, 1H); 8.22 (d, 1H); 11.61 (s, br, 1H) | 381 | Example 108 |
| 275 | 2-((3S,4R)-4-{[(4-bromo-5-methyl-1H-pyrrol-2-yl)carbonyl]amino}-3-fluoropiperidin-1-yl)-1,3-thiazole-5-carboxylic acid | 1.94 (m, 1H), 1.98 (m, 1H), 2.14 (s, 3H); 3.31 (m 2H); 4.01 (m, 1H); 4.28 (m, 2H); 4.86 (d, br, 1H); 6.94 (s, 1H); 7.75 (s, 1H); 8.02 (d, 1H); 11.73 (s, 1H). | 432 | Example 103 |

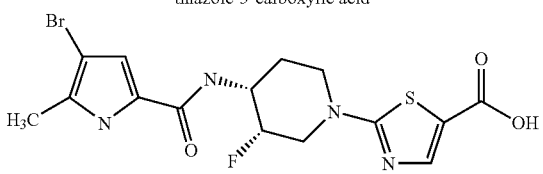

| 276 | 2-((3S,4R)-4-{[(4-bromo-5-methyl-1H-pyrrol-2-yl)carbonyl]amino}-3-fluoropiperidin-1-yl)isonicotinic acid | 1.72 (m, 1H); 1.92 (m, 1H); 2.15 (s, 3H); 3.10 (m, 1H); 3.30 (m, 1H); 4.24 (m, 1H); 4.44 (m, 2H); 4.69 (m, 1H); 4.86 (d, br, 1H); 6.96 (s, 1H); 7.05 (d, 1H); 7.33 (s, 1H); 7.95 (d, 1H); 8.24 (d, 1H); 11.74 (s, br, 1H). | 426 | Example 109 |
| 277 | 2-((3S,4R)-4-{[(4-bromo-3-chloro-5-methyl-1H-pyrrol-2-yl)carbonyl]amino}-3-fluoropiperidin-1-yl)-1,3-thiazole-5-carboxylic acid | 1.86 (m, 2H), 2.19 (s, 3H); 3.48 (m 1H); 3.53 (m, 1H); 4.01 (m, 1H); 4.33 (m, 2H); 4.96 (d, br, 1H); 7.32 (d, 1H); 7.76 (s, 1H); 12.24 (s, 1H); 12.69 (br, 1H). | 466 | Example 104 |
| 278 | 2-((3S,4R)-4-{[(4-bromo-3-chloro-5-methyl-1H-pyrrol-2- | 1.85 (m, 2H), 2.19 (s, 3H); 3.31 (m 2H); 3.95 (m, 1H); 4.23 (m, | 466 | Example 105 |

| Ex | Compound | NMR | m/z | SM |
|---|---|---|---|---|
| | yl)carbonyl]amino}-3-fluoropiperidin-1-yl)-1,3-thiazole-4-carboxylic acid | 2H); 4.90 (d, br, 1H); 7.45 (d, 1H); 7.63 (s, 1H); 12.39 (s, br, 1H). | | |
| 279 | 2-((3S,4R)-4-{[(4-bromo-3-chloro-5-methyl-1H-pyrrol-2-yl)carbonyl]amino}-3-fluoropiperidin-1-yl)-4-(methoxymethyl)-1,3-thiazole-5-carboxylic acid | 1.86 (m, 2H); 2.19 (s, 3H); 3.29 (s, 2H); 3.60 (m 2H); 4.04 (m, 1H); 4.30 (m, 1H); 4.57 (s, 3H); 4.90 (d, br, 1H); 7.32 (d, 1H); 12.25 (s, 1H); 12.78 (br, 1H) | 510 | Example 107 |
| 280 | 2-((3S,4R)-4-{[(4-bromo-3-chloro-5-methyl-1H-pyrrol-2-yl)carbonyl]amino}-3-fluoropiperidin-1-yl)isonicotinic acid | 1.86 (m, 2H); 2.19 (s, 3H); 3.07 (m, 1H); 4.04 (m, 1H); 4.28 (m, 2H); 4.69 (m, 1H); 4.90 (d, br, 1H); 7.01 (d, 1H); 7.27 (s, 1H); 7.82 (m, 1H); 8.02 (m, 1H); 13.38 (s, br, 1H) | 460 | Example 106 |
| 281 | Cis(±)-2-[4-{[(3,4-Dichloro-5-methyl-1H-pyrrol-2-yl)carbonyl]amino}-3-(2-methoxyethoxy)piperidin-1-yl]-1,3-thiazole-5-carboxylic acid | 1.74-1.76 (m, 2H), 2.17 (s, 3H), 3.14 (s, 3H), 3.25-3.42 (m, 4H), 3.50-3.60 (m, 1H), 3.67-3.73 (m, 2H), 3.75-4.00 (m, 2H), 4.20-4.35 (m, 2H), 7.14 (d, 1H), 7.72 (s, 1H), 12.14 (brs, 1H) | 477 | Example 110 |
| 282 | Cis(±)-2-[4-{[(3,4-Dichloro-5-methyl-1H-pyrrol-2-yl)carbonyl]amino}-3-(2-methoxyethoxy)piperidin-1-yl]-1,3-thiazole-4-carboxylic acid | 1.74-1.80 (m, 2H), 2.17 (s, 3H), 3.14 (s, 3H), 3.25-3.42 (peaks overlapping with H₂O signal), 3.50-3.60 (m, 1H), 3.67-3.73 (m, 2H), 3.86-3.90 (m, 1H), 4.12-4.35 (m, 2H), 7.15 (d, 1H), 7.57 (s, 1H), 12.13 (brs, 1H), 12.55 (brs, 1H) | 477 | Example 111 |
| 283 | Cis(±)-2-[4-{[(3,4-Dichloro-5-methyl-1H-pyrrol-2-yl)carbonyl]amino}-3-(2-methoxyethoxy)piperidin-1-yl]isonicotinic acid | 1.70-1.75 (m, 2H), 2.17 (s, 3H), 3.05-3.20 (m, 2H), 3.09 (s, 3H), 3.25-3.35 (m, 2H), 3.45--3.73 (peaks overlapping with H₂O signal), 4.20-4.25 (m, 2H), 4.60-4.70 (m, 1H), 6.97 (d, 1H), 7.13 (d, 1H), 7.26 (s, 1H), 8.19 (d, 1H), 12.13 (s, 1H) | 471 | Example 113 |
| 284 | Cis(±)-2-[4-{[(3,4-Dichloro-5-methyl-1H-pyrrol-2-yl)carbonyl]amino}-3-(2-methoxyethoxy)piperidin-1-yl]-1,3-benzothiazole-7-carboxylic acid | 1.79-1.75 (m, 2H), 2.19 (s, 3H), 3.12 (s, 3H), 3.27-3.45 (peaks overlapping with H₂O signal), 3.51-3.62 (m, 1H), 3.72-3.80 (m, 2H), 4.05-4.13 (m, 1H), 4.24-4.42 (m, 2H), 7.18 (d, 1H), 7.39 (t, 1H), 7.65 (t, 2H), 12.16 (s, 1H), 13.48 (brs, 1H) | 527 | Example 114 |
| 285 | Cis(±)-2-[4-{[(3,4-Dichloro-5-methyl-1H-pyrrol-2-yl)carbonyl]amino}-3-(2-methoxyethoxy)piperidin-1-yl]-4-methyl-1,3-thiazole-5-carboxylic acid | 1.70-1.75 (m, 2H), 2.17 (s, 3H), 2.39 (s, 3H), 3.15 (s, 3H), 3.32-3.40 (m, buried under water peak), 3.50-3.60 (m, 1H), 3.68-3.75 (m, 2H), 3.86-3.98 (m, 1H), 4.20-4.30 (m, 2H), 7.14 (d, 1H), 12.14 (s, 1H), 12.38 (brs, 1H) | 490 | Example 112 |
| 286 | 2-((3S,4R)-4-{[(4-chloro-1H-pyrrol-2-yl)carbonyl]amino}-3- | 1.62-1.76 (m, 1H), 1.85-2.03 (m, 1H), 3.22 (s, 3H), 3.36-3.45 (m, | 373 | Example 115 |

| Ex | Compound | NMR | m/z | SM |
|---|---|---|---|---|
| | fluoropiperidin-1-yl)-1,3-thiazole-5-carboxylic acid | 1H), 3.50 (dd, 1H), 3.75 (s, 1H), 4.02-4.10 (m, 1H), 4.15-4.36 (m, 2H), 4.90 (d, 1H), 6.94-6.97 (m, 2H), 7.85 (s, 1H), 8.10 (d, 1H), 11.82 (s, 1H) | | |
| 287 | 2-((3S,4R)-4-{[(4-chloro-5-methyl-1H-pyrrol-2-yl)carbonyl]amino}-3-fluoropiperidin-1-yl)-4-methyl-1,3-thiazole-5-carboxylic acid | 1.62-1.74 (m, 1H), 1.84-2.05 (m, 1H), 2.13 (s, 3H), 2.41 (s, 3H), 3.19-3.30 (m, 1H), 3.50 (dd, 1H), 3.96-4.02 (m, 1H), 4.20-4.31 (m, 2H), 4.87 (d, 1H), 6.89 (d, 1H), 7.97 (d, 1H), 11.65 (s, 1H) | 401 | Example 116 |
| 288 | 2-((3S,4R)-4-{[(4-chloro-1H-pyrrol-2-yl)carbonyl]amino}-3-fluoropiperidin-1-yl)-4-methyl-1,3-thiazole-5-carboxylic acid | 1.68-1.74 (m, 1H), 1.85-2.00 (m, 1H), 2.39 (s, 3H), 3.30-3.54 (peaks buried under water peak), 3.94-4.00 (m, 1H), 4.10-4.32 (m, 2H), 4.82 (d, 1H), 6.94-6.97 (m, 2H), 8.11 (d, 1H), 11.84 (s, 1H) | 387 | Example 117 |
| 289 | 2-((3S,4R)-4-{[(4,5-dichloro-1H-pyrrol-2-yl)carbonyl]amino}-3-fluoropiperidin-1-yl)-4-methyl-1,3-thiazole-5-carboxylic acid | 1.69-1.74 (m, 1H), 1.86-2.00 (m, 1H), 2.40 (s, 3H), 3.25-3.35 (m, 1H, buried under water peak), 3.51 (dd, 1H), 3.96-4.00 (m, 1H), 4.16-4.31 (m, 2H), 4.87 (d, 1H), 7.06 (d, 1H), 8.15 (d, 1H), 12.48 (brs, 1H), 12.78 (s, 1H) | 419 | Example 118 |
| 290 | 2-((3S,4R)-4-{[(4,5-Dichloro-1H-pyrrol-2-yl)carbonyl]amino}-3-fluoropiperidin-1-yl)-1,3-thiazole-5-carboxylic acid | 1.64-1.74 (m, 1H), 1.85-2.00 (m, 1H), 3.30-3.40 (m, 1H, buried under water peak), 3.53 (dd, 1H), 4.00-4.08 (m, 1H), 4.12-4.40 (m, 2H), 4.89 (d, 1H), 7.06 (d, 1H), 7.75 (s, 1H), 8.16 (d, 1H), 12.78 (s, 1H) | 405 | Example 119 |
| 291 | Cis(±)-2-[4-{[(3,4-dichloro-5-methyl-1H-pyrrol-2-yl)carbonyl]amino}-3-(2-hydroxypropoxy)piperidin-1-yl]-1,3-thiazole-5-carboxylic acid | 0.95 (d, 3H), 1.73-1.85 (m, 2H), 2.16 (s, 3H), 3.19-3.36 (m, 6 H, broad peaks), 3.61-3.67 (m, 3H), 3.94-4.30 (m, difficult to integrate as the peaks are buried under water peak), 7.16 (d, 1H), 7.71 (s, 1H), 12.11 (s, 1H) | 477 | Example 120 |
| 292 | Cis(±)-2-[4-{[(3,4-dichloro-5-methyl-1H-pyrrol-2-yl)carbonyl]amino}-3-(2-methoxypropoxy)piperidin-1-yl]-1,3-thiazole-5-carboxylic acid | 0.96 (d, 3H), 1.73-1.76 (m, 2H), 2.17 (s, 3H), 3.14 (s, 1H), 3.28-3.67 (difficult to integrate as the peaks are buried under water peak), 3.89-3.92 (m, 1H), 4.20-4.45 (m, 2H), 7.12 (d, 1H), 7.72 (s, 1H), 12.15 (s, 1H) | 491 | Example 121 |
| 293 | 2-((3R,4S)-4-{[(3,4-dichloro-5-methyl-1H-pyrrol-2-yl)carbonyl]amino}-3-methoxypiperidin-1-yl)-1,3-benzothiazole-7-carboxylic | 1.85 (m, 2H), 2.25 (s, 3H), 3.41-3.48 (m, 6H), 4.16 (m, 1H), 5.35 (m, 1H), 4.41 (m, 1H), 7.26 (d, 1H), 7.49 (t, 1H), 7.72 (t, 2H0, 12.23 (s, 1H) | 483 | Example 123 |
| 294 | 2-((3S,4R)-4-{[(3,4-dichloro-5-methyl-1H-pyrrol-2-yl)carbonyl]amino}-3-methoxypiperidin-1-yl)-1,3-benzothiazole-7-carboxylic acid | 1.85 (m, 2H), 2.25 (s, 3H), 3.41-3.48 (m, 6H), 4.16 (m, 1H), 5.35 (m, 1H), 4.41 (m, 1H), 7.26 (d, 1H), 7.49 (t, 1H), 7.72 (t, 2H), 12.23 (s, 1H) | 483 | Example 122 |

| Ex | Compound | NMR | m/z | SM |
| --- | --- | --- | --- | --- |
| 295 | Cis(±)2-((3S,4R)-4-{[(3,4-dichloro-5-methyl-1H-pyrrol-2-yl)carbonyl]amino}-3-fluoropiperidin-1-yl)-1,3-thiazole-4-carboxylic acid | 1.74 (m, 2H), 2.10 (s, 3H), 3.29 (m, 1H), 3.48 (d, 1H), 3.85 (d, 1H), 4.14 (m, 1H), 4.29 (m, 1H), 4.83 (d, 1H), 7.18 (d, 1H), 7.53 (s, 1H), 12.03 (s, 1H) | 421 | Example 124 |
| 296 | 2-((3S,4R)-4-{[(4-chloro-5-methyl-1H-pyrrol-2-yl)carbonyl]amino}-3-methoxypiperidin-1-yl)-1,3-benzothiazole-7-carboxylic acid | 1.85 (m, 1H), 2.14 (m, 1H), 2.23 (s, 3H), 3.33 (s, 3H), 3.62-3.81 (m, 2H), 4.29 (m, 1H), 4.43 (m, 1H), 4.51 (m, 1H), 7.09 (s, 1H), 7.59 (t, 1H), 7.82-7.90 (m, 2H), 11.84 (s, 1H) | 449 | Example 125 |
| 297 | Cis(±)2-(4-{[(4-chloro-3,5-dimethyl-1H-pyrrol-2-yl)carbonyl]amino}-3-methoxypiperidin-1-yl)-1,3-thiazole-5-carboxylic acid | 1.47 (m, 1H), 1.62 (m, 1H), 1.95 (s, 3H0, 1.98 (s, 3H), 3.13 (m, 1H), 3.32 (m, 1H), 3.42 (s, 3H), 3.68 (m, 1H), 4.04 (m, 2H), 6.89 (d, 1H), 7.53 (s, 1H), 11.22 (s, 1H) | 413 | Example 126 |
| 299 | 2-((3S,4R)-4-{[(3,4-dichloro-5-methyl-1H-pyrrol-2-yl)carbonyl]amino}-3-fluoropiperidin-1-yl)-1,3-thiazole-4-carboxylic acid | 1.74 (m, 2H), 2.10 (s, 3H), 3.29 (m, 1H), 3.48 (d, 1H), 3.85 (d, 1H0, 4.14 (m, 1H), 4.29 (m, 1H), 4.83 (d, 1H), 7.18 (d, 1H), 7.53 (s, 1H), 12.03 (s, 1H) | 421 | Example 128 |
| 300 | 2-((3S,4R)-4-{[(4-chloro-3,5-dimethyl-1H-pyrrol-2-yl)carbonyl]amino}-3-fluoropiperidin-1-yl)-1,3-thiazole-4-carboxylic acid | 1.69 (m, 1H), 1.82 (m, 1H), 2.09 (s, 3H), 2.13 (s, 3H), 3.19-3.30 (m, 2H), 3.89 (m, 1H), 4.14 (m, 2H), 4.83 (d, 1H), 7.38 (d, 1H), 7.56 (s, 1H), 11.29 (s, 1H) | 401 | Example 129 |
| 301 | 2-((3R,4S)-4-{[(3,4-dichloro-5-methyl-1H-pyrrol-2-yl)carbonyl]amino}-3-fluoropiperidin-1-yl)-1,3-thiazole-4-carboxylic acid | 1.74 (m, 2H), 2.10 (s, 3H), 3.29 (m, 1H), 3.48 (d, 1H), 3.85 (d, 1H0, 4.14 (m, 1H), 4.29 (m, 1H), 4.83 (d, 1H), 7.18 (d, 1H), 7.53 (s, 1H), 12.03 (s, 1H) | 421 | Example 130 |
| 302 | Cis(±)2-(3-chloro-4-{[(3,4-dichloro-5-methyl-1H-pyrrol-2-yl)carbonyl]amino}piperidin-1-yl)-1,3-thiazole-5-carboxylic acid | 1.87 (m, 1H), 1.93 (m, 1H), 2.20 (s, 3H), 3.41 (m, 1H), 3.82 (d, 1H), 4.01 (d, 1H), 4.27 (d, 1H), 4.75 (s, 1H), 7.18 (d, 1H), 7.75 (s, 1H), 12.15 (s, 1H) | 437 | Example 131 |
| 303 | 2-{(3S,4R)-4-[({4-chloro-3-[(E)-(methoxyimino)methyl]-5-methyl-1H-pyrrol-2-yl}carbonyl)amino]-3-fluoropiperidin-1-yl}-1,3-thiazole-5-carboxylic acid | 1.86 (m, 2H), 2.35 (s, 3H), 3.33 (m, 1H), 3.61 (dd, 1H), 3.82 (s, 3H), 4.00 (d, 1H), 4.34 (m, 2H), 4.93 (d, 1H), 7.28 (d, 1H), 7.76 (s, 1H), 8.02 (s, 1H), 12.14 (s, 1H), 12.66 (s, 1H) | 444 | Example 132 |
| 304 | Cis(±)-2-(3-chloro-4-{[(3,4-dichloro-5-methyl-1H-pyrrol-2-yl)carbonyl]amino}piperidin-1-yl)[1,3]thiazolo[4,5-b]pyridine-7-carboxylic acid | 1.82 (m, 2H), 2.25 (s, 3H), 3.41 (m, 1H), 3.42 (m, 2H), 4.19 (m, 1H), 5.35 (m, 1H), 4.41 (m, 1H), 7.28 (d, 1H), 7.43 (t, 1H), 7.72 (t, 2H), 12.23 (s, 1H) | 489 | Example 133 |

-continued

| Ex | Compound | NMR | m/z | SM |
|---|---|---|---|---|
| 305 | Cis(±)-2-(3-chloro-4-{[(3,4-dichloro-5-methyl-1H-pyrrol-2-yl)carbonyl]amino}piperidin-1-yl)-4-(hydroxymethyl)-1,3-thiazole-5-carboxylic acid | 1.84 (m, 1H), 1.91 (m, 1H), 2.20 (s, 3H), 3.33 (m, 1H), 3.79 (m, 1H), 4.04 (m, 1H), 4.21 (m, 1H), 4.48 (m, 1H), 4.59 (m, 2H), 4.75 (s, 1H), 7.20 (d, 1H), 12.17 (s, 1H) | 468 | Example 134 |
| 306 | Cis(±)-2-(3-chloro-4-{[(4-chloro-5-methyl-1H-pyrrol-2-yl)carbonyl]amino}piperidin-1-yl)-1,3-thiazole-5-carboxylic acid | 1.72 (m, 1H), 2.07 (m, 1H), 2.14 (s, 3H), 3.34 (t, 1H), 3.81 (d, 1H), 4.03 (d, 1H), 4.22 (d, 1H), 4.36 (m, 1H), 4.73 (s, 1H), 6.91 (s, 1H), 7.75 (s, 1H), 7.95 (d, 1H), 11.70 (s, 1H) | 403 | Example 135 |
| 307 | Cis(±)-2-(3-chloro-4-{[(3,4-dichloro-5-methyl-1H-pyrrol-2-yl)carbonyl]amino}piperidin-1-yl)-4-(methoxymethyl)-1,3-thiazole-5-carboxylic acid | 1.83 (m, 1H), 1.92 (m, 1H), 2.20 (s, 3H), 3.28 (s, 3H0, 3.35 (m, 1H), 3.80 (d, 1H), 4.01 (m, 1H), 4.22 (m, 1H), 4.43 (m, 1H), 4.56 (m, 2H), 4.75 (s, 1H), 7.18 (d, 1H), 12.15 (s, 1H) | 481 | Example 136 |
| 308 | Cis(±)-2-(4-{[(3,4-dichloro-5-methyl-1H-pyrrol-2-yl)carbonyl]amino}-3-hydroxypiperidin-1-yl)-1,3-benzothiazole-7-carboxylic acid | 1.78 (m, 1H), 1.91 (m, 1H), 2.19 (s, 3H), 3.32 (m, 2H), 3.55 (d, 1H), 3.90 (s, 1H), 4.03 (m, 1H), 4.17 (m, 1H), 5.53 (d, 1H), 7.15 (d, 1H), 7.41 (t, 1H), 7.64 (t, 2H), 12.15 (s, 1H), 13.47 (s, 1H) | 470 | Intermediate 131 and 2-bromo-1,3-benzthiazole-7-carboxylate |
| 309 | Cis(±)-2-(4-{[(3,4-dichloro-5-methyl-1H-pyrrol-2-yl)carbonyl]amino}-3-methoxypiperidin-1-yl)-5-nitroisonicotinic acid | 1.65 (m, 1H), 1.8 (m, 1H), 2.2 (s, 3H), 3.3 (m, 1H), 3.55 (s, 1H), 4.3 (m, 1H), 7.1 (m 2H), 8.9 (s, 1H), 12.2 (s, 1H), 13.9 (s, 1H) | 500 | Example 137 |
| 310 | Cis(±)-2-(4-{[(3,4-dichloro-5-methyl-1H-pyrrol-2-yl)carbonyl]amino}-3-methoxypiperidin-1-yl)-5-[(methoxycarbonyl)amino]isonicotinic acid | 1.7 (m, 2H), 2.2 (s, 3H), 2.4-2.5 (m), 3.0-3.2 (m 2H), 3.3 (s, 3H), 3.5 (m 1H), 3.6 (s, 3H), 4.1 (m, 1H), 4.2 (m, 1H), 4.5 (m, 1H), 7.1 (m, 2H), 8.6 (s, 1H), 12.1 (s, 1H), 13.7 (s, 1H) | 500 | Example 195 |
| 311 | Cis(±)-2-(4-{[(3,4-dichloro-5-methyl-1H-pyrrol-2-yl)carbonyl]amino}-3-methoxypiperidin-1-yl)-5-[(methylsulfonyl)amino]isonicotinic acid | 1.7 (m, 2H) 2.2 (s, 3H), 2.9 (s, 3H), 3.1 (m, 2H), 3.3-3.5 (m), 3.5 (m, 1H), 4.2 (m, 2H), 4.6 (d, 1H), 7.1 (m, 2H), 8.1 (s, 1H), 12.1 (s, 1H). | 506 | Example 196 |
| 312 | Cis(±)-2-(4-{[(3,4-dichloro-5-methyl-1H-pyrrol-2-yl)carbonyl]amino}-3-methylpiperidin-1-yl)-1,3-thiazole-5-carboxylic acid | 0.9 (d, 3H), 1.8 (m, 2H), 2.2 (m, 4H), 3.3-3.8 (m, 4H), 4.25 (m, 1H), 4.25 (m, 1H), 7.2 (d, 1H), 7.8 (s, 1H), 12.0 (s, 1H), 12.6 (s, 1H) | 431 | Example 138 |
| 313 | Cis(±)-2-(4-{[(3,4-dichloro-5-methyl-1H-pyrrol-2-yl)carbonyl]amino}-2-methylpiperidin-1-yl)-1,3-thiazole-5-carboxylic acid | 1.3 (d, 1H), 1.8-2.1 (m, 4H), 2.2 (s, 3H), 3.6 (m, 1H), 3.8 (m 1H), 4.1 (m, 2H), 7.3 (s, 1H), 7.8 (s, 1H), 12.1 (s, 1H) | 417; | Example 139 |

-continued

| Ex | Compound | NMR | m/z | SM |
|---|---|---|---|---|
| 314 | Cis(±)-2-(4-{[(3,4-dichloro-5-methyl-1H-pyrrol-2-yl)carbonyl]amino}-3-methoxypiperidin-1-yl)-6-methylisonicotinic acid | 0.9 (m, 1H), 1.3 (d, 6H), 1.7, (m, 1H), 2.2 (s, 3H), 2.4 (s, 3H), 3.1 (m, 2H), 3.5 (m, 1H), 4.2 (m, 2H), 4.7 (d, 1H), 5.1 (m, 1H), 6.8 (s, 1H), 7.0 (s, 1H), 7.15 (s, 1H), 12.1 (s, 1H). | 441 | Example 140 |
| 315 | Cis(±)-5-chloro-4-(4-{[(3,4-dichloro-5-methyl-1H-pyrrol-2-yl)carbonyl]amino}-3-methoxypiperidin-1-yl)pyridine-2-carboxylic acid | NMR: 1.8, (m, 3H), 2.2 (s, 3H), 3.3 (s, 3H), 3.6 (m, 2H), 4.0 (m, 1H), 4.2 (m, 1H), 7.2 (s, 1H), 7.7 (s, 1H), 8.5 (s, 1H), 12.1 (s, 1H), 12.4 (s, broad, 1H). | 461 | Example 141 |
| 316 | 2-((3S,4R)-4-{[(3,4-dichloro-5-methyl-1H-pyrrol-2-yl)carbonyl]amino}-3-fluoropiperidin-1-yl)-4-(hydroxymethyl)-1,3-thiazole-5-carboxylic acid | NMR: 1.85 (m, 2H), 2.2 (s, 3H), 3.3-3.7 (m, 2H), 4.0 (m, 1H), 4.3 (m, 2H), 4.6 (s, 2H), 4.95 (d, 1H), 7.3 (d, 1H), 12.1 (s, 1H), 12.7 (s, 1H). | 451<br>215 | Example 142 and Intermediate |
| 317 | Cis(±)-2-(4-{[(3,4-dichloro-5-methyl-1H-pyrrol-2-yl)carbonyl]amino}-3-methoxypiperidin-1-yl)-4-(hydroxymethyl)-1,3-thiazole-5-carboxylic acid | NMR: 1.2 (t, 3H), 1.7 (m, 2H), 2.2 (s, 3H), 3.4 (s, 3H), 3.55 (m, 1H), 4.0 (m, 1H), 4.1-4.4 (m, 4H), 4.6 (s, 2H), 7.1 9d, 1H), 12.1 (s, 1H). | 463 | Example 143 |
| 318 | Cis(±)-2-(4-{[(4-chloro-3-cyano-5-methyl-1H-pyrrol-2-yl)carbonyl]amino}-3-methoxypiperidin-1-yl)-1,3-thiazole-5-carboxylicacid | NMR: 1.6-1.9 (m, 2H), 2.2 (s, 3H), 3.3 (s, 3H), 3.6 (m, 1H), 3.7 (s, 3H), 3.9 (m, 1H), 4.3 (m, 2H), 7.75 (m, 2H), 12.6 (2s, 2H). | 424 | Example 144 |
| 319 | Cis(±)-2-(4-{[(4-chloro-3-cyano-5-methyl-1H-pyrrol-2-yl)carbonyl]amino}-3-methoxypiperidin-1-yl)-1,3-benzothiazole-7-carboxylic acid | NMR: 1.6-2.0 (m, 2H), 2.2 (s, 3H), 3.3 (s, 3H), 3.4 (m, 1H), 3.6 (s, 3H), 4.1 (m, 1H), 4.2-4.4 (m, 2H), 7.4 (t, 1H), 7.65 (m, 2H), 7.8 (m, 1H), 12.6 (s, 1H), 13.5 (s, 1H). | 479 | Example 145 |
| 320 | Cis(±)-2-(4-{[(4-chloro-3-cyano-5-methyl-1H-pyrrol-2-yl)carbonyl]amino}-3-methoxypiperidin-1-yl)-1,3-thiazole-5-carboxylic acid | NMR: 1.7 (m, 2H), 2.2 (s, 3H), 3.0-3.7 (m), 4.2 (m, 2H), 4.6 (m, 1H), 7.0 (s, 1H), 7.25 (s, 1H), 7.7 (s, 1H), 8.2 (s, 1H), 12.6 (s, 1H), 13.5 (s, 1H). | 418 | Example 146 |
| 322 | 2-((3S,4R)-4-{[(4-chloro-3-cyano-5-methyl-1H-pyrrol-2-yl)carbonyl]amino}-3-fluoropiperidin-1-yl)-1,3-benzothiazole-7-carboxylic acid | NMR: 1.9 (m, 2H), 2.2 (s, 3H), 3.4 (m, 1H), 3.4 (m, 1H), 3.6 (s, 3H), 4.1 (m, 1H), 4.3 (m, 1H), 4.4 (q, 2H), 7.7 (m, 2H), 7.8 (m, 1H), 7.9 (t, 1H), 12.7 (s, 1H), 13.5 (s, 1H). | 462 | Example 148 |
| 323 | 2-((3S,4R)-4-{[(4-chloro-3-cyano-5-methyl-1H-pyrrol-2-yl)carbonyl]amino}-3-fluoropiperidin-1-yl)isonicotinic acid | NMR: 1.8 (m, 2H), 2.2 (s, 3H), 3.0 (m, 2H), 3.3 (m), 4.0-4.5 (m, 2H), 4.7 (m, 1H), 4.95 (d, 1H), 7.0 9d, 1H), 7.3 (m, 1H), 8.05 (m, 1H), 8.25 (d, 1H), 12.6 (s, 1H), 13.4 (s, 1H). | 406 | Example 149 |
| 324 | Cis(±)-2-(4-{[(3,4-dichloro-5-methyl-1H-pyrrol-2-yl)carbonyl]amino}-3-methoxypiperidin-1-yl)-5-(morpholin-4-ylcarbonyl)-1,3-thiazole-4-carboxylic acid | NMR: 1.7 (m, 2H), 2.2 (s, 3H), 3.3 (m), 3.4 (m, 4H), 3.5 (m, 4H), 3.8-3.9 (m, 4H), 4.0-4.2 (m, 4H), 7.3 (s, 1H), 12.3 (s, 1H), 12.9 (s, 1H). | 546 | Example 150 |

-continued

| Ex | Compound | NMR | m/z | SM |
|---|---|---|---|---|
| 325 | Cis(±)-6-cyano-4-(4-{[(3,4-dichloro-5-methyl-1H-pyrrol-2-yl)carbonyl]amino}-3-methoxypiperidin-1-yl)pyridine-2-carboxylic acid | NMR: 1.7 (m, 2H), 2.1 (s, 3H), 3.3 (s, 3H), 3.45 (m, 1H), 4.0 (d, 1H), 4.2 (m, 1H), 4.4 (d, 1H), 7.0 (d, 1H), 7.5 (s, 1H), 7.7 (s, 1H), 12.1 (s, 1H), 13.3 (s, 1H). | 452 | Example 151 |
| 326 | 2-((3S,4R)-4-{[(3,5-dichloro-4-methyl-1H-pyrrol-2-yl)carbonyl]amino}-3-fluoropiperidin-1-yl)-1,3-thiazole-5-carboxylic acid | NMR: 1.8 (m, 2H), 1.9 (s, 3H), 3.3 (m, 1H), 3.5 (dd, 1H), 4.0 (m, 1H), 4.3 (m, 2H), 5.0 (d, 1H), 7.35 (d, 1H), 7.8 (s, 1H), 12.6 (s, 1H), 12.7 (s, 1H). | 421 | Example 155 |
| 327 | 4-acetyl-2-((3S,4R)-4-{[(3,4-dichloro-5-methyl-1H-pyrrol-2-yl)carbonyl]amino}-3-methoxypiperidin-1-yl)-1,3-thiazole-5-carboxylic acid | NMR: 1.7 (m, 2H), 2.2 (s, 3H), 3.3 (s, 3H), 3.9 (m, 2H), 4.3 (m, 2H), 7.15 (m, 1H), 12.2 (s, 1H), 13.2 (s, 1H). | 475 | Example 157 |
| 328 | 2-((3S,4R)-4-{[(3,4-dichloro-5-methyl-1H-pyrrol-2-yl)carbonyl]amino}-3-methoxypiperidin-1-yl)-4-(1-hydroxy-1-methylethyl)-1,3-thiazole-5-carboxylic acid | NMR: 1.5 (s, 6H), 1.7 (m, 2H), 2.2 (s, 3H), 3.3 (s, 3H), 3.5 (m, 1H), 3.8 (m, 2H), 4.3 (m, 1H), 4.4 (m, 1H), 7.15 (d, 1H), 12.2 (s, 1H). | 491 | Example 158 |
| 329 | 2-((3S,4R)-4-{[(3,4-dichloro-5-methyl-1H-pyrrol-2-yl)carbonyl]amino}-3-methoxypiperidin-1-yl)thieno[2,3-d][1,3]thiazole-6-carboxylic acid | NMR: 1.8 (m, 2H), 2.2 (s, 3H), 3.3 (s, 3H), 3.6 (m, 1H), 4.0 (m, 1H), 4.3 (m, 2H), 7.2 (d, 1H), 7.9 (s, 1H), 12.2 (s, 1H), 13.1 (s, 1H). | 489 | Example 159 |
| 330 | Cis(±)-2-(3-(cyclopropylmethoxy)-4-{[(3,4-dichloro-5-methyl-1H-pyrrol-2-yl)carbonyl]amino}piperidin-1-yl)-1,3-thiazole-5-carboxylic acid | 0.10 (m, 2H), 0.38 (m, 2H), 0.91 (m, 1H), 1.75 (m, 1H), 2.17 (s, 3H), 3.15-3.43 (m, 4H), 3.67 (m, 1H), 3.92 (m, 1H), 4.26 (m, 2H), 7.14 (d, 1H), 7.72 (s, 1H), 12.16 (s, 1H), 12.60 (bs, 1H). | 473 | Example 160 |
| 331 | 2-[4-{[(3,4-dichloro-5-methyl-1H-pyrrol-2-yl)carbonyl]amino}-3-(1,3-thiazol-2-ylmethoxy)piperidin-1-yl]-1,3-thiazole-5-carboxylic acid | 1.80 (m, 2H), 2.16 (s, 3H), 3.40 (d, 2H), 3.94 (m, 2H), 4.33 (td, 1H), 4.46 (d, 1H), 4.81-4.99 (dd, 2H), 7.13 (d, 1H), 7.65 (d, 1H), 7.69 (s, 1H), 7.71 (d, 1H), 12.12 (s, 1H), 12.60 (bs, 1H). | 515 | Example 161 |

| Ex | Compound | NMR | m/z | SM |
|---|---|---|---|---|
| 332 | Cis(±)-2-(4-{[(3,4-dichloro-5-methyl-1H-pyrrol-2-yl)carbonyl]amino}-3-ethoxypiperidin-1-yl)-1,3-thiazole-5-carboxylic acid | 1.05 (t, 3H); 1.74 (m, 2H); 2.17 (s, 3H); 3.35-3.45 (m, 3H); 3.63-3.73 (m, 2H); 3.97 (m, 1H); 4.25 (m, 2H); 7.12 (d, 1H); 7.72 (s, 1H); 12.16 (s, 1H); 12.55 (br s, 1H). | 447, 449 | Example 162 |
| 333 | Cis(±)-2-(4-{[(3,4-dichloro-5-methyl-1H-pyrrol-2-yl)carbonyl]amino}-3-ethoxypiperidin-1-yl)-4-(methoxymethyl)-1,3-thiazole-5-carboxylic acid | 1.06 (t, 3H); 1.74 (m, 2H); 2.17 (s, 3H); 3.27 (m, 4H); 3.42 (m, 1H); 3.62-3.71 (m, 2H); 3.82 (m, 1H); 4.08-4.21 (overlapping m, 3H); 4.55 (s, 2H); 6.64 (s, 1H); 7.11 (d, 1H); 12.16 (s, 1H). | 435, 437 | Example 163 |
| 334 | 2-((3S,4R)-4-{[(3,4-Dichloro-5-methyl-1H-pyrrol-2-yl)carbonyl]amino}-3-fluoropiperidin-1-yl)-4-methyl-1,3-thiazole-5-carboxylic acid | 1.83 (m, 2H); 2.18 (s, 3H); 2.40 (s, 3H); 3.32 (m, overlapping water); 3.50 (dd, 1H); 3.97 (m, 1H); 4.21-4.31 (m, 2H); 4.93 (d, 1H); 7.26 (d, 1H); 12.11 (s, 1H); 12.44 br s, 1H). | 435, 437 | Example 165 |
| 335 | 2-((3S,4R)-4-{[(3,4-Dichloro-5-methyl-1H-pyrrol-2-yl)carbonyl]amino}-3-methoxypiperidin-1-yl)-4-methyl-1,3-thiazole-5-carboxylic acid | 1.72 (m, 2H); 2.17 (s, 3H); 2.39 (s, 3H); 3.26-3.35 (m overlapping with water, 5H); 3.52 (m, 1H); 3.90 (m, 1H); 4.25 (m, 2H); 7.14 (d, 1H); 12.15 (s, 1H); 12.40 (s, 1H). | 447, 449 | Example 166 |
| 337 | Trans(±)2-[4-{[(3,4-dichloro-5-methyl-1H-pyrrol-2-yl)carbonyl]amino}-3-(morpholin-4-ylcarbonyl)piperidin-1-yl]-1,3-thiazole-5-carboxylic acid | 1.89 (m, 1H), 2.14 (m, 1H), 2.17 (s, 3H), 3.24-3.70 (m, 11H [under H₂O peak]), 3.74 (dd, 1H), 3.90 (dd, 1H), 4.51 (m, 1H), 7.33 (d, 1H), 7.74 (s, 1H), 12.09 (s, 1H), 12.64 (s, 1H) | 516 | Example 167 |
| 338 | Cis(±)2-[4-{[(3,4-dichloro-5-methyl-1H-pyrrol-2-yl)carbonyl]amino}-3-(morpholin-4-ylcarbonyl)piperidin-1-yl]-1,3-thiazole-5-carboxylic acid | 1.79 (dq, 1H), 1.89 (m, 1H), 2.15 (s, 3H), 3.21-3.42 (m, 6H), 3.49-3.72 (m, 5H), 3.95 (m, 1H), 4.02 (m, 1H), 4.40 (m, 1H), 7.17 (d, 1H), 7.78 (s, 1H), 12.02 (s, 1H), 12.69 (s, 1H) | 516 | Example 168 |
| 339 | Cis(±)-2-[4-{[(3,4-dichloro-5-methyl-1H-pyrrol-2-yl)carbonyl]amino}-3-(2-morpholin-4-yl-2-oxoethoxy)piperidin-1-yl]-1,3-thiazole-5-carboxylic acid | 1.51 (dq, 1H), 1.98 (m, 1H), 2.18 (s, 3H), 3.18 (m, 2H), 3.23-3.56 (m, 10H [under H₂O peak]), 3.77 (m, 1H), 4.04 (m, 2H), 4.32 (q, 2H), 7.36 (s, 1H), 8.26 (broad s, 2H) | 546 | Example 169 |
| 340 | 2-(4-{[(3,4-dichloro-5-methyl-1H-pyrrol-2-yl)carbonyl]amino}-3-{[(ethylamino)carbonyl]oxy}piperidin-1-yl)-1,3-thiazole-5-carboxylic acid | MS (ES) MH⁺: 490, 492 for $C_{18}H_{21}Cl_2N_5O_5S$; NMR: 0.96 (t, 3H), 1.82 (m, 2H), 2.17 (s, 3H), 2.96 (m, 2H), 3.19-3.40 (m, 2H) [under H₂O peak]), 3.47 (d, 1H), 3.95 (m, 1H), 4.08 (m, 1H), 4.33 (m, 1H), 4.83 (m, 1H), 6.84 (broad s, 1H), 7.14 (d, 1H), 7.21 (t, 1H), 7.46 (s, 1H) | 490 | Example 172 |
| 341 | 2-(3-{[(allylamino)carbonyl]oxy}-4-{[(3,4-dichloro-5-methyl-1H-pyrrol-2-yl)carbonyl]amino}piperidin-1-yl)-1,3-thiazole-5-carboxylic acid | NMR: 1.22 (s, 1H), 1.84 (m, 2H), 2.17 (s, 3H), 3.52 (m, 1H), 3.57, (m, 1H), 4.03 (m, 1H), 4.14 (m, 1H), 4.36 (m, 1H), 4.78-4.91 (m, 2H), 4.99 (dd, 1H), 5.07 (dd, 1H), 5.52 (broad s, 1H), 5.73 (m 1H), 7.00 (d, 1H), 7.10 (broad s, 1H), 7.44 (t, 1H), 7.62 (s, 1H) | 502 | Example 173 |

-continued

| Ex | Compound | NMR | m/z | SM |
|---|---|---|---|---|
| 342 | Cis(±)-4-(4-{[(4-chloro-5-methyl-1H-pyrrol-2-yl)carbonyl]amino}-3-methoxypiperidin-1-yl)pyridine-2-carboxylic acid | 1.56-1.72 (m, 2H) 2.08-2.20 (m, 3H) 3.24 (s, 3H) 3.55 (s, 2 H) 3.71-3.86 (m, 2H) 4.16 (s, 2 H) 6.88 (d, 1H) 7.44 (s, 1H) 7.68 (s, 1H) 7.97 (d, 1H) 11.69 (s, 1H) | 393 | Example 177 |
| 343 | Cis(±)-4-(aminocarbonyl)-2-(4-{[(3,4-dichloro-5-methyl-1H-pyrrol-2-yl)carbonyl]amino}-3-methoxypiperidin-1-yl)-1,3-thiazole-5-carboxylic acid | 1.74 (s, 2H) 2.19 (s, 3H) 3.38 (s, 3H) 3.55 (s, 2H) 4.01 (s, 1H) 4.25 (s, 3H) 4.49 (s, 1H) 7.16 (d, 1H) 8.93 (s, 2H) 12.16 (s, 1 H | 476 | Example 242 |
| 344 | 4-((3S,4R)-4-{[(3,4-dichloro-5-methyl-1H-pyrrol-2-yl)carbonyl]amino}-3-fluoropiperidin-1-yl)pyridine-2-carboxylic acid | 1.81-1.95 (m, 2H) 2.14-2.21 (m, 3H) 3.73 (s, 2H) 4.26 (t, 2 H) 4.62 (s, 1H) 4.93 (s, 1H) 7.22 (s, 1H) 7.36 (s, 1H) 7.49 (s, 1H) 7.69 (s, 1H) 8.04 (d, 1H) 12.30 (s, 1H) | 415 | Example 174 |
| 345 | 2-((3S,4R)-4-{[(3,4-dichloro-5-methyl-1H-pyrrol-2-yl)carbonyl]amino}-3-fluoropiperidin-1-yl)isonicotinic acid | 1.80 (m, 2H) 2.13-2.26 (s, 3H) 4.14 (dd, 1H) 4.27 (s, 1H) 4.41 (s, 2H) 4.72 (s, 1H) 4.84-5.00 (d, 1H) 7.02 (d, 1H) 7.17-7.32 (m, 1H) 7.66-7.78 (m, 1H) 8.24 (d, 1H) 12.11 (s, 1H) | 415 | Example 179 |
| 346 | 2-((3S,4R)-4-{[(3,4-dichloro-5-methyl-1H-pyrrol-2-yl)carbonyl]amino}-3-fluoropiperidin-1-yl)-4-(methoxymethyl)-1,3-thiazole-5-carboxylic acid | 1.85 (s, 2H) 2.19 (s, 3H) 3.28 (s, 3H) 3.50-3.64 (dd, 1H) 3.98 (s, 1H) 4.32 (s, 2H) 4.57 (s, 2H) 4.88-5.04 (d, 1H) 7.29 (d, 1H) 12.12 (s, 1H) 12.79 (s, 1H) | 465 | Example 180 |
| 347 | 4-((3S,4R)-4-{[(3,4-dichloro-5-methyl-1H-pyrrol-2-yl)carbonyl]amino}-3-fluoropiperidin-1-yl)quinoline-2-carboxylic acid | 2.00 (s, 2H) 2.21 (s, 3H) 3.33 (s, 1H) 3.78 (d, 1H) 4.08 (s, 2H) 4.32-4.42 (m, 1H) 4.95-5.11 (d, 1H) 7.34 (d, 1H) 7.60 (s, 2H) 7.69 (t, 1H) 7.84 (t, 1H) 8.08-8.22 (m, 2H) 12.15 (s, 1H) | 465 | Example 181 |
| 348 | Cis(±)-2-(4-{[(4-chloro-5-methyl-1H-pyrrol-2-yl)carbonyl]amino}-3-methoxypiperidin-1-yl)isonicotinic acid | 1.57 (d, 1H) 1.86 (d, 1H) 2.14 (s, 3H) 3.04-3.18 (m, 2H) 3.19-3.25 (s, 3H) 3.49 (s, 1H) 4.19 (s, 1H) 4.21 (d, 1H) 4.55 (d, 1 H) 6.89 (d, 1H) 6.96 (d, 1H) 7.23 (s, 1H) 7.64 (d, 1H) 8.22 (d, 1H) 11.62 (s, 1H) 13.39 (s, 1H) | 393 | Example 182 |
| 349 | 2-((3S,4R)-4-{[(3,4-dichloro-5-methyl-1H-pyrrol-2-yl)carbonyl]amino}-3-methoxypiperidin-1-yl)-4-(methoxymethyl)-1,3-thiazole-5-carboxylic acid | 1.68 (s, 2H) 2.12 (s, 3H) 3.21 (s, 3H) 3.33 (m, 5H) 3.48 (s, 1H) 3.85 (s, 1H) 4.19 (s, 2H) 4.49 (s, 2H) 7.08 (s, 1H) 12.09 (s, 1H) | 477 | Example 183 |
| 350 | 2-((3R,4S)-4-{[(3,4-dichloro-5-methyl-1H-pyrrol-2-yl)carbonyl]amino}-3-methoxypiperidin-1-yl)-4-(methoxymethyl)-1,3-thiazole-5-carboxylic acid | 1.68 (s, 2H) 2.12 (s, 3H) 3.21 (s, 3H) 3.25 (m, 2H) 3.30 (s, 3H) 3.48 (s, 1H) 3.84 (s, 1H) 4.19 (s, 2H) 4.49 (s, 2H) 7.09 (d, 1H) 12.09 (s, 1H) | 477 | Example 184 |

-continued

| Ex | Compound | NMR | m/z | SM |
|---|---|---|---|---|
| 351 | Cis(±)-4-(4-{[(3,4-dichloro-5-methyl-1H-pyrrol-2-yl)carbonyl]amino}-3-methoxypiperidin-1-yl)pyridine-2,6-dicarboxylic acid | 1.68 (s, 1H) 1.77 (s, 1H) 2.18 (s, 3H) 3.21 (s, 2H) 3.31 (s, 3H) 3.55 (s, 1H) 4.02 (s, 1H) 4.28 (s, 1H) 4.41 (s, 1H) 7.13 (s, 1H) 7.61 (s, 2H) 12.13 (s, 1H) | 471 | Example 185 |
| 352 | 4-((3S,4R)-4-{[(3,4-dichloro-5-methyl-1H-pyrrol-2-yl)carbonyl]amino}-3-fluoropiperidin-1-yl)-6-[(dimethylamino)carbonyl]pyridine-2-carboxylic acid | 1.71-1.86 (m, 2H) 2.22 (s, 3H) 2.93-3.04 (m, 3H) 3.04-3.15 (m, 3H) 3.80-3.96 (m, 1H) 4.08 (s, 1H) 4.28-4.43 (m, 2H) 4.77 (s, 1H) 4.94 (s, 1H) 6.87 (d, 1H) 7.10 (d, 1H) 7.58 (d, 1H) 9.33 (s, 2H) | 486 | Example 187 |
| 353 | Cis(±)-2-(4-{[(3,4-dichloro-5-methyl-1H-pyrrol-2-yl)carbonyl]amino}-3-methoxypiperidin-1-yl)-1,3-thiazole-4,5-dicarboxylic acid | 1.75 (s, 2H) 2.18 (s, 3H) 3.33 (s, 2H) 3.37 (s, 3H) 3.55 (s, 1H) 3.92 (s, 1H) 4.26 (s, 2H) 7.15 (d, 1H) 12.14 (s, 1H) | 477 | Example 175 |
| 354 | 2-((3S,4R)-4-{[(3,4-dichloro-5-methyl-1H-pyrrol-2-yl)carbonyl]amino}-3-fluoropiperidin-1-yl)-1,3-thiazole-4,5-dicarboxylic acid | 1.85 (s, 2H) 2.19 (s, 3H) 3.33 (s, 1H) 3.60 (s, 1H) 3.99 (s, 1H) 4.31 (s, 2H) 4.88-5.04 (s, 1H) 7.28 (s, 1H) 12.09 (s, 1H) | 465 | Example 176 |
| 355 | Cis(±)-2-(4-{[(3,4-dichloro-5-methyl-1H-pyrrol-2-yl)carbonyl]amino}-3-methoxypiperidin-1-yl)-4-formyl-1,3-thiazole-5-carboxylic acid | 1.75 (s, 2H) 2.18 (s, 3H) 3.17 (s, 1H) 3.36 (s, 3H) 3.56 (s, 1H) 4.01 (s, 2H) 4.25 (s, 2H) 7.15 (d, 1H) 10.35 (s, 1H) 12.15 (s, 1H) | 461 | Example 252 |
| 356 | Cis(±)-2-(4-{[(3,4-dichloro-5-methyl-1H-pyrrol-2-yl)carbonyl]amino}-3-methoxypiperidin-1-yl)-4-[(dimethylamino)carbonyl]-1,3-thiazole-5-carboxylic acid | 1.69 (s, 2H) 2.12 (s, 3H) 2.72 (s, 3H) 2.82-2.88 (m, 3H) 3.22 (s, 1H) 3.29 (s, 3H) 3.32 (s, 1H) 3.48 (d, 1H) 3.81 (s, 1H) 4.21 (s, 2H) 7.09 (d, 1H) 12.03-12.13 (m, 1H) 12.68 (s, 1H) | 504 | Example 203 |
| 357 | Cis(±)-2-(4-{[(3,4-dichloro-5-methyl-1H-pyrrol-2-yl)carbonyl]amino}-3-methoxypiperidin-1-yl)-4-(morpholin-4-ylcarbonyl)-1,3-thiazole-5-carboxylic acid | 1.75 (s, 2H) 2.18 (s, 3H) 3.12-3.22 (m, 2H) 3.35 (s, 3H) 3.53 (d, 6H) 3.60 (d, 2H) 3.85 (s, 2H) 4.27 (s, 2H) 7.14 (d, 1H) 12.13 (s, 1H) 12.81 (s, 1H) | 546 | Example 204 |
| 358 | 2-((3S,4R)-4-{[(3,4-dichloro-5-methyl-1H-pyrrol-2-yl)carbonyl]amino}-3-fluoropiperidin-1-yl)-4-(morpholin-4-ylcarbonyl)-1,3-thiazole-5-carboxylic acid | 1.84 (s, 2H) 2.18 (s, 3H) 3.16 (s, 2H) 3.51 (s, 2H) 3.52-3.64 (m, 5H) 3.96 (s, 1H) 4.29 (s, 2H) 4.37 (s, 1H) 4.87-5.04 (s, 1H) 7.26 (d, 1H) 12.07 (s, 2H) | 534 | Example 205 |
| 359 | Cis(±)-2-(4-{[(3,4-dichloro-5-methyl-1H-pyrrol-2-yl)carbonyl]amino}-3-methoxypiperidin-1-yl)-4-[(methoxyamino)carbonyl]-1,3-thiazole-5-carboxylic acid trifluoroacetate | 1.79 (s, 2H) 2.19 (s, 3H) 3.38 (s, 3H) 3.56 (s, 2H) 3.64 (s, 1H) 3.75 (s, 3H) 4.03 (s, 1H) 4.25 (s, 2H) 7.16 (d, 1H) 12.16 (s, 1H) | 506 | Example 206 |

| Ex | Compound | NMR | m/z | SM |
|---|---|---|---|---|
| 360 | 2-((3S,4R)-4-{[(3,4-dichloro-5-methyl-1H-pyrrol-2-yl)carbonyl]amino}-3-fluoropiperidin-1-yl)-4-[(methoxyamino)carbonyl]-1,3-thiazole-5-carboxylic acid 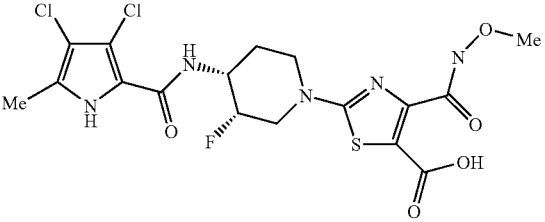 [SMILES: CONC(=O)c1nc(N2CC[C@@H](NC(=O)c3[nH]c(C)c(Cl)c3Cl)[C@@H](F)C2)sc1C(=O)O] | 1.83-1.92 (m, 2H) 2.19 (s, 3H) 3.50-3.63 (dd, 1H) 3.76 (s, 3H) 4.11 (s, 1H) 4.30 (s, 1H) 4.42 (s, 2H) 4.90-5.07 (s, 1H) 7.29 (d, 1+nlH) 12.11 (s, 1H) 12.39 (s, 1H) | 494 | Example 207 |
| 361 | Cis(±)-2-(4-{[(3,4-dichloro-5-methyl-1H-pyrrol-2-yl)carbonyl]amino}-3-methoxypiperidin-1-yl)-4-(piperidin-1-ylcarbonyl)-1,3-thiazole-5-carboxylic acid | 1.51 (s, 3H) 1.57 (s, 1H) 1.75 (s, 2H) 2.18 (s, 3H) 3.07-3.17 (m, 2H) 3.35 (s, 3H) 3.54 (d, 2H) 3.87 (s, 1H) 4.27 9s, 2H) 7.16 (d, 1H) 12.16 (s, 1H) 12.76 (s, 1H) | 544 | Example 208 |
| 362 | 4-(aminocarbonyl)-2-((3S,4R)-4-{[(3,4-dichloro-5-methyl-1H-pyrrol-2-yl)carbonyl]amino}-3-methoxypiperidin-1-yl)-1,3-thiazole-5-carboxylic acid | 1.74 (d, 2H) 2.19 (s, 3H) 3.32 (s, 2H) 3.38 (s, 1H) 3.55 (s, 1H) 4.25 (s, 2H) 4.49 (s, 1H) 7.17 (d, 1H) 8.87 (s, 1H) 12.17 (s, 1H) | 476 | Example 243 |
| 363 | 4-(aminocarbonyl)-2-((3S,4R)-4-{[(3,4-dichloro-5-methyl-1H-pyrrol-2-yl)carbonyl]amino}-3-fluoropiperidin-1-yl)-1,3-thiazole-5-carboxylic acid | 1.84 (s, 2H) 2.19 (s, 3H) 3.19 (s, 1H) 3.95 (s, 2H) 4.24 (s, 2H) 4.86-5.02 (s, 1H) 7.28 (d, 1H) 12.12 (s, 1H) | 464 | Example 244 |
| 364 | Cis(±)-2-(4-{[(3,4-dichloro-5-methyl-1H-pyrrol-2-yl)carbonyl]amino}-3-methoxypiperidin-1-yl)-5-{[(2-hydroxyethyl)amino]carbonyl}-1,3-thiazole-4-carboxylic acid trifluoroacetate (salt) | 1.60-1.73 (m, 2H) 2.12 (s, 3H) 3.14-3.25 (m, 2H) 3.30 (s, 3H) 3.41 (t, 2H) 3.86 (s, 2H) 4.19 (s, 2H) 7.09 (d, 1H) 9.66 (t, 1H) 12.09 (s, 1H) | 520 | Example 212 |
| 365 | Cis(±)-2-(4-{[(3,4-dichloro-5-methyl-1H-pyrrol-2-yl)carbonyl]amino}-3-methoxypiperidin-1-yl)-4-{[(2-hydroxyethyl)amino]carbonyl}-1,3-thiazole-5-carboxylic acid 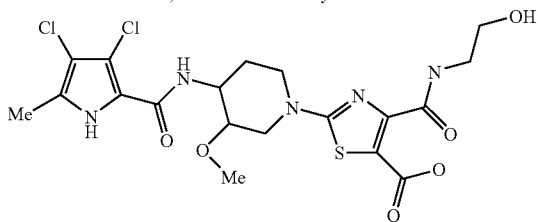 | 1.69 (s, 2H) 2.12 (s, 3H) 3.25 (s, 2H) 3.31 (s, 3H) 3.43-3.53 (m, 2H) 4.03 (s, 1H) 4.23 (s, 2H) 4.80 (s, 1H) 7.07-7.22 (m, 1H) 9.23 (s, 1H) 12.09 (s, 1H) | 520 | Example 212 |
| 366 | 2-((3S,4R)-4-{[(3,4-dichloro-5-methyl-1H-pyrrol-2-yl)carbonyl]amino}-3-fluoropiperidin-1-yl)-5-[(methylamino)carbonyl]-1,3-thiazole-4-carboxylic acid | 1.84 (s, 2H) 2.18 (s, 3H) 2.76 (s, 3H) 3.31 (s, 1H) 3.40 (s, 1H) 3.61 (s, 1H) 3.98 (s, 1H) 4.29 (s, 1H) 4.87-5.03 (s, 1H) 7.26 (s, 1 H) 9.43 (s, 1H) 12.11 (s, 1H) | 478 | Example 211 |
| 367 | 2-((3S,4R)-4-{[(3,4-dichloro-5-methyl-1H-pyrrol-2-yl)carbonyl]amino}-3-fluoropiperidin-1-yl)-4-[(methylamino)carbonyl]-1,3-thiazole-5-carboxylic acid | 1.87 (s, 2H) 2.19 (s, 3H) 2.87 (s, 3H) 3.53 (s, 1H) 4.13 (s, 1H) 4.30 (s, 1H) 4.43 (s, 2H) 4.91-5.07 (d, 1H) 7.31 (s, 1H) 9.40 (s, 1H) 12.11 (s, 1H) | 478 | Example 211 |
| 368 | Cis(±)-2-(4-{[(3,4-dichloro-5-methyl-1H-pyrrol-2-yl)carbonyl]amino}-3-methoxypiperidin-1-yl)-4-[(hydroxyimino)methyl]-1,3-thiazole-5-carboxylic acid | 1.76 (s, 2H) 2.19 (s, 3H) 2.91 (q, 1H) 3.03 (d, 1H) 3.35-3.38 (m, 3H) 3.53 (s, 1H) 3.93 (s, 1H) 4.03 (d, 1H) 4.23 (s, 1H) 7.20 (d, 1H) 7.54 (s, 1H) 7.83 (s, 1H) 8.76 (s, 1H) | 476 | Example 355 |
| 369 | Cis(±)-2-(4-{[(3,4-dichloro-5-methyl-1H-pyrrol-2- | 1.70-1.82 (m, 2H) 2.19 (s, 3H) 3.32 (s, 3H) 3.38 (s, 3H) 3.41 (s, | 490 | Example 214 |

| Ex | Compound | NMR | m/z | SM |
|---|---|---|---|---|
| | yl)carbonyl]amino}-3-methoxypiperidin-1-yl)-4-[(methylamino)carbonyl]-1,3-thiazole-5-carboxylic acid | 1H) 3.56 (s, 1H) 4.09 (s, 1H) 4.29 (d, 2H) 4.46 (s, 1H) 7.17 (d, 1H) 9.38 (s, 1H) 12.17 (s, 1 H) | | |
| 370 | Cis(±)-2-(4-{[(3,4-dichloro-5-methyl-1H-pyrrol-2-yl)carbonyl]amino}-3-methoxypiperidin-1-yl)-4-[(E)-(methoxyimino)methyl]-1,3-thiazole-5-carboxylic acid | 1.69 (s, 2H) 2.12 (s, 3H) 3.31 (s, 3H) 3.49 (s, 2H) 3.84 (s, 3H) 3.96 (s, 2H) 4.21 (s, 2H) 7.10 (d, 1H) 8.62 (s, 1H) 12.10 (s, 1H) | 490 | Example 251 |

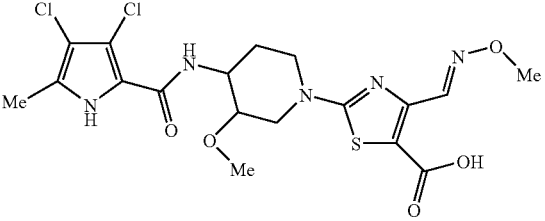 [SMILES: CO/N=C/c1nc(N2CCC(NC(=O)c3[nH]c(C)c(Cl)c3Cl)C(OC)C2)sc1C(=O)O]

| Ex | Compound | NMR | m/z | SM |
|---|---|---|---|---|
| 371 | Cis(±)-2-(4-{[(3,4-dichloro-5-methyl-1H-pyrrol-2-yl)carbonyl]amino}-3-methoxypiperidin-1-yl)-4-(morpholin-4-ylmethyl)-1,3-thiazole-5-carboxylic acid | 1.61-1.71 (m, 2H) 2.10-2.14 (m, 3H) 2.68 (s, 3H) 3.29 (s, 3 H) 3.47 (d, 1H) 3.58 (s, 4H) 3.67-3.80 (m, 2H) 3.84 (d, 2H) 4.19 (t, 2H) 7.10 (d, 1H) 12.12 (s, 1H) | 532 | Example 246 |
| 372 | Cis(±)-2-(4-{[(3,4-dichloro-5-methyl-1H-pyrrol-2-yl)carbonyl]amino}-3-methoxypiperidin-1-yl)-4-(difluoromethyl)-1,3-thiazole-5-carboxylic acid | 1.60-1.74 (m, 2H) 2.12 (s, 3H) 3.27 (s, 1H) 3.30 (s, 3H) 3.34 (s, 1H) 3.49 (s, 1H) 3.87 (s, 1H) 4.21 (s, 2H) 7.10 (d, 1H) 7.27 (s, 1H) 12.10 (s, 1H) | 483 | Example 253 |
| 373 | Cis(±)-4-[(tert-butylamino)methyl]-2-(4-{[(3,4-dichloro-5-methyl-1H-pyrrol-2-yl)carbonyl]amino}-3-methoxypiperidin-1-yl)-1,3-thiazole-5-carboxylic acid | 1.26 (s, 9H) 1.72 (s, 2H) 2.18 (s, 3H) 3.32 (m, 3H) 3.36 (s, 3H) 3.52 (s, 1H) 3.95 (s, 2H) 4.18 (s, 2H) 7.15 (d, 1H) 12.18 (s, 1H) | 518 | Example 247 |
| 374 | Cis(±)-2-(4-{[(3,4-dichloro-5-methyl-1H-pyrrol-2-yl)carbonyl]amino}-3-methoxypiperidin-1-yl)-4-{[(2-hydroxy-1-methylethyl)amino]carbonyl}-1,3-thiazole-5-carboxylic acid | 1.11-1.20 (m, 3H) 1.76 (s, 2H) 2.19 (s, 3H) 3.38 (s, 3H) 3.48 (d, 3H) 3.57 (s, 1H) 4.04 (s, 1H) 4.27 (s, 2H) 4.91 (s, 2H) 7.17 (d, 1H) 8.83 (s, 1H) 12.16 (s, 1H) | 534 | Example 216 |
| 375 | Cis(±)-2-(4-{[(3,4-dichloro-5-methyl-1H-pyrrol-2-yl)carbonyl]amino}-3-methoxypiperidin-1-yl)-4-{[(2-methoxyethyl)amino]carbonyl}-1,3-thiazole-5-carboxylic acid | 1.79 (s, 3H) 2.19 (s, 3H) 3.23-3.28 (m, 3H) 3.38 (s, 3H) 3.42 (s, 2H) 3.46-3.52 (m, 2H) 3.57 (s, 1H) 4.30 (d, 2H) 7.17 (d, J = 8.48 Hz, 1H) 9.38 (s, 1H) 12.16 (s, 1H) | 534 | Example 215 |
| 376 | Cis(±)-2-(4-{[(3,4-dichloro-5-methyl-1H-pyrrol-2-yl)carbonyl]amino}-3-methoxypiperidin-1-yl)-5-{[(2-hydroxypropyl)amino]carbonyl}-1,3-thiazole-4-carboxylic acid | 1.06 (d, 3H) 1.69-1.79 (m, 3H) 2.18 (s, 3H) 3.37 (s, 3H) 3.54 (s, 2H) 3.71 (s, 1H) 3.94 (s, 1H) 4.25 (s, 3H) 4.79 (s, 1H) 6.55 (s, 1H) 7.17 (s, 1H) 9.78 (s, 1H) 12.16 (s, 1H) | 534 | Example 217 |
| 377 | Cis(±)-2-(4-{[(3,4-dichloro-5-methyl-1H-pyrrol-2-yl)carbonyl]amino}-3-methoxypiperidin-1-yl)-4-{[(2-hydroxypropyl)amino]carbonyl}-1,3-thiazole-5-carboxylic acid | 1.06 (dd, 3H) 1.75 (s, 2H) 2.19 (s, 3H) 3.24 (s, 2H) 3.38 (s, 3H) 3.43 (s, 1H) 3.56 (s, 1H) 3.83 (s, 1H) 4.05 (s, 1H) 4.26 (s, 2H) 4.90 (s, 1H) 7.17 (d, 1H) 9.21 (s, 1H) 12.16 (s, 1H) | 534 | Example 217 |
| 378 | Cis(±)-2-(4-{[(3,4-dichloro-5-methyl-1H-pyrrol-2-yl)carbonyl]amino}-3-methoxypiperidin-1-yl)-4- | 1.69 (s, 6H) 2.18 (s, 3H) 3.34 (s, 3H) 3.40 (m, 3H) 3.54 (s, 5H) 4.24 (s, 4H) 7.14 (d, 1H) 12.16 (s, 1H) | 530 | Example 248 |

| Ex | Compound | NMR | m/z | SM |
|---|---|---|---|---|
| 379 | (piperidin-1-ylmethyl)-1,3-thiazole-5-carboxylic acid<br>2-((3S,4R)-4-{[(3,4-dichloro-5-methyl-1H-pyrrol-2-yl)carbonyl]amino}-3-methoxypiperidin-1-yl)-1,3-thiazole-4-carboxylic acid | 1.75 (s, 2H) 2.19 (s, 3H) 3.17 (d, 1H) 3.27 (s, 1H) 3.36 (s, 3H) 3.54 (s, 1H) 3.85 (s, 1H) 4.21 (d, 2H) 7.16 (d, 1H) 7.58 (s, 1H) 12.16 (s, 1H) 12.57 (s, 1H) | 433 | Example 192 |
| 380 | 2-((3S,4R)-4-{[(3,4-dichloro-5-methyl-1H-pyrrol-2-yl)carbonyl]amino}-3-methoxypiperidin-1-yl)-4-[(3-hydroxypyrrolidin-1-yl)methyl]-1,3-thiazole-5-carboxylic acid | 1.73 (d, 3H) 2.07 (s, 1H) 2.18 (s, 3H) 2.95 (s, 2H) 3.26 (s, 2H) 3.36 (s, 3H) 3.53 (s, 1H) 3.85 (s, 1H) 4.15 (s, 4H) 4.35 (s, 1H) 5.20 (s, 1H) 7.16 (d, 1H) 12.16 (s, 1H) | 532 | Example 249 |
| 381 | 4-{[(1-carboxycyclopropyl)amino]carbonyl}-2-((3S,4R)-4-{[(3,4-dichloro-5-methyl-1H-pyrrol-2-yl)carbonyl]amino}-3-methoxypiperidin-1-yl)-1,3-thiazole-5-carboxylic acid | 1.25 (s, 2H) 1.48 (s, 2H) 1.75 (s, 2H) 2.19 (s, 3H) 3.39 (s, 4H) 3.56 (s, 2H) 4.26 (s, 2H) 4.42 (s, 1H) 7.15 (s, 1H) 9.80 (s, 1H) 12.15 (s, 1H) 12.78 (s, 1H) 16.05 (s, 1H) | 560 | Example 402 |

Example 382

Cis(±)-5-(aminocarbonyl)-2-(4-{[(3,4-dichloro-5-methyl-1H-pyrrol-2-yl)carbonyl]amino}-3-methoxypiperidin-1-yl)-1,3-thiazole-4-carboxylic acid A solution of 55 mg (23 mmol) of Cis(±)-3,4-dichloro-N-[3-methoxypiperidin-4-yl]-5-methyl-1H-pyrrole-2-carboxamide (Intermediate 50), 55 mg (0.23 mmol) of ethyl 5-(aminocarbonyl)-2-chloro-1,3-thiazole-4-carboxylate (Intermediate 220) and 33 mg (0.23 mmol) $K_2CO_3$ in 3 ml NMP was heated at 150° C. for 1 h in a microwave reactor. Water (0.1 ml) was added and the mixture was heated at 150° C. for another hour. The solution was diluted with water and acidified with 1N HCl before being extracted 2 times with EtOAc. The EtOAc extracts were washed with brine, dried ($MgSO_4$) and concentrated to give a solid that was triturated with MeOH to give 41 mg of a white solid. MS (ES) MH$^+$: 479 for $C_{17}H_{19}Cl_2N_5O_5S$; NMR: 1.75 (m, 2H), 2.2 (s, 3H), 3.3 (s), 3.5 (s, 1H), 3.9 (m, 1H), 4.2 (m, 2H), 7.15 (d, 1H), 7.8 (s, 1H), 8.9 (s, 1H), 12.2 (s, 1H).

Example 383

Cis(±)-5-(aminocarbonyl)-2-(4-{[(3,4-dichloro-5-methyl-1H-pyrrol-2-yl)carbonyl]amino}-3-methoxypiperidin-1-yl)isonicotinic acid A mixture of 85 mg (0.17 mmol) of Cis(±)-ethyl 5-(aminocarbonyl)-2-(4-{[(3,4-dichloro-5-methyl-1H-pyrrol-2-yl)carbonyl]amino}-3-methoxypiperidin-1-yl)isonicotinate (Example 198) and 86 mg (0.50 mmol) Ba(OH)$_2$ in 3 ml MeOH and 2 ml water was heated at 120° C. for 1 h. The mixture was acidified to about pH=4 with 1N HCl and extracted 4 times with EtOAc. The EtOAc was concentrated and the residue was purified by reverse phase HPLC (20-40% $CH_3CN$ gradient in water with 0.1% TFA) to afford 8 mg of product as a white solid. MS (ES) MH$^+$: 470 for $C_{19}H_{21}Cl_2N_5O_5$; NMR: 1.5-1.8, (m, 3H), 2.2 (s, 3H), 3.0-3.2 (m, 2H), 3.3 (s, 3H), 3.5 (m, 2H), 4.2-4.5 (m, 2H), 4.9 (d, 1H), 6.9 (s, 1H), 7.1-7.3 (m, 2H), 7.8 (s, 1H), 8.4 (s, 1H), 12.1 (s, 1H), 13.1 (s, 1H).

Examples 384-385

The following Examples were synthesized by an analogous method to Example 383 from the starting materials (SM) given in the table below.

| Ex | Compound | NMR | m/z | SM |
|---|---|---|---|---|
| 384 | 2-((3S,4R)-4-{[(3,5-dichloro-4-methyl-1H-pyrrol-2-yl)carbonyl]amino}-3-fluoropiperidin-1-yl)-4-{[(2-morpholin-4-ylethyl)amino]carbonyl}-1,3-thiazole-5-carboxylic acid | NMR: 1.8 (m, 2H), 1.9 (s, 3H), 3.5-4.0 (m, 8H), 4.0-4.4 (m, 3H), 5.0 (d, 1H), 7.4 (d, 1H), 9.5 (s, 1H), 12.6 (s, 1H). | MS (ES) MH$^+$: 577 for $C_{22}H_{27}Cl_2FN_6O_5S$ | Intermediate 138 |

-continued

| Ex | Compound | NMR | m/z | SM |
|---|---|---|---|---|
| 385 | 4-(aminocarbonyl)-2-((3S,4R)-4-{[(3,5-dichloro-4-methyl-1H-pyrrol-2-yl)carbonyl]amino}-3-fluoropiperidin-1-yl)-1,3-thiazole-5-carboxylic acid 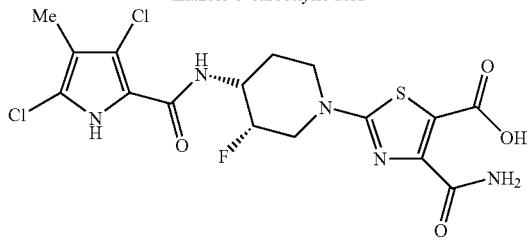 | NMR: 1.8 (m, 2H), 1.9 (s, 3H), 3.5-4.0 (m, 8H), 4.0-4.4 (m, 3H), 5.0 (d, 1H), 7.4 (d, 1H), 9.5 (s, 1H, 12.6 (s, 1H.) | MS (ES) MH+: 464 for $C_{16}H_{16}Cl_2FN_5O_4S$ | Example 202 |

Example 386

2-((3S,4R)-4-{[(3,4-dichloro-5-methyl-1H-pyrrol-2-yl)carbonyl]amino}-3-methoxypiperidin-1-yl)-4-[(methylamino)carbonyl]-1,3-thiazole-5-carboxylic acid To a suspension/solution of ethyl 2-((3S,4R)-4-{[(3,4-dichloro-5-methyl-1H-pyrrol-2-yl)carbonyl]amino}-3-methoxypiperidin-1-yl)-4-[(methylamino)carbonyl]-1,3-thiazole-5-carboxylate (0.078 g, 0.15 mmol, Example 218) in methanol (2 mL) was added barium hydroxide (0.052 g, 0.30 mmol) and water (0.5 mL). After stirring several hours the reaction was complete. The reaction was acidified with 1N HCl and then concentrated to remove methanol. The residue was extracted with EtOAc (×3), dried with MgSO4 and concentrated to a white solid (0.059 g). MS (ES) M+H+: 490 for $C_{18}H_{21}Cl_2N_5O_5S$; NMR: 1.76 (s, 2 H) 2.18 (s, 3 H) 2.86 (s, 3 H) 3.38 (s, 3 H) 3.56 (s, 2 H) 4.02 (s, 1 H) 4.27 (s, 2 H) 4.40 (s, 1 H) 7.15 (s, 1 H) 9.38 (s, 1 H) 12.15 (s, 1 H).

Examples 387-412

The following Examples were prepared by the procedure described in Example 386 from the starting materials (SM) indicated.

| Ex | Compound | Data | SM |
|---|---|---|---|
| 387 | 2-((3S,4R)-4-{[(3,4-dichloro-5-methyl-1H-pyrrol-2-yl)carbonyl]amino}-3-methoxypiperidin-1-yl)-4-{[(2-methoxyethyl)amino]carbonyl}-1,3-thiazole-5-carboxylic acid | MS (ES) MH+: 534 for $C_{20}H_{25}Cl_2N_5O_6S$; NMR: 1.72 (s, 2H) 2.18 (s, 3H) 3.24 (s, 3H) 3.36 (s, 3H) 3.51 (s, 2H) 3.84 (s, 2H) 4.15 (s, 2H) 7.15 (s, 1H) 12.16 (s, 1H) 13.18 (s, 1H) | Example 219 |
| 388 | 2-((3S,4R)-4-{[(3,4-dichloro-5-methyl-1H-pyrrol-2-yl)carbonyl]amino}-3-methoxypiperidin-1-yl)-4-({[(1S)-2-hydroxy-1-methylethyl]amino}carbonyl)-1,3-thiazole-5-carboxylic acid | MS (ES) MH+: 534 for $C_{20}H_{25}Cl_2N_5O_6S$; NMR: 1.19 (s, 3H) 1.77 (s, 2H) 2.19 (s, 3H) 3.38 (s, 3H) 3.47 (s, 3H) 3.58 (s, 1H) 4.04 (s, 1H) 4.29 (s, 2H) 4.91 (s, 1H) 7.18 (s, 1H) 8.79-8.94 (m, 1H) 12.16 (s, 1H) | Example 220 |
| 389 | 2-((3S,4R)-4-{[(3,4-dichloro-5-methyl-1H-pyrrol-2-yl)carbonyl]amino}-3-methoxypiperidin-1-yl)-4-({[(1R)-2-hydroxy-1-methylethyl]amino}carbonyl)-1,3-thiazole-5-carboxylic acid | MS (ES) MH+: 534 for $C_{20}H_{25}Cl_2N_5O_6S$ | Example 221 |

| Ex | Compound | Data | SM |
|---|---|---|---|
| 390 | Cis(±)-2-(4-{[(3,4-dichloro-5-methyl-1H-pyrrol-2-yl)carbonyl]amino}-3-methoxypiperidin-1-yl)-4-{[(2,2-difluoroethyl)amino]carbonyl}-1,3-thiazole-5-carboxylic acid 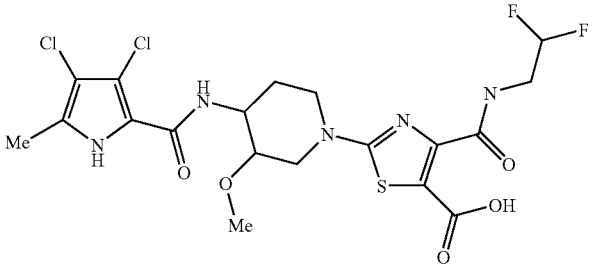 [SMILES: COC1CN(c2nc(C(=O)NCC(F)F)c(C(=O)O)s2)CCC1NC(=O)c1[nH]c(C)c(Cl)c1Cl] | MS (ES) MH$^+$: 540 for C$_{19}$H$_{21}$Cl$_2$F$_2$N$_5$O$_5$S; NMR: 1.76 (s, 2H) 2.19 (s, 3H) 3.38 (s, 3H) 3.44 (s, 1H) 3.57 (s, 2H) 3.73 (s, 3H) 4.10 (s, 1H) 4.27 (d, 2H) 4.43 (s, 1H) 7.17 (d, 1H) 9.60 (s, 1H) 12.16 (s, 1+nlH) 15.77 (s, 1H) | Example 222 |
| 391 | Cis(±)-2-(4-{[(3,4-dichloro-5-methyl-1H-pyrrol-2-yl)carbonyl]amino}-3-methoxypiperidin-1-yl)-4-[(isoxazol-3-ylamino)carbonyl]-1,3-thiazole-5-carboxylic acid | MS (ES) MH$^+$: 543 for C$_{20}$H$_{20}$Cl$_2$N$_6$O$_6$S; NMR: 1.74 (s, 2H) 2.19 (s, 3H) 3.22 (s, 2H) 3.38 (s, 3H) 3.52 (s, 1H) 3.88 (s, 1H) 4.24 (s, 2H) 6.99 (d, 1H) 7.16 (s, 1H) 8.75 (s, 1H) 12.16 (s, 1H) | Example 223 |
| 392 | Cis(±)-2-(4-{[(3,4-dichloro-5-methyl-1H-pyrrol-2-yl)carbonyl]amino}-3-methoxypiperidin-1-yl)-4-{[(3R)-tetrahydrofuran-3-ylamino]carbonyl}-1,3-thiazole-5-carboxylic acid | MS (ES) MH$^+$: 546 for C$_{21}$H$_{25}$Cl$_2$N$_5$O$_6$S; NMR: 1.76 (s, 3H) 1.94-2.08 (m, 1H) 2.19 (s, 3H) 3.38 (s, 3H) 3.44 (s, 1H) 3.56 (s, 1H) 3.63-3.76 (m, 2H) 3.81-3.92 (m, 2H) 4.12 (s, 1H) 4.26 (s, 1H) 4.51 (s, 1H) 7.16 (d, 1H) 9.17 (d, 1H) 12.15 (s, 1H) 15.97 (s, 1H) | Example 224 |
| 393 | Cis(±)-2-(4-{[(3,4-dichloro-5-methyl-1H-pyrrol-2-yl)carbonyl]amino}-3-methoxypiperidin-1-yl)-4-({[(1R,2S)-2-fluorocyclopropyl]amino}carbonyl)-1,3-thiazole-5-carboxylic acid | MS (ES) MH$^+$: 534 for C$_{20}$H$_{22}$Cl$_2$FN$_5$O$_5$S; NMR: 1.23 (dd, 2H) 1.75 (s, 2H) 2.19 (s, 3H) 2.87 (s, 1H) 3.37 (d, 3H) 3.42 (s, 1H) 3.56 (s, 2H) 4.10 (s, 1H) 4.26 (s, 3H) 4.45 (s, 1H) 4.73 (d, 1H) 4.96 (s, 1H) 7.16 (d, 1H) 9.29 (dd, 1H) 12.15 (s, 2H) 16.02 (d, 1H) | Example 225 |
| 394 | 4-(azidomethyl)-2-((3S,4R)-4-{[(3,4-dichloro-5-methyl-1H-pyrrol-2-yl)carbonyl]amino}-3-methoxypiperidin-1-yl)-1,3-thiazole-5-carboxylic acid | MS (ES) MH$^+$: 488 for C$_{17}$H$_{19}$Cl$_2$N$_7$O$_4$S; NMR: 1.76 (s, 2H) 2.18 (s, 3H) 3.37 (s, 5H) 3.56 (s, 1H) 3.92 (s, 1H) 4.28 (s, 2H) 4.54 (d, 2H) 7.18 (s, 1H) 12.16 (s, 1H) 12.97 (s, 1H) | Example 254 |
| 395 | 2-((3S,4R)-4-{[(3,4-dichloro-5-methyl-1H-pyrrol-2-yl)carbonyl]amino}-3-methoxypiperidin-1-yl)-4-({[(1S)-2-methoxy-1-methylethyl]amino}carbonyl)-1,3-thiazole-5-carboxylic acid 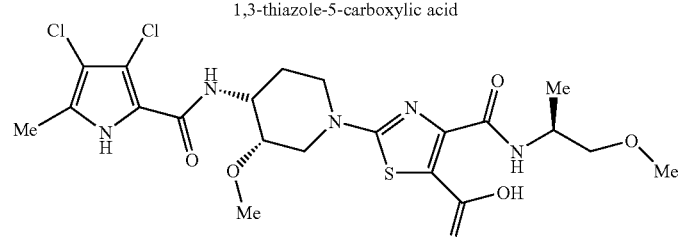 | MS (ES) MH$^+$: 548 for C$_{21}$H$_{27}$Cl$_2$N$_5$O$_6$S; NMR: 1.18 (d, 3H) 1.76 (s, 2H) 2.18 (s, 3H) 3.24 (s, 3H) 3.38 (s, 3H) 3.49 (s, 2H) 3.57 (s, 1H) 4.06 (s, 1H) 4.26 (s, 2H) 7.15 (s, 1H) 8.95 (s, 1H) 12.16 (s, 1H) 16.33 (s, 1H) | Example 226 |
| 396 | 2-((3S,4R)-4-{[(3,4-dichloro-5-methyl-1H-pyrrol-2-yl)carbonyl]amino}-3-methoxypiperidin-1-yl)-4-[(prop- | MS (ES) MH$^+$: 514 for C$_{20}$H$_{21}$Cl$_2$N$_5$O$_5$S; NMR: 1.76 (s, 2H) 2.19 (s, 3H) 3.26 (s, 2H) 3.38 (s, 3H) 3.57 (s, | Example 227 |

| Ex | Compound | Data | SM |
|---|---|---|---|
| | 2-yn-1-ylamino)carbonyl]-1,3-thiazole-5-carboxylic acid | 2H) 4.10 (d, 2H) 4.27 (s, 2H) 7.17 (d, 1H) 9.78 (s, 1H) 12.16 (s, 1H) 15.96 (s, 1H) | |
| 397 | 2-((3S,4R)-4-{[(3,4-dichloro-5-methyl-1H-pyrrol-2-yl)carbonyl]amino}-3-methoxypiperidin-1-yl)-4-{[(2-hydroxy-1,1-dimethylethyl)amino]carbonyl}-1,3-thiazole-5-carboxylic acid | MS (ES) MH$^+$: 548 for $C_{21}H_{27}Cl_2N_5O_6S$; NMR: 1.29 (s, 6H) 1.73 (s, 2H) 2.17 (s, 3H) 3.37 (m, 6H) 3.46 (s, 2H) 3.54 (s, 1H) 3.91 (s, 1H) 4.23 (s, 2H) 7.16 (s, 1H) 12.19 (s, 1H) | Example 228 |
| 398 | 2-((3S,4R)-4-{[(3,4-dichloro-5-methyl-1H-pyrrol-2-yl)carbonyl]amino}-3-methoxypiperidin-1-yl)-4-{[(3R)-tetrahydrofuran-3-ylamino]carbonyl}-1,3-thiazole-5-carboxylic acid | MS (ES) MH$^+$: 546 for $C_{21}H_{25}Cl_2N_5O_6S$; NMR: 1.23 (s, 1H) 1.76 (s, 2H) 2.00 (d, 1H) 2.19 (s, 3H) 3.38 (s, 6H) 3.43 (s, 1H) 3.56 (s, 1H) 3.64-3.77 (m, 2H) 3.79-3.94 (m, 2H) 4.26 (s, 2H) 4.51 (s, 1H) 7.16 (d, 1H) 9.17 (s, 1H) 12.16 (s, 1H) 15.98 (s, 1H) | Example 224 |
| 399 | 2-((3S,4R)-4-{[(3,4-dichloro-5-methyl-1H-pyrrol-2-yl)carbonyl]amino}-3-methoxypiperidin-1-yl)-4-({[(1R,2S)-2-fluorocyclopropyl]amino}carbonyl)-1,3-thiazole-5-carboxylic acid | MS (ES) MH$^+$: 534 for $C_{20}H_{22}Cl_2FN_5O_5S$; NMR: 1.21 (d, 1H) 1.40 (s, 1H) 1.76 (s, 2H) 2.19 (s, 3H) 2.85 (s, 1H) 3.38 (s, 3H) 3.43 (s, 3H) 3.56 (s, 1H) 4.26 (s, 1H) 4.74-4.97 (m, 1H) 7.17 (d, 1H) 9.27 (d, 1H) 12.16 (s, 2H) 16.01 (s, 2H) | Example 229 |
| 400 | 2-((3S,4R)-4-{[(3,4-dichloro-5-methyl-1H-pyrrol-2-yl)carbonyl]amino}-3-methoxypiperidin-1-yl)isonicotinic acid | MS (ES) MH$^+$: 427 for $C_{18}H_{20}Cl_2N_4O_4$ NMR: 1.72 (s, 2H) 2.18 (s, 3H) 3.13 (d, 2H) 3.30 (s, 3H) 3.49 (s, 1H) 4.17-4.31 (m, 2H) 4.68 (d, 1H) 6.97 (d, 1H) 7.15 (d, 1+nlH) 7.23 (s, 1H) 8.22 (d, 1H) 12.16 (s, 1H) 13.39 (s, 1H) | Example 193 |
| 401 | 4-[(cyclopropylamino)carbonyl]-2-((3S,4R)-4-{[(3,4-dichloro-5-methyl-1H-pyrrol-2-yl)carbonyl]amino}-3-methoxypiperidin-1-yl)-1,3-thiazole-5-carboxylic acid | MS (ES) MH$^+$: 516 for $C_{20}H_{23}Cl_2N_5O_5S$; NMR: 0.77 (d, 2H) 0.80 (s, 2H) 1.76 (s, 2H) 2.19 (s, 3H) 2.86-2.99 (m, 1H) 3.30 (s, 1H) 3.37 (s, 3H) 3.56 (s, 1H) 4.16 (s, 1H) 4.26 (d, 2H) 4.41 (s, 1H) 7.16 (d, 1H) 9.22 (d, 1H) 12.15 (s, 1H) | Example 231 |
| 402 | 1-({[2-((3S,4R)-4-{[(3,4-dichloro-5-methyl-1H-pyrrol-2-yl)carbonyl]amino}-3-methoxypiperidin-1-yl)-5-(methoxycarbonyl)-1,3-thiazol-4-yl]carbonyl}amino)cyclopropane carboxylic acid | MS (ES) MH$^+$: 574 for $C_{22}H_{25}Cl_2N_5O_7S$; | Example 230 |
| 403 | 4-{[(1-carboxy-2-hydroxyethyl)amino]carbonyl}-2-((3S,4R)-4-{[(3,4-dichloro-5-methyl-1H-pyrrol-2-yl)carbonyl]amino}-3-methoxypiperidin-1-yl)-1,3-thiazole-5-carboxylic acid | MS (ES) MH$^+$: 564 for $C_{20}H_{23}Cl_2N_5O_8S$; NMR: 1.78 (s, 2H) 2.19 (s, 3H) 3.39 (s, 3H) 3.47 (s, 2H) 3.59 (s, 1H) 3.87 (s, 2H) 4.30 (s, 2H) 4.53 (s, 1H) 7.16 (s, 1H) 9.03 (s, 1H) 12.16 (s, 1H) 15.97 (s, 1H) | Example 233 |

-continued

| Ex | Compound | Data | SM |
|---|---|---|---|
| 404 | 2-((3S,4R)-4-{[(3,4-dichloro-5-methyl-1H-pyrrol-2-yl)carbonyl]amino}-3-methoxypiperidin-1-yl)-4-{[(2-morpholin-4-ylethyl)amino]carbonyl}-1,3-thiazole-5-carboxylic acid | MS (ES) MH$^+$: 589 for C$_{23}$H$_{30}$Cl$_2$N$_6$O$_6$S; NMR: 1.76 (s, 2H) 2.19 (s, 3H) 3.14 (d, 2H) 3.39 (s, 4H) 3.57 (s, 3H) 3.72 (s, 3H) 3.78 (s, 1H) 3.96 (s, 2H) 4.27 (s, 2H) 7.18 (d, 1H) 9.59 (s, 1H) 12.21 (s, 1H) | Example 234 |
| 405 | 2-((3S,4R)-4-{[(3,4-dichloro-5-methyl-1H-pyrrol-2-yl)carbonyl]amino}-3-methoxypiperidin-1-yl)-4-{[(1,3-dioxolan-2-ylmethyl)amino]carbonyl}-1,3-thiazole-5-carboxylic acid | MS (ES) MH$^+$: 562 for C$_{21}$H$_{25}$Cl$_2$N$_5$O$_7$S; NMR: 1.77 (s, 2H) 2.19 (s, 3H) 3.39 (s, 9H) 3.44-3.52 (m, 2H) 3.58 (s, 1H) 3.79-3.87 (m, 2H) 3.89-3.97 (m, 2H) 4.27 (s, 2H) 5.05 (t, 1H) 7.17 (d, 1H) 9.39 (t, 1H) 12.16 (s, 1H) 16.20 (s, 1H) | Example 235 |
| 406 | 2-((3S,4R)-4-{[(3,4-dichloro-5-methyl-1H-pyrrol-2-yl)carbonyl]amino}-3-methoxypiperidin-1-yl)-4-{[(pyridin-2-ylmethyl)amino]carbonyl}-1,3-thiazole-5-carboxylic acid | MS (ES) MH$^+$: 567 for C$_{23}$H$_{24}$Cl$_2$N$_6$O$_5$S; NMR: 1.77 (s, 2H) 2.19 (s, 3H) 3.40 (s, 3H) 3.58 (s, 2H) 4.28 (s, 2H) 4.67 (s, 2H) 7.16 (s, 1H) 7.31-7.45 (m, 2H) 7.85 (s, 1H) 8.56 (s, 1H) 9.97 (s, 1H) 12.17 (s, 1H) 16.14 (s, 1H) | Example 237 |
| 407 | 2-((3S,4R)-4-{[(3,4-dichloro-5-methyl-1H-pyrrol-2-yl)carbonyl]amino}-3-methoxypiperidin-1-yl)-4-({[3-(2-oxopyrrolidin-1-yl)propyl]amino}carbonyl)-1,3-thiazole-5-carboxylic acid | MS (ES) MH$^+$: 601 for C$_{24}$H$_{30}$Cl$_2$N$_6$O$_6$S; NMR: 1.71 (s, 1H) 1.74 (d, 3H) 1.85-2.00 (m, 2H) 2.19 (s, 3H) 2.20-2.27 (m, 2H) 3.19-3.35 (m, 11H) 3.39 (s, 4H) 3.56 (s, 1H) 4.20-4.34 (m, 1H) 7.17 (d, 1H) 9.45 (t, 1H) 12.16 (s, 1H) | Example 236 |
| 408 | Cis(±)-4-[cyano(morpholin-4-yl)methyl]-2-(4-{[(3,4-dichloro-5-methyl-1H-pyrrol-2-yl)carbonyl]amino}-3-methoxypiperidin-1-yl)-1,3-thiazole-5-carboxylic acid | MS (ES) MH$^+$: 557 for C$_{22}$H$_{26}$Cl$_2$N$_6$O$_5$S; NMR: 1.75 (s, 2H) 2.18 (s, 3H) 2.71 (s, 3H) 3.39 (s, 2H) 3.43 (s, 5H) 3.59 (s, 4H) 3.80 (s, 2H) 4.27 (s, 2H) 4.44 (s, 1H) 7.14 (s, 1H) 12.15 (s, 1H) | Example 255 |
| 409 | 2-((3S,4R)-4-{[(3,4-dichloro-5-methyl-1H-pyrrol-2-yl)carbonyl]amino}-3-methoxypiperidin-1-yl)-4-({[2-(methylsulfonyl)ethyl]amino}carbonyl)-1,3-thiazole-5-carboxylic acid | MS (ES) MH$^+$: 582 for C$_{20}$H$_{25}$Cl$_2$N$_5$O$_7$S$_2$ NMR: 1.76 (s, 2H) 2.19 (s, 3H) 3.06 (s, 3H) 3.38 (s, 5H) 3.44 (t, 3H) 3.57 (s, 1H) 3.68-3.81 (m, 2H) 4.26 (s, 2H) 7.16 (d, 1H) 9.45-9.56 (m, 1H) 12.15 (s, 1H) | Example 256 |

-continued

| Ex | Compound | Data | SM |
|---|---|---|---|
| 410 | 2-((3S,4R)-4-{[(3,4-dichloro-5-methyl-1H-pyrrol-2-yl)carbonyl]amino}-3-methoxypiperidin-1-yl)-4-{[(1,3-oxazol-2-ylmethyl)amino]carbonyl}-1,3-thiazole-5-carboxylic acid | MS (ES) MH$^+$: 557 for C$_{21}$H$_{22}$Cl$_2$N$_6$O$_6$S; NMR: 1.76 (s, 2H) 2.19 (s, 3H) 3.38 (s, 3H) 3.45 (s, 1H) 3.57 (s, 1H) 4.26 (d, 2H) 4.65 (s, 2H) 7.11-7.24 (m, 2H) 8.09 (s, 1H) 9.98 (s, 1H) 12.16 (s, 1H) 15.92 (s, 1H) | Example 239 |
| 411 | 2-((3S,4R)-4-{[(3,4-dichloro-5-methyl-1H-pyrrol-2-yl)carbonyl]amino}-3-methoxypiperidin-1-yl)-4-{[(2-fluoroethyl)amino]carbonyl}-1,3-thiazole-5-carboxylic acid | MS (ES) MH$^+$: 522 for C$_{19}$H$_{22}$Cl$_2$FN$_5$O$_5$S; NMR: 1.76 (s, 2H) 2.19 (s, 3H) 3.38 (s, 4H) 3.45 (s, 1H) 3.58 (s, 2H) 3.68 (s, 1H) 4.14 (s, 1H) 4.27 (s, 2H) 4.47-4.54 (m, 1H) 4.67 (t, 1H) 7.26 (d, J = 8.29 Hz, 1H) 9.55 (s, 1H) 12.29 (s, 1H) 16.19 (s, 1H) | Example 240 |
| 412 | 2-((3S,4R)-4-{[(3,4-dichloro-5-methyl-1H-pyrrol-2-yl)carbonyl]amino}-3-methoxypiperidin-1-yl)-4-{[(2-hydroxy-2-methylpropyl)amino]carbonyl}-1,3-thiazole-5-carboxylic acid | MS (ES) MH$^+$: 548 for C$_{21}$H$_{27}$Cl$_2$N$_5$O$_6$S; NMR: 1.11 (d, 6H) 1.77 (s, 2H) 2.18 (s, 3H) 3.23 (s, 3H) 3.38 (s, 3H) 3.57 (s, 1H) 4.29 (s, 1H) 4.76 (s, 1H) 7.18 (s, 1H) 8.94 (s, 1H) 12.16 (s, 1H) | Example 241 |

Example 413

4-{[(1-cyanocyclopropyl)amino]carbonyl}-2-((3S,4R)-4-{[(3,4-dichloro-5-methyl-1H-pyrrol-2-yl)carbonyl]amino}-3-methoxypiperidin-1-yl)-1,3-thiazole-5-carboxylic acid To a solution of ethyl 4-{[(1-cyanocyclopropyl)amino]carbonyl}-2-((3S,4R)-4-{[(3,4-dichloro-5-methyl-1H-pyrrol-2-yl)carbonyl]amino}-3-methoxypiperidin-1-yl)-1,3-thiazole-5-carboxylate (0.09 g, 0.16 mmol, Example 230) in methanol (2 mL) was added potassium carbonate (0.022 g, 0.16 mmol) and water (0.5 mL). After heating in the microwave for 30 min at 80°, reaction was complete by LCMS analysis. The reaction mixture was diluted with water and acidified with 1N HCl. After concentrating to remove methanol, the resulting white precipitate was filtered, washed with water and dried (0.071 g). MS (ES) M+H$^+$: 541 for C$_{21}$H$_{22}$Cl$_2$N$_6$O$_5$S; NMR: 1.33-1.41 (m, 2 H) 1.64 (s, 2 H) 1.75 (s, 2 H) 2.19 (s, 3 H) 3.37 (s, 3H) 3.43 (s, 1 H) 3.57 (s, 1 H) 4.08 (s, 1 H) 4.27 (d, 2 H) 4.40 (s, 1 H) 7.16 (d, 1 H) 9.87 (s, 1 H) 12.17 (s, 1 H).

Example 414

The following Example was prepared by the procedure described in Example 413 from the starting materials (SM) indicated.

| Ex | Compound | Data | SM |
|---|---|---|---|
| 414 | 4-{[(1-cyano-1-methylethyl)amino]carbonyl}-2-((3S,4R)-4-{[(3,4-dichloro-5-methyl-1H-pyrrol-2-yl)carbonyl]amino}-3-methoxypiperidin-1-yl)-1,3-thiazole-5-carboxylic acid | MS (ES) MH$^+$: 543 for C$_{21}$H$_{24}$Cl$_2$N$_6$O$_5$S; NMR: 1.68 (s, 6 H) 1.76 (s, 2 H) 2.19 (s, 3 H) 3.38 (s, 4 H) 3.44 (s, 1 H) 3.56 (s, 1 H) 4.11 (s, 1 H) 4.25 (s, 2 H) 7.14 (s, 1 H) 9.10 (s, 1 H) 12.17 (s, 1 H) | Example 232 |

Example 415

2-((3S,4R)-4-{[(3,4-dichloro-5-methyl-1H-pyrrol-2-yl)carbonyl]amino}-3-fluoropiperidin-1-yl)-N-methoxy-N-methyl-1,3-thiazole-5-carboxamide

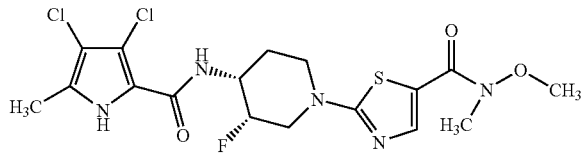

2-((3S,4R)-4-{[(3,4-dichloro-5-methyl-1H-pyrrol-2-yl)carbonyl]amino}-3-fluoropiperidin-1-yl)-1,3-thiazole-5-carboxylic acid (10 mg, 0.024 mmol) was dissolved in dry DMF (10 ml), HATU (9.1 mg, 0.024 mmol), triethylamine (7.27 mg, 0.072 mmol) and N,O-dimethylhydroxyamine (4.65 mg, 0.048 mmol) were added. The mixture was stirred at room temperature for 30 minutes, then was poured into cold water (30 ml), the precipitate was filtered, washed with water and collected as the desired product (off white solid, 10 mg).

MS (ESP): 465 (MH$^+$) for $C_{17}H_{20}Cl_2FN_5O_3S$.

NMR (CDCl$_3$) δ: 1.87 (m, 2H); 2.19 (s, 3H); 3.07 (m, 2H); 3.21 (s, 3H); 3.72 (s, 3H); 4.01 (m, 1H); 4.30 (m, 2H); 4.96 (d, br, 1H); 7.28 (d, 1H); 7.85 (s, 1H); 12.09 (s, 1H).

The following compound was produced following the procedure described for Example 415 from Example 334 and N-methoxy amine hydrochloride.

Example 416

2-((3S,4R)-4-{[(3,4-Dichloro-5-methyl-1H-pyrrol-2-yl)carbonyl]amino}-3-methoxypiperidin-1-yl)-N-methoxy-4-methyl-1,3-thiazole-5-carboxamide MS (ES) MH$^+$: 476 for $C_{18}H_{23}Cl_2N_5O_4S$; NMR: 1.66-1.79 (m, 1H), 2.17(s, 3H), 2.37 (s, 3H), 3.20-3.35 (m, buried under water peak), 3.35 (s, 3H), 33.50-3.55 (m, 1H), 3.61 (s, 3H), 3.82-3.91 (m, 1H), 4.15-4.31 (m, 2H), 7.14 (d, 1H), 10.79 (s, 1H), 12.14 (s, 1H).

Example 417 sodium 2-((3S,4R)-4-{[(3,4-dichloro-5-methyl-1H-pyrrol-2-yl)carbonyl]amino}-3-methoxypiperidin-1-yl)-4-{[(2-methoxyethyl)amino]carbonyl}-1,3-thiazole-5-carboxylate Sodium hydroxide (0.056 mL, 0.056 mmol, Acros 1N) was added to a suspension of 2-((3S,4R)-4-{[(3,4-dichloro-5-methyl-1H-pyrrol-2-yl)carbonyl]amino}-3-methoxypiperidin-1-yl)-4-{[(2-methoxyethyl)amino]carbonyl}-1,3-thiazole-5-carboxylic acid (0.03 g, 0.056 mmol, Example 387) in methanol (5 mL). After stirring five minutes the reaction was homogeneous. The reaction mixture was concentrated and the resulting white solid was dried overnight (0.030 g). MS (ES) MH$^+$: 534 for $C_{20}H_{24}Cl_2N_5O_6SNa$; NMR: 1.73 (s, 2 H) 2.19 (s, 3 H) 3.24 (s, 3 H) 3.32 (s, 2 H) 3.36 (s, 3 H) 3.51 (s, 1 H) 3.84 (s, 1 H) 4.22 (d, 2 H) 7.17 (d, 1 H) 12.17 (s, 1 H) 13.26 (s, 1 H).

Examples 419-423

The following Examples were prepared by the procedure described in Example 417 from the starting materials (SM) indicated.

| Ex | Compound | Data | SM |
|---|---|---|---|
| 419 | sodium 2-((3S,4R)-4-{[(3,4-dichloro-5-methyl-1H-pyrrol-2-yl)carbonyl]amino}-3-methoxypiperidin-1-yl)-4-({[(1S)-2-methoxy-1-methylethyl]amino}carbonyl)-1,3-thiazole-5-carboxylate | MS (ES) MH$^+$: 548 for $C_{21}H_{26}Cl_2N_5O_6SNa$ NMR: 1.04-1.15 (m, 3H) 1.71 (s, 2H) 2.18 (s, 3H) 3.08-3.21 (m, 3H) 3.25 (s, 3H) 3.36 (s, 4 H) 3.50 (s, 1H) 3.87 (d, 1H) 3.99 (dt, 1H) 4.11 (s, 1H) 4.22 (s, 1 H) 7.21 (d, 1H) 13.17 (d, 1H) | Example 395 |
| 420 | sodium 2-((3S,4R)-4-{[(3,4-dichloro-5-methyl-1H-pyrrol-2-yl)carbonyl]amino}-3-methoxypiperidin-1-yl)-4-({[(1S)-2-methoxy-1-methylethyl]amino}carbonyl)-1,3-thiazole-5-carboxylate | MS (ES) MH$^+$: 582 for $C_{20}H_{24}Cl_2N_5O_7S_2Na$ NMR: 1.67-1.78 (m, 2H) 2.18 (s, 3H) 3.00 (s, 3H) 3.10-3.21 (m, 2H) 3.24-3.31 (m, 3H) 3.36 (s, 3H) 3.47-3.60 (m, 3H) 3.85 (s, 1H) 4.10 (s, 1H) 4.17 (s, 2H) 7.17 (d, 1H) 12.16 (s, 1H) 13.71 (s, 1H) | Example 409 |
| 421 | sodium 2-((3S,4R)-4-{[(3,4-dichloro-5-methyl-1H-pyrrol-2-yl)carbonyl]amino}-3-methoxypiperidin-1-yl)-4-{[(1,3-oxazol-2-ylmethyl)amino]carbonyl}-1,3- | MS (ES) MH$^+$: 556 for $C_{21}H_{21}Cl_2N_6O_6SNa$ NMR: 1.71 (d, 2H) 2.15 (s, 3H) 3.09-3.24 (m, 2H) 3.35 (s, 3H) 3.49 (s, 1H) 3.84 (s, 1H) 4.16 (s, 2H) 4.48 (d, 2H) 7.12 (s, 12H) | Example 410 |

| Ex | Compound | Data | SM |
|---|---|---|---|
| | thiazole-5-carboxylate | 7.18 (d, 1H) 8.01 (s, 1H) 12.17 (s, 1H) 13.95-14.07 (m, 1H) | |
| 422 | sodium 2-((3S,4R)-4-{[(3,4-dichloro-5-methyl-1H-pyrrol-2-yl)carbonyl]amino}-3-methoxypiperidin-1-yl)-4-({[(1R,2S)-2-fluorocyclopropyl]amino}carbonyl)-1,3-thiazole-5-carboxylate | MS (ES) MH$^+$: 534 for $C_{20}H_{21}Cl_2FN_5O_5SNa$ | Example 399 |
| 423 | Sodium-2-((3S,4R)-4-{[(3,4-dichloro-5-methyl-1H-pyrrol-2-yl)carbonyl]amino}-3-fluoropiperidin-1-yl)-1,3-thiazole-5-carboxylate | MS (ES) MH$^+$: 435,437 for $C_{16}H_{17}Cl_2FN_4O_3S$; NMR: 1.77-1.79 (m, 1H), 1.99 (m, 1H), 2.24 (s, 3H), 3.25-3.27 (m, 1H), 3.74 (d, 1H), 4.16 (m, 1H), 4.22 (m, 1H), 4.38 (t, 1H), 4.83 (d, 1H), 7.19 (s, 1H), 8.13 (br d, 1H) | Example 42 |

Example 424

N-ethylethanaminium 2-((3S,4R)-4-{[(3,4-dichloro-5-methyl-1H-pyrrol-2-yl)carbonyl]amino}-3-methoxypiperidin-1-yl)-4-{[(2-methoxyethyl)amino]carbonyl}-1,3-thiazole-5-carboxylate Diethylamine (0.0058 mL, 0.056 mmol, Aldrich) was added to a suspension of 2-((3S,4R)-4-{[(3,4-dichloro-5-methyl-1H-pyrrol-2-yl)carbonyl]amino}-3-methoxypiperidin-1-yl)-4-{[(2-methoxyethyl)amino]carbonyl}-1,3-thiazole-5-carboxylic acid (0.03 g, 0.056 mmol, Example 387) in methanol (5 mL). After stirring five minutes, methylene chloride was added until solution was homogeneous. The reaction was concentrated and the resulting solid was dried overnight (0.024 g). MS (ES) MH$^+$: 534 for $C_{24}H_{37}Cl_2N_6O_6S$; NMR: 1.16 (t, 3 H) 1.74 (s, 2 H) 2.19 (s, 3 H) 2.91 (q, 3 H) 3.25 (s, 3 H) 3.32 (s, 4 H) 3.37 (s, 3 H) 3.42 (d, 2 H) 3.53 (s, 1 H) 3.94 (s, 1 H) 4.22 (s, 2 H) 7.17 (d, 1 H).

Example 425

The following compound was synthesized according to the procedure described for Example 424.

Example 426

Potassium 2-((3S,4R)-4-{[(3,4-dichloro-5-methyl-1H-pyrrol-2-yl)carbonyl]amino}-3-fluoropiperidin-1-yl)-1,3-thiazole-5-carboxylate An aqueous solution of potassium hydroxide (0.1 M, 4.75 ml, 0.475 mmol) was added to a solution of 2-((3S,4R)-4-{[(3,4-dichloro-5-methyl-1H-pyrrol-2-yl)carbonyl]amino}-3-fluoropiperidin-1-yl)-1,3-thiazole-5-carboxylic acid (Example 42, 200 mg, 0.475 mmol) in methanol (35 ml). The mixture was stirred for 1 h and then concentrated under reduced pressure to provide the crude salt (230 mg). The salt was dissolved in acetone/water (50 ml; 48:2) and acetone was added slowly to the stirred mixture until it became cloudy. Stirring was continued and more acetone was added very slowly over 20 min. The mixture was stored at 4° C. overnight. The solid was collected by filtration and air dried for 24 h to provide the salt (160 mg).

MS (ESP): 421 (M+H) for $C_{15}H_{15}Cl_2FN_4O_3S$.

| Ex | Compound | Data | SM |
|---|---|---|---|
| 425 | N-ethylethanaminium-2-((3S,4R)-4-{[(3,4-dichloro-5-methyl-1H-pyrrol-2-yl)carbonyl]amino}-3-fluoropiperidin-1-yl)-1,3-thiazole-5-carboxylate | MS (ES) MH$^+$: 435,437 for $C_{16}H_{17}Cl_2FN_4O_3S$; NMR: 1.14 (t, 3H), 1.81 (m, 2H), 2.21 (s, 3H), 2.84 (q, 2H), 3.34 (m, 2H), 3.86 (m, 1H), 4.30 (m, 1H), 4.89 (d, 1H), 7.32 (s, 1H), 7.61 (d, 1H) | Example 42 |

¹H NMR (300 MHz, DMSO-d₆) δ: 1.75 (d, 1H); 2.04 (m, 1H); 2.24 (s, 3H); 3.34 (m, 2H); 3.75 (d, 1H); 4.20 (m, 1H); 4.39 (t, 1H); 4.83 (d, 1H); 7.17 (s, 1H); 8.18 (s, 1H); 14.12 (s, 1H).

Example 427

1,3-Dihydroxy-2-(hydroxymethyl)propan-2-aminium 2-((3S,4R)-4-{[(3,4-dichloro-5-methyl-1H-pyrrol-2-yl)carbonyl]amino}-3-fluoropiperidin-1-yl)-1,3-thiazole-5-carboxylate Tromethamine (43 mg, 0.36 mmol), 2-((3S,4R)-4-{[(3,4-dichloro-5-methyl-1H-pyrrol-2-yl)carbonyl]amino}-3-fluoropiperidin-1-yl)-1,3-thiazole-5-carboxylic acid (Example 42, 150 mg, 0.36 mmol), methanol (50 ml) and water (5 ml) were combined and stirred at 60° C. until the mixture was a homogeneous solution (30 min). The mixture was cooled to room temperature and concentrated under reduced pressure. The crude salt (80 mg) was dissolved in ethyl acetate/methanol (8 ml; 50:50) and ethyl acetate was added slowly to the stirred solution until it became cloudy. Stirring was continued and additional ethyl acetate (~15 ml) was added slowly to the mixture. The mixture was stored at 4° C. overnight. The solid was collected by filtration and air dried for 24 h to provide the salt (64 mg).

MS (ESP): 421 (M+H) for $C_{15}H_{15}Cl_2FN_4O_3S$.
¹H NMR (300 MHz, Methanol-d₄) δ: 2.00 (m, 2H); 2.25 (s, 3H); 3.33 (m, 2H); 3.30-3.55 (m, 2H); 3.67 (s, 6H); 4.10 (d, 1H); 4.35 (m, 2H); 4.90 (d, 1H); 7.57 (s, 1H).

Example 428

The following Example was prepared by the procedure described in Example 1 from the starting materials (SM) indicated in the table below.

| Ex | Compound | Data | SM |
|---|---|---|---|
| 428 | methyl 2-((3S,4R)-4-{[(4-chloro-3-fluoro-5-methyl-1H-pyrrol-2-yl)carbonyl]amino}-3-fluoropiperidin-1-yl)-1,3-thiazole-5-carboxylate | MS (ESP): 419 (MH⁺) for $C_{16}H_{17}ClF_2N_4O_3S$<br>¹H-NMR (CDCl₃) δ: 1.96 (m, 2H); 2.25 (s, 3H); 3.37 (m 2H); 3.84 (s, 3H); 4.17 (m, 1H); 4.38 (m, 1H); 4.56 (m, 1H); 4.87 (d, br, 1H); 6.21 (m, 1H); 7.87 (s, 1H); 9.35 (s, br, 1H); ¹⁹F-NMR (CDCl₃) δ: −158(s) | Intermediate 261 |

Example 429

The following Example was synthesized by an analogous method to Example 35 from the starting materials (SM) given in the table below.

| Ex | Compound | NMR | m/z | SM |
|---|---|---|---|---|
| 429 | 2-((3S,4R)-4-{[(4-chloro-3-fluoro-5-methyl-1H-pyrrol-2-yl)carbonyl]amino}-3-fluoropiperidin-1-yl)-1,3-thiazole-5-carboxylic acid | 1.85 (m, 2H); 2.15 (s, 3H); 3.31 (m 2H); 4.0 (m, 1H); 4.31 (m, 2H); 4.90 (d, br, 1H); 7.43 (d, 1H); 7.75 (s, 1H); 11.95 (s, br, 1H); ¹⁹F-NMR (CDCl₃) δ: −158(s)ppm | 405 | Example 428 |

Examples 430-433

The following Examples were prepared by the procedure described in Example 1 from the starting materials (SM) indicated in the table below.

| Ex | Compound | Data | SM |
|---|---|---|---|
| 430 | Ethyl 2-((3S,4R)-4-{[(3,4-dichloro-5-methyl-1H-pyrrol-2-yl)carbonyl]amino}-3-methoxypiperidin-1-yl)-4-({[(2R)-2-methoxypropyl]amino}carbonyl)-1,3-thiazole-5-carboxylate | MS (ES) MH: 575 for $C_{23}H_{31}Cl_2N_5O_6S$; NMR: 1.08 (d, 3H), 1.20 (t, 3H), 1.68-1.76 (m, 2H), 2.17 (s, 3H), 3.14-3.19 (m, 1H), 3.25 (s, 3H), 3.35 (s, 3H), 3.54 (brs, 1H), 3.90-4.05 (m, 2H), 4.15 (q, 2H), 4.20-4.30 (m, 2H), 7.15 (d, 1H), 8.32 (d, 1H), 12.16 (s, 1H) | Example 191 and Intermediate 1725-162 |
| 431 | Ethyl 2-((3S,4R)-4-{[(3,4-dichloro-5-methyl-1H-pyrrol-2-yl)carbonyl]amino}-3-methoxypiperidin-1-yl)-4-({[(2S)-2-methoxypropyl]amino}carbonyl)-1,3-thiazole-5-carboxylate | MS (ES) MH: 575 for $C_{23}H_{31}Cl_2N_5O_6S$; NMR: 1.09 (d, 3H), 1.21 (t, 3H), 1.68-1.76 (m, 2H), 2.18 (s, 3H), 3.15-3.21 (m, 1H), 3.26 (s, 3H), 3.36 (s, 3H), 3.54 (brs, 1H), 3.95-4.05 (m, 2H), 4.16 (q, 2H), 4.20-4.30 (m, 2H), 7.15 (d, 1H), 8.32 (d, 1H), 12.16 (s, 1H) | Example 191 and (2S)-2-methoxypropan-1-amine hydrochloride (1725-163) |
| 432 | Ethyl 2-((3S,4R)-4-{[(3,4-dichloro-5-methyl-1H-pyrrol-2-yl)carbonyl]amino}-3-methoxypiperidin-1-yl)-4-({[(1R)-2-methoxy-1-methylethyl]amino}carbonyl)-1,3-thiazole-5-carboxylate | MS (ES) MH$^+$: 576 for $C_{23}H_{31}Cl_2N_5O_6S$; NMR: 1.08 (d, 3H), 1.21 (t, 3H), 1.68-1.76 (m, 2H), 2.17 (s, 3H), 3.14-3.20 (m, 1H), 3.25 (s, 3H), 3.35 (s, 3H), 3.54 (brs, 1H), 3.95-4.05 (m, 2H), 4.16 (q, 2H), 4.20-4.30 (m, 2H), 7.14 (d, 1H), 8.30 (d, 1H), 12.15 (s, 1H) | Example 191 and (2R)-1-methoxypropan-2-amine hydrochloride (1725-177) |
| 433 | Cis(±)-methyl 2-(3-azido-4-{[(3,4-dichloro-5-methyl-1H-pyrrol-2-yl)carbonyl]amino}piperidin-1-yl)-1,3-thiazole-5-carboxylate | 1.8 (m, 2H), 2.19 (s, 3H), 3.35 (m, 1H), 3.6 (d, 1H), 3.75 (s, 3H), 3.95 (d, 1H), 4.24 (m, 3H), 7.23 (d, 1H), 7.86 (s, 1H), 12.1 (s, 1H). | Intermediate 272 and methyl 2-bromo-1,3-thiazole-5-carboxylate |

Examples 434-437

The following Examples were synthesized by an analogous method to Example 35 from the starting materials (SM) given in the table below.

| Ex | Compound | NMR | m/z | SM |
|---|---|---|---|---|
| 434 | 2-((3S,4R)-4-{[(3,4-Dichloro-5-methyl-1H-pyrrol-2-yl)carbonyl]amino}-3-methoxypiperidin-1-yl)-4-({[(2R)-2-methoxypropyl]amino}carbonyl)-1,3-thiazole-5-carboxylic acid | 1.07 (d, 3H), 1.70-1.76 (m, 2H), 2.17 (s, 3H), 3.25 (s, 3H), 3.36 (s, 3H), 3.37-3.50 (m, 2H), 3.55 (brs, 1H), 4.20-4.30 (m, 2H), 4.45 (brs, 1H), 7.16 (d, 1H), 8.98 (d, 1H), 12.13 (s, 1H), 16.30 (s, 1H) | 546 | Example 430 |

-continued

| Ex | Compound | NMR | m/z | SM |
|---|---|---|---|---|
| 435 | 2-((3S,4R)-4-{[(3,4-Dichloro-5-methyl-1H-pyrrol-2-yl)carbonyl]amino}-3-methoxypiperidin-1-yl)-4-({[(2S)-2-methoxypropyl]amino}carbonyl)-1,3-thiazole-5-carboxylic acid | 1.16 (d, 3H), 1.70-1.76 (m, 2H), 2.18 (s, 3H), 3.23 (s, 3H), 3.37 (s, 3H), 3.44-3.50 (m, 2H), 3.55 (brs, 1H), 4.20-4.30 (m, 2H), 4.45 (brs, 1H), 7.16 (d, 1H), 8.98 (d, 1H), 12.14 (s, 1H), 16.31 (s, 1H) | 546 | Example 431 |
| 436 | 2-((3S,4R)-4-{[(3,4-Dichloro-5-methyl-1H-pyrrol-2-yl)carbonyl]amino}-3-methoxypiperidin-1-yl)-4-({[(1R)-2-methoxy-1-methylethyl]amino}carbonyl)-1,3-thiazole-5-carboxylic acid | 1.16 (d, 3H), 1.70-1.76 (m, 2H), 2.17 (s, 3H), 3.26 (s, 3H), 3.38 (s, 3H), 3.46-3.52 (m, 2H), 3.55 (brs, 1H), 4.20-4.30 (m, 2H), 4.45 (brs, 1H), 7.16 (d, 1H), 8.96 (d, 1H), 12.14 (s, 1H), 16.31 (s, 1H) | 547 | Example 432 |
| 437 | Cis(±)-2-(3-azido-4-{[(3,4-dichloro-5-methyl-1H-pyrrol-2-yl)carbonyl]amino}piperidin-1-yl)-1,3-thiazole-5-carboxylic acid | .8 (m, 2H), 2.2 (s, 3H), 3.3 (m, 1H), 3.6 (d, 1H), 3.9 (d, 1H), 4.24 (m, 3H), 7.23 (d, 1H), 7.7 (s, 1H), 12.1 (s, 1H), 12.7 (S, 1H) | 444 | Example 433 |

Examples 438-440

The following Examples were prepared by the procedure described in Example 417 from the starting materials (SM) indicated

| Ex | Compound | Data | SM |
|---|---|---|---|
| 438 | sodium 2-((3S,4R)-4-{[(3,4-dichloro-5-methyl-1H-pyrrol-2-yl)carbonyl]amino}-3-methoxypiperidin-1-yl)-4-({[(2R)-2-methoxypropyl]amino}carbonyl)-1,3-thiazole-5-carboxylate | MS (ES) MH$^+$: 547 for $C_{21}H_{26}Cl_2N_5O_6S$; NMR: 1.07 (d, 3H), 1.60-1.75 (m, 2H), 2.14 (s, 3H), 3.10-3.19 (m, 3H), 3.24 (s, 3H), 3.34 (s, 3H), 3.47 (brs, 1H), 3.81-3.85 (m, 1H), 3.90-4.00 (m, 1H), 4.05-4.20 (m, 2H), 7.17 (d, 1H), 12.16 (brs, 1H), 13.22 (d, 1H) | Example 434 |
| 439 | Sodium 2-((3S,4R)-4-{[(3,4-dichloro-5-methyl-1H-pyrrol-2-yl)carbonyl]amino}-3-methoxypiperidin-1-yl)-4-({[(2S)-2-methoxypropyl]amino}carbonyl)-1,3-thiazole-5-carboxylate | MS (ES) MH$^+$: 547 for $C_{21}H_{26}Cl_2N_5O_6S$; NMR: 1.07 (d, 3H), 1.60-1.75 (m, 2H), 2.17 (s, 3H), 3.10-3.22(m, 3H), 3.24 (s, 3H), 3.35 (s, 3H), 3.49 (brs, 1H), 3.81-3.85 (m, 1H), 3.90-4.00 (m, 1H), 4.05-4.20 (m, 2H), 7.15 (d, 1H), 12.15 (brs, 1H), 13.22 (d, 1H) | Example 435 |

| Ex | Compound | Data | SM |
|---|---|---|---|
| 440 | Sodium 2-((3S,4R)-4-{[(3,4-dichloro-5-methyl-1H-pyrrol-2-yl)carbonyl]amino}-3-methoxypiperidin-1-yl)-4-({[(1R)-2-methoxy-1-methylethyl]amino}carbonyl)-1,3-thiazole-5-carboxylate 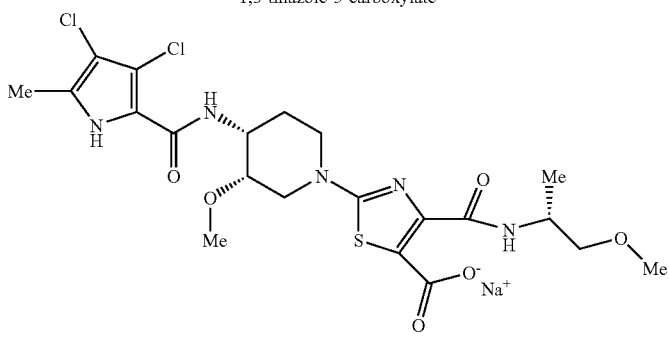 | MS (ES) MH$^+$: 547 for $C_{21}H_{26}Cl_2N_5O_6S$; NMR: 1.07 (d, 3H), 1.65-1.73 (m, 2H), 2.17 (s, 3H), 3.10-3.22 (m, 3H), 3.24 (s, 3H), 3.35 (s, 3H), 3.49 (brs, 1H), 3.81-3.85 (m, 1H), 3.90-4.00 (m, 1H), 4.05-4.20 (m, 2H), 7.17 (d, 1H), 12.18 (brs, 1H), 13.19 (d, 1H) | Example 436 |

Preparation of Starting Materials

Intermediate 83-278

Intermediate 83

Cis(±)-ethyl (4-{[(3,4-dichloro-5-methyl-1H-pyrrol-2-yl)carbonyl]amino}-3-methylpiperidine-1-carboxylate A solution of 167 mg (0.9 mmol) of Cis(±)-ethyl (4-amino-3-methylpiperidine-1-carboxylate (Intermediate 152), 235 μl (1.25 mmol) diisopropylethylamine and 280 mg (1.35) of 3,4-dichloro-5-methyl-1H-pyrrole-2-carbonyl chloride (Intermediate 202) was stirred at room temperature for 1 h. The mixture was diluted with EtOAc and washed with aqueous $Na_2CO_3$ and brine. Drying MgSO4 and removal of solvent gave an oil that was purified by chromatography (100% $CH_2Cl_2$ followed by gradient elution to 100% EtOAc) to afford 145 mg of product. MS (ES)(MH$^+$): 362 for $C_{15}H_{21}Cl_2N_3O_3$; NMR (d$_6$-DMSO): 0.8 (d, 3H), 1.2 (t, 3H), 1.65 (m, 2H), 1.9 (m, 1H), 2.2 (s, 3H), 3.5 (m, 1H), 4.0 (m, 2H), 4.1 (m, 1H), 7.1 (d, 1H), 12.0 (s, 1H).

Intermediates 84-114

The following Intermediates were synthesized by an analogous method to Intermediate 37 or Intermediate 83 from the starting materials (SW) given in the table below.

| Int | Compound | Data | SM |
|---|---|---|---|
| 84 | Cis(±)-tert-butyl 4-{[(3,4-dichloro-5-methyl-1H-pyrrol-2-yl)carbonyl]amino}-3-[(methylthio)methyl]piperidine-1-carboxylate | N/A | Intermediate 72 |
| 85 | Cis(±)-tert-butyl-4-{[(3,4-dichloro-5-methyl-1H-pyrrol-2-yl)carbonyl]amino}-3-(methylthio)piperidine-1-carboxylate | MS (ESP): 420.1 (M −+0H) for $C_{17}H_{25}Cl_2N_3O_3S$; NMR: 1.40 (s, 9H); 1.45-1.70 (m, 2H); 2.10 (s, 3H); 2.18 (s, 3H); 2.80-3.20 (m, 2H); 3.31 (m, 1H); 3.90 (m, 2H); 4.30 (m, 1H); 7.15 (d, 1H); 12.13 (s, 1H) | Intermediate 184 and Intermediate 1 |
| 86 | Cis(±)-ethyl 3-(benzyloxy)-4-{[(3,4-dichloro-5-methyl-1H-pyrrol-2-yl)carbonyl]amino}piperidine-1-carboxylate | MS (ESP): 454 (M ++0H) for $C_{21}H_{25}Cl_2N_3O_4$; NMR: 1.20 (q, 3H); 1.70 (m, 2H); 2.15 (s, 3H); 3.05 (m, 2H); 3.68 (s, 1H); 4.00 (m, 3H); 4.15 (m, 1H); 4.40 (m, 2H); 4.70 (d, 1H); 7.08 (d, 1H); 7.30 (m, 5H); 12.06 (s, 1H). | Intermediate 158 and Intermediate 1 |

| Int | Compound | Data | SM |
|---|---|---|---|
| 87 | Cis(±)-ethyl 4-{[(3,4-dichloro-5-methyl-1H-pyrrol-2-yl)carbonyl]amino}-3-(prop-2-yn-1-yloxy)piperidine-1-carboxylate | MS (ESP): 424 (M + Na) for $C_{17}H_{21}Cl_2N_3O_4$; $^1$H NMR (300 MHz, CDCl$_3$) δ: 1.27 (t, 3H); 1.79 (m, 2H); 2.27 (s, 3H); 2.40 (t, 1H); 2.90 (m, 2H); 3.85 (m, 1H); 4.10-4.55 (m, 7H); 7.25 (m, 1H); 9.53 (s, 1H). | Intermediate 256 and Intermediate 1 |
| 88 | Trans-(±)tert-butyl 4-{[(3,4-dichloro-5-methyl-1H-pyrrol-2yl)carbonyl]amino}3-hydroxypiperidine-1-carboxylate | MS (ES) MH$^+$: 392 for $C_{16}H_{23}Cl_2N_3O_4$; NMR: 1.45 (s, 9H), 1.54 (m, 1H), 2.02 (m, 1H), 2.27 (s, 3H), 2.67 (dd, 1H), 2.84 (brt, 1H), 3.34 (m, 1H), 3.50 (m, 1H), 3.90 (m, 1H), 4.11 (m, 1H), 4.27 (m, 1H), 6.75 (brd, 1H), 10.06 (br s, 1H) | Intermediate 185 and Intermediate 1 |
| 89 | tert-butyl (3S,4R)-4-{[(3-chloro-5-methyl-1H-pyrrol-2-yl)carbonyl]amino}-3-fluoropiperidine-1-carboxylate | MS (ES) MH$^+$: 360 for $C_{16}H_{23}ClFN_3O_3$ | Intermediate 196 and Intermediate 64 |
| 90 | tert-butyl (3S,4R)-4-{[(4-bromo-5-methyl-1H-pyrrol-2-yl)carbonyl]amino}-3-fluoropiperidine-1-carboxylate | MS (ESN): 404 (M − 1) for $C_{16}H_{23}BrN_3O_3$ NMR (CDCl$_3$) δ: 1.47 (t, 9H); 1.80 (m, 2H); 2.26 (s, 3H); 2.81 (s, 3H); 2.96 (m, 1H); 4.27 (m, 1H); 4.65 (d, br, 1H); 6.11 (d, 1H); 6.59 (s, 1H); 9.97 (s, br, 1H) | Intermediate 197 and Intermediate 64 |
| 91 | tert-butyl (3S,4R)-4-{[(4-bromo-3-chloro-5-methyl-1H-pyrrol-2-yl)carbonyl]amino}-3-fluoropiperidine-1-carboxylate | MS (ES) MH$^+$: 440 for $C_{16}H_{22}BrClFN_3O_3$ NMR (CDCl$_3$) δ: 1.47 (s, 9H); 1.85 (m, 2H); 2.29 (s, 3H); 2.85 (m, 2H); 4.24 (m, 2H); 4.50 (m, 1H); 4.72 (d, br, 1H); 6.96 (d, 1H); 9.30 (s, br, 1H) | Intermediate 198 and Intermediate 64 |
| 92 | Cis(±)-Ethyl (4-{[(3,4-dichloro-5-methyl-1H-pyrrol-2-yl)carbonyl]amino}-3-(2-methoxyethoxy)piperidine-1-carboxylate | MS (ES) MH$^-$: 420 for $C_{17}H_{25}Cl_2N_4O_5$ | Intermediate 159 and Intermediate 1 |
| 93 | Cis(±)-Ethyl 4-{[(3,4-dichloro-5-methyl-1H-pyrrol-2-yl)carbonyl]amino}-3-(2-methoxypropoxy)piperidine-1-carboxylate | MS (ES) MH$^+$: 436 for $C_{18}H_{27}Cl_2N_3O_5$ | Intermediate 160 and Intermediate 1 |
| 94 | Cis(±)-Ethyl 4-{[(3,4-dichloro-5-methyl-1H-pyrrol-2-yl)carbonyl]amino}-3-(2-hydroxypropoxy)piperidine-1-carboxylate | MS (ES) MH$^+$: 422 for $C_{17}H_{25}Cl_2N_3O_5$ | Intermediate 161 and Intermediate 1 |
| 95 | tert-Butyl (3S,4R)-4-{[(4-chloro-1H-pyrrol-2-yl)carbonyl]amino}-3-fluoropiperidine-1-carboxylate | $C_{15}H_{21}ClFN_3O_3$ NMR: 1.39 (s, 9H), 1.50-1.60 (m, 1H), 1.69-1.80 (m, 1H), 2.73-3.11 (m, 2H), 3.95-4.23 (m, 3H), 4.71 (d, 1H), 6.94-6.96 (m, 2H), 8.03 (d, 1H), 11.78 (s, 1H) | 2,2,2-trichloro-1-(4-chloro-1H-pyrrol-2-yl)ethanone (Tett lett. 27, 2505-2508, 1979) and Intermediate 64 |
| 96 | tert-Butyl (3S, 4R)-4- {[(4,5-dichloro-1H-pyrrol-2- | $C_{15}H_{21}ClFN_3O_3$ NMR: 1.39 (s, 9H), 1.50-1.60 | Intermediate 203 and Intermediate 64 |

| Int | Compound | Data | SM |
|---|---|---|---|
| | yl)carbonyl]amino}-3-fluoropiperidine-1-carboxylate | (m, 1H), 1.69-1.80 (m, 1H), 2.73-3.11 (m, 2H), 3.95-4.23 (m, 3H), 4.71 (d, 1H), 6.94-6.96 (m, 2H), 8.03 (d, 1H), 11.78 (s, 1H) | |
| 97 | Ethyl (3S,4R)-4-{[(4-chloro-5-methyl-1H-pyrrol-2-yl)carbonyl]amino}-3-methoxypiperidine-1-carboxylate | MS (ES) MH⁺: for $C_{15}H_{22}ClN_3O_4$; NMR: 1.18 (t, J = 7.06 Hz, 3H), 1.48 (d, J = 3.58 Hz, 1H), 1.75 (td, J = 12.29, 7.82 Hz, 1H), 2.10-2.18 (m, 3H), 2.95 (d, J = 13.38 Hz, 2H), 3.20-3.27 (m, 3H), 3.27-3.35 (m, 2H), 3.38 (s, 1H), 3.97-4.09 (m, J = 10.53, 7.08, 7.08, 3.39 Hz, 2H), 4.19 (s, 1H), 6.88 (d, J = 2.64 Hz, 1H), 7.62 (d, J = 7.91 Hz, 1H), 11.60 (s, 1H) | Intermediate 6 and Intermediate 25 |
| 98 | Cis(±)-ethyl-4-{[(4-chloro-3,5-dimethyl-1H-pyrrol-2-yl)carbonyl]amino}-3-methoxypiperidine-1-carboxylate | MS (ES) MH⁺: 358 for $C_{16}H_{24}ClN_3O_4$. | Intermediate 195 and Intermediate 26 |
| 99 | tert-butyl (Cis(±)-3-chloro-4-{[(3,4-dichloro-5-methyl-1H-pyrrol-2-yl)carbonyl]amino}piperidine-1-carboxylate | 1.40 (s, 9H), 1.67 (m, 2H), 2.19 (s, 3H), 2.68 (m, 1H), 3.43 (m, 1H), 4.02 (m, 1H), 4.17 (m, 1H), 4.36 (m, 1H), 4.58 (s, 1H), 7.05 (d, 1H), 12.12 (s, 1H) | Intermediate 1 and Intermediate 162 |
| 100 | tert-butyl (3S,4R)-4-[({4-chloro-3-[(E)-(methoxyimino)methyl]-5-methyl-1H-pyrrol-2-yl}carbonyl)amino]-3-fluoropiperidine-1-carboxylate | MS (ES) MH⁺: 415 for $C_{18}H_{26}ClFN_4O_4$; NMR: 1.40 (s, 9H), 1.70 (m, 2H), 2.34 (s, 3H), 3.29 (m, 1H), 3.31 (s, 3H), 3.35 (m, 1H), 3.99 (m, 1H), 4.24 (m, 2H), 4.78 (d, 1H), 7.19 (d, 1H), 8.02 (s, 1H), 12.11 (s, 1H) | Intermediate 199 and Intermediate 64 |
| 101 | tert-butyl Cis(±)-3-chloro-4-{[(4-chloro-5-methyl-1H-pyrrol-2-yl)carbonyl]amino}piperidine-1-carboxylate | 1.40 (s, 9H), 1.54 (m, 1H), 1.83 (m, 1H), 2.14 (s, 3H), 3.28 (m, 1H), 3.41 (m, 1H), 4.02-4.22 (m, 3H), 4.56 (s, 1H), 6.89 (s, 1H), 7.80 (d, 1H), 11.63 (s, 1H) | 162 and Intermediate 6 |
| 102a | Cis(±)-ethyl (4-{[(3,4-dichloro-5-methyl-1H-pyrrol-2-yl)carbonyl]amino}-2-methylpiperidine-1-carboxylate | MS (ES) (MH⁺): 362 for $C_{15}H_{21}Cl_2N_3O_3$; NMR (d₆-DMSO): 0.8 (d, 3H), 1.2 (t, 3H), 1.65 (m, 2H), 1.9 (m, 1H), 2.2 (s, 3H), 3.5 (m, 1H), 4.0 (m, 2H), 4.1 (m, 1H), 7.1 (d, 1H), 12.0 (s, 1H) | Intermediate 202 and Intermediate 164 |
| 102b | Cis(±)-ethyl (4-{[(4-chloro-3-cyano-5-methyl-1H-pyrrol-2-yl)carbonyl]amino}-3-methoxypiperidine-1-carboxylate | MS (ES) (MH⁺): 369 for $C_{16}H_{21}ClN_4O_4$; NMR (d₆-DMSO): 1.2 (t, 3H), 2.2 (s, 3H), 2.8-3.1 (m, 2H), 3.3 (s, 3H), 3.4 (m, 1H), 3.8-4.3 (m 5H), 7.7 (d, 1H), 12.7 (s, 1H) | Intermediate 200 and Intermediate 21 |
| 103 | tert-butyl (3S,4R)-4-{[(4-chloro-3-cyano-5-methyl-1H-pyrrol-2-yl)carbonyl]amino}-3-fluoropiperidine-1-carboxylate | MS (ES) (MH⁺): 383 for $C_{17}H_{22}ClFN_4O_3$; NMR (d₆-DMSO): 1.4 (s, 9H), 1.7 (m, 2H), 2.2 (s, 3H), 3.8-4.2 (m, 4H), 4.8 (d, 1H), 8.0 (d, 1H), 12.5 (s, 1H) | Intermediate 200 and Intermediate 59 |

-continued

| Int | Compound | Data | SM |
|---|---|---|---|
| 104 | tert-butyl (3S,4R)-4-{[(3,5-dichloro-4-methyl-1H-pyrrol-2-yl)carbonyl]amino}-3-fluoropiperidine-1-carboxylate | MS (ES) (MH$^+$): 394 for $C_{16}H_{22}Cl_2FN_3O_3$; NMR (d$_6$-DMSO): 1.4 (s, 9H), 1.6-1.8 (m, 2H), 1.9 (s, 3H), 2.9 (m, 2H), 4.0-4.3 (m, 3H), 4.8 (d, 1H), 7.3 (d, 1H), 12.5 (s, 1H) | Intermediate 201 and Intermediate 59 |
| 105 | Cis(±)-Ethyl3-(cyclopropylmethoxy)-4-{[(3,4-dichloro-5-methyl-1H-pyrrol-2-yl)carbonyl]amino}piperidine-1-carboxylate | MS (ESI) M: 418 for $C_{18}H_{25}Cl_2N_3O_4$; NMR: 0.22 (m, 2H), 0.50 (m, 2H), 1.04 (m, 1H), 1.24 (t, 3H), 1.69 (m, 2H), 2.24 (s, 3H), 2.87-3.09 (m, 2H), 3.28 (m, 1H), 3.59 (bs, 1H), 3.92-4.36 (m, 5H), 7.20 (m, 1H), 12.21 (bs, 1H) | Interemdiate 165 and Intermediate 1 |
| 106 | Cis(±)-ethyl 4-{[(3,4-dichloro-5-methyl-1H-pyrrol-2-yl)carbonyl]amino}-3-(1,3-thiazol-2-ylmethoxy)piperidine-1-carboxylate | MS (ESI) M: 461 for $C_{18}H_{22}Cl_2N_4O_4S$; NMR (DMSO): 1.10 (m, 3H), 1.65 (m, 2H), 2.16 (s, 3H), 2.82-3.10 (m, 2H), 3.79 (bs, 1H), 3.97 (m, 3H), 4.21 (dt, 1H), 4.35 (t, 1H), 4.78 (d, 1H), 4.95 (d, 1H), 7.10 (d, 1H), 7.72 (dd, 2H), 12.12 (bs, 1H) | Intermediate 166 and Intermediate 1 |
| 107 | Cis(±)-Ethyl (rel 3S,4R)-4-{[(3,4-dichloro-5-methyl-1H-pyrrol-2-yl)carbonyl]amino}-3-ethoxypiperidine-1-carboxylate | MS (ES) MH$^+$: 392, 394 for $C_{16}H_{23}Cl_2N_3O_4$; NMR: 1.04-1.21 (m, 6H); 1.60 (m, 2H); 2.17 (s, 3H); 2.95 (m, 2H); 3.48 (br s, 1H); 3.65 (m, 1H); 3.92 (br s, 1H); 3.98-4.05 (m, 2H); 4.09-4.25 (m, 2H); 7.09 (d, 1H) 12.14 (s, 1H) | Intermediate 257 and Intermediate 1 |
| 108 | 1-tert-butyl 3-methyl 4-{[(3,4-dichloro-5-methyl-1H-pyrrol-2-yl)carbonyl]amino}piperidine-1,3-dicarboxylate | MS (ES) MH$^+$: 434, 436 for $C_{18}H_{25}Cl_2N_3O_5$; NMR (CDCl$_3$): 1.45 (s, 9H), 1.60 (m, 1H), 2.16 (m, 1H), 2.27 (s, 3H), 2.45 (dt, 1H), 2.93 (m, 1H), 3.10 (m, 1H), 3.66 (s, 3H), 4.05 (m, 1H), 4.29 (m, 2H), 6.68 (d, 1H), 9.66 (s, 1H) | Intermediate 167 and Intermediate 1 |
| 109 | 1-(tert-butoxycarbonyl)-4-{[(3,4-dichloro-5-methyl-1H-pyrrol-2-yl)carbonyl]amino}piperidine-3-carboxylic acid | MS (ES) MH$^+$: 420, 422 for $C_{17}H_{23}Cl_2N_3O_5$. | Intermediate 108 and Intermediate 1 |

-continued

| Int | Compound | Data | SM |
|---|---|---|---|
| 110 | Cis(±)tert-butyl 4-{[(3,4-dichloro-5-methyl-1H-pyrrol-2-yl)carbonyl]amino}-3-(morpholin-4-ylcarbonyl)piperidine-1-carboxylate | MS (ES) MH$^+$: 489, 491 for C$_{21}$H$_{30}$Cl$_2$N$_4$O$_5$; NMR: 1.40 (s, 9H), 1.54 (m, 1H), 1.82 (m, 1H), 2.15 (s, 3H), 2.81 (broad s, 2H), 3.14 (dt, 1H), 3.24-3.40 (m, 2H [under H$_2$O peak]), 3.41-3.68 (m, 6H), 3.93 (m, 2H), 4.24 (m, 1H), 7.14 (d, 1H), 11.98 (s, 1H) | Intermediate 109 and Intermediate 1 |
| 111 | Trans(±)tert-butyl 4-{[(3,4-dichloro-5-methyl-1H-pyrrol-2-yl)carbonyl]amino}-3-(morpholin-4-ylcarbonyl)piperidine-1-carboxylate | MS (ES) MH$^+$: 489, 491 for C$_{21}$H$_{30}$Cl$_2$N$_4$O$_5$; NMR: 1.37 (s, 9H), 1.64 (m, 1H), 2.11 (m, 1H), 2.16 (s, 3H), 3.14 (m, 1H), 3.18-3.68 (m, 11H [under H$_2$O peak]), 3.73 (dd, 1H), 4.37 (m, 1H), 7.24 (d, 1H), 12.08 (s, 1H) | Intermediate 109 and Intermediate 1 |
| 112 | Cis(±)ethyl 3-(2-tert-butoxy-2-oxoethoxy)-4-{[(3,4-dichloro-5-methyl-1H-pyrrol-2-yl)carbonyl]amino}piperidine-1-carboxylate | MS (ES) MH$^+$: 478, 480 for C$_{20}$H$_{29}$Cl$_2$N$_3$O$_6$; NMR: 1.17 (t, 3H), 1.41 (s, 9H), 1.90 (m, 1H), 2.16 (s, 3H), 2.78-3.06 (m, 3H), 3.46 (m, 1H), 3.74 (m, 1H), 3.94 (m, 1H), 4.03 (q, 2H), 4.09 (s, 2H), 4.12 (m, 1H), 7.39 (d, 1H), 11.97 (s, 1H) | Intermediate 240 and Intermediate 1 |
| 113 | Trans(±)ethyl 3-(2-tert-butoxy-2-oxoethoxy)-4-{[(3,4-dichloro-5-methyl-1H-pyrrol-2-yl)carbonyl]amino}piperidine-1-carboxylate | NMR: 1.17 (t, 3H), 1.38 (s, 9H), 1.58 (m, 1H), 1.68 (m, 1H), 2.17 (s, 3H), 2.81-3.02 (m, 2H), 3.66 (m, 1H), 3.86-4.27 (m, 7H), 7.40 (d, 1H), 12.07 (s, 1H) | Intermediate 240 and Intermediate 1 |
| 114 | Ethyl 3-{[tert-butyl(dimethyl)silyl]oxy}-4-{[(3,4-dichloro-5-methyl-1H-pyrrol-2-yl)carbonyl]amino}piperidine-1-carboxylate | MS (ES)MH$^+$: 478, 480 for C$_{20}$H$_{33}$Cl$_2$N$_3$O$_4$Si; NMR: -0.07 (s, 3H), 0.07 (s, 3H), 0.83 (s, 9H), 1.16 (t, 3H), 1.56 (m, 1H), 1.72 (m, 1H), 2.17 (s, 3H), 3.04 (m, 2H), 3.85-4.11 (m, 6H), 6.66 (m, 1H), 12.12 (s, 1H) | Intermediate 112 and Intermediate 1 |

Intermediates 115-144

The following Intermediates were synthesized by an analogous method to Intermediate 50 or Intermediate 74 from the starting materials (SM) given in the table below.

| Int | Compound | Data | SM |
|---|---|---|---|
| 115 | Cis(±)-3,4-dichloro-N-[3-(hydroxymethyl)piperidin-4-yl]-5-methyl-1H-pyrrole-2-carboxamide hydrochloride | MS (ES) MH$^+$: 306, 308 for C$_{12}$H$_{17}$Cl$_2$N$_3$O$_2$. | Intermediate 71 |

-continued

| Int | Compound | Data | SM |
|---|---|---|---|
| 116 | Cis(±)-3,4-dichloro-5-methyl-N-{3-[(methylthio)methyl]piperidin-4-yl}-1H-pyrrole-2-carboxamide hydrochloride | MS (ES) MH$^+$: 336, 338 for $C_{13}H_{19}Cl_2N_3OS$. | Intermediate 84 |
| 117 | Cis(±)-3,4-dichloro-5-methyl-N-[3-(methylthio)piperidin-4-yl]-1H-pyrrole-2-carboxamide | MS (ESP): 463.1 (M + H) for $C_{17}H_{20}Cl_2N_4O_3S_2$; NMR: 1.90 (m, 2H); 2.14 (s, 3H); 2.28 (s, 3H); 3.28-3.45 (m, 2H); 3.74 (s, 3H); 3.77 (m, 1H); 3.95 (m, 2H); 4.44 (m, 1H); 7.25 (d, 1H); 7.85 (s, 1H); 12.14 (s, 1H) | Intermediate 85 |
| 118 | Cis(±)-N-[3-(benzyloxy)piperidin-4-yl]-3,4-dichloro-5-methyl-1H-pyrrole-2-carboxamide | MS (ESP): 382 (M + H) for $C_{18}H_{21}Cl_2N_3O_2$ | Intermediate 86 |
| 119 | Cis(±)-3,4-dichloro-5-methyl-N-[3-(prop-2-yn-1-yloxy)piperidin-4-yl]-1H-pyrrole-2-carboxamide | MS (ESP): 330 (M + H) for $C_{14}H_{17}Cl_2N_3O_2$ | Intermediate 87 |
| 120 | Trans(±)3,4-dichloro-N-[3-hydroxypiperidin-4-yl]-5-methyl-1H-pyrrole-2-carboxamide trifluoroacetate 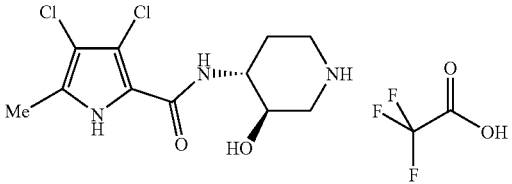 | MS (ES) MH$^+$: 292 for $C_{11}H_{15}Cl_2N_3O_2$ | Intermediate 88 |
| 121 | 3-chloro-N-[(3S,4R)-3-fluoropiperidin-4-yl]-5-methyl-1H-pyrrole-2-carboxamide | MS (ES) MH$^+$: 260 for $C_{11}H_{15}ClFN_3O$; 1.91 (m, 2H); 2.17 (s, 3H); 3.13 (m, 1H); 3.35 (m, 2H); 3.57 (s, 1H); 4.35 (m, 1H); 5.05 (d, br, 1H); 5.96 (s, 1H); 7.26 (d, 1H); 8.67 (br, 1H); 9.16 (br, 1H); 11.70 (s, br, 1H) | Intermediate 89 |
| 122 | 4-bromo-N-[(3S,4R)-3-fluoropiperidin-4-yl]-5-methyl-1H-pyrrole-2-carboxamide | MS (ES) MH$^+$: 306 for $C_{11}H_{15}BrN_3O$ | Intermediate 90 |
| 123 | 4-bromo-3-chloro-N-[(3S,4R)-3-fluoropiperidin-4-yl]-5-methyl-1H-pyrrole-2-carboxamide | MS (ES) MH$^+$: 340 for $C_{11}H_{14}BrN_3O$ NMR δ: 1.91 (m, 2H); 2.20 (s, 3H); 3.13 (m, 1H); 3.35 (m, 2H); 3.62 (m, 1H); 4.35 (m, 1H); 5.05 (d, br, 1H); 7.39 (d, 1H); 8.60 (s, br, 1H); 8.99 (s, br, 1H); 12.17 (s, br, 1H) | Intermediate 91 |
| 124 | Cis(±)-3,4-dichloro-N-[(3-(2-methoxyethoxy)piperidin-4-yl]-5-methyl-1H-pyrrole-2-carboxamide | MS (ES) MH$^+$: 350 for $C_{14}H_{21}Cl_2N_3O_3$ | Intermediate 92 |
| 125 | Cis(±)-3,4-Dichloro-N-[3-(2-methoxypropoxy)piperidin-4-yl]-5-methyl-1H-pyrrole-2-carboxamide 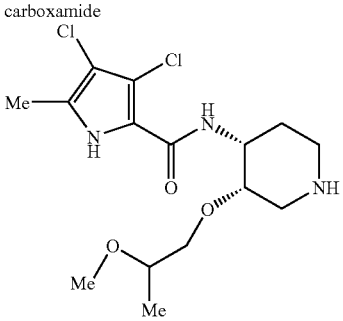 | MS (ES) MH$^+$: 364 for $C_{15}H_{23}Cl_2N_3O_3$ | Intermediate 93 |
| 126 | Cis(±)-3,4-Dichloro-N-3-(2-hydroxypropoxy)piperidin-4-yl]-5-methyl-1H-pyrrole-2- | MS (ES): MH$^+$: 350 for $C_{14}H_{21}Cl_2N_3O_3$; | Intermediate 94 |

| Int | Compound | Data | SM |
|---|---|---|---|
| 127 | carboxamide<br>4-Chloro-N-[(3S,4R)-3-fluoropiperidin-4-yl]-1H-pyrrole-2-carboxamide hydrochloride | MS (ES) MH+: 246 for $C_{10}H_{13}ClFN_3O$ | Intermediate 95 |
| 128 | 4,5-dichloro-N-[(3S,4R)-3-fluoropiperidin-4-yl]-1H-pyrrole-2-carboxamide hydrochloride | MS (ES) MH+: 280 for $C_{10}H_{12}Cl_2FN_3O$ | Intermediate 96 |
| 129 | 4-chloro-N--[(3S,4R)-(3-methoxypiperidin-4-yl)]-5-methyl-1H-pyrrole-2-carboxamide | 1.41 (s, 1H), 1.67 (s, 1H), 2.13 (s, 3H), 2.47 (s, 1H), 2.55 (s, 1H), 2.86 (s, 1H), 3.08 (d, J = 13.19 Hz, 1H), 3.25 (s, 3H), 3.31 (s, 1H), 6.89 (d, J = 2.45 Hz, 1H), 7.52 (s, 1H), 11.59 (s, 1H) | Intermediate 97 |
| 130 | Cis(±)-4-chloro-N-[(3S,4R)-3-methoxypiperidin-4-yl]-3,5-dimethyl-1H-pyrrole-2-carboxamide | MS (ES) MH+: 287 for $C_{13}H_{20}ClN_3O_2$. | Intermediate 98 |
| 131 | 3,4-dichloro-N-[Cis(±)-3-chloropiperidin-4-yl]-5-methyl-1H-pyrrole-2-carboxamide hydrochloride | MS (ES) MH+: 310 for $C_{11}H_{14}Cl_3N_3O$ | Intermediate 99 |
| 132 | 4-chloro-N-[(3S,4R)-3-fluoropiperidin-4-yl]-3-[(E)-(methoxyimino)methyl]-5-methyl-1H-pyrrole-2-carboxamide hydrochloride | MS (ES) MH+: 317 for $C_{17}H_{18}ClFN_4O_2$ | Intermediate 100 |
| 133 | Cis(±)-3-chloro-N-[3-chloropiperidin-4-yl]-5-methyl-1H-pyrrole-2-carboxamide hydrochloride | MS (ES) MH+: 276 for $C_{11}H_{15}Cl_2N_3O$ | Intermediate 101 |
| 134 | Cis(±)-3,4-dichloro-5-methyl-N-[(3-methylpiperidin-4-yl]-1H-pyrrole-2-carboxamide | MS (ES) (MH+): 290 for $C_{12}H_{17}Cl_2N_3O$. | Intermediate 83 |
| 135 | Cis(±)-3,4-dichloro-5-methyl-N-[2-methylpiperidin-4-yl]-1H-pyrrole-2-carboxamide | MS (ES) (MH+): 290 for $C_{12}H_{17}Cl_2N_3O$.<br>NMR: 1.0 (d, 3H), 1.2-1.4 (m, 1H), 1.7-1.9 (m, 1H), 2.2 (s, 3H), 2.5-2.7 (m, 2H), 3.0 (m, 1H), 3.3 (m, 1H), 3.7-3.8 (m, 1H), 7.1 (d, 1H) | Intermediate 101 |
| 136 | Cis(±)-4-chloro-3-cyano-N-[(3-methoxypiperidin-4-yl]-5-methyl-1H-pyrrole-2-carboxamide | MS (ES) (MH+): 297 for $C_{12}H_{17}Cl_2N_3O_2$.<br>NMR: 1.6-1.9 (m, 2H), 2.2 (s, 3H), 2.8 (m, 2H), 3.0 (m, 1H), 3.3 (s, 3H), 3.5 (s, 1H), 4.15 (m, 1H), 7.7 (d, 1H), 8.7 (s, broad, 1H) | Intermediate 102 |
| 137 | 4-chloro-3-cyano-N-[(3S,4R)-3-fluoropiperidin-4-yl]-5-methyl-1H-pyrrole-2-carboxamide | MS (ES) (MH+): 285 for $C_{11}H_{14}Cl_2FN_3O$.<br>NMR: 1.6 (m, 2H), 2.2 (s, 3H), 2.3 (m, 1H), 2.3 (m, 1H), 2.5-3.0 (m, 2H), 3.1-3.3 (m, 1H), 3.5 (s, 1H), 4.0-4.2 (dd, 1H), 4.7 (d, 1H), 7.9 (d, 2H) | Intermediate 103 |
| 138 | (3S,4R)-4-{[(3,5-dichloro-4-methyl-1H-pyrrol-2-yl)carbonyl]amino}-3-fluoropiperidinium chloride | MS (ES) (MH+): 294 for $C_{11}H_{14}Cl_2FN_3O$.<br>NMR: 1.9 (s, 3H), 3.0-3.7 (m, 4H), 4.3 (m, 1H), 5.0 (d, 1H), 7.65 (d, 1H), 8.7 (s, broad, 1H), 9.4 (s, broad, 1H), 12.7 (s, 1H) | Intermediate 104 |

-continued

| Int | Compound | Data | SM |
|---|---|---|---|
| 139 | Cis(±)-3,4-dichloro-N-[3-(cyclopropylmethoxy)piperidin-4-yl]-5-methyl-1H-pyrrole-2-carboxamide | MS (ES) MH$^+$: 347 for C$_{15}$H$_{21}$Cl$_2$N$_3$O$_2$; NMR: 0.17 (m, 2H), 0.44 (m, 2H), 1.01 (m, 1H), 1.34 (s, 1H), 1.62 (m, 2H), 2.17 (s, 3H), 2.55-2.70 (m, 2H), 2.89 (m, 2H), 3.10-3.23 (m, 2H), 3.38-3.49 (m, 1H), 4.09 (m, 1H), 7.12 (d, 1H), 12.10 (bs, 1H). | Intermediate 105 |
| 140 | Cis(±)-3,4-dichloro-5-methyl-N-[3-(1,3-thiazol-2-ylmethoxy)piperidin-4-yl]-1H-pyrrole-2-carboxamide | MS (ESI) M: 389 for C$_{15}$H$_{18}$Cl$_2$N$_4$O$_2$S | Intermediate 106 |
| 141 | Cis(±)-3,4-Dichloro-N-[(rel 3S,4R)-3-ethoxypiperidin-4-yl]-5-methyl-1H-pyrrole-2-carboxamide | MS (ES): MH$^+$: 320 for C$_{13}$H$_{19}$Cl$_2$N$_3$O$_2$; NMR: 1.14 (t, 3H); 1.60 (br s, 2H); 2.17 (s, 3H); 2.62 (m, 2H); 2.89 (m, 2H); 3.14 (m, 2H); 3.64 (m, 2H); 4.05 (m, 2H); 7.10 (d, 1H) | Intermediate 107 |
| 142 | Trans(±)3,4-dichloro-5-methyl-N-[3-(morpholin-4-ylcarbonyl)piperidin-4-yl]-1H-pyrrole-2-carboxamide hydrochloride | MS (ES) MH$^+$: 389, 391 for C$_{16}$H$_{22}$Cl$_2$N$_4$O$_3$ | Intermediate 111 |
| 143 | Cis(±)3,4-dichloro-5-methyl-N-[3-(morpholin-4-ylcarbonyl)piperidin-4-yl]-1H-pyrrole-2-carboxamide hydrochloride | MS (ES) MH$^+$: 389, 391 for C$_{16}$H$_{22}$Cl$_2$N$_4$O$_3$ | Intermediate 110 |
| 144 | Cis(±)[(4-{[(3,4-dichloro-5-methyl-1H-pyrrol-2-yl)carbonyl]amino}piperidin-3-yl)oxy]acetic acid | MS (ES)[(M + H)$^+$]: 350, 352 for C$_{13}$H$_{17}$Cl$_2$N$_3$O$_4$ | Intermediate 112 |

Intermediates 145-157

The following Intermediates were synthesized by an analogous method to Intermediate 59 from the starting materials (SM) given in the table below.

| Int | Compound | Data | SM |
|---|---|---|---|
| 145 | Cis(±)-ethyl 3-(benzyloxy)-4-[(tert-butoxycarbonyl)amino]piperidine-1-carboxylate | MS (ES): 401 (M + Na) for $C_{20}H_{30}N_2O_5$; NMR (CDCl$_3$) δ: 1.25 (m, 3H); 1.43 (s, 9H); 1.65-1.85 (m, 2H); 2.81 (m, 2H); 3.58 (s, 1H); 3.71 (m, 1H); 4.05-4.30 (m, 3H); 4.30 (m, 2H); 4.76 (t, 1H); 4.94 (m, 1H); 7.26-7.38 (m, 5H) | cis(±)ethyl 4-[(tert-butoxycarbonyl)-amino]-3-hydroxypiperidine-1-carboxylate (WO9412494) and Benzyl bromide |
| 146 | Cis(±)-ethyl 4-[(tert-butoxycarbonyl)amino]-3-(prop-2-yn-1-yloxy)piperidine-1-carboxylate | NMR: (CDCl$_3$) 1.26 (t, 3H); 1.45 (s, 9H); 1.67 (m, 2H); 2.43 (t, 1H); 2.79 (m, 2H); 3.74 (m, 2H); 4.00-4.45 (m, 6H); 5.00 (s, 1H) | cis(±)ethyl 4-[(tert-butoxycarbonyl)amino]-3-hydroxypiperidine-1-carboxylate (WO9412494) and Propargyl bromide |
| 147 | Cis(±)-Ethyl (4-benzylamino)-3-(2-methoxyethoxy)piperidine-1-carboxylate | MS (ES) MH⁺: 337 for $C_{18}H_{28}N_2O_4$ | Intermediate 169 |
| 148 | Cis(±)-Ethyl 4-[(tert-butoxycarbonyl)amino]-3-(2-methoxypropoxy)piperidine-1-carboxylate | MS (ES) M + Na: 383 for $C_{17}H_{32}N_2O_6$ | Intermediate 149 and methyl iodide |
| 149 | Cis(±)-Ethyl 4-[(tert-butoxycarbonyl)amino]-3-(2-hydroxypropoxy)piperidine-1-carboxylate | MS (ES) M + Na: 369 for $C_{16}H_{30}N_2O_6$ | Intermediate 150 (J. Org. Chem, 60, 4922-4924, 1995) |
| 150 | Cis(±)-Ethyl 4-[(tert-butoxycarbony)amino]-3-(oxiran-2-ylmethoxy)piperidine-1-carboxylate | MS (ES) M + Na: 367 for $C_{16}H_{28}N_2O_6$ | Intermediate 27 and m-CPBA |
| 151 | tert-butyl (Cis(±)-4-(benzylamino)-3-chloropiperidine-1-carboxylate | 1.39 (s, 9H), 1.54 (m, 2H), 1.93 (m, 1H), 2.80 (m, 2H), 3.20 (m, 1H), 3.75 (q, 2H), 4.06 (m, 1H), 4.57 (s, 1H), 7.22-7.36 (m, 5H). | Intermediate 170 |
| 152 | Cis(±)-ethyl 4-(benzylamino)-3-methylpiperidine-1-carboxylate | NMR (CDCl$_3$): 0.9 (d, 3H),1.2 (t, 3H), 1.6 (m, 2H), 2.0 (m, 1H), 2.8 (m, 1H), 2.9-3.2 (m, 2H), 3.7 (m, 1H), 3.8 (s, 2H), 4.1 (m, 2H), | ethyl 3-methyl-4-oxopiperidine-1-carboxylate (Ebnoether, A.; |

| Int | Compound | Data | SM |
|---|---|---|---|
| | | 7.2-7.4 (m, 5H). | Niklaus, P.; Suess, R. Helvetica Chimica Acta (1969), 52(3), 629-38) |
| 153 | Cis(±)-ethyl (4-(benzylamino)-2-methylpiperidine-1-carboxylate | MS (ES) (MH+): 277 for $C_{16}H_{24}N_2O_2$: NMR ($d_6$-DMSO): 1.25 (t, 3H), 1.3 (d, 3H), 1.3-1.5 (m, 2H), 1.65 (s, broad, 2H), 1.8-2.0 (m, 2H), 3.2-3.4 (m, 2H), 3.8 (m, 1H), 4.1 (3, 3H) | Intermediate 164 |
| 154 | Cis(±)-Ethyl 4-(benzylamino)-3-(cyclopropylmethoxy)piperidine-1-carboxylate | MS (ES) MH+: 333 for $C_{19}H_{28}N_2O_3$; NMR: 0.14 (m, 2H), 0.42 (m, 2H), 0.97 (m, 1H), 1.15 (t, 3H), 1.51 (m, 2H), 2.67 (m, 1H), 2.79-3.01 (m, 2H), 3.19 (m, 1H), 3.53 (m, 1H), 3.73 (m, 3H), 3.88-4.02 (m, 3H), 7.18-7.35 (m, 5H) | Intermediate 171 |
| 155 | Cis(±)-ethyl 4-[(tert-butoxycarbonyl)amino]-3-(1,3-thiazol-2-ylmethoxy)piperidine-1-carboxylate | MS (ES) MH+: 386 for $C_{17}H_{27}N_3O_5S$; NMR (CDCl$_3$): 1.24 (t, 3H), 1.42 (s, 9H), 1.63 (s, 1H), 1.69-1.81 (m, 2H), 2.82 (m, 2H), 3.67 (m, 2H), 4.10 (q, 2H), 4.40-4.60 (m, 1H), 4.76 (d, 1H), 4.94-5.25 (m, 2H), 7.31 (d, 1H), 7.74 (d, 1H) | Intermediate 235 |
| 156 | Cis(±)-Ethyl (4-(benzylamino)-3-ethoxypiperidine-1-carboxylate | MS (ES) MH+: 307 for $C_{17}H_{26}N_2O_3$; NMR: 1.08 (t, 3H); 1.15 (t, 3H); 1.50 (m, 2H); 1.75 (br s, 1H); 2.65 (br s, 1H); 2.92 (m, 2H); 3.47 (br s, 1H); 3.55 (m, 1H); 3.71 (m, 3H); 3.88 (br s, 1H); 3.98-4.05 (m, 2H); 7.18-7.34 (m 5H) | Intermediate 172 |
| 157 | Cis(±)-ethyl 4-(benzylamino)-3-methoxypiperidine-1-carboxylate | MS (ES) MH+: 293 for $C_{16}H_{24}N_2O_3$. NMR: 1.16 (t, 3H), 1.50 (m, 2H), 1.89 (s, 2H), 2.66 (m, 1H), 2.89 (dd, 2H), 3.26 (s, 3H), 3.67-3.83 (m, 3H), 3.99 (m, 3H), 7.18-7.37 (m, 5H) | Intermediate 168 |

Intermediates 158-167

The following Intermediates were synthesized by an analogous method to Intermediate 28 or Intermediate 59 from the starting materials (SM) given in the table below.

| Int | Compound | Data | SM |
|---|---|---|---|
| 158 | Cis(±)-ethyl 4-amino-3-(benzyloxy)piperidine-1-carboxylate | MS (ESP): 279 (M + H) for $C_{15}H_{22}N_2O_3$ | Intermediate 145 |

| Int | Compound | Data | SM |
|---|---|---|---|
| 160 | Cis(±)-Ethyl 4-amino-3-(2-methoxypropoxy)piperidine-1-carboxylate hydrochloride | MS (ES) MH+: 261 for $C_{12}H_{24}N_2O_4$ | Intermediate 148 |
| 161 | Cis(±)-Ethyl 4-amino-3-(2-hydroxypropoxy)piperidine-1-carboxylate hydrochloride | MS (ES) MH+: 247 for $C_{11}H_{22}N_2O_4$ | Intermediate 149 |
| 162 | tert-butyl Cis(±)-4-amino-3-chloropiperidine-1-carboxylate | 1.39 (s, 9H), 1.45 (m, 1H), 1.58 (m, 2H), 2.95 (m, 1H), 3.31 (m, 1H), 3.82 (m, 1H), 4.03 (m, 1H), 4.26 (m, 1H) | Intermediate 151 |
| 163 | ethyl Cis(±)-4-amino-3-methylpiperidine-1-carboxylate | NMR (CDCl$_3$): 0.9 (d, 3H), 1.2 (t, 3H), 1.5 (m, 2H), 1.6 (m, 1H), 2.2 (s, broad, 2H), 3.0 (m, 1H), 3.2 (m, 2H), 3.4 (m, 1H), 4.0-4.2 (m, 2H) | Intermediate 152 |
| 164 | Cis(±)-ethyl (4-amino-2-methylpiperidine-1-carboxylate | NMR: 1.25 (t, 3H), 1.3 (d, 3H), 1.3-1.5 (m, 2H), 1.65 (s, broad, 2H), 1.8-2.0 (m, 2H), 3.2-3.4 (m, 2H), 3.9 (m, 1H), 4.1 (3, 3H) | ethyl 2-methyl-4-oxopiperidine-1-carboxylate (EP 121972 A2) |
| 165 | Cis(±)-Ethyl 4-amino-3-(cyclopropylmethoxy)piperidine-1-carboxylate | MS (ES) MH+: 243 for $C_{12}H_{22}N_2O_3$; NMR (CDCl$_3$): 0.19 (m, 2H), 0.49 (m, 2H), 1.05 (m, 1H), 1.24 (t, 3H), 1.65-1.84 (m, 2H), 2.93 (d, 2H), 3.09 (m, 1H), 3.25-3.44 (m, 2H), 3.52 (bs, 1H), 3.85-4.21 (m, 6H) | Intermediate 154 |
| 166 | Cis(±)-ethyl 4-amino-3-(1,3-thiazol-2-ylmethoxy)piperidine-1-carboxylate | MS (ES) MH+: 286 for $C_{12}H_{19}N_3O_3S$; NMR (DMSO): 1.00 (t, 1.8H), 1.15 (t, 1.2H), 1.70 (m, 2H), 2.79-3.03 (m, 2H), 3.44 (m, 1H), 3.74-4.02 (m, 4H), 4.29 (m, 1H), 4.91 (t, 2H), 7.25 (bs, 1H), 7.77 (dd, 2H), 8.34 (s, 1H) | Intermediate 155 |
| 167 | 1-tert-butyl 3-methyl-4-aminopiperidine-1,3-dicarboxylate | MS (GC-EI)[(M)+]: 258 for $C_{12}H_{22}N_2O_4$ | Intermediate 237 |

Intermediate 168 ethyl 3-methoxy-4-oxopiperidine-1-carboxylate

To a stirred solution of the methoxyketal (Intermediate 173, 55.15 g, 223 mmol, crude) in dry THF (30 mL), at room temperature and under ambient atmosphere, was added an aqueous solution of H$_2$SO$_4$ (5%, v/v, 190 mL). Temperature was increased to 60° C.; the reaction was stirred at this temperature. Complete conversion was suggested after 2 hours by TLC (50% ethyl acetate in hexanes; Hanessian's stain; Rf~0.43). The reaction mixture was allowed to come to room temperature. THF was removed under vacuum. To the aqueous solution was added solid sodium bicarbonate until basic, and solid sodium chloride until saturated, with the addition of more water necessary. Crude product was extracted with methylene chloride (3×300 mL); the organic layers were combined, dried over magnesium sulfate, and concentrated. The crude material was used without further purification; yield was assumed quantitative.

MS (ESI) M: 201 for $C_9H_{15}NO_4$. $^1$H NMR (CDCl$_3$): 1.28 (t, 3H), 2.38-2.60 (m, 2H), 3.30-3.41 (m, 2H), 3.45 (s, 3H), 3.69 (m, 1H), 4.05 (m, 2H), 4.17 (q, 2H).

Intermediates 169-172

The following Intermediates were synthesized by an analogous method to Intermediate 168 from the starting materials (SM) given in the table below.

| Int | Compound | Data | SM |
|---|---|---|---|
| 169 | Ethyl 3-(2-methoxyethoxy)-4-oxopiperidine-1-carboxylate | MS (ES) MH$^+$: 246 for $C_{11}H_{19}NO_5$ | Intermediate 174 |
| 170 | tert-butyl 3-chloro-4-oxopiperidine-1-carboxylate | 1.30 (m, 1H), 1.34 (s, 9H), 2.45 (t, 2H), 3.34 (m, 1H), 3.17 (m, 1H), 4.10 (m, 1H), 4.66 (m, 1H) | J. Org. Chem., 1994, 59, 6955-6964. |
| 171 | Ethyl 3-(cyclopropylmethoxy)-4-oxopiperidine-1-carboxylate | MS (ES) MH$^+$: 242 for $C_{12}H_{19}NO_4$; NMR (CDCl$_3$): 0.21 (m, 2H), 0.53 (m, 2H), 1.07 (m, 1H), 1.28 (t, 3H), 2.37-2.58 (m, 2H), 3.32-3.51 (m, 4H), 3.85 (bs, 1H), 4.04-4.41 (m, 4H) | Intermediate 255 and cyclopropylmethyl bromide |
| 172 | Ethyl 3-ethoxy-4-oxopiperidine-1-carboxylate | MS (ES) NMa$^+$: 238 for $C_{10}H_{17}NO_4$—Na adduct; NMR: 1.09 (t, 3H); 1.20 (t, 3H); 2.31 (m, 1H); 3.12 (br s, 1H); 3.45 (m, 1H); 3.59 (m, 1H); 3.94 (m, 2H); 4.03-4.11 (m, 4H). | Intermediate 175 |

Intermediate 173 ethyl 3,4,4-trimethoxypiperidine-1-carboxylate

To a stirred solution of sodium hydride (6.96 g, 290 mmol) in dry THF (100 mL), at 0° C. and under an atmosphere of $N_2$, was added a solution of the hydroxyketal (Intermediate 255, 223 mmol) in THF (125 mL) over approximately 30 minutes, via addition funnel. The resulting solution was stirred at 0° C. under an atmosphere of $N_2$ for approximately 15 minutes; to it was then added methyl iodide (18.0 mL, 41.0 g, 290 mmol) portionwise, via syringe, over approximately 5 minutes. The reaction was stirred overnight under an atmosphere of $N_2$, gradually reaching room temperature. Complete conversion was suggested by TLC (50% ethyl acetate in hexanes; Hanessian's stain; Rf~0.57) in the morning. The reaction was quenched with a small volume of water, then concentrated under vacuum. To the residue was added approximately 50 mL of water; from this mixture was extracted the crude product with ethyl acetate (3×150 mL). The organic layers were combined, dried over magnesium sulfate, and concentrated. The crude material was used without further purification; yield was assumed quantitative.

MS (ESI) M: 247 for $C_{11}H_{21}NO_5$. $^1$H NMR (CDCl$_3$): 1.24 (t, 3H), 1.72-1.83 (m, 2H), 2.82 (m, 2H), 2.98 (t, 1H), 3.20 (s, 3H), 3.21 (s, 3H), 3.41 (s, 3H), 4.10 (q, 2H), 4.20-4.37 (m, 2H).

Intermediates 174-175

The following Intermediates were synthesized by an analogous method to Intermediate 173 from the starting materials (SM) given in the table below.

| Int | Compound | Data | SM |
|---|---|---|---|
| 174 | Ethyl 4,4-dimethoxy-3-(2-methoxyethoxy)piperidine-1-carboxylate | NMR (CDCl$_3$): 1.23 (t, 3H), 1.73-1.85 (m, 2H), 2.75-2.88 (m, 1H), 2.93-3.10 (m, 1H), 3.19 (s, 3H), 3.23 (s, 3H), 3.34 (s, 3H), 3.40-3.60 (m, 4H), 3.68-3.80 (m, 2H), 4.11 (q, 2H), 3.98-4.30 (m, 1H) | Intermediate 255 and 1-bromo-2-methoxyethane |
| 175 | Ethyl 3-ethoxy-4,4-dimethoxypiperidine-1-carboxylate | MS (ES) MNa$^+$: 284 for $C_{12}H_{23}NO_5$—Na adduct; NMR: 1.07 (t, 3H); 1.15 (t, 3H); 1.52 (m, 1H); 1.66 (m, 1H); 3.08 (s, 3H); 3.10 (s, 3H); 3.59 (m, 1H); 3.81 (m, 2H); 3.96-4.07 (m, 4H); 4.12 (m, 1H) | Intermediate 255 and ethyl iodide |

Intermediate 176

Ethyl 2-oxobutanoate

Diethyl oxalate (10 g; 68 mmol) was dissolved in Et$_2$O (100 ml) and cooled to −78 C. Ethyl magnesium bromide (1.0 M in THF; 72 ml; 71.8 mmol; 1.05 equiv.) was added slowly via syringe. The dry ice/acetone bath was allowed to melt and warm to 10 C. Monitored the reaction by $^1$H NMR. The reaction was cooled to 0 C and quenched with saturated NH$_4$Cl. Dilute with H$_2$O and separate phases. The organic layer was dried over Na$_2$SO$_4$, filtered and concentrated. Isolation gave 7.6 g of a crude yellow oil in 86% yield. No further purification.

Intermediate 177

Ethyl 3-bromo-2-oxobutanoate

CuBr$_2$ (39.3 g; 176 mmol; 3 equiv.) was suspended in EtOAc (160 ml). A CHCl$_3$ solution containing ethyl 2-oxobutanoate (Intermediate 176, 7.6 g; 58.7 mmol) was added dropwise. The suspension was then heated to reflux for 6 hours and monitored by $^1$H NMR. The solids were filtered through a pad of Celite and the mother liquor was concentrated. The crude oil was passed through a short plug of silica gel and eluted with a 1:1 mixture of EtOAc/hexanes. The yellow band was collected and concentrated to give 12.2 g of product. No further purification.

Intermediate 178

Ethyl 2-amino-5-methyl-1,3-thiazole-4-carboxylate

Ethyl 3-bromo-2-oxobutanoate (Intermediate 177, 12.2 g; 58.7 mmol) and thiourea (4.46 g; 76.1; 58.7 mmol) were combined and heated to reflux. The solution was allowed to cool to room temperature and stir for 12 hours. The reaction was monitored by LC/MS. The base was precipitated with 20% NH$_4$OH (10 ml) and then redissolved with 1N HCl (100 ml) and then finally reprecipitated with 20% NH$_4$OH. The precipitate was collected and washed with H$_2$O. The crude product was then crystallized from 9:1 ethanol/water to give 5.95 g of product in 55% yield. MS (ES) MH$^+$: 187 for C$_7$H$_{10}$N$_2$O$_2$S.

Intermediate 179

Ethyl 2-chloro-5-methyl-1,3-thiazole-4-carboxylate

Ethyl 2-amino-5-methyl-1,3-thiazole-4-carboxylate (Intermediate 178, 3 g; 16.1 mmol) and anhydrous CuCl$_2$ (3.25 g; 24.2 mmol; 1.5 equiv.) were combined in dry acetonitrile (28 ml). t-butyl nitrite (90% tech; 2.77 g; 24.2 mmol; 1.5 equiv.) was added dropwise. The suspension was stirred at room temperature for 12 hours and monitored by LC/MS. The acetonitrile was removed in vacou and the solid was redissolved in CHCl$_3$ and H$_2$O. The aqueous layer was acidified with 2N HCl and the phases were separated. Back extracted the aqueous with CHCl$_3$. The organic extracts were combined, dried over Na$_2$SO$_4$ and decolorizing carbon for 1 hour. Filtered through a pad of Celite and concentrated to an oil. Isolation gave 2.62 g of the title compound in 80% yield. The compound can be further purified via flash column chromatography and crystallization. MS (ES) MH$^+$: 206, 208 for C$_7$H$_8$ClNO$_2$S.

Intermediate 180

Ethyl 5-(bromomethyl)-2-chloro-1,3-thiazole-4-carboxylate

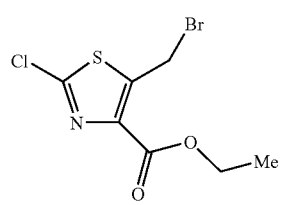 [SMILES: CCOC(=O)c1nc(Cl)sc1CBr]

Ethyl 2-chloro-5-methyl-1,3-thiazole-4-carboxylate (Intermediate 179, 2.8 g; 13.6 mmol) was dissolved in CCl$_4$ (25 ml). NBS (2.3 g; 13 mmol) and AIBN (2.12 g; 13 mmol) were added in a single portion and the resultant reaction mixture was heated to reflux for 24 hours. Additional NBS (690 mg; 0.3 equiv.) and AIBN (636 mg; 0.3 mmol) were added to push the reaction to completion. Continued to heat for another 4 hours. Cooled to room temperature, filtered and concentrated the mother liquor. Redissolved in minimal DMSO (7 ml) and purified by Gilson HPLC (5-95% ACN/0.1% TFA; run time=35 min). Isolated 1.15 g of desired product in 29% yield MS (ES) MH$^+$: 284, 286, 288 for C$_7$H$_7$BrClNO$_2$S.

Intermediate 181

Ethyl 2-chloro-5-formyl-1,3-thiazole-4-carboxylate

Ethyl 5-(bromomethyl)-2-chloro-1,3-thiazole-4-carboxylate (Intermediate 180, 920 mg; 3.2 mmol) was dissolved in acetonitrile dried over molecular sieves. The solution was cooled to 0 C and NMO (570 mg; 1.5 equiv.) was added in a single portion. The reaction was monitored by LC/MS. An additional 1.5 equivalents of NMO was added in two portions over two hours. The reaction was concentrated to a solid residue, redissolved in EtOAc and washed with H$_2$O. Dried the organic over Na$_2$SO$_4$, filtered and concentrated. No further purification. MS (ES) MH$^+$: 220, 222 for C$_7$H$_6$ClNO$_3$S.

Intermediate 182 tert-Butyl 3-bromo-4-oxopiperidine-1-carboxylate

Chlorotrimethylsilane (5.6 ml, 44 mmol) was added slowly to a solution of tert-butyl 4-oxopiperidine-1-carboxylate (commercial, 8 g, 40 mmol), triethylamine (12.3 ml, 88 mmol) and DMF (40 ml) at room temperature. The resultant solution was heated to 75° C. and stirred overnight under nitrogen. The reaction mixture was cooled to room temperature and then in an ice bath. Cold hexane (250 ml) was added slowly to the reaction mixture followed by cold (saturated) aqueous sodium bicarbonate (50 ml). The organic phase was separated and washed with brine, dried over sodium sulfate, filtered and concentrated under reduced pressure. The crude silyl enolether was dissolved in THF (15 ml) and cooled to 0° C. N-Bromosuccinimide (7.1 g, 40 mmol) was dissolved in THF (120 ml) and added slowly (45 min.) to the reaction mixture. The resultant mixture was allowed to slowly warm to room temperature and stirred overnight. The reaction mixture was concentrated under reduced pressure. The crude residue was purified by flash chromatography (hexanes/ethyl acetate, 5:1) to provide the title compound as a white solid (11 g).

MS (ESP): 222.1 (M-tBu) for $C_{10}H_{16}BrNO_3$.

$^1$H NMR (300 MHz, DMSO-$d_6$) δ: 1.25 (s, 9H); 2.30 (m, 1H); 2.55 (m, 1H); 3.42-3.80 (m, 3H); 3.93 (m, 1H); 4.60 (m, 1H).

Intermediate 183 tert-Butyl 3-(methylthio)-4-oxopiperidine-1-carboxylate

Sodium thiomethoxide (805 mg, 11.5 mmol) was added to a solution of tert-butyl 3-bromo-4-oxopiperidine-1-carboxylate (Intermediate 182, 3.20 g, 11.5 mmol) and THF (15 ml) at 0° C. The resultant mixture was allowed to slowly warm to room temperature and stirred overnight. The reaction was quenched with water (15 ml) and diluted with ethyl acetate (150 ml). The organic phase was separated and washed with brine. The combined aqueous phase was back extracted with ethyl acetate (50 ml). The combined organic layer was dried over magnesium sulfate, filtered, and concentrated under reduced pressure. The crude residue was purified by flash chromatography (hexanes/ethyl acetate, 7:1) to provide the title compound (2.4 g).

MS (ESP): 190.2 (M-tBu) for $C_{11}H_{19}NO_3S$.

$^1$H NMR (300 MHz, CDCl$_3$) δ: 1.43 (s, 9H); 2.02 (s, 3H); 2.23 (dt, 1H); 2.95 (m, 1H); 3.20-3.40 (m, 2H); 3.65 (m, 1H); 3.90-4.20 (m, 2H).

Intermediate 184

Cis(±)-tert-butyl-4-amino-3-(methylthio)piperidine-1-carboxylate

Sodium cyanoborohydride (344 mg, 5.48 mmol) was added to a solution of tert-butyl 3-(methylthio)-4-oxopiperidine-1-carboxylate (Intermediate 183, 1.07 g, 4.40 mmol), ammonium acetate (3.24 g, 42 mmol) and methanol (15 ml). The resultant mixture was stirred for 4 h. The reaction was quenched by addition of 1N HCl (3 ml). Aqueous sodium bicarbonate (saturated, 50 ml) was added slowly to the reaction mixture followed by extraction with ethyl acetate (3×75 ml). The combined organic phase was dried over sodium sulfate, filtered and concentrated under reduced pressure to yield the crude amine MS (ESP): 247.3 (M+H) for $C_{11}H_{22}N_2O_2S$.

Intermediate 185

Trans(±)tert-butyl 4-amino-3-hydroxypiperidine-1-carboxylate

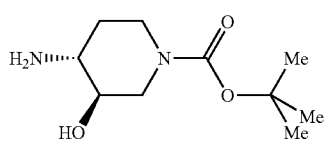

The title compound was prepared as described in Marquis R. W. et al. *J. Med. Chem.* 1998, 41,3563-3567 and/or WO 9805336. MS (ES) MH$^+$: 217 for $C_{10}H_{20}N_2O_3$; NMR: 1.45 (s, 9H), 1.80 (m, 1H), 1.95 (m, 1H), 2.21 (m, 1H), 2.62 (m, 1H), 2.75 (m, 1H), 3.28 (m, 1H), 3.47 (m, 1H), 3.81 (m, 1H), 4.11 (m, 1H), 4.28 (m, 1H), 8.20 (m, 1H).

Intermediate 186

Ethyl 3-chloro-5-methyl-1H-pyrrole-2-carboxylate

The compound was prepared by the procedure described for Intermediate 2.

MS (ESP): 188 (MH$^+$) for $C_8H_{10}ClNO_2$.

$^1$H-NMR (CDCl$_3$) δ: 1.37 (t, 3H); 2.26 (s, 3H); 4.32 (q, 2H); 5.96 (s, 1H); 8.81 (br, 1H).

Intermediate 187

Ethyl 4-bromo-5-methyl-1H-pyrrole-2-carboxylate

The compound was prepared by the procedure described for Intermediate 2.

MS (ESP): 234 (MH$^+$) for $C_8H_{10}BrNO_2$.

$^1$H-NMR δ: 1.27 (t, 3H); 2.17 (s, 3H); 4.22 (q, 2H); 6.74 (s, 1H); 12.10 (s, br, 1H).

Intermediate 188

4 Ethyl 4-bromo-3-chloro-5-methyl-1H-pyrrole-2-carboxylate

Ethyl 4-bromo-5-methyl-1H-pyrrole-2-carboxylate (Intermediate 187, 2.87 g, 12.4 mmol) was dissolved in dry DMF (30 ml), N-chlorosuccinimide (1.66 g, 12.4 mmol) was added and resulting mixture was stirred at room temperature over night, more N-chlorosuccinimide (0.83 g, 6.2 mmol) was added and the reaction temperature was increased to 35° C., stirred for 4 hours. The mixture was poured into cold sodium hydroxide aqueous solution (2M) (50 ml), extracted with diethyl ether (2×50 ml). The organic phase was then washed with water (20 ml) and brine (20 ml), dried over anhydrous sodium sulfate and purified by column chromatography(hexanes/ethyl acetate, gradient) to give the desired product as a white crystal. (1.2 g).

MS (ESP): 268 (MH$^1$) for $C_8H_9BrClNO_2$.

$^1$H-NMR (CDCl$_3$) δ: 1.38 (t, 3H); 2.30 (s, 3H); 4.34 (q, 2H); 9.0 (br, 1H).

Intermediate 189 ethyl 4-chloro-3,5-dimethyl-1H-pyrrole-2-carboxylate

N-Chlorosuccinimide (1.77 g, 13.25 mmol) was added to a solution of ethyl 3,5-dimethyl-2-pyrrole carboxylate (2.11 g, 12.62 mmol) in chloroform (45 mL). The reaction mixture was stirred at room temperature for 24 h and then poured into 2 N NaOH. The organic layer was washed with water and brine, dried over sodium sulfate, filtered, and concentrated under reduced pressure to give a crude solid. The crude solid was dissolved in hot MeOH, cooled to room temperature, and the precipitate was collected by filtration (493 mg, 19%). MS (ES) MH$^+$: 174 for $C_9H_{12}ClNO_2$.

Intermediate 190 ethyl 4-chloro-3-[(E)-(methoxyimino)methyl]-5-methyl-1H-pyrrole-2-carboxylate

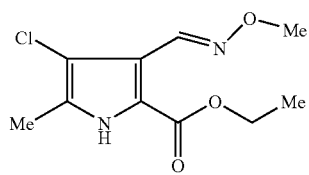 [SMILES: CCOC(=O)c1[nH]c(C)c(Cl)c1/C=N/OC]

A solution of Intermediate 191 (300 mg, 1.39 mmol) in MeOH (5 mL) and pyridine (1.5 mL) with methylamine hydrochloride (255 mg, 3.06 mmol) was heated to 60° C. overnight. The reaction was cooled to room temperature and then partitioned between methylene chloride and 10% HCl. The organic layer was dried over sodium sulfate, filtered, and concentrated under reduced pressure to give an off-white solid.

MS (ES) MH$^+$: 245 for $C_{10}H_{13}ClN_2O_3$;
NMR (DMSO-$d_6$): 1.29 (t, 3H), 2.36 (s, 3H), 3.83 (s, 3H), 4.27 (q, 2H), 8.03 (s, 1H), 12.31 (s, 1H).

Intermediate 191 ethyl 4-chloro-3-formyl-5-methyl-1H-pyrrole-2-carboxylate

POCl$_3$ in 1,2-dichloroethane (14 mL) was slowly added to a solution of DMF (4.37 mL, 59.79 mmol) in 1,2-dichloroethane (10 mL). The reaction mixture was stirred for 15 min and then Intermediate 7 (2.04 g, 10.87 mmol) was added. The reaction mixture was heated at reflux for 3 h and then cooled to room temperature. The reaction mixture was treated with sodium acetate (10 g) in water (25 mL) and stirred for 1 h. The mixture was extracted with methylene chloride, washed with water, dried over sodium sulfate, filtered, and concentrated under reduced pressure. Purification by flash column chromatography (silica, 2:1 hexanes/ethyl acetate) gave the desired compound (720 mg).

MS (ES) MH$^+$: 216 for $C_9H_{10}ClNO_3$.

Intermediate 192 ethyl 3-bromo-4-chloro-5-methyl-1H-pyrrole-2-carboxylate

Bromine (0.56 ml, 11 mmol) was added to a solution of 1 g (5.3 mmol) of ethyl 4-chloro-5-methyl-1H-pyrrole-2-carboxylate (Intermediate 7) and 0.8 ml (5.7 mmol) Et$_3$N in CH$_2$Cl$_2$. After stirring at room temperature for 2 h, aqueous NaHSO$_3$ was added and the CH$_2$Cl$_2$ was removed and the aqueous residue was partitioned between water and EtOAc. The EtOAc was separated and washed with brine. Drying (MgSO$_4$) and removal of solvent gave 1.5 g of product as a solid. MS (ES) (MH$^+$): 240 for $C_8H_9BrClNO_2$; NMR ($d_6$-DMSO): 1.3 (t, 3H), 2.2 (s, 3H), 4.2 (q, 2H), 12.3 (s, 1H).

Intermediate 193 ethyl 4-chloro-3-cyano-5-methyl-1H-pyrrole-2-carboxylate

Nitrogen gas was bubbled through a mixture of 1.4 g (5.25 mmol) of ethyl 3-bromo-4-chloro-5-methyl-1H-pyrrole-2-carboxylate (Intermediate 192), 470 g (4 mol) Zn(CN)$_2$, 250 mg (0.26 mmol) Pd$_2$(dba)$_3$ and 302 mg (0.26 mmol) dppf in 15 ml DMF for 15 min. The mixture was heated at 130° C. for 1 h. Additional Zn(CN)$_2$ (1 g), Pd$_2$(dba)$_3$ (500 mg) and dppf (604 mg) were added. After bubbling through N$_2$ for 15 min and heating at 130° C. for 2 h, additional Zn(CN)$_2$ (0.5 g), Pd$_2$(dba)$_3$ (250 mg) and dppf (302 mg) were added. Heating was continued at 130° C. for 2h. Solvent was removed and the residue was partitioned between EtOAc and water. The EtOAc was separated and washed with brine. Combined aqueous layers were extracted again with EtOAc, which was washed with brine. Combined EtOAc extracts were dried (MgSO$_4$) and concentrated. The residue was purified by silica gel chromatography (100% CH$_2$Cl$_2$ followed by gradient elution to 5% MeOH in CH$_2$Cl$_2$) to afford 750 mg of product as a solid. MS (ES) (MH$^+$): 213 for $C_9H_9ClN_2O_2$; NMR ($d_6$-DMSO): 1.3 (t, 3H), 2.2 (s, 3H), 4.3 (q, 2H), 13.1 (s, 1H).

Intermediate 194 ethyl 3,5-dichloro-4-methyl-1H-pyrrole-2-carboxylate

Et$_3$N (5.5 ml, 39 mmol) was added slowly to a solution of 2.0 g (13 mmol) of ethyl 4-methyl-1H-pyrrole-2-carboxylate and 3.1 ml SO$_2$Cl$_2$ in 30 ml CH$_2$Cl$_2$ cooled in an ice water bath. The mixture was warmed to room temperature with stirring overnight. After treatment with aqueous NaHSO$_3$, the CH$_2$Cl$_2$ was removed and the aqueous residue was diluted with water and extracted twice with EtOAc. The EtOAc extracts were washed with brine, dried (MgSO$_4$) and concentrated. The solid residue was twice recrystallized from 50% aqueous EtOH to afford 1.38 g of product as a white solid. MS (ES) (M−H$^-$): 222 for $C_8H_9Cl_2NO_2$; NMR ($d_6$-DMSO): 1.3 (t, 3H), 1.9 (s, 3H), 4.25 (q, 2H), 12.8 (s, 1H).

Intermediate 195

4-chloro-3,5-dimethyl-1H-pyrrole-2-carboxylic acid

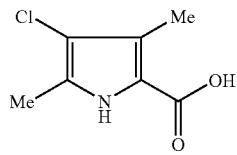 [SMILES: Cc1[nH]c(C(=O)O)c(C)c1Cl]

Prepared using the procedure described for Intermediate 1 using Intermediate 189 as the starting material.
MS (ES) MH$^+$: 174 for $C_7H_8ClNO_2$.

Intermediate 196

3-chloro-5-methyl-1H-pyrrole-2-carboxylic acid

Prepared using the procedure described for Intermediate 1 using Intermediate 186 as the starting material.

MS (ESP): 160 (MH$^+$) for $C_6H_6ClNO_2$.
$^1$H-NMR (CDCl$_3$) δ: 2.29 (s, 3H); 6.02 (s, 1H); 8.83 (br, 1H).

Intermediate 197

4-bromo-5-methyl-1H-pyrrole-2-carboxylic acid

Prepared by the procedure described for Intermediate 1 using Intermediate 187 as the starting material.
MS (ESP): 206 (MH$^+$) for $C_6H_6BrNO_2$.
NMR (CDCl$_3$) δ: 2.31 (s, 3H); 6.97 (s, 1H); 9.08 (s, br, 1H).

Intermediate 198

4-bromo-3-chloro-5-methyl-1H-pyrrole-2-carboxylic acid

Prepared using the procedure described for Intermediate 1 and Intermediate 188. MS (ESP): 240 (MH$^+$) for $C_6H_5BrClNO_2$.

Intermediate 199

4-chloro-3-[(E)-(methoxyimino)methyl]-5-methyl-1H-pyrrole-2-carboxylic acid

Synthesized as described for Intermediate 1 from Intermediate 190.
MS (ES) MH$^+$: 217 for $C_9H_9ClN_2O_3$.

Intermediate 200

4-chloro-3-cyano-5-methyl-1H-pyrrole-2-carboxylic acid

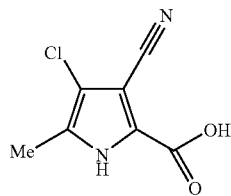 [SMILES: Cc1[nH]c(C(=O)O)c(C#N)c1Cl]

A solution of 670 mg (3.2 mmol) of ethyl 4-chloro-3-cyano-5-methyl-1H-pyrrole-2-carboxylate (Intermediate 193) and 3.2 ml (3.2 mmol) 1N NaOH in 20 ml MeOH was heated at 100° C. in a microwave reactor for 2 h. The mixture was diluted with water and extracted with EtOAc. The EtOAc was washed with 1N NaOH. The combined aqueous layers were acidified with concentrated HCl and extracted 2 times with EtOAc, each extract being washed with brine. Drying (MgSO$_4$) and removal of solvent gave 535 mg of product as a solid. MS (ES) (M–H$^-$): 183 for $C_7H_5ClN_2O_2$; NMR (d$_6$-DMSO): 2.2 (s, 3H), 12.9 (s, 1H), 13.3 (s, 1H).

Intermediate 201

3,5-dichloro-4-methyl-1H-pyrrole-2-carboxylic acid

A solution of 1.1 gm (4.95 mmol) of ethyl 3,5-dichloro-4-methyl-1H-pyrrole-2-carboxylate (Intermediate 194) and 1.7 g (9.9 mmol) of Ba(OH)$_2$ in 50 ml 1:1 EtOH—H$_2$O was heated at 85° C. for 9 h. The mixture was diluted with water, acidified with 20 ml 1N HCl and extracted 3 times with ether. The ether was washed with water, dried (MgSO$_4$) and concentrated to give 1.0 g of product as a solid. MS (ES) (M–H$^-$): 194 for $C_6H_5Cl_2NO_2$; NMR (d$_6$-DMSO): 1.9 (s, 3H), 12.7 (s, 1H), 12.8 (s, 1H).

Intermediate 202

3,4-dichloro-5-methyl-1H-pyrrole-2-carbonyl chloride

A solution of 10.4 g (54 mmol) of 3,4-Dichloro-5-methyl-1H-pyrrole-2-carboxylic acid (Intermediate 1) in 100 ml SOCl$_2$ was heated at reflux for 30 min. Solvent was removed to afford product. NMR (CDCl$_3$): 2.3 (s, 1H), 8.8 (s, 1H).

Intermediate 203

2,2,2-trichloro-1-(4,5-dichloro-1H-pyrrol-2-yl)ethanone

To a solution of 2,2,2-trichloro-1-(1H-pyrrol-2-yl)ethanone (1.00 g, 47.06 mmol) in dichloromethane (8 mL), sulfuryl chloride (1.60 mL, 0.188 mol) was added slowly at room temperature. The reaction was stirred overnight and quenched with water and extracted with dichloromethane. The extract was washed with saturated sodium bicarbonate, water and brine. Then it was dried over magnesium sulfate and concentrated to give the desired product as a white solid (0.90 g).
MS (ES) M$^-$: 279 for $C_6H_2Cl_5O$.

Intermediate 204 ethyl 2-bromo[1,3]thiazolo[4,5-b]pyridine-7-carboxylate

To a 0° C. mixture of CuBr$_2$ (229 mg, 1.02 mmol) in acetonitrile (3 mL) was slowly added t-Butyl nitrite (0.15 mL, 1.28 mmol). The reaction mixture was stirred for 15 min and then added Intermediate 205 (250 mg, 0.85 mmol). The reaction mixture was stirred for 2 h, partitioned between diethyl ether and water, and filtered through diatomaceous earth. The organic layer was washed with water and brine, dried over sodium sulfate, filtered, and concentrated under reduced pressure. Purification by flash column chromatography (silica, 1:1 hexanes/ethyl acetate) gave the desired product (38 mg, 16%).
MS (ES) MH$^+$: 174 for $C_9H_7BrN_2O_2S$.

Intermediate 205 ethyl 2-amino[1,3]thiazolo[4,5-b]pyridine-7-carboxylate

To a solution of Intermediate 206 (944 mg, 4.20 mmol) in acetic acid (12 mL) was added benzyltrimethyl ammonium tribromide (1.67 g, 4.28 mmol). The reaction mixture was stirred at room temperature for 2 h and the solid that formed was collected by filtration to provide the desired compound as the acetic acid salt (1.20 g).
MS (ES) MH$^+$: 224 for $C_9H_9N_3O_2S$.

Intermediate 206 ethyl 2-[(aminocarbonothioyl)amino]isonicotinate

A solution of Intermediate 207 (2.10 g, 6.38 mmol) in ethanol (20 mL) and potassium carbonate (882 mg, 6.38 mmol) was heated to 80° C. for 2 h. The reaction mixture was cooled to room temperature and the solid that formed was collected by filtration to give the desired compound.

MS (ES) MH$^+$: 226 for $C_9H_{11}N_3O_2S$;

NMR (DMSO-d$_6$): 1.17 (t, 3H), 4.18 (q, 2H), 7.29 (m, 1H), 7.59 (s, 1H), 8.25 (m, 1H), 8.87 (s, 1H), 10.24 (s, 1H), 10.63 (s, 1H).

Intermediate 207 ethyl 2-{[(benzoylamino)carbonothioyl]amino}isonicotinate

To a 0° C. solution of benzyl isothiocyanate (1.25 mL, 9.27 mmol) in acetone (15 mL) was slowly added ethyl 2-aminoisonicotinate (1.4 g, 8.43 mmol). The reaction mixture was stirred for 1 h and then poured onto ice. The solid that formed was collected by filtration and washed with water to give the desired product (2.10 g).

MS (ES) MH$^+$: 330 for $C_{16}H_{15}N_3O_3S$.

Intermediate 208

2-chloro-5-nitroisonicotinic acid

A solution of 13.7 g (46 mmol) of $Na_2Cr_2O_3$ in 100 ml concentrated $H_2SO_4$ was added slowly to a solution of 3.0 g (17.4 mmol) of 2-chloro-4-methyl-5-nitropyridine dissolved in 100 ml concentrated $H_2SO_4$ while cooling in ice water. Allowed to warm to room temperature and stir overnight. The solution was poured onto 600 ml ice and extracted twice with EtOAc, each extract being washed with brine. The combined organic extracts were dried (MgSO$_4$) and concentrated to afford product as a gummy oil. MS (ES) MH$^+$: 203 for $C_6H_3ClN_2O_4$.

Intermediate 209 ethyl 2-amino-4-(hydroxymethyl)-1,3-thiazole-5-carboxylate

A solution of 5.0 g (37 mmol) of 3-chlorofuran-2,4(3H,5H)-dione and 3.3 g (43 mmol) of thiourea in 50 ml EtOH was heated at reflux for 4 h. Solvent was removed and the residue was dissolved in water with 1N HCl added. The aqueous solution was basified with aqueous $Na_2CO_3$. Thick solids that formed were filtered, rinsed with water and dried in vacuo. NMR: 1.2 (t, 3H), 4.2 (q, 2H), 4.6 (s, 2H), 4.9 (s, broad, 1H), 7.8 (s, 2H).

Intermediate 210 ethyl 2-amino-4-({[tert-butyl(dimethyl)silyl]oxy}methyl)-1,3-thiazole-5-carboxylate

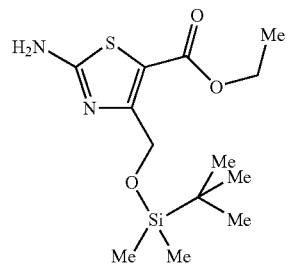 [SMILES: CCOC(=O)c1sc(N)nc1CO[Si](C)(C)C(C)(C)C]

To a solution of 2.0 g (9.8 mmol) of ethyl 2-amino-4-(hydroxymethyl)-1,3-thiazole-5-carboxylate (Intermediate 209) and 1.3 g (19.4 mmol) of imidazole in 20 ml DMF was added 1.6 g (10.6 mmol) of t-butyldimethylsilyl chloride. After stirring for 2 h, solvent was removed and the residue was taken up in water. Insoluble solids were collected, ground up, washed with water and dried in vacuo to afford 2.95 g of product. MS (ES) (MH$^+$): 317 for $C_{13}H_{24}N_2O_3SSi$; NMR (d$_6$-DMSO): 0.03 (s, 6H), 0.86 (s, 9H), 1.2 (t, 3H), 4.1 (q, 2H), 4.8 (s, 2H), 7.8 (s, 2H).

Intermediate 211 ethyl 4-({[tert-butyl(dimethyl)silyl]oxy}methyl)-2-chloro-1,3-thiazole-5-carboxylate t-Butylnitrite (1.8 ml (14 mmol) was added slowly to a mixture of 2.9 g (9.2 mmol) of ethyl 2-amino-4-({[tert-butyl(dimethyl)silyl]oxy}methyl)-1,3-thiazole-5-carboxylate (Intermediate 210) and 1.95 g (14 mmol) CuCl$_2$ in CH$_3$CN. After stirring at room temperature for 2 h, solvent was removed and the residue was taken up in EtOAc, which was washed 2 times with 1NHCl and once with brine. Drying (MgSO$_4$) and removal of solvent gave 2.95 g of product as an oil. NMR (CDCl$_3$): 0.1 (s, 6H), 0.9 (s, 9H), 1.35 (t, 3H), 4.3 (q, 2H), 5.0 (s, 2H).

Intermediate 212

The following Intermediate was synthesized by an analogous method to Intermediate 211 from the starting materials (SM) given in the table below

| Int | Compound | Data | SM |
|---|---|---|---|
| 212 | methyl 4-acetyl-2-chloro-1,3-thiazole-5-carboxylate | NMR (CDCl$_3$): 2.6 (s, 3H), 3.9 (s, 3H) | Intermediate 222 |

Intermediate 214 methyl 2-chloro-4-(1-hydroxy-1-methylethyl)-1,3-thiazole-5-carboxylate

A solution of 5.6 ml (11.2 mmol) 2N AlMe$_3$ in toluene was added to a dry ice-acetone bath of 1.14 g (5.2 mol) of methyl 4-acetyl-2-chloro-1,3-thiazole-5-carboxylate (Intermediate 212) in 20 ml dry CH$_2$Cl$_2$. The mixture was allowed to warm to room temperature slowly before being quenched with MeOH. After stirring at room temperature overnight, the mixture was diluted with 1N HCl and stirred 15 min before being diluted with water and extracted twice with EtOAc. The EtOAc was washed with brine, dried (MgSO$_4$) and concentrated to give an oil that was purified by chromatography (50% hexanes in CH$_2$Cl$_2$ with gradient elution to 100% CH$_2$Cl$_2$) affording 720 mg of product as an oil. NMR (CDCl$_3$): 1.5 (s, 6H), 3.8 (s, 3H), 5.7 (s, broad, 1H).

Intermediate 215 ethyl 2-chloro-4-(hydroxymethyl)-1,3-thiazole-5-carboxylate

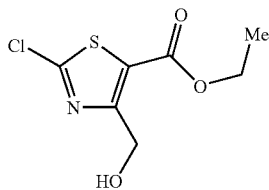 [SMILES: CCOC(=O)c1sc(Cl)nc1CO]

A solution of 17.7 g (53 mmol) of ethyl 4-({[tert-butyl(dimethyl)silyl]oxy}methyl)-2-chloro-1,3-thiazole-5-carboxylate (Intermediate 211) and 53 ml (53 mmol) of 1N HCl in dioxane was stirred at room temperature for 1 h. The mixture was extracted 3 times with EtOAc, which was dried (MgSO$_4$) and concentrated to give 11.3 g of an orange oil. Purification by silica gel chromatography affords a solid. NMR (CDCl$_3$): 1.2 (t, 3H), 3.1 (s, broad, 1H), 4.2 (q, 2H), 4.8 (s, 2H).

Intermediate 216

4-{[4-({[tert-butyl(dimethyl)silyl]oxy}methyl)-2-chloro-1,3-thiazol-5-yl]carbonyl}morpholine A solution of 2N Me$_3$Al in hexanes (0.91 ml, 1.82 mmol) was added slowly to a solution of 0.16 ml (1.8 mmol) of morpholine in 4 ml CH$_2$Cl$_2$. After stirring for 15 min, a solution of 0.5 g (1.5 mmol) of ethyl 4-({[tert-butyl(dimethyl)silyl]oxy}methyl)-2-chloro-1,3-thiazole-5-carboxylate (Intermediate 218) in 4 ml CH$_2$Cl$_2$ was added. The solution was heated at 80° C. in a microwave reactor for 1 hour before pouring into dilute aqueous HCl. The mixture was extracted 3 times with CH$_2$Cl$_2$, which was washed with brine, dried (MgSO$_4$) and concentrated. The residue was purified by silica gel chromatography (100% CH$_2$Cl$_2$ followed by gradient elution to 30% EtOAc in CH$_2$Cl$_2$ to give 315 mg of product. MS (ES) (MH$^+$): 377 for C$_{15}$H$_{25}$ClN$_2$O$_3$SSi; NMR (d$_6$-DMSO): 0.1 (s, 6H), 0.9 (s, 9H), 3.6 (m, 4H), 3.7 (m, 4H), 4.1 (q, 2H), 4.75 (s, 2H).

Intermediate 217

The following Intermediate was synthesized by an analogous method to Intermediate 216 from the starting materials (SM) given in the table below.

| Int | Compound | Data | SM |
|---|---|---|---|
| 217 | 4-({[tert-butyl(dimethyl)silyl]oxy}methyl)-2-chloro-N-(1-methyl-1-phenylethyl)-1,3-thiazole-5-carboxamide | NMR (d$_6$-DMSO): 0.04 (s, 6H), 0.8 (s, 9H), 1.6 (s, 6H), 4.9 (s, 2H), 7.2 (7, 1H), 7.3 (t, 2H), 7.4 (d, 2H), 8.6 (s, 1H). | Intermediate 211 and cumylamine |

Intermediate 218

2-chloro-5-(morpholin-4-ylcarbonyl)-1,3-thiazole-4-carboxylic acid

A solution of 173 mg (1.7 mmol) CrO$_3$ in 1 ml of 4:1 water/H$_2$SO$_4$ was added to as solution of 310 mg (0.82 mmol) of 4-{[4-({[tert-butyl(dimethyl)silyl]oxy}methyl)-2-chloro-1,3-thiazol-5-yl]carbonyl}morpholine (Intermediate 216) in 3 ml acetone cooled in an ice water bath. The mixture was stirred with warming room temperature over 90 min. A few drops of isopropanol were added, and the mixture was diluted with water and extracted 2 times with EtOAc. The EtOAc extracts were washed with brine, dried (MgSO$_4$) and concentrated to give 190 mg of a white solid. MS (ES) (MH$^+$): 277 for C$_9$H$_9$ClN$_2$O$_4$S; NMR (d$_6$-DMSO): 3.3 (m, 4H), 3.6 (m, 4H), 13.7 (s, 1H).

Intermediate 219

The following Intermediate was synthesized by an analogous method to Intermediate 218 from the starting materials (SM) given in the table below.

| Int | Compound | Data | SM |
|---|---|---|---|
| 219 | 2-chloro-5-{[(1-methyl-1-phenylethyl)amino]carbonyl}-1,3-thiazole-4-carboxylic acid | MS (ES) (M − H$^-$): 323 for C$_{14}$H$_{13}$ClN$_2$O$_2$S | Intermediate 217 |

Intermediate 220 ethyl 5-(aminocarbonyl)-2-chloro-1,3-thiazole-4-carboxylate

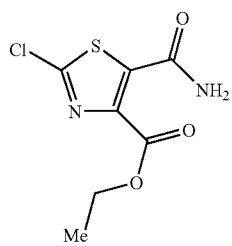 [SMILES: CCOC(=O)c1nc(Cl)sc1C(N)=O]

A solution of 210 mg of ethyl 2-chloro-5-{[(1-methyl-1-phenylethyl)amino]carbonyl}-1,3-thiazole-4-carboxylate (Intermediate 233) in 5 ml TFA was stirred at room temperature overnight. Solvent was removed and the residue was dissolved in 5 ml MeOH. Solvent was again removed and the residue was triturated with ether to give 57 mg of a white solid. NMR ($d_6$-DMSO): 1.3 (t, 3H), 4.3 (q, 2H), 8.2 (s, 1H), 8.8 (s, 1H).

Intermediate 221 methyl 2-chloro-4,4-dimethoxy-3-oxopentanoate $SO_2Cl_2$ (2.2 ml, 27 mmol) was added slowly to a solution of 5.0 g (26 mmol) of methyl 4,4-dimethoxy-3-oxopentanoate in 30 ml $CH_2Cl_2$ cooled in an ice water bath. The solution was warmed to room temperature and stirred for 1 h. Solvent was removed and the residue was taken up in EtOAc, which was washed with water and brine. Drying ($MgSO_4$) and removal of solvent gave 6.1 g of an oil. NMR: ($CDCl_3$): 1.5 (s, 3H), 3.25 (2s, 6H), 4.8 (s, 3H), 5.3 (s, 1H).

Intermediate 222 methyl 4-acetyl-2-amino-1,3-thiazole-5-carboxylate

A solution of 4.37 g (19 mmol) methyl 2-chloro-4,4-dimethoxy-3-oxopentanoate (Intermediate 221) and 1.8 g (24 mmol) thiourea in 50 ml EtOH was heated at reflux for 3 h. Solvent was removed and the residue was dissolved in 1:1 acetone-5N HCl and the solution was heated at reflux for 4 h. Acetone was removed and the aqueous residue was neutralized with 50% NaOH and then basified with aqueous $Na_2CO_3$. Precipitated solids were filtered, washed with water and dried in vacuo. NMR ($d_6$-DMSO): 2.4 (s, 3H), 3.7 (s, 3H), 8.0 (s, 2H).

Intermediate 223 isopropyl 4-chloropyridine-2-carboxylate 1-oxide

A solution of 2.55 g (14 mmol) of isopropyl 4-chloropyridine-2-carboxylate (Intermediate 232) and 1.4 g (26 mmol) of m-CPBA in 30 ml $CH_2Cl_2$ was stirred at room temperature for 2 d. The mixture was quenched with aqueous $NaHSO_3$ and $CH_2Cl_2$ was removed. The aqueous residue was basified with aqueous $Na_2CO_3$, saturated with NaCl and extracted repeatedly with EtOAc. The EtOAc was dried ($MgSO_4$) and concentrated. The residue was taken up in ether and insoluble material was filtered off. The filtrate was concentrated and the residue was chromatographed on silica gel (100% $CH_2Cl_2$ with gradient elution to 100% EtOAc) to afford 2.1 g of product as an oil. NMR ($d_6$-DMSO): 1.3 (d, 6H), 5.3 (septet, 1H), 7.25 (m, 1H), 7.5 (d, 1H), 8.1 (d, 1H).

Intermediate 224 isopropyl 4-chloro-6-cyanopyridine-2-carboxylate

A solution of 200 mg (0.86 mmol) of isopropyl 4-chloropyridine-2-carboxylate 1-oxide (Intermediate 223), 0.14 ml (1 mmol) $Et_3N$ and 0.36 ml (2.7 mmol) of trimethylsilylcyanide in 3 ml $CH_3CN$ was heated at 90° C. overnight. The solution was diluted with EtOAc and washed with water and brine. Drying ($MgSO_4$) and removal of solvent gave an oil that was purified by chromatography on silica gel (100% $CH_2Cl_2$ followed by gradient elution to 10% EtOAc in $CH_2Cl_2$) to afford 130 mg of product as a white solid. MS (ES) ($MH^+$): 224 for $C_{19}H_9ClN_2O_2$; NMR ($d_6$-DMSO): 1.35 (d, 6H), 5.2 (septet, 1H), 8.4 (s, 1H), 8.6 (s, 1H).

Intermediate 225 ethyl 2-chloro-5-formylisonicotinate

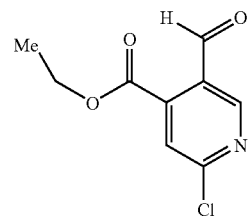 [SMILES: CCOC(=O)c1cc(Cl)ncc1C=O]

A solution of 51 ml (128 mmol) of 2.5 N n-butyllithium in hexanes was added slowly to a THF solution of 16 ml (95 mmol) of tetramethylpiperidine cooled in a dry ice-acetone bath. The solution was warmed to −30° C. and cooled to −60° C. before 5.0 g (32 mmol) of 6-chloronicotinic acid was added portion wise. The mixture was warmed to −25° C. and stirred for 30 min. It was then cooled to −70° C. and 10 ml (129 mmol) DMF was added quickly. After quenching with 1N HCl, the solution was warmed to room temperature. The pH was brought to about 4 with additional 1N HCl and the solution was continuously extracted with EtOAc overnight. The EtOAc was dried ($MgSO_4$) and concentrated. The residue was dissolved in 100 ml EtOH and 2 ml concentrated $H_2SO_4$ was added. The solution was heated at reflux for 24 h. The mixture was brought to about pH=4 with 50% NaOH and was extracted twice with ether. The ether was dried ($MgSO_4$) and concentrated to gave an oil that was chromatographed on silica gel (50% hexanes in $CH_2Cl_2$ with gradient elution to 100% $CH_2Cl_2$) to afford 1 g of product as an oil that slowly solidified. NMR ($CDCl_3$): 1.4 (t, 3H), 4.5 (q, 2H), 7.7 (s, 1H), 9.1 (s, 1H), 10.7 (s, 1H).

Intermediate 226 ethyl 2-chloro-5-nitroisonicotinate

A mixture of 2-chloro-5-nitroisonicotinic acid (Intermediate 208) and 16 ml triethylorthoacetate in 100 ml toluene was heated at reflux for 2 h. The mixture as stirred with 1N HCl for 30 min before being partitioned between EtOAc and water. The EtOAc was separated, washed with water and brine, dried ($MgSO_4$) and concentrated. Chromatographed on silica gel (100% hexanes with gradient elution to 100% $CH_2Cl_2$ to give product as an oil. MS (ES) ($MH^+$): 231 for $C_8H_7ClN_2O_4$; NMR ($d_6$-DMSO): 1.3 (t, 3H), 4.4 (m, 2H), 8.1 (s, 1H), 9.2 (s, 1H).

Intermediates 227-233

The following compounds were prepared in a manner analogous to Intermediate 226 from the starting material (SM) indicated.

| Int | Compound | Data | SM |
|---|---|---|---|
| 227 | isopropyl 2-chloro-6-methylisonicotinate | MS (ES) (MH+): 214 for $C_{10}H_{12}ClNO_2$; NMR ($d_6$-DMSO): 1.3 (d, 6H), 2.55 (s, 3H), 5.2 (septet, 1H), 7.65 (s, 1H), 7.7 (s, 1H) | 2-chloro-6-methylisonicotinate and trisopropylorthoformate |
| 228 | isopropyl 4-chloropyridine-2-carboxylate | NMR ($CDCl_3$): 1.35 (d, 6H), 5.3 (septet, 1H), 7.4 (dd, 1H), 8.05 (d, 1H), 8.6 (d, 1H) | 4-chloropyridine-2-carboxylate and trisopropylformate |
| 229 | isopropyl 4,5-dichloropyridine-2-carboxylate | NMR ($CDCl_3$): 1.35 (d, 6H), 5.3 (septet, 1H), 8.1 (s, 1H), 8.7 (s, 1H) | 4,5-dichloropyridine-2-carboxylate (Graf, R. J. fuer Prakt. Chem. (Leipzig) (1932), 133 36-50) and trisopropylorthoformate |
| 230 | isopropyl 2-fluoroisonicotinate | NMR ($CDCl_3$): 1.4 (d, 6H), 5.3 (septet, 3H), 7.5 (m, 1H), 7.7 (m, 1H), 8.35 (d, 1H) | 2-fluoroisonicotinic acid and trisopropylorthoformate |
| 231 | ethyl 2-chloro-5-(morpholin-4-ylcarbonyl)-1,3-thiazole-4-carboxylate | NMR: 1.3 (t, 3H), 3.3 (m, 2H), 3.5 (m, 2H), 3.6 (m, 2H), 3.65 (m 2H), 4.3 (q, 2H) | Intermediate 218 and triethylorthoacetate |
| 232 | isopropyl 4-chloropyridine-2-carboxylate | NMR ($CDCl_3$): 1.35 (d, 6H), 5.3 (septet, 1H), 7.4 (dd, 1H), 8.05 (d, 1H), 8.6 (d, 1H) | 4-chloropyridine-2-carboxylic acid and trisopropylorthoformate |
| 233 | ethyl 2-chloro-5-{[(1-methyl-1-phenylethyl)amino]carbonyl}-1,3-thiazole-4-carboxylate | MS (ES) (MH+−): 353 for $C_{16}H_{17}ClN_2O_2S$ | Intermediate 219 and triethylorthoacetate |

Intermediate 234

1,3-thiazol-2-ylmethanol

To a stirred solution of commercially available 1,3-thiazole-2-carbaldehyde (5.36 g, 47 mmol) in dry methanol (100 mL), at 0° C. and under an atmosphere of $N_2$, was added sodium borohydride (2.15 g, 57 mmol) as a solid over approximately 20 minutes. The reaction was stirred for an hour at ambient temperature, under an atmosphere of $N_2$. Complete conversion was suggested by TLC (50% ethyl acetate in hexanes; Rf~0.23). The reaction was concentrated under vacuum. To the residue was added 15 mL of an aqueous solution of ammonium chloride, and 15 mL of an aqueous solution of sodium chloride; from this mixture was extracted the crude product with ethyl acetate (4×50 mL). The organic layers were combined, dried over magnesium sulfate, and concentrated. The crude material was used without further purification.

MS (ES) MH+: 116 for $C_4H_5NOS$. $^1H$ NMR (DMSO): 4.72 (d, 2H), 6.03 (t, 1H), 7.61 (d, 1H), 7.71 (d, 1H).

Intermediate 235

2-(bromomethyl)-1,3-thiazole

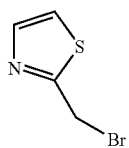

This compound was synthesized from Intermediate 234 above, using the procedure described in Tetrahedron 61 (2005), p. 137. The crude material was purified by column chromatography (silica gel, 15% ethyl acetate in hexanes). A pale orange liquid (57% yield) was obtained; this material decomposed rapidly, and was used immediately in the next step.

MS (ES) MH$^+$: 179 for C$_4$H$_4$BrNS. $^1$H NMR (CDCl$_3$): 4.75 (s, 2H), 7.37 (d, 1H), 7.74 (d, 1H).

Intermediate 236

Ethyl 2-chloro-4-methyl-1,3-thiazole-5-carboxylate

Synthesized according to the procedure described for Intermediate 17. MS (ES) MH$^+$: 206, 208 for C$_7$H$_8$ClNO$_2$S; $^1$H-NMR (300 MHz; DMSO-d$_6$) δ: 1.28 (t, 3H); 2.60 (s, 3H); 4.28 (q, 2H).

Intermediate 237

1-tert-butyl 3-methyl 4-hydroxy-5,6-dihydropyridine-1,3(2H)-dicarboxylate

Methyl 4-oxopiperidine-3-carboxylate hydrochloride (13.0 g) was suspended in anhydrous DCM (100 mL) under an argon atmosphere. DIEA (29.2 mL) was added slowly via syringe, producing a slightly cloudy solution. The reaction was cooled to 0° C., and di-tert-butyl dicarboxylate (16.1 g) was added, resulting in an exothermic reaction. The reaction mixture was left stirring overnight, slowly warming to room temperature. The reaction mixture was then concentrated in vacuo and partitioned between EtOAc (500 mL) and saturated aqueous NH$_4$Cl (350 mL). The EtOAc layer was washed with brine (125 mL), dried over anhydrous MgSO$_4$ and concentrated in vacuo, producing a yellow oil. The product was purified by silica gel chromatography (1-25% EtOAc in hexanes), producing the title compound as a clear, colourless oil (14.7 g, 85.1%). MS (ES)[(M−H)$^−$]: 256 for C$_{12}$H$_{19}$NO$_5$; NMR (CDCl$_3$): 1.46 (s, 9H), 2.36 (t, 2H), 3.55 (t, 2H), 3.76 (s, 3H) 4.04 (s, 2H), 11.97 (s, 1H).

Intermediate 238

Ethyl 4-azido-3-hydroxypiperidine-1-carboxylate

Ethyl 4-bromo-3-hydroxypiperidine-1-carboxylate (Preparation: Izamanishi, T. et al; 1982, Chem. Pharm. Bull., 30: 3617-3623) (5.1 g) was dissolved in anhydrous DMF (20 mL) under an argon atmosphere, followed by the addition of 18-crown-6 (0.27 g) and sodium azide (2.89 g). The reaction was heated at 90° C. for twenty-three hours, then stirred overnight, slowly cooling to room temperature. The reaction was then added to deionised water (150 mL) to quench it, saturated with solid sodium chloride, and extracted with EtOAc (2×200 mL). The combined EtOAc layers were washed with brine (100 mL), dried over anhydrous MgSO$_4$ and concentrated in vacuo, yielding the title compound (4.3 g, 100%). MS (GC-EI)[(M-N$_2$)$^+$]: 186 for C$_8$H$_{14}$BrN$_4$O$_3$.

Intermediate 239

Ethyl 4-azido-3-(2-tert-butoxy-2-oxoethoxy)piperidine-1-carboxylate

Ethyl 4-azido-3-hydroxypiperidine-1-carboxylate (Intermediate 238, 1.71 g) was dissolved in anhydrous THF (15 mL) and cooled to 0° C. Sodium hydride (60% in mineral oil) (0.42 g) was added as a shot, stirred for twenty minutes at 0° C., followed by the slow addition of tert-butyl bromo acetate (0.86 mL) via syringe, and stirred for an additional two hours at 0° C. The reaction was partitioned between EtOAc (250 mL) and saturated aqueous NaHCO$_3$ (200 mL), and the aqueous layer was washed with EtOAc (200 mL). The combined EtOAc layers were washed with brine (50 mL), dried over anhydrous MgSO$_4$ and concentrated in vacuo, yielding the title compound as a crude product (1.78 g, 103%). MS (GC-EI)[(M-N$_2$)$^+$]: 300 for C$_{14}$H$_{24}$N$_4$O$_5$.

Intermediate 240

Ethyl 4-amino-3-(2-tert-butoxy-2-oxoethoxy)piperidine-1-carboxylate

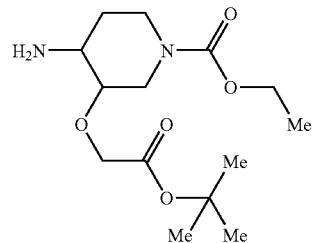 [SMILES: CCOC(=O)N1CCC(N)C(OCC(=O)OC(C)(C)C)C1]

Ethyl 4-azido-3-(2-tert-butoxy-2-oxoethoxy)piperidine-1-carboxylate (Intermediate 239, 1.75 g) was dissolved in THF (60 mL), followed by the addition of deionised water (5 mL) and PS-triphenylphosphine resin (10.6 g), and stirred at room temperature over the week-end. The reaction mixture was filtered, and the resin was rinsed repeatedly with MeOH and a 1:5 MeOH:DCM mixture, and the filtrate was concentrated in vacuo, yielding the title compound (1.20 g, 75%). MS (GC-EI)[(M)$^+$]: 302 for C$_{14}$H$_{26}$N$_2$O$_5$.

Intermediate 241

Ethyl 4-bromo-3-{[tert-butyl(dimethyl)silyl]oxy}piperidine-1-carboxylate

Ethyl 4-bromo-3-hydroxypiperidine-1-carboxylate (Preparation: Izamanishi, T. et al; 1982, Chem. Pharm. Bull., 30: 3617-3623) (10.17 g) was dissolved in anhydrous DCM (100 mL) under an argon atmosphere and cooled to 0° C. tert-Butyldimethylsilyl trifluoromethylsulfonate (10.2 mL) was added dropwise via syringe, followed by 2,6-lutidine (4.7 mL), also added dropwise via syringe. The reaction was stirred overnight, slowly warming to room temperature, then diluted with DCM (200 mL) and washed with saturated aqueous NaHCO$_3$ (150 mL), saturated aqueous NH$_4$Cl ((150 mL), brine (100 mL), dried over anhydrous MgSO$_4$ and concentrated in vacuo, yielding the title compound as a crude product (15.1 g, 102%). MS (GC-EI)[(M-C$_4$H$_7$)$^+$]: 310, 312 for C$_{14}$H$_{28}$BrNO$_3$Si; NMR (CDCl$_3$): 0.10 (s, 3H), 0.12 (s, 3H), 0.88 (s, 9H), 1.24 (t, 3H), 1.87 (m, 1H), 2.34 (m, 1H), 2.84-3.40 (m, 2H), 3.69 (m, 2H), 3.93 (m, 2H), 4.13 (q, 2H).

Intermediate 242

Ethyl 4-azido-3-{[tert-butyl(dimethyl)silyl]oxy}piperidine-1-carboxylate

The title compound was prepared in a manner analogous to (Intermediate 238) starting with ethyl 4-bromo-3-{[tert-butyl(dimethyl)silyl]oxy}piperidine-1-carboxylate (Intermediate 241). MS (GC-EI)[(M-N$_2$)$^+$]: 300 for C$_{14}$H$_{28}$N$_4$O$_3$Si.

Intermediate 243

Ethyl 4-amino-3-{[tert-butyl(dimethyl)silyl]oxy}piperidine-1-carboxylate

The title compound was prepared in a manner analogous to (Intermediate 240) starting with ethyl 4-azido-3-{[tert-butyl(dimethyl)silyl]oxy}piperidine-1-carboxylate (Intermediate 242. MS (GC-EI)[(M)$^+$]: 302 for $C_{14}H_{30}N_2O_3Si$.

Intermediate 244

3,4-dichloro-N-(3-hydroxypiperidin-4-yl)-5-methyl-1H-pyrrole-2-carboxamide

Ethyl 3-{[tert-butyl(dimethyl)silyl]oxy}-4-{[(3,4-dichloro-5-methyl-1H-pyrrol-2-yl)carbonyl]amino}piperidine-1-carboxylate (Intermediate 114, 0.805 g) was dissolved in a mixture of MeOH (10 mL) and 1,4-dioxane (15 mL), to which was added 1N NaOH (10 mL) and heated to reflux for twenty-four hours. An additional 5 mL of 1N NaOH was added, with 5 mL of 1,4-dioxane, and the reaction was heated for an additional forty-two hours, then cooled to 0° C. and acidified to ~pH 9 with 2N HCl (6 mL). The cold mixture was filtered and washed with deionised water, yielding the title compound as a crude product. MS (ES) MH$^+$: 292, 294 for $C_{11}H_{15}Cl_2N_3O_2$.

Intermediate 245

The following Intermediate was prepared by the procedure described in Intermediate 16 from the starting materials (SM) indicated.

| Int | Compound | Data | SM |
|---|---|---|---|
| 245 | ethyl 4-{[(1-methyl-1-phenylethyl)amino]carbonyl}-2-(methylsulfonyl)-1,3-thiazole-5-carboxylate 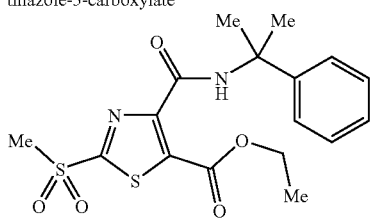 | MS (ES) MH$^+$: 397 for $C_{17}H_{20}N_2O_5S_2$ NMR: 1.24-1.32 (m, 3H) 1.66 (s, 6H) 3.57 (s, 3H) 4.36 (q, 2H) 7.22 (t, 1H) 7.34 (t, 2H) 7.41-7.50 (m, 2H) 8.91 (s, 1H) | Intermediate 246 |

Intermediate 246 ethyl 4-{[(1-methyl-1-phenylethyl)amino]carbonyl}-2-(methylthio)-1,3-thiazole-5-carboxylate Diisopropylamine (5.3 ml) was dissolve in anhydrous THF (100 ml) was cooled to −78° C. and to this was added n-butyl lithium (15 ml) slowly. The solution was slowly warmed to 0° C. and then cooled back to −78° C. A solution of N-(1-methyl-1-phenylethyl)-2-(methylthio)-1,3-thiazole-4-carboxamide (Intermediate 13; 3.7 g) in anhydrous THF was added slowly maintaining the temperature below −70° C. After stirring for 30 min, a solution of ethyl cyano formate (2.5 ml) in anhydrous THF was added in one portion and the reaction was stirred at −78° C. for 30 min followed by slow warming to room temperature. The reaction mixture was diluted with water and extracted with ethyl acetate (×3), dried with $MgSO_4$ and concentrated to a black oil (0.84 g) NMR: 1.22-1.29 (m, 3 H) 1.63 (s, 6 H) 2.76 (s, 3 H) 4.28 (q, 2 H) 7.20 (t, 1 H) 7.32 (t, 2 H) 7.46 (d, 2 H) 8.75 (s, 1 H).

Intermediate 247 diethyl 2-chloro-1,3-thiazole-4,5-dicarboxylate

To a solution of tert-butyl nitrite (3.4 mL, 28 mmol) and copper (II) chloride (3.7 g, 28 mmol) in acetonitrile (50 mL) was added diethyl 2-amino-1,3-thiazole-4,5-dicarboxylate (4.6 g, 19 mmol, Intermediate 248) all in one portion. Gas evolution was observed. After 45 min of stirring at room temperature LCMS indicated complete product formation. After concentrating to remove acetonitrile the residue was partitioned with chloroform and 1N HCl (Fisher), washed with chloroform, dried with $MgSO_4$ and concentrated to an orange oil. Purification by flash column yielded a pale yellow oil (4.2 g, 85%). MS (ES): 264; NMR: 1.25-1.29 (t, 3 H) 1.29-1.33 (t, 3 H) 4.28-4.33 (q, 2 H) 4.33-4.39 (q, 2 H).

Intermediate 248 diethyl 2-amino-1,3-thiazole-4,5-dicarboxylate

A solution of thiourea (1.7 g, 22 mmol) and diethyl 2-chloro-3-oxosuccinate (5.0 g, 22 mmol) in absolute ethanol (50 mL) was heated at reflux for one hour. After cooling to room temperature the solvent was removed leaving a white solid. The solid was dissolved in water (100 mL) and the resulting precipitate was filtered and dried (4.6 g, 87%). MS (ES): 245; NMR: 1.21 (t, 3 H) 1.26 (t, 3 H) 4.16 (q, 2 H) 4.26 (q, 2 H) 8.04 (s, 2 H).

Intermediate 249 isopropyl 4-chloro-6-(morpholin-4-ylcarbonyl)pyridine-2-carboxylate n-butyllithium (1.92 mL, 2.5M in hexanes) was added dropwise to a −78° C. solution of morpholine (0.42 mL, 4.8 mmol) in anhydrous THF followed by slow warming to room temperature. The solution was transferred to an addition funnel via cannulation and then added dropwise to a solution of dimethyl 4-chloropyridine-2,6-dicarboxylate (1.0 g, 4.4 mmol, Intermediate 251) in anhydrous THF. A slight precipitate was observed during the addition. After stirring two hrs at room temperature an additional 0.5 equivalence of the morpholino-lithium reagent was added to the reaction and after an additional two hrs of stirring another 0.5 equivalence was added followed by stirring one hour to reach completion. The solvent was removed under reduced pressure and the residue was suspended in methylene chloride and the product was extracted with a sat. sodium bicarbonate solution (×3). The sodium bicarbonate portion was acidified with conc. HCl to pH 3 and then extracted with EtOAc (×10), followed by drying with MgSO$_4$ and concentrating to a solid (0.8 g, 70%). MS (ES) MH$^+$: 271 for C$_{11}$H$_{11}$ClN$_2$O$_4$. The solid was suspended in anhydrous toluene (75 mL) and to this was added triisopropylorthoformate (1.97 mL, 8.9 mmol) slowly followed by heating to reflux for 12 hours. After cooling to room temperature the solvent was removed under reduced pressure and the residue was suspended in 1N HCl. Basification to pH8 with saturated sodium bicarbonate followed by extraction with EtOAc (×3), drying with MgSO$_4$ and removal of solvent yielded a tan solid. Purification by silica gel flash column (gradient elution to 3:1 EtOAc:CH$_2$Cl$_2$) yielded a white solid (0.23 g) MS (ES) MH$^+$: 313 for C$_{14}$H$_{17}$ClN$_2$O$_4$; NMR: 1.33 (s, 3 H) 1.35 (s, 3 H) 3.41 (s, 2 H) 3.44 (d, 2 H) 3.58 (d, 2 H) 3.68 (s, 4 H) 5.17 (dt, 1 H) 8.01 (d, 1H) 8.13 (d, 1 H).

Intermediate 250

The following Intermediate was prepared by the procedure described in Intermediate 249 from the starting materials (SM) indicated.

| Int | Compound | Data | SM |
| --- | --- | --- | --- |
| 250 | isopropyl 4-chloro-6-[(dimethylamino)carbonyl]pyridine-2-carboxylate | MS (ES) MH$^+$: 271 for C$_{12}$H$_{15}$ClN$_2$O$_3$ NMR: 1.35 (d, 6H) 2.93 (s, 3H) 3.03 (s, 3H) 5.18 (dt, 1H) 7.96 (d, 1H) 8.11 (d, 1H) | Intermediate 251 and dimethylamine |

Intermediate 251 dimethyl 4-chloropyridine-2,6-dicarboxylate

Phosphorus pentachloride (45.5 g, 218 mmol) was weighed into a closed flask and suspended in chloroform. 4-hydroxypyridine-2,6-dicarboxylic acid (10.0 g, 55 mmol) was added and after heating at a gentle reflux for 3 days the reaction was complete (60% conversion). After cooling to 0° C. anhydrous methanol (150 mL) was added dropwise. Once the exotherm subsided the solvent was removed under reduced pressure and the residue was partitioned with EtOAc and water and the insoluble material was filtered, washed with EtOAc and dried (6.7 g). The EtOAc layer was washed with water, dried with MgSO$_4$ and concentrated. Recrystallization with methanol yielded additional pure product (0.64 g). MS (ES) MH$^+$: 230 for C$_9$H$_8$ClNO$_4$; NMR: 3.94 (s, 3 H) 8.32 (s, 1 H).

Intermediate 252

2-chloro-5-(ethoxycarbonyl)-1,3-thiazole-4-carboxylic acid

To a solution of ethyl 2-chloro-4-(hydroxymethyl)-1,3-thiazole-5-carboxylate (2.5 g, 11 mmol, Intermediate 215) in acetone at 0° C. was slowly added a solution of chromium trioxide (2.26 g, 22 mmol) in 20% conc. Sulfuric acid in water (20 mL). After stirring at room temperature for 2 hrs, isopropanol (1 mL) was added to quench unreacted chromium trioxide. The reaction was diluted with water and the acetone was removed. Partitioning with methylene chloride (×3), drying with MgSO4 and concentrating yielded a white solid (2.3 g, 90%). MS (ES) MH$^+$: 236 for C$_7$H$_6$ClNO$_4$S; NMR: 1.26 (t, 3 H) 4.31 (q, 2 H) 13.99-14.15 (m, 1 H).

Intermediate 253

3,4-Dichloro-5-chloromethyl-1H-pyrrole-2-carboxylic acid ethyl ester

To a 4-neck 22 L round bottom flask equipped with an overhead stirrer, liquid addition funnel, nitrogen inlet and an internal temperature probe was charged (Intermediate 254, 2000 g, 13.6 mol) and carbon tetrachloride (12 L). The reaction mixture was cooled to −5° C. and sulfuryl chloride was added at a rate that the temperature did not exceed 0° C. (1 h). Resulting reaction mixture became very thick (as precipitate becomes heavy, significant gas evolution was observed) and was allowed to stir at 0° C. for a total of 4 h after addition. Precipitate was filtered and solid azeotroped with toluene to remove excess sulfuryl chloride. The solid was and dried in convection oven at 50° C. yielding 3 (2077 g, 62%) as a dark purple solid.

Intermediate 254

5-Methyl-1H-pyrrole-2-carboxylic acid ethyl ester

To a 4-neck 22 L round bottom flask equipped with an overhead stirrer, liquid addition funnel, nitrogen inlet and an internal temperature probe was charged ethyl 3-oxobutanoate (1952 g, 15.0 mol) and glacial acetic acid (5 L). The resulting solution was cooled to 0° C. with an ice water bath and an aqueous solution of sodium nitrite (1242 g, 18.0 mol, 1.2 eq, in 1875 ml of water) was added slowly (4.5 h) not allowing the internal temperature above 10° C. The homogeneous red solution was allowed to warm to ambient and stirred for 48 h. The solution color changed from light red to yellow. Reaction vessel was then placed in a heating mantle, fitted with a reflux condenser and acetylacetaldehyde dimethyl acetal (1982 g, 15.0 mol, 1 eq) was added in one portion (the top of the reflux condenser was left open to air to allow for the rapid gas evolution during the addition of the zinc). Zinc (dust, 2156 g, 33 mol, 2.2 eq) was added in portions (at a rate such that gas evolution was controlled) over 4 h. The addition of zinc brought the reaction to reflux and after addition the dark red solution was heated at reflux for an additional 1.5 h. Contents of the reaction were poured hot into a 50 L container with 20 kg of ice and allowed to stir for 16 h. Resulting suspension was filtered, dried in convection oven and recrystallized with hot heptane yielding a light yellow solid (312 g, 13.6% yield).

Intermediate 255 ethyl 3-hydroxy-4,4-dimethoxypiperidine-1-carboxylate

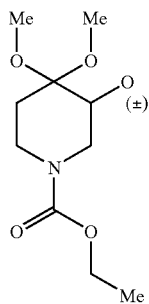

To a stirred solution of potassium hydroxide (42 g, 752 mmol) in dry methanol (100 mL), at 0° C. and under an atmosphere of $N_2$, was added a solution of ethyl 4-oxopiperidine-1-carboxylate (26.4 mL, 29.96 g, 175 mmol) in dry methanol (75 mL) via syringe. The resulting solution was stirred for an additional 30 minutes under an atmosphere of $N_2$ at 0° C. To it, in small portions over approximately 90 minutes, was added iodobenzene diacetate (84.6 g, 262 mmol). Temperature was kept near 0° C. throughout this time. The reaction was stirred overnight under an atmosphere of $N_2$, gradually reaching room temperature. Complete conversion was suggested by TLC (50% ethyl acetate in hexanes; Hanessian's stain; Rf~0.25) in the morning. The reaction was concentrated under vacuum. To the residue was added approximately 50 mL water; from this mixture was extracted the crude product with ethyl acetate (3×200 mL). The organic layers were combined, dried over magnesium sulfate, and concentrated. The crude product was purified using column chromatography (silica gel; 10-65% ethyl acetate in hexanes), yielding 26.74 g (66%) of a pale yellow oil.

MS (ESI) M: 233 for $C_{10}H_{19}NO_5$. $^1$H NMR (CDCl$_3$): 1.22 (t, 3H), 1.69-1.86 (m, 2H), 2.20 (m, 2H), 2.86 (t, 1H), 3.22 (s, 3H), 3.23 (s, 3H), 3.74 (m, 1H), 3.95 (m, 2H), 4.11 (q, 2H).

Intermediates 256-257

The following Intermediates were synthesized by an analogous method to Intermediate 28 or Intermediate 59 from the starting materials (SM) given in the table below.

| Int | Compound | Data | SM |
|---|---|---|---|
| 256 | Cis(±)-ethyl 4-amino-3-(prop-2-yn-1-yloxy)piperidine-1-carboxylate | MS (ESP): 227 (M + H) for $C_{11}H_{18}N_2O_3$ | Intermediate 146 |
| 257 | Cis(±)-Ethyl (4-amino-3-ethoxypiperidine-1-carboxylate | MS (ES) MH$^+$: 217 for $C_{10}H_{20}N_2O_3$ | Intermediate 156 |

Intermediates 258-259

The following Intermediates were synthesized by an analogous method to Intermediate 37 or Intermediate 83 from the starting materials (SM) given in the table below.

| Int | Compound | Data | SM |
|---|---|---|---|
| 258 | tert-Butyl (3S,4R)-4-{[(4-chloro-5-methyl-1H-pyrrol-2-yl)carbonyl]amino}-3-fluoropiperidine-1-carboxylate | MS (ES) MH$^+$: 360 for $C_{16}H_{23}ClFN_3O_3$; | Intermediate 64 and Intermediate 6 |
| 259 | tert-butyl (3S,4R)-4-{[(4-chloro-3-fluoro-5-methyl-1-{[2-(trimethylsilyl)ethoxy]methyl}-1H-pyrrol-2-yl)carbonyl]amino}-3-fluoropiperidine-1-carboxylate | MS (ESP): 530 (MNa$^+$) for $C_{22}H_{36}ClF_2N_3O_4Si$ | Intermediate 263 and Intermediate 64 |

Intermediates 260-261

The following Intermediates were synthesized by an analogous method to Intermediate 50 or Intermediate 74 from the starting materials (SM) given in the table below.

| Int | Compound | Data | SM |
|---|---|---|---|
| 260 | 4-Chloro-N-[(3S,4R)-3-fluoropiperidin-4-yl]-5-methyl-1H-pyrrole-2-carboxamide 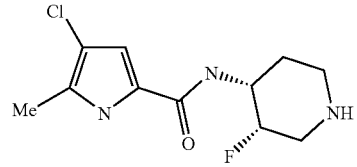 [SMILES: Cc1[nH]c(C(=O)N[C@@H]2CCNC[C@@H]2F)cc1Cl] | MS (ES): MH$^+$: 260 for $C_{11}H_{15}ClFN_3O$ | Intermediate 258 |

-continued

| Int | Compound | Data | SM |
|---|---|---|---|
| 261 | 4-chloro-3-fluoro-N-[(3S,4R)-3-fluoropiperidin-4-yl]-5-methyl-1H-pyrrole-2-carboxamide | MS(ESP): 278 (MH$^+$) for C$_{11}$H$_{14}$ClF$_2$N$_3$O | Intermediate 262 |

Intermediate 262 tert-butyl (3S,4R)-4-{[(4-chloro-3-fluoro-5-methyl-1H-pyrrol-2-yl)carbonyl]amino}-3-fluoropiperidine-1-carboxylate tert-butyl (3S,4R)-4-{[(4-chloro-3-fluoro-5-methyl-1-{[2-(trimethylsilyl)ethoxy]methyl}-1H-pyrrol-2-yl)carbonyl]amino}-3-fluoropiperidine-1-carboxylate (Intermediate 259, 80 mg, 0.16 mmol) was dissolved in anhydrous THF (6 ml), followed by the addition of tetra-butyl ammonium fluoride (1 ml, 1M in THF) and ethylene diamine (1 mmol), the mixture was then stirred at 50° C. over night. After cooling down to room temperature, the reaction mixture was diluted with ethyl acetate (20 ml) and washed with saturated aqueous sodium bicarbonate (10 ml) and brine (10 ml), dried over anhydrous sodium sulfate, concentrated and purified by column chromatography (100%~70% hexanes/ethyl acetate) to give the desired product (55 mg).
MS (ESP): 378 (MNa$^+$) for C$_{16}$H$_{22}$ClF$_2$N$_3$O$_3$.
$^1$H-NMR (CDCl$_3$) δ: 1.46 (s, 9H); 1.84 (m, 2H); 2.24 (s, 3H); 2.89 (m, 2H); 4.28 (m, 2H); 4.50 (m, 1H); 4.70 (m, br, 1H); 6.32 (m, 1H); 9.36 (br, 1H).

Intermediate 263

4-chloro-3-fluoro-5-methyl-1-{[2-(trimethylsilyl)ethoxy]methyl}-1H-pyrrole-2-carboxylic acid tert-butyl 4-chloro-3-fluoro-5-methyl-1-{[2-(trimethylsilyl)ethoxy]methyl}-1H-pyrrole-2-carboxylate (Intermediate 264, 100 mg) was dissolved in N-methylpyrrolidinone (10 ml), heated to 200° C. for 30 minutes. The resulting solution was carried on to the next step without further purification.
MS (ESP): 307 (M$^-$) for C$_{12}$H$_{19}$ClFNO$_3$Si.

Intermediate 264 tert-butyl 4-chloro-3-fluoro-5-methyl-1-{[2-(trimethylsilyl)ethoxy]methyl}-1H-pyrrole-2-carboxylate tert-butyl 3-bromo-4-chloro-5-methyl-1-{[2-(trimethylsilyl)ethoxy]methyl}-1H-pyrrole-2-carboxylate (Intermediate 265, 480 mg, 1.13 mmol) was dissolved in dry THF (8 ml), cooled down to −78° C., n-BuLi (2.5M in Hexane, 3.39 mmol) was added dropwise into the mixture via syringe and the mixture was stirred at −78° C. for 30 min followed by a quick addition of N-Fluorobenzensulfonimide (1.25 g, 3.96 mmol in 5 ml of THF/Toluene 1:1), the resulting mixture was then stirred at −78° C. for 30 min and slowly warmed up to room temperature during a period of 12 hrs. The reaction was quenched at 0° C. with drops of saturated NH$_4$Cl solution and further diluted with EtOAc (50 ml). The organic phase was washed with brine and dried over anhydrous MgSO$_4$, concentrated to an oil and purified by flash column chromatography eluted with 10% EtOAc in Hexanses. The desired product was obtained as an oil (125 mg).

MS (ESP): 364 (MH$^+$) for C$_{16}$H$_{27}$ClFNO$_3$Si.
$^1$H-NMR (CDCl$_3$) δ: 0.00 (s, 9H); 0.90 (t, 2H); 1.58 (s, 9H); 2.31 (s, 3H); 3.52 (t, 2H); 5.70 (s, 2H).
$^{19}$F-NMR (CDCl$_3$) δ: −148.85.

Intermediate 265 tert-butyl 3-bromo-4-chloro-5-methyl-1-{[2-(trimethylsilyl)ethoxy]methyl}-1H-pyrrole-2-carboxylate

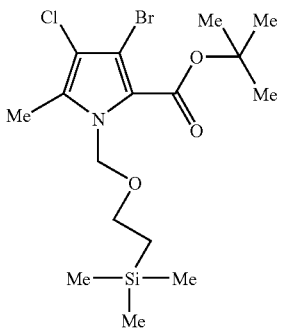 [SMILES: Cc1c(Cl)c(Br)c(C(=O)OC(C)(C)C)n1COCC[Si](C)(C)C]

Ethyl 3-bromo-4-chloro-5-methyl-1-{[2-(trimethylsilyl)ethoxy]methyl}-1H-pyrrole-2-carboxylate (Intermediate 266, 564 mg, 1.42 mmol), t-Butylacetate (330 mg, 2.84 mmol) and potassium t-butoxide (0.14 mmol) were mixed together and stirred at room temperature for 10 minutes, concentrated to an oil under vacuum. t-Butylacetate (330 mg, 2.84 mmol) and potassium t-butoxide (0.14 mmol) were added again into the reaction mixture, repeated the same procedure again. The resulting reaction crude was filtered through a short pass silica gel, washed with ethyl acetate, the combined filtrate was concentrated to an oil and purified by column chromatography (2% ethyl acetate in hexanes) to give the desired product as an oil (485 mg).
$^1$H-NMR (CDCl$_3$) δ: 0.00 (s, 9H); 0.90 (t, 2H); 1.58 (s, 9H); 2.33 (s, 3H); 3.52 (t, 2H); 5.75 (s, 2H).

Intermediate 266

Ethyl 3-bromo-4-chloro-5-methyl-1-{[2-(trimethylsilyl)ethoxy]methyl}-1H-pyrrole-2-carboxylate To a suspension of sodium hydride (76 mg, 3.16 mmol) in dry DMF (5 ml), solution of ethyl 3-bromo-4-chloro-5-methyl-1H-pyrrole-2-carboxylate (Intermediate 267, 420 mg, 1.58 mg) was added, the resulting mixture was stirred at 0° C. for 30 minutes until gas evolution seized. Trimethylsilylethylmethyl chloride (315 mg, 1.89 mmol) was added drop wise and stirred over night while allowing the reaction mixture warmed up to room temperature slowly. The reaction was quenched with cold water, diluted with ether (20 ml), washed with water and brine, the organic layer was dried over anhydrous sodium sulfate, concentrated and purified by column chromatography (95% hexanes in ethyl acetate) to give the desired product as an oil (624 mg).

MS (ESP): 397 (MH$^+$) for C$_{14}$H$_{23}$BrClNO$_3$Si.

$^1$H-NMR (CDCl$_3$) δ: 0.00 (s, 9H); 0.90 (t, 2H); 1.43 (t, 3H); 2.38 (s, 3H); 3.55 (t, 2H); 4.34 (q, 2H); 5.75 (s, 2H).

Intermediate 267

Ethyl 3-bromo-4-chloro-5-methyl-1H-pyrrole-2-carboxylate

Ethyl 4-chloro-5-methyl-1H-pyrrole-2-carboxylate (Intermediate 7, 300 mg, 1.6 mmol) was dissolved in dry dichloromethane (10 ml), N-bromosuccinimide (285 mg, 1.6 mmol) was added at 0° C. and resulting mixture was stirred at room temperature over night. The mixture was poured into cold sodium hydroxide aqueous solution (2M) (20 ml), extracted with diethyl ether (2×20 ml). The organic phase was then washed with water (20 ml) and brine (20 ml), dried over anhydrous sodium sulfate, concentrated and purified by column chromatography (hexanes/ethyl acetate, gradient) to give the desired product as a yellowish solid. (424 mg).

MS (ESP): 266 (MH$^+$) for C$_8$H$_9$BrClNO$_2$.

$^1$H-NMR (CDCl$_3$) δ: 1.39 (t, 3H); 2.32 (s, 3H); 4.34 (q, 2H); 9.04 (s, br, 1H).

Intermediate 268

Trans(±)-tert-butyl-4-[(diphenylmethylene)amino]-3-hydroxypiperidine-1-carboxylate tert-butyl-4-amino-3-hydroxypiperidine-1-carboxylate (11.9 g; 55 mmol) and benzophenone imine (10 g; 59 mmol; 1.05 eq.) were dissolved in anhydrous toluene and heated to reflux for 18 hrs. Monitored the reaction by TLC (30% EtOAc/hexanes with 0.1% triethylamine). The crude reaction was concentrated and purified by flash column chromatography. Isolation gave 18.4 g of the title compound in an 86% yield. LC/MS (ES$^+$)[(M+H)$^+$]: 381 for C$_{23}$H$_{28}$N$_2$O$_3$.

Intermediate 269

Cis(±)-tert-butyl-3-azido-4-[(diphenylmethylene)amino]piperidine-1-carboxylate

In a flame-dried flask triphenylphosphine (3.86 g; 14.7 mmol; 2 eq.) was dissolved in anhydrous THF (15 ml) and cooled to 0 C. DIAD (2.97 g; 14.7 mmol; 2 eq.) was slowly added dropwise. Upon addition a white precipitate formed. A THF solution containing tert-butyl-4-[(diphenylmethylene) amino]-3-hydroxypiperidine-1-carboxylate (Intermediate 268, 2.8 g; 7.36 mmol) was added (amount of THF added was such that the final concentration of alcohol was ca. 0.5-1M). The resultant reaction slurry was stirred at 0 C for 30 minutes. (PhO)$_2$PON$_3$ (4.05 g; 14.7 mmol; 2 eq.) was then added and the reaction was allowed to warm to RT and stirred for 12 hrs. Monitored by LC/MS. The reaction was concentrated and purified by flash column chromatography (0-30% EtOAc/ hexanes with 0.1% triethylamine). Isolation gave 2.13 g of the title compound in 71% yield. LC/MS (ES$^+$)[(M+H)$^+$]: 406 for C$_{23}$H$_{27}$N$_5$O$_2$.

Intermediate 270

Cis(±)tert-butyl-4-amino-3-azidopiperidine-1-carboxylate

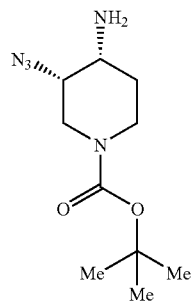

tert-butyl-3-azido-4-[(diphenylmethylene)amino]piperidine-1-carboxylate (Intermediate 269, 1.36 g; 3.3 mmol) was dissolved in 10 ml's of aqueous THF (5% H$_2$O). PPTS (850 mg; 3.4 mmol; 1.03 eq.) was added in a single portion. The initial cloudy solution became clear within minutes. Upon completion (as determined by LC/MS analysis) the reaction was concentrated and azeotropically dried with acetonitrile. No further purification. (LC/MS: see disappearance of starting material and formation of Ph$_2$C=O. Product is not observable due to lack of chromophore).

Intermediate 271

Cis(±)tert-butyl-3-azido-4-{[(3,4-dichloro-5-methyl-1H-pyrrol-2-yl)carbonyl]amino}piperidine-1-carboxylate Crude tert-butyl-4-amino-3-azidopiperidine-1-carboxylate (Intermediate 270, 3.3 mmol) was dissolved in anhydrous CH$_2$Cl$_2$ (10 ml) and DIEA (1.27 g; 1.6 ml; 9.9 mmol; 3 eq.). The solution was cooled to 0 C and 3,4-dichloro-5-methyl-1H-pyrrole-2-carbonyl chloride (736 mg; 3.5 mmol; 1.05 eq.) was added. The reaction was complete within 30 minutes. Dilute with CH$_2$Cl$_2$ and wash with H$_2$O (×2), brine and dried over Na$_2$SO$_4$. Filter and concentrate. Purify by flash column chromatography (0-60% EtOAc/hexanes). Isolation gave 967 mg in 69% yield over the two-step sequence. LC/MS (ES$^-$) [(M−H)$^+$]: 415, 417 for C$_{16}$H$_{22}$Cl$_2$N$_6$O$_3$.

Intermediate 272

Cis(±)N-(-3-azidopiperidin-4-yl)-3,4-dichloro-5-methyl-1H-pyrrole-2-carboxamide hydrochloride tert-butyl-3-azido-4-{[(3,4-dichloro-5-methyl-1H-pyrrol-2-yl)carbonyl]amino}piperidine-1-carboxylate (Intermediate 271, 967 mg; 2.3 mmol) was dissolved in 4N HCl in dioxanes (20 ml) and methanol (10 ml). The solution was stirred for 2 hours and monitored by LC/MS. Upon completion the solvent was removed and the crude reaction mixture was azeotroped with methanol to remove excess HCl. No further purification. LC/MS (ES$^+$)[(M+H)$^+$]: 317, 319 for C$_{11}$H$_{14}$Cl$_2$N$_6$O.

Intermediate 273

(2R)-2-Methoxypropan-1-amine hydrochloride (1725-162)

tert-Butyl [(2R)-2-methoxypropyl]carbamate (Intermediate 277, 0.33 g, 1.74 mmol) and Hydrochloric acid (4 M, 1.5 mL) were combined and stirred at room temperature for two hours. Then it was concentrated and triturated with diethyl ether to give white crystalline solid (0.20 g) as the product.

NMR: 1.14 (d, 3H), 3.30 (s, 3H), 3.35-3.45 (m, 2H), 7.99 (brs, 3H).

Intermediates 274-275

The following compounds were produced according to the procedure for Intermediate 273 or by hydrogenation using the starting materials listed.

| Int | Compound | Data | SM |
|---|---|---|---|
| 274 | (2S)-2-methoxypropan-1-amine hydrochloride | NMR: 1.14 (d, 3H), 3.30 (s, 3H), 3.35-3.45 (m, 2H), 7.99 (brs, 3H) | Intermediate 278 |
| 275 | (2R)-1-Methoxypropan-2-amine hydrochloride | NMR: 1.14 (d, 3H), 3.29 (s, 3H), 8.07 (brs, 3H), rest of the peaks are buried under huge water peak | Intermediate 276 |

Intermediate 276

Benzyl [(1R)-2-methoxy-1-methylethyl]carbamate

To a solution of benzyl [(1R)-2-hydroxy-1-methylethyl] carbamate (0.5 g, 2.38 mmol) in acetonitrile (20 mL), silver oxide (3.8 g, 13.09 mmol) is added followed by the addition of methyl iodide (1.94 mL, 23.8 mmol). The resultant mixture was stirred overnight at room temperature. The insoluble salt was filtered off and the filtrate was concentrated. The residue was flashed using silica and Ethyl acetate/hexanes system as eluent to give the desired product as clear oil (0.38 g).

MS (ES) MH+Na: 246 for $C_{12}H_{17}NO_3$;

NMR: 1.01 (d, 3H), 3.12-3.17 (m, 1H), 3.22 (s, 3H), 3.25-3.26 (m, 1H), 3.60-3.75 (m, 1H), 5.00 (s, 2H), 7.16 (d, 1H), 7.29-7.36 (m, 5H).

Intermediate 277 tert-Butyl [(2R)-2-methoxypropyl]carbamate

To a solution of tert-butyl [(2R)-2-hydroxypropyl]carbamate (0.4 g, 2.28 mmol) in THF (5 mL), sodium hydride (0.06 g, 2.51 mmol) was added at 0° C. The resulting solution was stirred for 30 minutes at that temperature and then methyl iodide (0.14 mL, 2.28 mmol) was added. The reaction was warmed to room temperature slowly and allowed to stir for an additional two hours. The reaction was quenched by adding water and extracted with ethyl acetate. The extract was washed with sodium bicarbonate solution, water and brine. It was dried over magnesium sulfate and concentrated. The desired product was obtained as clear oil (0.31 g) and it did not need any further purification.

NMR (CDCl$_3$): 1.15 (d, 3H), 1.43 (s, 9H), 3.31-3.33 (m, 2H), 3.34 (s, 3H), 3.77-3.81 (m, 1H), 4.66 (brs, 1H).

Intermediate 278 tert-Butyl [(2S)-2-methoxypropyl]carbamate

The title compound was synthesized by using the method analogous to the synthesis of Intermediate 277 starting with tert-butyl [(2S)-2-hydroxypropyl]carbamate and alkylating it with methyl iodide.

NMR (CDCl$_3$): 1.15 (d, 3H), 1.43 (s, 9H), 3.31-3.33 (m, 2H), 3.34 (s, 3H), 3.77-3.81 (m, 1H), 4.66 (brs, 1H).

Example 441

The following Example was prepared by the procedure described in Example 203 from the starting materials (SM) indicated.

| Ex | Compound | Data | SM |
|---|---|---|---|
| 441 | ethyl 2-((3S,4R)-4-{[(3,4-dichloro-5-methyl-1H-pyrrol-2-yl)carbonyl]amino}-3-methoxypiperidin-1-yl)-4-({[2-methoxy-1-(methoxymethyl)ethyl]amino}carbonyl)-1,3-thiazole-5-carboxylate | MS (ES) MH+: 605 for $C_{24}H_{33}Cl_2N_5O_7S$; | Example 188 and [2-methoxy-1-(methoxymethyl)ethyl]amine (ChemPacific) |

Example 442

The following Example was prepared by the procedure described in Example 383 from the starting materials (SM) indicated.

| Ex | Compound | Data | SM |
|---|---|---|---|
| 442 | 2-((3S,4R)-4-{[(3,4-dichloro-5-methyl-1H-pyrrol-2-yl)carbonyl]amino}-3-methoxypiperidin-1-yl)-4-({[2-methoxy-1-(methoxymethyl)ethyl]amino}carbonyl)-1,3-thiazole-5-carboxylic acid | MS (ES) MH$^+$: 578 for $C_{22}H_{29}Cl_2N_5O_7S$ NMR: 1.77 (s, 2H) 2.19 (s, 3H) 3.24 (s, 3H) 3.27 (s, 3H) 3.38 (s, 5H) 3.49 (s, 6H) 4.32 (s, 2H) 7.18 (s, 1H) 8.93 (s, 1H) 12.16 (s, 1H) 16.17 (s, 1H) | Example 441 |

Example 443

The following Example was prepared by the procedure described in Example 417 from the starting materials (SM) indicated

| Ex | Compound | Data | SM |
|---|---|---|---|
| 443 | sodium 2-((3S,4R)-4-{[(3,4-dichloro-5-methyl-1H-pyrrol-2-yl)carbonyl]amino}-3-methoxypiperidin-1-yl)-4-({[2-methoxy-1-(methoxymethyl)ethyl]amino}carbonyl)-1,3-thiazole-5-carboxylate | MS (ES) MH$^+$: 578 for $C_{22}H_{28}Cl_2N_5O_7SNa$ NMR: 1.70 (s, 2H) 2.17 (s, 3H) 3.21-3.26 (m, 6H) 3.34 (s, 4H) 3.35-3.38 (m, 6H) 3.49 (s, 1H) 3.86 (d, 1H) 4.04-4.16 (m, 3H) 4.22 (s, 1H) 7.18 (d, 1H) 12.17 (s, 1H) 13.33 (d, 1H) Adduct (Salt) Na$^+$ | Example 442 |

What is claimed is:

1. A compound:

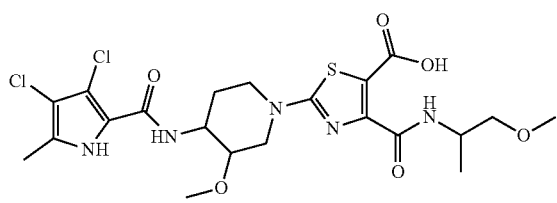 [SMILES: COCC(C)NC(=O)c1nc(N2CCC(NC(=O)c3[nH]c(C)c(Cl)c3Cl)C(OC)C2)sc1C(=O)O]

and/or a pharmaceutically acceptable salt thereof.

2. A compound:

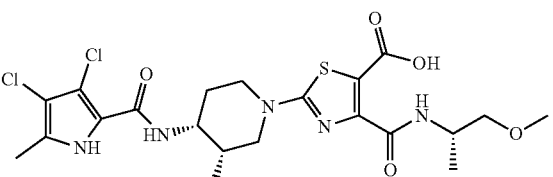

and/or a pharmaceutically acceptable salt thereof.

3. The compound of claim 2, in the form of a free acid.

4. The compound of claim 2, in the form of a mixture of a free acid and a pharmaceutically acceptable salt thereof.

5. The compound of claim 2, in the form of a pharmaceutically acceptable salt.

6. The compound of claim 5, in the form of a potassium salt.

7. The compound of claim 5, in the form of a sodium salt.

8. A pharmaceutical composition comprising a compound of claim 2, and/or a pharmaceutically acceptable salt thereof, and a pharmaceutically acceptable diluent and/or carrier.

9. The pharmaceutical composition of claim 8, wherein the compound is in the form of a potassium salt.

* * * * *